(12) United States Patent
Chen et al.

(10) Patent No.: US 11,840,513 B2
(45) Date of Patent: *Dec. 12, 2023

(54) SUBSTITUTED NICOTINIMIDE INHIBITORS OF BTK FOR TREATING CANCER

(71) Applicant: GUANGZHOU INNOCARE PHARMA TECH CO., LTD., Guangzhou (CN)

(72) Inventors: Xiangyang Chen, Beijing (CN); Yingxiang Gao, Beijing (CN); Chong Liu, Beijing (CN); Haihong Ni, Beijing (CN)

(73) Assignee: Guangzhou Innocare Pharma Tech Co., Ltd, Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/804,012

(22) Filed: May 25, 2022

(65) Prior Publication Data

US 2022/0298153 A1 Sep. 22, 2022

Related U.S. Application Data

(60) Division of application No. 16/421,197, filed on May 23, 2019, now Pat. No. 11,345,695, which is a continuation of application No. 15/942,772, filed on Apr. 2, 2018, now Pat. No. 10,301,297, which is a continuation of application No. 15/025,654, filed as application No. PCT/US2014/058084 on Sep. 29, 2014, now Pat. No. 9,951,056.

(60) Provisional application No. 61/884,958, filed on Sep. 30, 2013.

(30) Foreign Application Priority Data

Oct. 16, 2013 (CN) .......................... 201310485048.1

(51) Int. Cl.
| | | |
|---|---|---|
| *A61K 31/444* | (2006.01) | |
| *A61P 35/00* | (2006.01) | |
| *C07D 417/04* | (2006.01) | |
| *C07D 401/14* | (2006.01) | |
| *C07D 213/82* | (2006.01) | |
| *C07D 231/14* | (2006.01) | |
| *C07D 401/04* | (2006.01) | |
| *C07D 403/04* | (2006.01) | |
| *C07D 413/04* | (2006.01) | |
| *C07D 277/56* | (2006.01) | |
| *C07D 211/34* | (2006.01) | |
| *C07D 295/185* | (2006.01) | |
| *C07D 401/12* | (2006.01) | |

(52) U.S. Cl.
CPC .......... *C07D 417/04* (2013.01); *A61K 31/444* (2013.01); *A61P 35/00* (2018.01); *C07D 211/34* (2013.01); *C07D 213/82* (2013.01); *C07D 231/14* (2013.01); *C07D 277/56* (2013.01); *C07D 295/185* (2013.01); *C07D 401/04* (2013.01); *C07D 401/12* (2013.01); *C07D 401/14* (2013.01); *C07D 403/04* (2013.01); *C07D 413/04* (2013.01)

(58) Field of Classification Search
CPC ............................ C07D 401/14; A61K 31/444
See application file for complete search history.

(56) References Cited

U.S. PATENT DOCUMENTS

| | | |
|---|---|---|
| 9,951,056 B2 | 4/2018 | Chen et al. |
| 10,301,297 B2 | 5/2019 | Chen et al. |
| 2010/0144705 A1 | 6/2010 | Miller |

FOREIGN PATENT DOCUMENTS

| | | |
|---|---|---|
| CN | 101060842 A | 10/2007 |
| CN | 101460466 B | 6/2012 |
| CN | 101610676 B | 3/2013 |
| CN | 103848810 A | 6/2014 |
| CN | 201410519430.4 | 11/2015 |
| JP | 2008-513500 A | 5/2008 |
| WO | 2006034317 A2 | 3/2006 |
| WO | 2006099075 A2 | 9/2006 |
| WO | 2007117692 A2 | 10/2007 |
| WO | 2008033834 A1 | 3/2008 |
| WO | 2008039218 A2 | 4/2008 |
| WO | 2008121742 A2 | 10/2008 |
| WO | 2009158571 A1 | 12/2009 |

(Continued)

OTHER PUBLICATIONS

Meredith et al., Journal of Medicinal Chemistry, 2010, 53(15), 5422-5438.

(Continued)

*Primary Examiner* — Susanna Moore
(74) *Attorney, Agent, or Firm* — Viola Kung; Perkins Coie LLP

(57) ABSTRACT

Compounds of Formula I, as shown below and defined herein:

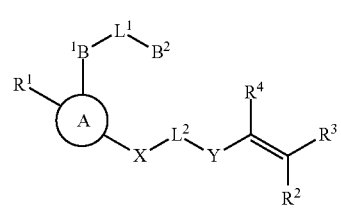

and pharmaceutically acceptable salts, syntheses, intermediates, formulations, and methods of treating diseases including cancer, inflammation, and autoimmune disease mediated at least in part by Bruton's Tyrosine Kinase (BTK).

8 Claims, No Drawings

(56) References Cited

FOREIGN PATENT DOCUMENTS

| | | |
|---|---|---|
| WO | 2010055304 A2 | 5/2010 |
| WO | 2012170976 A2 | 12/2012 |
| WO | 2012171337 A1 | 12/2012 |
| WO | 2014025976 A1 | 2/2014 |
| WO | 2014068527 A1 | 5/2014 |
| WO | 2014078578 A1 | 5/2014 |
| WO | 2014082598 A1 | 6/2014 |
| WO | 2014151620 A1 | 9/2014 |
| WO | 2014173289 A1 | 10/2014 |
| WO | 2014210255 A1 | 12/2014 |
| WO | WO-2015061247 A2 * 4/2015 ......... A61K 31/4409 | |

OTHER PUBLICATIONS

Chinese Second Office Action dated Apr. 22, 2016 for corresponding Chinese Patent Application No. 201410519430.4.
International Search Report in corresponding PCT Application No. PCT/US2014/058084, dated Mar. 19, 2015.
Chinese Office Action dated Nov. 23, 2015 for the corresponding Chinese Patent Application No. 201410519430.4 (an English translation attached hereto).
Extended European Search Report in the corresponding European patent application No. 14848083.3, dated Feb. 27, 2017.
International Search Report of corresponding PCT Application No. PCT/US2013/054096, dated Sep. 30, 2013.
Written Opinion of Singaporean Patent Application No. 11201602070T, dated Mar. 2, 2017.

* cited by examiner

SUBSTITUTED NICOTINIMIDE INHIBITORS OF BTK FOR TREATING CANCER

This application is a divisional of U.S. application Ser. No. 16/421,197, filed May 23, 2019; which is a continuation of U.S. application Ser. No. 15/942,772, filed Apr. 2, 2018, now U.S. Pat. No. 10,301,297; which is a continuation of U.S. application Ser. No. 15/025,654, filed Mar. 30, 2016, now U.S. Pat. No. 9,951,056; which is a 371 national phase application of PCT/US2014/058084, filed Sep. 29, 2014; which claims priority under 35 U.S.C. 119(e) to U.S. Provisional Patent Application No. 61/884,958, filed on Sep. 30, 2013, and under 35 U.S.C. 119(a) to Chinese Patent Application No. 201310485048.1, filed on Oct. 16, 2013, The entire contents of each of the above-referenced applications are incorporated herein by reference.

FIELD AND BACKGROUND

The present invention relates to chemical compounds, pharmaceutical compositions including these compounds, and their use in treatment of disease. In particular, the present invention relates to the use of substituted nicotinimides as irreversible inhibitors of tyrosine kinases useful in the treatment of diseases mediated by Bruton's Tyrosine Kinase (BTK) including cancer, inflammation and autoimmune disease.

BTK is a Tec family non-receptor protein kinase which plays a role in multiple signal-transduction pathways regulating survival, activation, proliferation, and differentiation of B-lineage lymphoid cells. BTK is overexpressed and active in several B-lineage lymphoid malignancies. BTK is expressed in malignant cells in humans with B-Cell Precursor (BCP)-Acute Lymphoblastic Leukemia (ALL), Chronic Lymphocytic Leukemia (CLL), and Non-Hodgkin's Lymphoma (NHL). BTK is an upstream activator of anti-apoptotic signaling molecules and networks, including: Signal Transducer and Activator of Transcription 5 (STAT5) protein, Phosphatidylinositol (PI), 3-kinase/AKT/Mammalian Target of Rapamycin (mTOR) pathway, and Nuclear Factor kappa B (NF-κB). D'Cruz, Osmond J., *OncoTargets and Therapy* 2013: 6, 161-176.

PCT/CN2012/000971 to De Man et al. describes that BTK is expressed in B cells and myeloid cells, and is a terminal enzyme in the B-Cell antigen Receptor (BCR) signaling pathway. Mutations in human BTK leads to X-Linked Agammaglobulinemia (XLA), an immunodeficiency disease related to a failure to generate mature B cells leading to reduced immunoglobulin in serum. BTK is therefore implicated in regulation of the production of autoantibodies in autoimmune diseases. Furthermore, BTK may play a role in treatment of autoimmune diseases characterized by production of pro-inflammatory cytokines and chemokines by B cells due to BTK's position in the BCR pathway. BTK inhibitors may be used for treatment of B cell lymphomas due to BTK's involvement in the regulation of proliferation and apoptosis of B cells. Inhibition of BTK is relevant in particular for B cell lymphomas due to chronic active BCR signaling. Davis et al., *Nature,* 463 (2010), 88-94.

Adaptive immune responses may involve B lymphocyte activation and absence of B lymphocyte activation is an indication of autoimmune disease. Treatment of autoimmune disease, such as Rheumatoid Arthritis (RA), with Rituximab, an anti-CD20 therapy, demonstrates that B cell therapies are effective. Additionally, treatment with Rituximab has been shown to improve disease symptoms in Relapsing Remitting Multiple Sclerosis (RRMS) and Systemic Lupus Erythematosus (SLE) patients. Accordingly, targeting B cell immunity is effective for treatment of autoimmune diseases.

SUMMARY

The present invention includes certain substituted compounds described herein, their pharmaceutically acceptable salts, solvates and hydrates, preparation of the compounds, intermediates, pharmaceutical compositions and formulations thereof, and methods of treating disease including cancers, inflammation, and autoimmune diseases therewith.

The present invention includes compounds of Formula I and pharmaceutically acceptable salts thereof as provided below and further defined herein:

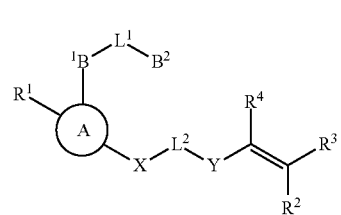

I

In some aspects, compounds of the invention are irreversible inhibitors of kinases, including Bruton's Tyrosine Kinase (BTK). In some aspects, compounds of the invention are selective inhibitors of BTK.

In some aspects, the invention includes methods of treating proliferative disease, particularly cancers, conditions causing inflammation, and autoimmune diseases mediated at least in part by BTK, alone or in combination regimens with other therapies.

Compounds of the present invention, and pharmaceutically acceptable compositions thereof, are useful as inhibitors of protein kinases. In some embodiments, the compounds are effective as inhibitors of Bruton's Tyrosine Kinase (BTK). In some aspects, the invention includes pharmaceutically acceptable salts of the compounds of Formula I:

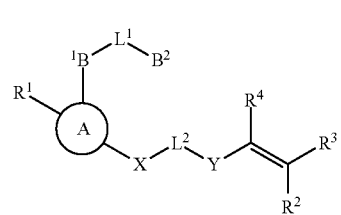

I wherein:
A is selected from $C_{3-12}$cycloalkyl, $C_{3-12}$heterocycloalkyl, $C_{3-12}$aryl, or $C_{3-12}$heteroaryl, any of which is optionally substituted with $G^1$ substituents;

$B^1$ is selected from $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^2$ substituents;

$B^2$ is selected from $C_{0-12}$alkyl, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^3$ substituents;

$L^1$ is selected from —$C_{0-2}$alkyl-, —$CR^5R^6$—, —$C_{0-3}$alkyl $(R^5)(OH)$—, —$C(O)$—, —$CH_2O$—, —$OCH_2$—, —$CF_2$—, —$SCR^5R^6$—, —$CR^5R^6S$—, —$N(R^5)$—, —$N(R^5)C(O)$—, —$C(O)N(R^5)$—, —$N(R^5)C(O)N(R^6)$—, —O—, —S—, —$S(O)_{m1}$—, —$N(R^5)S(O)_{m1}$—, or —$S(O)_{m1}N(R^5)$—;

$L^2$ is selected from —$C_{0-4}$alkyl-, —$C(O)$—, —$N(R^7)$—, —$N(R^7)C(O)$—, or —$N(R^7)S(O)_{m2}$—;

X is selected from $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^4$ substituents;

Y is selected from —$C(O)$—, —$N(R^8)$—, —$N(R^8)C(O)$—, —$S(O)_{m3}$—, or —$N(R^8)S(O)_{m3}$—;

$R^1$ is selected from —$C(O)R^9$, —$C(O)NR^9R^{10}$, —$C(O)OR^9$, $C_{1-4}$alkynyl, $OR^9$, $S(O)_{m4}R^9R^{10}$, or —CN;

$R^2$, $R^3$, and $R^4$ are each independently selected from $C_{0-12}$alkyl, —CN, halo, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^5$ substituents;

$R^5$, $R^6$, $R^7$, $R^8$, $R^9$, and $R^{10}$ are each independently selected from $C_{0-12}$alkyl, $C_{3-12}$cycloalkyl-$C_{0-12}$alkyl-, $C_{3-12}$heterocycloalkyl-$C_{0-12}$alkyl-, aryl- $C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^6$ substituents;

$G^1$, $G^2$, $G^3$, $G^4$, $G^5$, and $G^6$ are each independently selected from one or more of $C_{0-12}$alkyl, —$C_{2-12}$alkenyl, —$C_{2-12}$alkynyl, D, —$CD_3$, —$OCD_3$, halo, —CN, -oxo-, —$CF_3$, —$OCF_3$, —$OCHF_2$, —$NO_2$, —$B(OH)_2$, —$P(O)C_{0-3}$ alkyl, —$PO(OR^{11})_2$, —$PO(OR^{11})R^{12}$, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, heteroaryl-$C_{3-12}$heterocycloalkyl-, —$C_{0-6}$alkyl$OR^{11}$, —$OC(O)NR^{11}R^{12}$, —$C(O)OR^{11}$, —$C(O)NR^{11}R^{12}$, —$C(O)R^{11}$, —$NR^{11}R^{12}$, —$NR^{11}C(O)R^{12}$, —$NR^{13}C(O)NR^{11}R^{12}$, —$S(O)_{m5}R^{11}$, and —$NR^{11}S(O)_{m5}R^{12}$, any of which is optionally substituted with $Q^1$ substituents;

$Q^1$ is selected from one or more of $C_{0-12}$alkyl-, —$C_{2-12}$alkenyl, —$C_{2-12}$alkynyl, D, halo, —CN, —$CD_3$, —$OCD_3$, -oxo-, —$CF_3$, —$OCF_3$, —$OCHF_2$, —$NO_2$, —$B(OH)_2$, —$PO(OR^{14})_2$, —$PO(OR^{14})R^{15}$, $NR^{14}R^{15}$, —$C(O)NR^{14}OH$, —$C_{0-6}$alkyl$OR^{14}$, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —$C(O)$—$C(O)$ $NR^{14}R^{15}$, —$C(O)$—$C(O)OR^{14}$, —$NR^{14}C$ $(O)R^{15}$, —$NR^{14}S(O)_{m6}R^{15}$, —$(CR^{15}R^{16})_{n1}C(O)R^{14}$, —$(CR^{15}R^{16})_{n1}C(O)OR^{14}$, —$(CR^{15}R^{16})_{n1}C(O)$ $NR^{14}R^{17}$, —$(CR^{15}R^{16})_{n1}S(O)_{m6}NR^{14}R^{17}$, —$(CR^{15}R^{16})_{n1}NR^{14}R^{17}$, —$(CR^{15}R^{16})_{n1}OR^{14}$, —$(CR^{15}R^{16})_{n1}S(O)_{m6}R^{14}$, —$NR^{16}C(O)NR^{14}R^{15}$, and —$NR^{16}S(O)_{m6}NR^{14}R^{15}$, any of which is optionally substituted with independently selected $E^1$ substituents;

$E^1$ is selected from one or more of $C_{0-12}$alkyl-, —$C_{2-12}$alkenyl, —$C_{2-12}$alkynyl, D, halo, —CN, -oxo-, —$CD_3$, —$OCD_3$, —$CF_3$, —$OCF_3$, —$OCHF_2$, —$NO_2$, —$B(OH)_2$, —$PO(OR^{18})_2$, —$PO(OR^{18})R^{19}$, —$C(O)$ $NR^{18}OH$, —$C(O)NR^{18}R^{19}$, —$C_{0-12}$alkyl$OR^{18}$, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —$C(O)$—$C(O)$ $NR^{18}R^{19}$, —$C_{0-12}$alkyl$C(O)OR^{18}$, —$C(O)$—$C(O)$ $OR^{18}$, —$OC(O)R^{18}$, —$NR^{18}C(O)R^{19}$, —$NR^{18}C(O)$ $OR^{19}$, —$NR^{18}S(O)_{m7}R^{19}$, —$(CR^{19}R^{20})_{n2}C(O)R^{18}$, —$(CR^{19}R^{20})_{n2}C(O)OR^{18}$, —$(CR^{19}R^{20})_{n2}C(O)$ $NR^{18}R^{21}$, —$(CR^{19}R^{20})_{n2}S(O)_{m7}NR^{18}R^{21}$, —$(CR^{19}R^{20})_{n2}NR^{18}R^{21}$, —$(CR^{19}R^{20})_{n20}R^{18}$, —$(CR^{19}R^{20})_{n2}S(O)_{m7}R^{18}$, —$NR^{20}C(O)NR^{18}R^{19}$, and —$NR^{20}S(O)_{m7}NR^{18}R^{19}$ substituents;

$R^{11}$, $R^{12}$, $R^{13}$, $R^{14}$, $R^{15}$, $R^{16}$, $R^{17}$, $R^{18}$, $R^{19}$, $R^{20}$, and $R^{21}$ are each independently selected from H, $C_{1-6}$alkyl-, $C_{3-8}$cycloalkyl-$C_{0-6}$alkyl-, $C_{3-8}$heterocycloalkyl-$C_{0-6}$alkyl-, aryl-$C_{0-6}$alkyl-, aryl-$C_{3-8}$cycloalkyl-, aryl-$C_{3-8}$heterocycloalkyl-, heteroaryl-$C_{1-6}$alkyl-, heteroaryl-$C_{3-8}$cycloalkyl-, or heteroaryl-$C_{3-8}$heterocycloalkyl-;

$R^3$ and $R^4$ are taken together with the carbon atoms to which they are attached to form a 3-12 membered partially saturated or unsaturated ring, wherein said ring optionally includes one or more additional heteroatoms selected from O, N, or $S(O)_{m8}$;

m1, m2, m3, m4, m5, m6, m7, m8, n1, and n2 are each independently selected from 0, 1, or 2;

or a pharmaceutically acceptable salt, solvate or a prodrug thereof.

In some aspects of Formula I, compounds of the present invention are a subgenus of Formula I, having the Formula Ia:

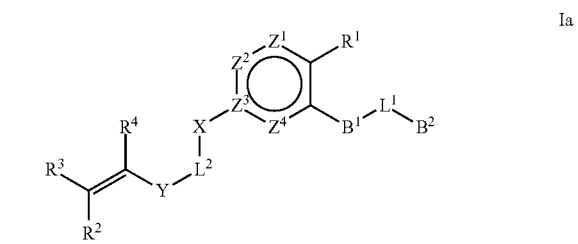

Ia wherein:

$B^1$ is selected from $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^2$ substituents;

$B^2$ is selected from $C_{0-12}$alkyl, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl- $C_{3-12}$cycloalkyl-, or heteroaryl-$C_{3-12}$heterocycloalkyl-, any of which is optionally substituted with $G^3$ substituents;

$L^1$ is selected from —$C_{0-2}$alkyl-, —$CR^5R^6$—, —$C_{0-3}$alkyl($R^5$)(OH)—, —C(O)—, —$CH_2O$—, —$OCH_2$—, —$CF_2$—, —$SCR^5R^6$—, —$CR^5R^6S$—, —N($R^5$)—, —N($R^5$)C(O)—, —C(O)N($R^5$)—, —N($R^5$)C(O)N($R^6$)—, —O—, —S—, —S(O)$_{m1}$—, —N($R^5$)S(O)$_{m1}$—, or —S(O)$_{m1}$N($R^5$)—;

$L^2$ is selected from —$C_{0-4}$alkyl-, —C(O)—, —N($R^7$)—, —N($R^7$)C(O)—, or —N($R^7$)S(O)$_{m2}$—;

X is selected from $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^4$ substituents;

Y is selected from —C(O)—, —N($R^8$)—, —N($R^8$)C(O)—, —S(O)$_{m3}$—, or —N($R^8$)S(O)$_{m3}$—;

$Z^1$ is $(CR^a)_{0-1}$;

$Z^2$ is selected from $CR^b$, $NR^b$, O, or S;

$Z^3$ is selected from C or N;

$Z^4$ is selected from CRC, NRC, O, or S;

$R^1$ is selected from —C(O)$R^9$, —C(O)$NR^9R^{10}$, —C(O)$OR^9$, $C_{1-4}$alkynyl, $OR^9$, S(O)$_{m4}R^9R^{10}$, or —CN;

$R^2$, $R^3$, $R^4$, $R^a$, $R^b$, and $R^c$ are each independently selected from $C_{0-12}$alkyl, —CN, halo, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^5$ substituents;

$R^5$, $R^6$, $R^7$, $R^8$, $R^9$, and $R^{10}$ are each independently selected from $C_{0-12}$alkyl, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^6$ substituents;

$G^1$, $G^2$, $G^3$, $G^4$, $G^5$, and $G^6$ are each independently selected from one or more of $C_{0-12}$alkyl, —$C_{2-12}$alkenyl, —$C_{2-12}$alkynyl, D, —$CD_3$, —$OCD_3$, halo, —CN, -oxo-, —$CF_3$, —$OCF_3$, —$OCHF_2$, —$NO_2$, —$B(OH)_2$, —$P(O)C_{0-3}$ alkyl, —$PO(OR^{11})_2$, —$PO(OR^{11})R^{12}$, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, heteroaryl-$C_{3-12}$heterocycloalkyl-, —$C_{0-6}$alkyl$OR^{11}$, —OC(O)$NR^{11}R^{12}$, —C(O)$OR^{11}$, —C(O)$NR^{11}R^{12}$, —C(O)$R^{11}$, —$NR^{11}R^{12}$, —$NR^{11}$C(O)$R^{12}$, —$NR^{13}$C(O)$NR^{11}R^{12}$, —S(O)$_{m5}R^{11}$, and —$NR^{11}$S(O)$_{m5}R^{12}$, any of which is optionally substituted with independently selected $Q^1$ substituents;

$Q^1$ is selected from one or more of $C_{0-12}$alkyl-, —$C_{2-12}$alkenyl, —$C_{2-12}$alkynyl, D, halo, —CN, —$CD_3$, —$OCD_3$, -oxo-, —$CF_3$, —$OCF_3$, —$OCHF_2$, —$NO_2$, —$B(OH)_2$, —$PO(OR^{14})_2$, —$PO(OR^{14})R^{15}$, $NR^{14}R^{15}$, —C(O)$NR^{14}$OH, —$C_{0-6}$alkyl$OR^{14}$, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{3-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —C(O)—C(O)$NR^{14}R^{15}$, —C(O)—C(O)$OR^{14}$, —OC(O)$R^{14}$, —$NR^{14}$C(O)$R^{15}$, —$NR^{14}$S(O)$_{m6}R^{15}$, —$(CR^{15}R^{16})_{n1}$C(O)$R^{14}$, —$(CR^{15}R^{16})_{n1}$C(O)$OR^{14}$, —$(CR^{15}R^{16})_{n1}$C(O)$NR^{14}R^{17}$, —$(CR^{15}R^{16})_{n1}$S(O)$_{m6}NR^{14}R^{17}$, —$(CR^{15}R^{16})_{n1}NR^{14}R^{17}$, —$(CR^{15}R^{16})_{n1}OR^{14}$, —$(CR^{15}R^{16})_{n1}$S(O)$_{m6}R^{14}$, —$NR^{16}$C(O)$NR^{14}R^{15}$, and —$NR^{16}$S(O)$_{m6}NR^{14}R^{15}$, any of which is optionally substituted with independently selected $E^1$ substituents;

$E^1$ is selected from one or more of $C_{0-12}$alkyl-, —$C_{2-12}$alkenyl, —$C_{2-12}$alkynyl, D, halo, —CN, -oxo-, —$CD_3$, —$OCD_3$, —$CF_3$, —$OCF_3$, —$OCHF_2$, —$NO_2$, —$B(OH)_2$, —$PO(OR^{18})_2$, —$PO(OR^{18})R^{19}$, —C(O)$NR^{18}$OH, —C(O)$NR^{18}R^{19}$, —$C_{0-12}$alkyl$OR^{18}$, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —C(O)—C(O)$NR^{18}R^{19}$, —$C_{0-12}$alkylC(O)$OR^{18}$, —C(O)—C(O)$OR^{18}$, —OC(O)$R^{18}$, —$NR^{18}$C(O)$R^{19}$, —$NR^{18}$C(O)$OR^{19}$, —$NR^{18}$S(O)$_{m7}R^{19}$, —$(CR^{19}R^{20})_{n2}$C(O)$R^{18}$, —$(CR^{19}R^{20})_{n2}$C(O)$OR^{18}$, —$(CR^{19}R^{20})_{n2}$C(O)$NR^{18}R^{21}$, —$(CR^{19}R^{20})_{n2}$S(O)$_{m7}NR^{18}R^{21}$, —$(CR^{19}R^{20})_{n2}NR^{18}R^{21}$, —$(CR^{19}R^{20})_{n2}OR^{18}$, —$(CR^{19}R^{20})_{n2}$S(O)$_{m7}R^{18}$, —$NR^{20}$C(O)$NR^{18}R^{19}$, and —$NR^{20}$S(O)$_{m7}NR^{18}R^{19}$ substituents;

$R^{11}$, $R^{12}$, $R^{13}$, $R^{14}$, $R^{15}$, $R^{16}$, $R^{17}$, $R^{18}$, $R^{19}$, $R^{20}$, and $R^{21}$ are each independently selected from H, $C_{1-6}$alkyl-, $C_{3-8}$cycloalkyl-$C_{0-6}$alkyl-, $C_{3-8}$heterocycloalkyl-$C_{0-6}$alkyl-, aryl-$C_{0-6}$alkyl-, aryl-$C_{3-8}$cycloalkyl-, aryl-$C_{3-8}$heterocycloalkyl-, heteroaryl-$C_{1-6}$alkyl-, heteroaryl-$C_{3-8}$cycloalkyl-, or heteroaryl-$C_{3-8}$heterocycloalkyl-;

$R^3$ and $R^4$ are taken together with the carbon atoms to which they are attached to form a 3-12 membered partially saturated or unsaturated ring, wherein said ring optionally includes one or more additional heteroatoms selected from O, N, or S(O)$_{m8}$;

m1, m2, m3, m4, m5, m6, m7, m8, n1, and n2 are each independently selected from 0, 1, or 2;

or a pharmaceutically acceptable salt, solvate or a prodrug thereof.

In some aspects of Formula I, compounds of the present invention are a subgenus of Formula I selected from one of Formulas Ib-Ii:

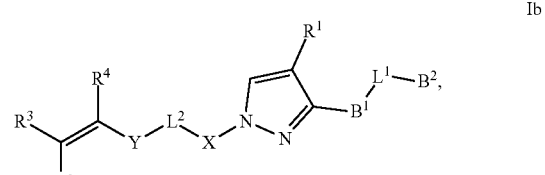

Ib

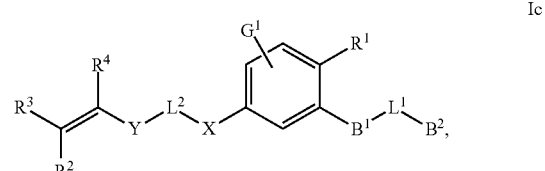

Ic

-continued

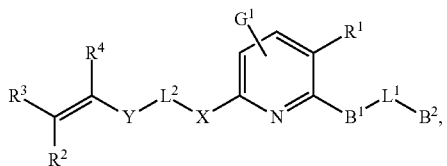

Id

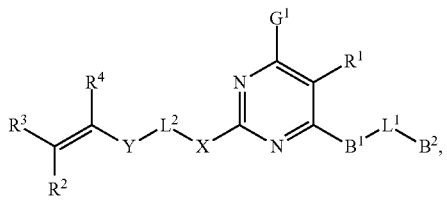

Ie

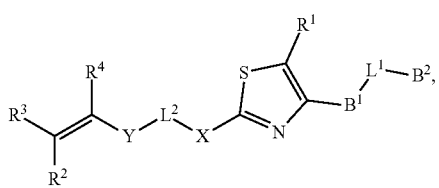

If

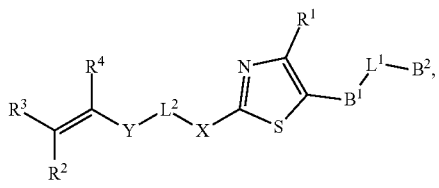

Ig

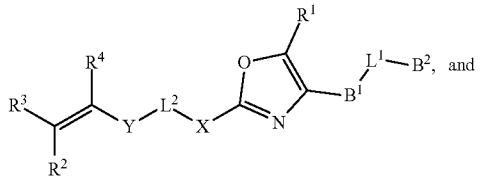

Ih

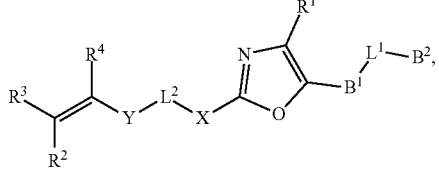

Ii wherein:
$B^1$ is selected from $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^2$ substituents;
$B^2$ is selected from $C_{0-12}$alkyl, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^3$ substituents;
$L^1$ is selected from —$C_{0-2}$alkyl-, —$CR^5R^6$—, —$C_{0-3}$alkyl($R^5$)(OH)—, —C(O)—, —$CH_2O$—, —$OCH_2$—, —$CF_2$—, —$SCR^5R^6$—, —$CR^5R^6S$—, —N($R^5$)—, —N($R^5$)C(O)—, —C(O)N($R^5$)—, —N($R^5$)C(O)N($R^6$)—, —O—, —S—, —S(O)$_{m1}$—, —N($R^5$)S(O)$_{m1}$—, or —S(O)$_{m1}$N($R^5$)—;
$L^2$ is selected from —$C_{0-4}$alkyl-, —C(O)—, —N($R^7$)—, —N($R^7$)C(O)—, or —N($R^7$)S(O)$_{m2}$—;
X is selected from $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^4$ substituents;
Y is selected from —C(O)—, —N($R^8$)—, —N($R^8$)C(O)—, —S(O)$_{m3}$—, or —N($R^8$)S(O)$_{m3}$—;
$R^1$ is selected from —C(O)$R^9$, —C(O)N$R^9R^{10}$, —C(O)O$R^9$, $C_{1-4}$alkynyl, O$R^9$, S(O)$_{m4}R^9R^{10}$ or —CN;
$R^2$, $R^3$, and $R^4$ are each independently selected from $C_{0-12}$alkyl, —CN, halo, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^5$ substituents;
$R^5$, $R^6$, $R^7$, $R^8$, $R^9$, and $R^{10}$ are each independently selected from $C_{0-12}$alkyl, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, or heteroaryl-$C_{3-12}$heterocycloalkyl-, any of which is optionally substituted with $G^6$ substituents;
$G^1$, $G^2$, $G^3$, $G^4$, $G^5$, and $G^6$ are each independently selected from one or more of $C_{0-12}$alkyl, —$C_{2-12}$alkenyl, —$C_{2-12}$alkynyl, D, —$CD_3$, —$OCD_3$, halo, —CN, -oxo-, —$CF_3$, —$OCF_3$, —$OCHF_2$, —$NO_2$, —$B(OH)_2$, —P(O)$C_{0-3}$ alkyl, —PO(O$R^{11}$)$_2$, —PO(O$R^{11}$)$R^{12}$, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, heteroaryl-$C_{3-12}$heterocycloalkyl-, —$C_{0-6}$alkylO$R^{11}$, —OC(O)N$R^{11}R^{12}$, —C(O)O$R^{11}$, —C(O)N$R^{11}R^{12}$, —C(O)$R^{11}$, —N$R^{11}R^{12}$, —N$R^{11}$C(O)$R^{12}$, —N$R^{13}$C(O)N$R^{11}R^{12}$, —S(O)$_{m5}R^{11}$, and —N$R^{11}$S(O)$_{m5}R^{12}$, any of which is optionally substituted with independently selected $Q^1$ substituents;
$Q^1$ is selected from one or more of $C_{0-12}$alkyl-, —$C_{2-12}$alkenyl, —$C_{2-12}$alkynyl, D, halo, —CN, —$CD_3$, —$OCD_3$, -oxo-, —$CF_3$, —$OCF_3$, —$OCHF_2$, —$NO_2$, —$B(OH)_2$, —PO(O$R^{14}$)$_2$, —PO(O$R^{14}$)$R^{15}$, N$R^{14}R^{15}$, —C(O)N$R^{14}$OH, —$C_{0-6}$alkylO$R^{14}$, aryl-$C_{0-12}$alkyl-, heteroaryl-$C_{0-12}$alkyl-, $C_{3-12}$cycloalkyl-$C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —C(O)—C(O)N$R^{14}R^{15}$, —C(O)—C(O)O$R^{14}$, —OC(O)$R^{14}$, —N$R^{14}$C(O)$R^{15}$, —N$R^{14}$S(O)$_{m6}R^{15}$, —(C$R^{15}R^{16}$)$_{n1}$C(O)$R^{14}$, —(C$R^{15}R^{16}$)$_{n1}$C(O)O$R^{14}$, —(C$R^{15}R^{16}$)$_{n1}$C(O)N$R^{14}R^{17}$, —(C$R^{15}R^{16}$)$_{n1}$S(O)$_{m6}$N$R^{14}R^{17}$, —(C$R^{15}R^{16}$)$_{n1}$N$R^{14}R^{17}$, —(C$R^{15}R^{16}$)$_{n1}$O$R^{14}$, —(C$R^{15}R^{16}$)$_{n1}$S(O)$_{m6}R^{14}$, —N$R^{16}$C(O)N$R^{14}R^{15}$, —N$R^{16}$S(O)$_{m6}$N$R^{14}R^{15}$, any of which is optionally substituted with independently selected $E^1$ substituents;
$E^1$ is selected from one or more of $C_{0-12}$alkyl-, —$C_{2-12}$alkenyl, —$C_{2-12}$alkynyl, D, halo, —CN, -oxo-, —$CD_3$, —$OCD_3$, —$CF_3$, —$OCF_3$, —$OCHF_2$, —$NO_2$, —$B(OH)_2$, —PO(O$R^{18}$)$_2$, —PO(O$R^{18}$)$R^{19}$, —C(O)N$R^{18}$OH, —C(O)N$R^{18}R^{19}$, —$C_{0-12}$alkylO$R^{18}$, aryl-$C_{0-12}$alkyl-, heteroaryl-$C_{0-12}$alkyl-, $C_{3-12}$cycloalkyl- $C_{0-12}$alkyl-, $C_{3-12}$heterocycloalkyl-$C_{0-12}$alkyl-, aryl-$C_{0-12}$cycloalkyl-, heteroaryl-$C_{3-12}$cycloalkyl-, $C_{3-12}$heterocycloalkyl-$C_{3-12}$cycloalkyl-, $C_{3-12}$cycloalkyl-$C_{3-12}$cycloalkyl-, $C_{3-12}$heterocycloalkyl-$C_{3-12}$heterocycloalkyl-, aryl-$C_{3-12}$heterocycloalkyl-, heteroaryl-$C_{3-12}$heterocycloalkyl-, —C(O)—C(O)NR$^{18}$R$^{19}$, —C$_{0-12}$alkylC(O)OR$^{18}$, —C(O)—C(O)OR$^{18}$, —OC(O)R$^{18}$, —NR$^{18}$C(O)R$^{19}$, —NR$^{18}$C(O)OR$^{19}$, —NR$^{18}$S(O)$_{m7}$R$^{19}$, —(CR$^{19}$R$^{20}$)$_{n2}$C(O)R$^{18}$, —(CR$^{19}$R$^{20}$)$_{n2}$C(O)OR$^{18}$, —(CR$^{19}$R$^{20}$)$_{n2}$C(O)NR$^{18}$R$^{21}$, —(CR$^{19}$R$^{20}$)$_{n2}$S(O)$_{m7}$NR$^{18}$R$^{21}$, —(CR$^{19}$R$^{20}$)$_{n2}$NR$^{18}$R$^{21}$, —(CR$^{19}$R$^{20}$)$_{n2}$OR$^{18}$, —(CR$^{19}$R$^{20}$)$_{n2}$S(O)$_{m7}$R$^{18}$, —NR$^{20}$C(O)NR$^{18}$R$^{19}$, and —NR$^{20}$S(O)$_{m7}$NR$^{18}$R$^{19}$ substituents;

R$^{11}$, R$^{12}$, R$^{13}$, R$^{14}$, R$^{15}$, R$^{16}$, R$^{17}$, R$^{18}$, R$^{19}$, R$^{20}$, and R$^{21}$ are each independently selected from H, $C_{1-6}$alkyl-, $C_{3-8}$cycloalkyl-$C_{0-6}$alkyl-, $C_{3-8}$heterocycloalkyl-$C_{0-6}$alkyl-, aryl-$C_{0-6}$alkyl-, aryl-$C_{3-8}$cycloalkyl-, aryl-$C_{3-8}$heterocycloalkyl-, heteroaryl-$C_{1-6}$alkyl-, heteroaryl-$C_{3-8}$cycloalkyl-, or heteroaryl-$C_{3-8}$heterocycloalkyl-;

R$^{3}$ and R$^{4}$ are taken together with the carbon atoms to which they are attached to form a 3-12 membered partially saturated or unsaturated ring, wherein said ring optionally includes one or more additional heteroatoms selected from O, N, or S(O)$_{m8}$;

m1, m2, m3, m4, m5, m6, m7, m8, n1, and n2 are each independently selected from 0, 1, or 2;

or a pharmaceutically acceptable salt, solvate or a prodrug thereof.

In some embodiments of Formulas I, and Ia-Ii, B$^{1}$ is selected from $C_{4-8}$cycloalkyl-$C_{0-12}$alkyl-, $C_{4-8}$heterocycloalkyl-$C_{0-12}$alkyl-, $C_{4-8}$aryl-$C_{0-12}$alkyl-, or $C_{4-8}$heteroaryl-$C_{0-12}$alkyl-, any of which is optionally substituted with G$^{2}$ substituents.

In some embodiments of Formulas I, and Ia-Ii, B$^{2}$ is selected from $C_{4-8}$cycloalkyl-$C_{0-12}$alkyl-, $C_{4-8}$heterocycloalkyl-$C_{0-12}$alkyl-, $C_{4-8}$aryl-$C_{0-12}$alkyl-, or $C_{4-8}$heteroaryl-$C_{0-12}$alkyl-, any of which is optionally substituted with G$^{3}$ substituents.

In some embodiments of Formulas I, and Ia-Ii, L$^{1}$ is selected from —$C_{0-2}$alkyl-, —CR$^{5}$R$^{6}$—, —$C_{0-3}$alkyl(R$^{5}$)(OH)—, —C(O)—, —CH$_{2}$O—, —OCH$_{2}$—, —CF$_{2}$—, —N(R$^{5}$)—, —N(R$^{5}$)C(O)—, —C(O)N(R$^{5}$)—, —O—, or —S(O)$_{m1}$—.

In some embodiments of Formulas I, and Ia-Ii, L$^{1}$ is selected from —$C_{0-2}$alkyl-, —CR$^{5}$R$^{6}$—, —$C_{1-2}$alkyl(R$^{5}$)(OH)—, —C(O)—, —CF$_{2}$—, —N(R$^{5}$)—, —N(R$^{5}$)C(O)—, —C(O)N(R$^{5}$)—, —O—, or —S(O)$_{m1}$—.

In some embodiments of Formulas I, and Ia-Ii, L$^{2}$ is selected from —$C_{0-2}$alkyl-, —C(O)—, or —N(R$^{7}$)—.

In some embodiments of Formulas I, and Ia-Ii, X is selected from $C_{4-8}$cycloalkyl-$C_{0-12}$alkyl-, $C_{4-8}$heterocycloalkyl-$C_{0-12}$alkyl-, $C_{4-8}$aryl-$C_{0-12}$alkyl-, or $C_{4-8}$heteroaryl-$C_{0-12}$alkyl-.

In some embodiments of Formulas I, and Ia-Ii, Y is selected from —C(O)—, —N(R$^{8}$)—, —N(R$^{8}$)C(O)—, or —S(O)$_{m3}$—.

In some embodiments of Formulas I, and Ia-Ii, R$^{1}$ is selected from —C(O)R$^{9}$, —C(O)NR$^{9}$R$^{10}$, —C(O)OR$^{9}$, $C_{1-4}$alkynyl, or —CN.

In some embodiments of Formulas I, and Ia-Ii, R$^{2}$, R$^{3}$, and R$^{4}$ are each independently selected from $C_{0-12}$alkyl, —CN, halo, $C_{3-6}$cycloalkyl-$C_{0-12}$alkyl-, $C_{3-6}$heterocycloalkyl-$C_{0-12}$alkyl-any of which is optionally substituted with G$^{5}$ substituents.

In some embodiments of Formulas I, and Ia-Ii, G$^{1}$, G$^{2}$, G$^{3}$, G$^{4}$, G$^{5}$, and G$^{6}$ are each independently selected from one to three of $C_{0-12}$alkyl, —$C_{2-12}$alkenyl, —$C_{2-12}$alkynyl, D, —CD$_{3}$, —OCD$_{3}$, halo, —CN, -oxo-, —CF$_{3}$, —OCF$_{3}$, —OCHF$_{2}$, —NO$_{2}$, —B(OH)$_{2}$, —P(O)C$_{0-3}$ alkyl, —PO(OR$^{11}$)$_{2}$, —PO(OR$^{11}$)R$^{12}$, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, heteroaryl-$C_{3-12}$heterocycloalkyl-, —$C_{0-6}$alkylOR$^{11}$, —OC(O)NR$^{11}$R$^{12}$, —C(O)OR$^{11}$, —C(O)NR$^{11}$R$^{12}$, —C(O)R$^{11}$, —NR$^{11}$R$^{12}$, —NR$^{11}$C(O)R$^{12}$, —NR$^{13}$C(O)NR$^{11}$R$^{12}$, —S(O)$_{m5}$R$^{11}$, and —NR$^{11}$S(O)$_{m5}$R$^{12}$, any of which is optionally substituted with independently selected Q$^{1}$ substituents.

In some embodiments of Formulas I, and Ia-Ii, G$^{1}$, G$^{2}$, G$^{3}$, G$^{4}$, G$^{5}$, and G$^{6}$ are each independently selected from one to two of $C_{0-12}$alkyl, —$C_{2-12}$alkenyl, —$C_{2-12}$alkynyl, D, —CD$_{3}$, —OCD$_{3}$, halo, —CN, -oxo-, —CF$_{3}$, —OCF$_{3}$, —OCHF$_{2}$, —NO$_{2}$, —B(OH)$_{2}$, —P(O)C$_{0-3}$ alkyl, —PO(OR$^{11}$)$_{2}$, —PO(OR$^{11}$)R$^{12}$, $C_{3-12}$cycloalkyl-$C_{0-12}$alkyl-, $C_{3-12}$heterocycloalkyl-$C_{0-12}$alkyl-, aryl-$C_{0-12}$alkyl-, aryl-$C_{3-12}$cycloalkyl-, aryl-$C_{3-12}$heterocycloalkyl-, heteroaryl-$C_{0-12}$alkyl-, heteroaryl-$C_{3-12}$cycloalkyl-, heteroaryl-$C_{3-12}$heterocycloalkyl-, —$C_{0-6}$alkylOR$^{11}$, —OC(O)NR$^{11}$R$^{12}$, —C(O)OR$^{11}$, —C(O)NR$^{11}$R$^{12}$, —C(O)R$^{11}$, —NR$^{11}$R$^{12}$, —NR$^{11}$C(O)R$^{12}$, —NR$^{13}$C(O)NR$^{11}$R$^{12}$, —S(O)$_{m5}$R$^{11}$, and —NR$^{11}$S(O)$_{m5}$R$^{12}$, any of which is optionally substituted with independently selected Q$^{1}$ substituents.

In some aspects, the present invention includes a pharmaceutical composition including the compound or salt of any one of the compounds of Formula I, formulated with or without one or more pharmaceutical carriers.

In some aspects, the present invention includes a method for the treatment of at least one of cancer, chronic inflammation, and autoimmune disease mediated at least in part by BTK including administering to a subject in need thereof a therapeutically effective amount of a compound or salt of the compound of Formula I.

In some aspects, the present invention includes a method of treating cancer, chronic inflammation, or autoimmune disease in a mammal including administering a therapeutically effective amount of a compound of Formula I, or a pharmaceutically acceptable salt thereof, to the mammal in need thereof.

In some aspects, the present invention includes a method of irreversibly inhibiting tyrosine kinases, the method including administering to a patient a therapeutically effective amount of a tyrosine kinase inhibitor including a compound of Formula I.

In some aspects, the present invention includes a method of irreversibly inhibiting BTK, the method including administering to a patient a therapeutically effective amount of a BTK inhibitor including a compound according to Formula I.

The methods described herein include administering to a subject in need a composition containing a therapeutically effective amount of one or more BTK inhibitor compounds described herein. Without being bound by theory, the diverse roles played by BTK signaling in various hematopoietic cell functions, e.g., B-cell receptor activation, suggests that small molecule BTK inhibitors are useful for reducing the risk of or treating a variety of diseases affected by or affecting many cell types of the hematopoetic lineage including, e.g., autoimmune diseases, heteroimmune conditions or diseases, inflammatory diseases, cancer (e.g., B-cell proliferative disorders), and thromboembolic disorders. Further, the BTK inhibitor compounds described herein can be used to inhibit a small subset of other tyrosine kinases that share homology with BTK by having a cysteine residue (including a Cys 481 residue) that can form a covalent bond with the inhibitor. Thus, a subset of tyrosine kinases other than BTK may be useful as therapeutic targets in a number of health conditions.

The methods described herein can be used to treat an autoimmune disease, which includes, but is not limited to, rheumatoid arthritis, psoriatic arthritis, osteoarthritis, Still's disease, juvenile arthritis, lupus, diabetes (type I and type II), myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

The methods described herein can be used to treat heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, allergic asthma, and atopic dermatitis.

The methods described herein can be used to treat an inflammatory disease, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

The methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

The methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Disclosed herein is a method for treating a hematological malignancy in an individual in need thereof, comprising: administering to the individual a composition containing a therapeutic amount of at least one compound having the structure of Formulas I, Ia-Ii or IIa-IId.

The hematological malignancy is a chronic lymphocytic leukemia (CLL), small lymphocytic lymphoma (SLL), high risk CLL, or a non-CLL/SLL lymphoma. In some embodiments, the hematological malignancy is follicular lymphoma, diffuse large B-cell lymphoma (DLBCL), mantle cell lymphoma, Waldenstrom's macroglobulinemia, multiple myeloma, marginal zone lymphoma, Burkitt's lymphoma, non-Burkitt high grade B cell lymphoma, or extranodal marginal zone B cell lymphoma. In some embodiments, the hematological malignancy is acute or chronic myelogenous (or myeloid) leukemia, myelodysplastic syndrome, or acute lymphoblastic leukemia. In some embodiments, the hematological malignancy is relapsed or refractory diffuse large B-cell lymphoma (DLBCL), relapsed or refractory mantle cell lymphoma, relapsed or refractory follicular lymphoma, relapsed or refractory CLL; relapsed or refractory SLL; relapsed or refractory multiple myeloma. In some embodiments, the hematological malignancy is a hematological malignancy that is classified as high-risk. In some embodiments, the hematological malignancy is high risk CLL or high risk SLL.

B-cell lymphoproliferative disorders (BCLDs) are neoplasms of the blood and encompass, inter alia, non-Hodgkin lymphoma, multiple myeloma, and leukemia. BCLDs can originate either in the lymphatic tissues (as in the case of lymphoma) or in the bone marrow (as in the case of leukemia and myeloma), and they all are involved with the uncontrolled growth of lymphocytes or white blood cells. There are many subtypes of BCLD, e.g., chronic lymphocytic leukemia (CLL) and non-Hodgkin lymphoma (NHL). The disease course and treatment of BCLD is dependent on the BCLD subtype; however, even within each subtype the clinical presentation, morphologic appearance, and response to therapy is heterogeneous.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment (Freedman et al., "Non-Hodgkin's Lymphomas" Chapter 134, Cancer Medicine, (an approved publication of the American Cancer Society, B.C. Decker Inc., Hamilton, Ontario, 2003).

Disclosed herein is a method for treating a non-Hodgkin's lymphoma in an individual in need thereof, comprising: administering to the individual a composition containing a therapeutic amount of at least one compound having the structure of Formulas I, Ia-Ii or IIa-IId.

Further disclosed herein, is a method for treating relapsed or refractory non-Hodgkin's lymphoma in an individual in need thereof, comprising: administering to the individual a composition containing a therapeutic amount of at least one compound having the structure of Formulas I, Ia-Ii or IIa-IId. In some embodiments, the non-Hodgkin's lymphoma is relapsed or refractory diffuse large B-cell lymphoma (DLBCL), relapsed or refractory mantle cell lymphoma, or relapsed or refractory follicular lymphoma.

Non-Hodgkin lymphomas (NHL) are a diverse group of malignancies that are predominately of B-cell origin. NHL may develop in any organs associated with lymphatic system such as spleen, lymph nodes or tonsils and can occur at any age. NHL is often marked by enlarged lymph nodes, fever, and weight loss. NHL is classified as either B-cell or T-cell NHL. Lymphomas related to lymphoproliferative disorders following bone marrow or stem cell transplantation are usually B-cell NHL. In the Working Formulation classification scheme, NHL has been divided into low-, intermediate-, and high-grade categories by virtue of their natural histories (see "The Non-Hodgkin's Lymphoma Pathologic Classification Project," Cancer 49 (1982):2112-2135). The low-grade lymphomas are indolent, with a median survival of 5 to 10 years (Horning and Rosenberg (1984) N. Engl. J. Med. 311:1471-1475). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

A non-limiting list of the B-cell NHL includes Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lymphoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmacytic lymphoma, hairy cell leukemia, Waldenstrom's Macroglobulinemia, and primary central nervous system (CNS) lymphoma. Additional non-Hodgkin's lymphomas are contemplated within the scope of the present invention and apparent to those of ordinary skill in the art.

Disclosed herein is a method for treating a DLBCL in an individual in need thereof, comprising: administering to the individual a composition containing a therapeutic amount of at least one compound having the structure of Formulas I, Ia-Ii or IIa-IId.

As used herein, the term "Diffuse large B-cell lymphoma (DLBCL)" refers to a neoplasm of the germinal center B lymphocytes with a diffuse growth pattern and a high-intermediate proliferation index. DLBCLs represent approximately 30% of all lymphomas and may present with several morphological variants including the centroblastic, immunoblastic, T-cell/histiocyte rich, anaplastic and plasmoblastic subtypes. Genetic tests have shown that there are different subtypes of DLBCL. These subtypes seem to have different outlooks (prognoses) and responses to treatment. DLBCL can affect any age group but occurs mostly in older people (the average age is mid-60s).

Disclosed herein is a method for treating diffuse large B-cell lymphoma, activated B cell-like subtype (ABC-DLBCL), in an individual in need thereof, comprising: administering to the individual an irreversible BTK inhibitor in an amount from 300 mg/day up to, and including, 1000 mg/day. The ABC subtype of diffuse large B-cell lymphoma (ABC-DLBCL) is thought to arise from post germinal center B cells that are arrested during plasmatic differentiation. The ABC subtype of DLBCL (ABC-DLBCL) accounts for approximately 30% total DLBCL diagnoses. It is considered the least curable of the DLBCL molecular subtypes and, as such, patients diagnosed with the ABC-DLBCL typically display significantly reduced survival rates compared with individuals with other types of DLCBL. ABC-DLBCL is most commonly associated with chromosomal translocations deregulating the germinal center master regulator BCL6 and with mutations inactivating the PRDM1 gene, which encodes a transcriptional repressor required for plasma cell differentiation.

A particularly relevant signaling pathway in the pathogenesis of ABC-DLBCL is the one mediated by the nuclear factor (NF)-κB transcription complex. The NF-κB family comprises 5 members (p50, p52, p65, c-rel and RelB) that form homo- and heterodimers and function as transcriptional factors to mediate a variety of proliferation, apoptosis, inflammatory and immune responses and are critical for normal B-cell development and survival. NF-κB is widely used by eukaryotic cells as a regulator of genes that control cell proliferation and cell survival. As such, many different types of human tumors have misregulated NF-κB: that is, NF-κB is constitutively active. Active NF-κB turns on the expression of genes that keep the cell proliferating and protect the cell from conditions that would otherwise cause it to die via apoptosis.

The dependence of ABC DLBCLs on NF-κB depends on a signaling pathway upstream of IkB kinase comprised of CARD11, BCL10 and MALT1 (the CBM complex). Interference with the CBM pathway extinguishes NF-κB signaling in ABC DLBCL cells and induces apoptosis. The molecular basis for constitutive activity of the NF-κB pathway is a subject of current investigation but some somatic alterations to the genome of ABC DLBCLs clearly invoke this pathway. For example, somatic mutations of the coiled-coil domain of CARD11 in DLBCL render this signaling scaffold protein able to spontaneously nucleate protein-protein interaction with MALT1 and BCL10, causing IKK activity and NF-κB activation. Constitutive activity of the B cell receptor signaling pathway has been implicated in the activation of NF-κB in ABC DLBCLs with wild type CARD11, and this is associated with mutations within the cytoplasmic tails of the B cell receptor subunits CD79A and CD79B. Oncogenic activating mutations in the signaling adapter MYD88 activate NF-κB and synergize with B cell receptor signaling in sustaining the survival of ABC DLBCL cells. In addition, inactivating mutations in a negative regulator of the NF-κB pathway, A20, occur almost exclusively in ABC DLBCL.

Indeed, genetic alterations affecting multiple components of the NF-κB signaling pathway have been recently identified in more than 50% of ABC-DLBCL patients, where these lesions promote constitutive NF-κB activation, thereby contributing to lymphoma growth. These include mutations of CARD11 (~10% of the cases), a lymphocyte-specific cytoplasmic scaffolding protein that—together with MALT1 and BCL10—forms the BCR signalosome, which relays signals from antigen receptors to the downstream mediators of NF-κB activation. An even larger fraction of cases (~30%)

carry biallelic genetic lesions inactivating the negative NF-κB regulator A20. Further, high levels of expression of NF-κB target genes have been observed in ABC-DLBCL tumor samples. See, e.g., U. Klein et al., (2008), Nature Reviews Immunology 8:22-23; R. E. Davis et al., (2001), Journal of Experimental Medicine 194:1861-1874; G. Lentz et al., (2008), Science 319:1676-1679; M. Compagno et al., (2009), Nature 459:712-721; and L. Srinivasan et al., (2009), Cell 139:573-586).

Disclosed herein is a method for treating a follicular lymphoma in an individual in need thereof, comprising: administering to the individual a composition containing a therapeutic amount of at least one compound having the structure of Formulas I, Ia-Ii or IIa-IId.

As used herein, the term "follicular lymphoma" refers to any of several types of non-Hodgkin's lymphoma in which the lymphomatous cells are clustered into nodules or follicles. The term follicular is used because the cells tend to grow in a circular, or nodular, pattern in lymph nodes. The average age for people with this lymphoma is about 60.

Disclosed herein is a method for treating a CLL or SLL in an individual in need thereof, comprising: administering to the individual a composition containing a therapeutic amount of at least one compound having the structure of Formulas I, Ia-Ii or IIa-IId.

Chronic lymphocytic leukemia and small lymphocytic lymphoma (CLL/SLL) are commonly thought as the same disease with slightly different manifestations. Where the cancerous cells gather determines whether it is called CLL or SLL. When the cancer cells are primarily found in the lymph nodes, lima bean shaped structures of the lymphatic system (a system primarily of tiny vessels found in the body), it is called SLL. SLL accounts for about 5% to 10% of all lymphomas. When most of the cancer cells are in the bloodstream and the bone marrow, it is called CLL.

Both CLL and SLL are slow-growing diseases, although CLL, which is much more common, tends to grow slower. CLL and SLL are treated the same way. They are usually not considered curable with standard treatments, but depending on the stage and growth rate of the disease, most patients live longer than 10 years. Occasionally over time, these slow-growing lymphomas may transform into a more aggressive type of lymphoma.

Chronic lymphoid leukemia (CLL) is the most common type of leukemia. It is estimated that 100,760 people in the United States are living with or are in remission from CLL. Most (>75%) people newly diagnosed with CLL are over the age of 50. Currently CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes). Though CLL progresses slowly in most cases, it is considered generally incurable. Certain CLLs are classified as high-risk. As used herein, "high risk CLL" means CLL characterized by at least one of the following 1) 17p13-; 2) 11q22-; 3) unmutated IgVH together with ZAP-70+ and/or CD38+; or 4) trisomy 12.

CLL treatment is typically administered when the patient's clinical symptoms or blood counts indicate that the disease has progressed to a point where it may affect the patient's quality of life.

Small lymphocytic leukemia (SLL) is very similar to CLL described supra, and is also a cancer of B-cells. In SLL the abnormal lymphocytes mainly affect the lymph nodes. However, in CLL the abnormal cells mainly affect the blood and the bone marrow. The spleen may be affected in both conditions. SLL accounts for about 1 in 25 of all cases of non-Hodgkin lymphoma. It can occur at any time from young adulthood to old age, but is rare under the age of 50. SLL is considered an indolent lymphoma. This means that the disease progresses very slowly, and patients tend to live many years after diagnosis. However, most patients are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is 60 years.

Although SLL is indolent, it is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many patients develop fatal complications of recurrent disease. Considering the age of the individuals typically diagnosed with CLL and SLL, there is a need in the art for a simple and effective treatment of the disease with minimum side-effects that do not impede on the patient's quality of life. The instant invention fulfills this long standing need in the art.

Disclosed herein is a method for treating a Mantle cell lymphoma in an individual in need thereof, comprising: administering to the individual a composition containing a therapeutic amount of at least one compound having the structure of Formulas I, Ia-Ii or IIa-IId.

As used herein, the term, "Mantle cell lymphoma" refers to a subtype of B-cell lymphoma, due to CD5 positive antigen-naive pregerminal center B-cell within the mantle zone that surrounds normal germinal center follicles. MCL cells generally over-express cyclin D1 due to a t(11;14) chromosomal translocation in the DNA. More specifically, the translocation is at t(11;14)(q13;q32). Only about 5% of lymphomas are of this type. The cells are small to medium in size. Men are affected most often. The average age of patients is in the early 60s. The lymphoma is usually widespread when it is diagnosed, involving lymph nodes, bone marrow, and, very often, the spleen. Mantle cell lymphoma is not a very fast growing lymphoma, but is difficult to treat.

Disclosed herein, in certain embodiments, is a method for treating a marginal zone B-cell lymphoma in an individual in need thereof, comprising: administering to the individual a composition containing a therapeutic amount of at least one compound having the structure of Formulas I, Ia-Ii or IIa-IId.

As used herein, the term "marginal zone B-cell lymphoma" refers to a group of related B-cell neoplasms that involve the lymphoid tissues in the marginal zone, the patchy area outside the follicular mantle zone. Marginal zone lymphomas account for about 5% to 10% of lymphomas. The cells in these lymphomas look small under the microscope. There are 3 main types of marginal zone lymphomas including extranodal marginal zone B-cell lymphomas, nodal marginal zone B-cell lymphoma, and splenic marginal zone lymphoma.

Disclosed herein, in certain embodiments, is a method for treating a MALT in an individual in need thereof, comprising: administering to the individual a composition containing a therapeutic amount of at least one compound having the structure of Formulas I, Ia-Ii or IIa-IId.

The term "mucosa-associated lymphoid tissue (MALT) lymphoma", as used herein, refers to extranodal manifestations of marginal-zone lymphomas. Most MALT lymphoma are a low grade, although a minority either manifest initially as intermediate-grade non-Hodgkin lymphoma (NHL) or evolve from the low-grade form. Most of the MALT lymphoma occur in the stomach, and roughly 70% of gastric MALT lymphoma are associated with *Helicobacter pylori* infection. Several cytogenetic abnormalities have been identified, the most common being trisomy 3 or t(11;18). Many of these other MALT lymphoma have also been linked to infections with bacteria or viruses. The average age of patients with MALT lymphoma is about 60.

Disclosed herein, in certain embodiments, is a method for treating a nodal marginal zone B-cell lymphoma in an individual in need thereof, comprising: administering to the individual a composition containing a therapeutic amount of at least one compound having the structure of Formulas I, Ia-Ii or IIa-IId.

The term "nodal marginal zone B-cell lymphoma" refers to an indolent B-cell lymphoma that is found mostly in the lymph nodes. The disease is rare and only accounts for 1% of all Non-Hodgkin's Lymphomas (NHL). It is most commonly diagnosed in older patients, with women more susceptible than men. The disease is classified as a marginal zone lymphoma because the mutation occurs in the marginal zone of the B-cells. Due to its confinement in the lymph nodes, this disease is also classified as nodal.

Disclosed herein, in certain embodiments, is a method for treating a splenic marginal zone B-cell lymphoma in an individual in need thereof, comprising: administering to the individual a composition containing a therapeutic amount of at least one compound having the structure of Formulas I, Ia-Ii or IIa-IId.

The term "splenic marginal zone B-cell lymphoma" refers to specific low-grade small B-cell lymphoma that is incorporated in the World Health Organization classification. Characteristic features are splenomegaly, moderate lymphocytosis with villous morphology, intrasinusoidal pattern of involvement of various organs, especially bone marrow, and relative indolent course. Tumor progression with increase of blastic forms and aggressive behavior are observed in a minority of patients. Molecular and cytogenetic studies have shown heterogeneous results probably because of the lack of standardized diagnostic criteria.

Disclosed herein, in certain embodiments, is a method for treating a Burkitt lymphoma in an individual in need thereof, comprising: administering to the individual a composition containing a therapeutic amount of at least one compound having the structure of Formulas I, Ia-Ii or IIa-IId.

The term "Burkitt lymphoma" refers to a type of Non-Hodgkin Lymphoma (NHL) that commonly affects children. It is a highly aggressive type of B-cell lymphoma that often starts and involves body parts other than lymph nodes. In spite of its fast-growing nature, Burkitt's lymphoma is often curable with modern intensive therapies. There are two broad types of Burkitt's lymphoma—the sporadic and the endemic varieties: Endemic Burkitt's lymphoma and Sporadic Burkitt's lymphoma.

Endemic Burkitt's lymphoma involves children much more than adults, and is related to Epstein Barr Virus (EBV) infection in 95% cases. It occurs primarily in equatorial Africa, where about half of all childhood cancers are Burkitt's lymphoma. It characteristically has a high chance of involving the jawbone, a rather distinctive feature that is rare in sporadic Burkitt's. It also commonly involves the abdomen.

Sporadic Burkitt's lymphoma is a type of Burkitt's lymphoma that affects the rest of the world, including Europe and the Americas. Here too, it's mainly a disease in children. The link between Epstein Barr Virus (EBV) is not as strong as with the endemic variety, though direct evidence of EBV infection is present in one out of five patients. More than the involvement of lymph nodes, it is the abdomen that is notably affected in more than 90% of the children. Bone marrow involvement is more common than in the sporadic variety.

Disclosed herein, in certain embodiments, is a method for treating a Waldenstrom macroglobulinemia in an individual in need thereof, comprising: administering to the individual a composition containing a therapeutic amount of at least one compound having the structure of Formulas I, Ia-Ii or IIa-IId.

The term "Waldenstrom macroglobulinemia", also known as lymphoplasmacytic lymphoma, is cancer involving a subtype of white blood cells called lymphocytes. It is characterized by an uncontrolled clonal proliferation of terminally differentiated B lymphocytes. It is also characterized by the lymphoma cells making an antibody called immunoglobulin M (IgM). The IgM antibodies circulate in the blood in large amounts, and cause the liquid part of the blood to thicken, like syrup. This can lead to decreased blood flow to many organs, which can cause problems with vision (because of poor circulation in blood vessels in the back of the eyes) and neurological problems (such as headache, dizziness, and confusion) caused by poor blood flow within the brain. Other symptoms can include feeling tired and weak, and a tendency to bleed easily. The underlying etiology is not fully understood but a number of risk factors have been identified, including the locus 6p21.3 on chromosome 6. There is a 2- to 3-fold risk increase of developing WM in people with a personal history of autoimmune diseases with autoantibodies and particularly elevated risks associated with hepatitis, human immunodeficiency virus, and rickettsiosis.

Disclosed herein, in certain embodiments, is a method for treating a myeloma in an individual in need thereof, comprising: administering to the individual a composition containing a therapeutic amount of at least one compound having the structure of Formulas I, Ia-Ii or IIa-IId.

Multiple myeloma, also known as MM, myeloma, plasma cell myeloma, or as Kahler's disease (after Otto Kahler) is a cancer of the white blood cells known as plasma cells. A type of B cell, plasma cells are a crucial part of the immune system responsible for the production of antibodies in humans and other vertebrates. They are produced in the bone marrow and are transported through the lymphatic system.

Disclosed herein, in certain embodiments, is a method for treating a leukemia in an individual in need thereof, comprising: administering to the individual a composition containing a therapeutic amount of at least one compound having the structure of Formulas I, Ia-Ii or IIa-IId.

Leukemia is a cancer of the blood or bone marrow characterized by an abnormal increase of blood cells, usually leukocytes (white blood cells). Leukemia is a broad term covering a spectrum of diseases. The first division is between its acute and chronic forms: (i) acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children; (ii) chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Chronic leukemia mostly occurs in older people, but can theoretically occur in any age group. Additionally, the diseases are subdivided according to which kind of blood cell is affected. This split divides leukemias into lymphoblastic or lymphocytic leukemias and myeloid or myelogenous leukemias: (i) in lymphoblastic or lymphocytic leukemias, the cancerous change takes place in a type of marrow cell that normally goes on to form lymphocytes, which are infection-fighting immune system cells; (ii) in myeloid or myelogenous leukemias, the cancerous change takes place in a type of marrow cell that normally goes on to form red blood cells, some other types of white cells, and platelets.

Within these main categories, there are several subcategories including, but not limited to, Acute lymphoblastic leukemia (ALL), Acute myelogenous leukemia (AML), Chronic myelogenous leukemia (CML), and Hairy cell leukemia (HCL).

Symptoms, diagnostic tests, and prognostic tests for each of the above-mentioned conditions are known in the art. See, e.g., Harrison's Principles of Internal Medicine®," 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models are useful for establishing a range of therapeutically effective doses of BTK inhibitor compounds for treating any of the foregoing diseases.

For example, dosing of BTK inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), Am. J. Pathol 163:1827-1837.

In another example, dosing of BTK inhibitors for the treatment of B-cell proliferative disorders can be examined in, e.g., a human-to-mouse xenograft model in which human B-cell lymphoma cells (e.g. Ramos cells) are implanted into immunodeficient mice (e.g., "nude" mice) as described in, e.g., Pagel et al. (2005), Clin Cancer Res 11(13):4857-4866.

Animal models for treatment of thromboembolic disorders are also known.

The therapeutic efficacy of the compound for one of the foregoing diseases can be optimized during a course of treatment. For example, a subject being treated can undergo a diagnostic evaluation to correlate the relief of disease symptoms or pathologies to inhibition of in vivo BTK activity achieved by administering a given dose of a BTK inhibitor. Cellular assays known in the art can be used to determine in vivo activity of BTK in the presence or absence of an BTK inhibitor. For example, since activated BTK is phosphorylated at tyrosine 223 (Y223) and tyrosine 551 (Y551), phospho-specific immunocytochemical staining of P-Y223 or P-Y551-positive cells can be used to detect or quantify activation of BTK in a population of cells (e.g., by FACS analysis of stained vs unstained cells). See, e.g., Nisitani et al. (1999), Proc. Natl. Acad. Sci, USA 96:2221-2226. Thus, the amount of the BTK inhibitor compound that is administered to a subject can be increased or decreased as needed so as to maintain a level of BTK inhibition optimal for treating the subject's disease state.

Compounds disclosed herein irreversibly inhibit BTK and may be used to treat mammals suffering from Bruton's tyrosine kinase-dependent or Bruton's tyrosine kinase mediated conditions or diseases, including, but not limited to, cancer, autoimmune and other inflammatory diseases. Compounds disclosed herein have shown efficacy in a wide variety of diseases and conditions that are described herein.

A further aspect resides in the use of compounds of Formulas I, Ia-Ii or IIa-IId or a pharmaceutically acceptable salt thereof for the manufacture of a medicament to be used for the treatment of chronic B cell disorders in which T cells play a prominent role.

In yet another aspect, the compounds of Formulas I, Ia-Ii or IIa-IId are used for the manufacture of a medicament to be used for the treatment of BTK-mediated diseases or conditions. These include, but are not limited to, the treatment of B cell lymphomas resulting from chronic active B cell receptor signaling.

BTK mediated disorders or BTK mediated conditions as used herein, mean any disease state or other deleterious condition in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that can be treated or prevented with the compounds of Formulas I, Ia-Ii or IIa-IId further include rheumatic diseases (e.g. infectious arthritis, progressive chronic arthritis, deforming arthritis, traumatic arthritis, gouty arthritis, osteoporosis, Reiter's syndrome, polychondritis, acute synovitis and spondylitis), glomerulonephritis (with or without nephrotic syndrome), autoimmune hematologic disorders (e.g. hemolytic anemia, aplasic anemia, idiopathic thrombocytopenia, and neutropenia), and autoimmune inflammatory bowel diseases (e.g. ulcerative colitis and Crohn's disease), host versus graft disease, allograft rejection, chronic thyroiditis, scleroderma, primary billiary cirrhosis, systemic lupus erythematosis, contact dermatitis, eczema, skin sunburns, chronic renal insufficiency, Stevens-Johnson syndrome, inflammatory pain, idiopathic sprue, cachexia, sarcoidosis, kerato conjunctivitis, otitis media, periodontal disease, pulmonary interstitial fibrosis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that can be treated or prevented include, among others, allergies to foods, food additives, insect poisons, dust mites, pollen, animal materials and contact allergans, type I hypersensitivity allergic asthma, allergic conjunctivitis.

Infectious diseases that can be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

In some embodiments of Formula I, compounds are present as a material in substantially pure form.

In some embodiments of Formula I, compounds are selected from any one of the Examples herein or a pharmaceutically acceptable salt thereof.

Each variable definition above includes any subset thereof and the compounds of Formula I include any combination of such variables or variable subsets.

The present invention includes the compounds and salts thereof, their physical forms, preparation of the compounds, useful intermediates, and pharmaceutical compositions and formulations thereof.

The compounds of the present invention and the term "compound" in the claims include any pharmaceutically acceptable salts or solvates, and any amorphous or crystal forms, or tautomers, whether or not specifically recited in context.

The present invention includes all isomers of the compounds. Compounds may have one or more asymmetric carbon atoms and can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

The present invention includes any stereoisomers, even if not specifically shown, individually as well as mixtures, geometric isomers, and pharmaceutically acceptable salts thereof, including compounds exhibiting more than one type of isomerism. Where a compound or stereocenter is described or shown without definitive stereochemistry, it is to be taken to embrace all possible individual isomers, configurations, and mixtures thereof. Thus, a material sample containing a mixture of stereoisomers would be embraced by a recitation of either of the stereoisomers or a recitation without definitive stereochemistry. Also contemplated are any cis/trans isomers or tautomers of the compounds described. When a tautomer of the compound of Formula I exists, the compound of Formula I of the present invention includes any possible tautomers and pharmaceutically acceptable salts thereof, and mixtures thereof, except where specifically stated otherwise.

DETAILED DESCRIPTION OF THE INVENTION

Described herein are compounds of Formula I, which include compounds of Formulas Ia-Ii and IIa-IId, and compositions and formulations containing such compounds, and methods of using and making such compounds. These compounds are useful in treating diseases or conditions modulated at least in part by BTK.

In an embodiment, a compound according to Formula I and above embodiments is provided, wherein the compound of Formula I is represented by the compound of Formula IIa:

IIa

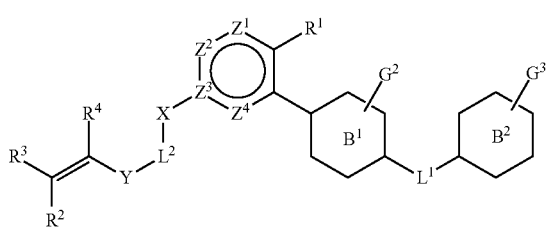

wherein, $R^1$-$R^4$, $G^2$, $G^3$, $L^1$, $L^2$, X, Y, and $Z^1$-$Z^4$, are as previously described for a compound of Formula I and B and $B^2$ are independently selected from $C_6$cycloalkyl, $C_6$heterocycloalkyl, $C_6$aryl, or $C_6$heteroaryl.

In an embodiment, a compound according to Formula I and above embodiments is provided, wherein the compound of Formula I is represented by the compound of Formula IIb:

IIb

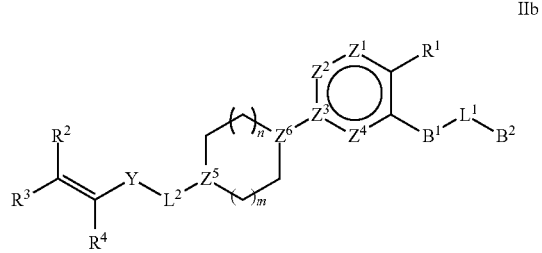

wherein, $R^1$-$R^4$, $B^1$, $B^2$, $L^1$, $L^2$, Y, and $Z^1$-$Z^4$, are as previously described for a compound of Formula I, $Z^5$ and $Z^6$ are each independently selected from $C(R^a)$ or N, where $R^a$ is alkyl or H, and n and m are each independently selected from 0, 1, or 2.

In an embodiment, a compound according to Formula I and above embodiments is provided, wherein the compound of Formula I is represented by the compound of Formula IIc:

IIc

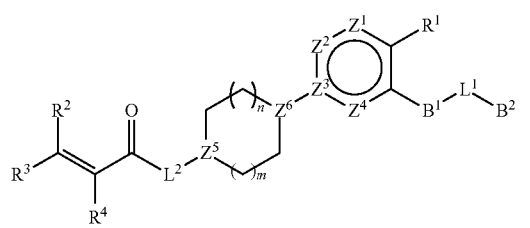

wherein, $R^1$-$R^4$, $B^1$, $B^2$, $L^1$, $L^2$, and $Z^1$-$Z^4$, are as previously described for a compound of Formula I, $Z^5$ and $Z^6$ are each independently selected from C or N, and n and m are each independently selected from 0, 1, or 2.

In an embodiment, a compound according to Formula I and above embodiments is provided, wherein the compound of Formula I is represented by the compound of Formula IId:

IId

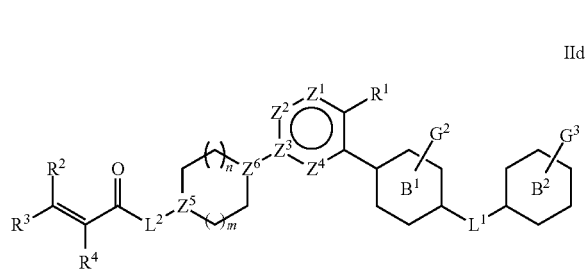

wherein, $R^1$-$R^4$, $L^1$, $L^2$, $G^2$, $G^3$, and $Z^1$-$Z^4$, are previously described for a compound of Formula I, $Z^5$ and $Z^6$ are each independently selected from C or N, $B^1$ and $B^2$ are independently selected from $C_6$cycloalkyl, $C_6$heterocycloalkyl, $C_6$aryl, or $C_6$heteroaryl, and n and m are each independently selected from 0, 1, or 2.

The present invention includes the compounds, intermediates, examples and synthetic methods described herein. Compounds of Formula I are prepared according to reaction schemes described herein. Unless otherwise indicated, the substituents in the schemes are defined as above.

Synthetic Methods:

Compounds of the present invention include the intermediates, examples, and synthetic methods described herein. Synthetic methods provided herein are generally preceded by their respective synthetic schemes. Where a procedure for an intermediate or example refers to an analogous procedure for an analogous intermediate or example, such reference includes the procedure for that analogous intermediate or example, the associated synthetic scheme as well as the procedures and schemes utilized for the synthesis of the analogous intermediate or example.

The compounds of Formulas I, Ia-Ii and IIa-d may be prepared by the methods described below, together with synthetic methods known in the art of organic chemistry, or modifications and derivatizations that are familiar to those of ordinary skill in the art. The starting materials used herein are commercially available or may be prepared by routine methods known in the art [such as those methods disclosed in standard reference books such as the Compendium of Organic Synthetic Methods, Vol. I-VI (Wiley-Interscience); or the Comprehensive Organic Transformations, by R. C. Larock (Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formulas I, Ia-Ii and IIa-d, or their pharmaceutically acceptable salts, can be prepared according to the reaction schemes discussed hereinbelow and utilizing ordinary skill in the art. Unless otherwise indicated, the substituents in the schemes are defined as above. Isolation and purification of the products is accomplished by standard procedures, which are known to a chemist of ordinary skill.

When a general or exemplary synthetic procedure is referred to, one skilled in the art can readily determine the appropriate reagents, if not indicated, extrapolating from the general or exemplary procedures. Some of the general procedures are given as examples for general preparation of compounds. One skilled in the art can readily adapt such procedures to the synthesis of other specific compounds. Representation of an unsubstituted position in structures shown or referred to in the general procedures is for convenience and does not preclude substitution as described elsewhere herein. For specific groups that can be present, either as groups in the general procedures or as optional substituents not shown, refer to the descriptions in the remainder of this document, including the claims and detailed description.

A general procedure for the synthesis of compounds of Formulas I, Ia-Ii and IIa-d is shown in the General Scheme, below.

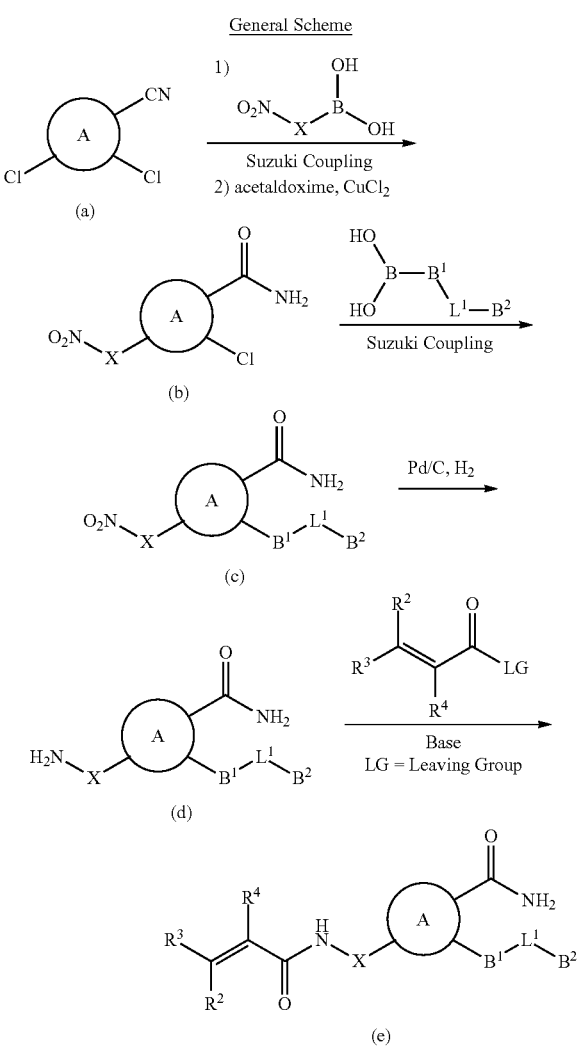

Where A, $B^1$, $B^2$, $L^1$, X, $R^2$, $R^3$, and $R^4$ are as defined previously for a compound of Formulas I, Ia-Ii and IIa-d and LG is equal to a suitable leaving group such as triflate, mesylate, tosylate, HATU, Cl, Br or I.

In a typical preparation of a compound of Formulas I, Ia-Ii and IIa-d, a compound of Formula (a) was reacted under Suzuki coupling conditions with a suitable boronic acid. Suitable conditions include, but are not limited to, treating compounds of Formula (a) with a suitable base, such as $Cs_2CO_3$ or $K_2CO_3$, and a suitable palladium catalyst, such as Pd(dppf)$Cl_2$·DCM. Suitable solvents for use in the above synthesis include 1,4-dioxane, water, DME and mixtures thereof. The mixture was degassed with nitrogen six times and refluxed for about 16 h under nitrogen atmosphere to afford the compound of Formula (b). The above process was carried out at temperatures between about 50° C. and about 150° C. Preferably, the reaction was carried out at about 100° C. The above process was preferably carried out at or about atmospheric pressure although higher or lower pressures may be used if desired. Substantially equimolar amounts of reactants were preferably used although higher or lower amounts may be used if desired.

The compound of Formula (b) was reacted with a suitable boronic acid under Suzuki coupling conditions. Suitable conditions include, but are not limited to, treating compounds of Formula (b) with a suitable base, such as Cs$_2$CO$_3$ or K$_2$CO$_3$, and a suitable palladium catalyst, such as Pd(dppf)Cl$_2$·DCM or Pd(PPh$_3$)$_4$. Suitable solvents for use in the above synthesis include 1,4-dioxane, water, DME and mixtures thereof. The mixture was degassed with nitrogen six times and refluxed for about 5 h under nitrogen atmosphere to afford the compound of Formula (c). The above process was carried out at temperatures between about 40° C. and about 120° C. Preferably, the reaction was carried out at about 90° C. The above process was preferably carried out at or about atmospheric pressure although higher or lower pressures may be used if desired. Substantially equimolar amounts of reactants were preferably used although higher or lower amounts may be used if desired.

The compound of Formula (c) was reacted under hydrogen atmosphere with palladium on carbon, preferably degassing the mixture with hydrogen about 6 times. Suitable solvents for use in the above synthesis include ethyl acetate and methanol. The above process was carried out at temperatures between about 10° C. and about 60° C., or preferably at ambient temperature, to afford the compound of Formula (d). The above process was preferably carried out at or about atmospheric pressure although higher or lower pressures may be used if desired. Substantially equimolar amounts of reactants were preferably used although higher or lower amounts may be used if desired.

The compound of Formula (d) was reacted with a suitable acryloyl chloride with a suitable base. Suitable bases include organic bases such as TEA or DIPEA. The above process was carried out at temperatures between about −10° C. and about ambient temperature, or preferably at 0° C., to afford the compound of Formula (d). The above process was preferably carried out at or about atmospheric pressure although higher or lower pressures may be used if desired. Substantially equimolar amounts of reactants were preferably used although higher or lower amounts may be used if desired.

EXAMPLES: PREPARATIONS AND INTERMEDIATES

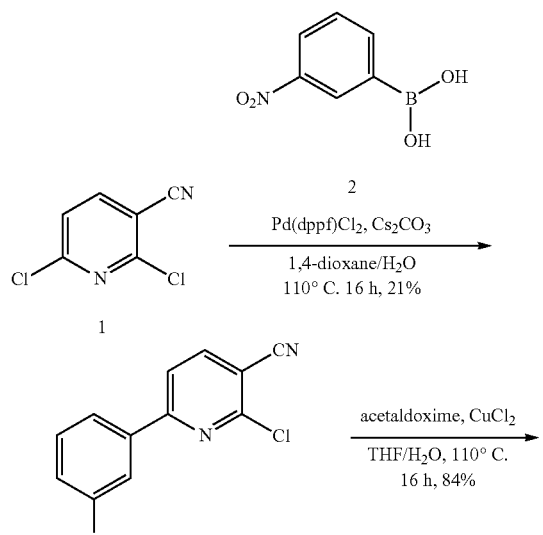

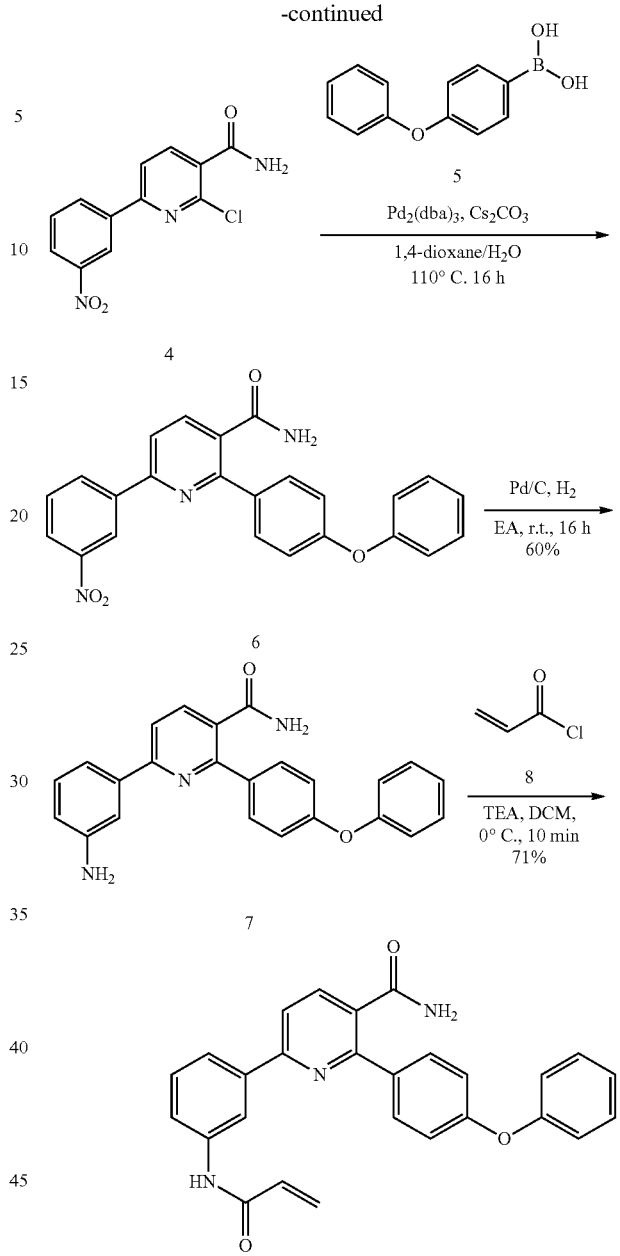

Example 1

2-chloro-6-(3-nitrophenyl)nicotinonitrile (3)

To a solution of 3-nitrophenylboronic acid 2 (5.19 g, 30 mmol), Cs$_2$CO$_3$ (19.56 g, 60 mmol) and 2,6-dichloronicotinonitrile 1 (5.51 g, 33 mmol) in dry 1,4-dioxane (100 mL) was added Pd(dppf)Cl$_2$·DCM (2.4 g, 3.0 mmol) under nitrogen atmosphere, and the mixture was degassed with nitrogen 6 times, then refluxed for 16 h under nitrogen atmosphere. After cooling to room temperature, the solvent was evaporated and the residue was purified by flash chromatography, eluting with 20:1 to 3:1 PE/EA to afford the title compound as a yellow solid (1.6 g, 21%).

2-chloro-6-(3-nitrophenyl)nicotinamide (4)

To a solution of 2-chloro-6-(3-nitrophenyl)nicotinonitrile 3 (259 mg, 1.0 mmol) and acetaldoxime (88 mg, 1.5 mmol)

in tetrahydrofuran (5 mL) and water (5 mL) was added CuCl₂ (15 mg, 0.1 mmol) under nitrogen atmosphere, and the mixture was degassed with nitrogen 6 times, then heated to 90° C. and stirred for 16 h under nitrogen atmosphere. After cooling to room temperature, the solvent was evaporated and the crude product was purified by flash chromatography, eluting with 20:1 DCM/MeOH to afford the title compound as a yellow solid (240 mg, 84%). MS (ESI): m/z=277.9 [M+H]⁺.

6-(3-nitrophenyl)-2-(4-phenoxyphenyl)nicotinamide (6)

To a solution of 2-chloro-6-(3-nitrophenyl)nicotinamide 4 (240 mg, 0.87 mmol), Cs₂CO₃ (567 mg, 1.74 mmol) and biphenyl-4-ylboronic acid 5 (203 mg, 0.95 mmol) in 1,4-dioxane (10 mL) and water (2.5 mL) was added Pd₂(dba)₃ (80 mg, 0.09 mmol) under nitrogen atmosphere, and the mixture was degassed with nitrogen 6 times, then refluxed for 16 h under nitrogen atmosphere. After cooling to room temperature, the solvent was evaporated and the crude product was purified by flash chromatography eluting with 150:1 DCM/MeOH to afford the title compound as a yellow solid (110 mg, crude).

6-(3-aminophenyl)-2-(4-phenoxyphenyl)nicotinamide (7)

To a solution of 6-(3-nitrophenyl)-2-(4-phenoxyphenyl)nicotinamide 6 (110 mg, 0.27 mmol) in ethyl acetate (5 mL) was added Pd/C (10 mg) under hydrogen atmosphere, and the mixture was degassed with hydrogen 6 times, then stirred for 16 h at ambient temperature under hydrogen atmosphere. The solution was filtered and the filtrate was evaporated to the crude product as red oil (61 mg, 60%). MS (ESI): m/z=382.1 [M+H]⁺.

Example 1

6-(3-acrylamidophenyl)-2-(4-phenoxyphenyl)nicotinamide

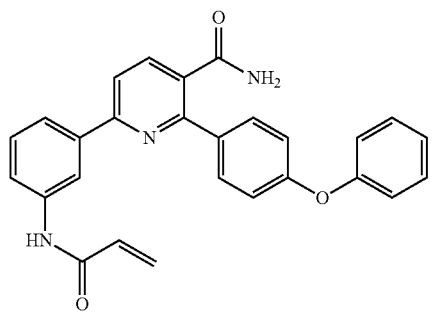 [SMILES: C=CC(=O)Nc1cccc(-c2ccc(C(N)=O)c(-c3ccc(Oc4ccccc4)cc3)n2)c1]

To a solution of 6-(3-aminophenyl)-2-(4-phenoxyphenyl)nicotinamide 7 (38 mg, 0.1 mmol) in DCM (5 mL) was added TEA (0.05 mL, 0.4 mmol) and acryloyl chloride 8 (9 mg, 0.1 mmol) at 0° C. The mixture was stirred at 0° C. for 10 minutes. The solvent was removed and the residue was purified by Prep-TLC eluting with 25:1 DCM/MeOH to afford the title compound (30 mg, 71%) as white solid. ¹H NMR (400 MHz, DMSO) δ 10.36 (s, 1H), 8.43 (s, 1H), 7.72-7.97 (m, 7H), 7.49 (s, 1H), 7.33-7.52 (m, 3H), 7.24 (t, J=6.9 Hz, 1H), 6.9-7.13 (m, 4H), 6.45 (dd, J=16.9, 10.0 Hz, 1H), 6.30 (d, J=16.9 Hz, 1H), 5.79 (d, J=10.5 Hz, 1H), MS (ESI, method A): m/z=436.0 [M+H]⁺, t_R=1.553 min., HPLC: 97.5% (214 nm), 98.0% (254 nm).

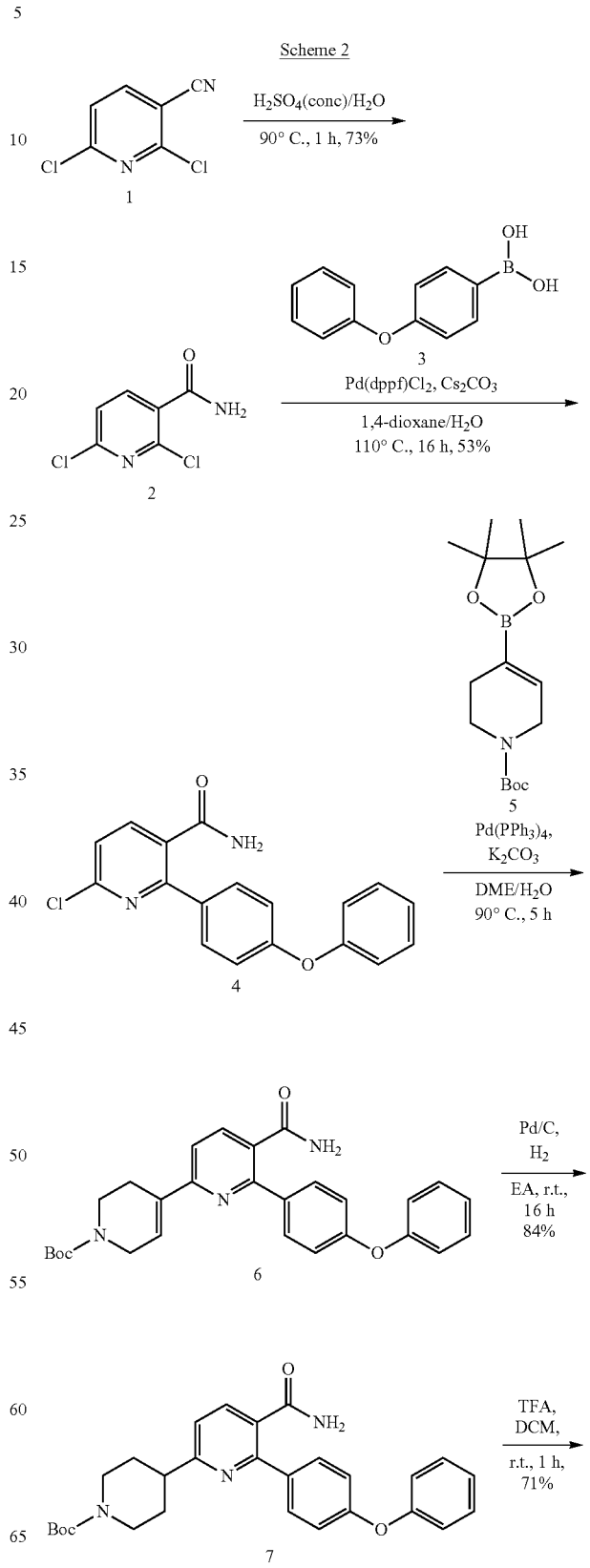

Scheme 2

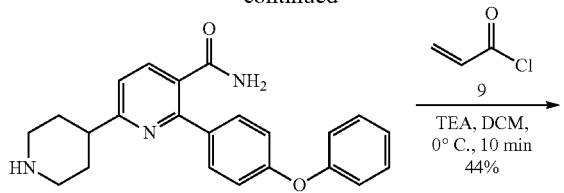

2,6-dichloronicotinamide (2)

To 2,6-dichloronicotinonitrile 1 (1.73 g, 10 mmol) was added conc $H_2SO_4$ (10 mL) and water (2 mL). The mixture was heated to 90° C. and stirred for 1 h. After cooling to room temperature, the solution was poured into ice-cold water, then adjusted to PH=8 with ammonia water. The precipitate was filtered, washed with water (20 mL) and dried under vacuum to afford the title compound as an brown solid (1.4 g, 73%). MS (ESI): m/z=191.1 $[M+H]^+$.

6-chloro-2-(4-phenoxyphenyl)nicotinamide (4)

To a solution of 2,6-dichloronicotinamide 2 (668 mg, 3.5 mmol), $Cs_2CO_3$ (1.14 g, 7 mmol) and 4-phenoxyphenylboronic acid 3 (749 mg, 3.5 mmol) in 1,4-dioxane (30 mL) was added Pd(dppf)Cl₂·DCM (285 mg, 0.35 mmol) under nitrogen atmosphere, and the mixture was degassed with nitrogen 6 times, then refluxed for 16 h under nitrogen atmosphere. After cooling to room temperature, the solvent was evaporated and the residue was purified by flash chromatography, eluting with 20:1 to 3:1 petroleum ether/ethyl acetate (PE/EA) to afford the title compound as a yellow solid (611 mg, 53%). MS (ESI): m/z=325.0 $[M+H]^+$.

tert-butyl-4-(5-carbamoyl-6-(4-phenoxyphenyl)pyridin-2-yl)-5,6-dihydropyridine-1(2H)-carboxylate (6)

To a solution of 4-(4,4,5,5-tetramethyl-1,3,2-dioxaborolan-2-yl)-1,2,3,6-tetrahydropyridine 5 (232 mg, 0.75 mmol), $K_2CO_3$ (207 mg, 1.50 mmol) and 6-chloro-2-(4-phenoxyphenyl)nicotinamide 4 (162 mg, 0.50 mmol) in 1,2-dimethoxyethane (5 mL) and water (1 mL) was added Pd(PPh₃)₄ (115 mg, 0.10 mmol) under nitrogen atmosphere, and the mixture was degassed with nitrogen 6 times, then heated to 90° C. and stirred for 5 h under nitrogen atmosphere. After cooling to room temperature, the solvent was evaporated and the crude product was purified by flash chromatography, eluting with 70:1 DCM/MeOH to afford the title compound as a white solid (232 mg, crude).

tert-butyl 4-(5-carbamoyl-6-(4-phenoxyphenyl)pyridin-2-yl)piperidine-1-carboxylate (7)

To a solution of 4-(5-carbamoyl-6-(4-phenoxyphenyl) pyridin-2-yl)-5,6-dihydropyridine-1(2H)-carboxylate 6 (232 mg, 0.75 mmol) in ethyl acetate (5 mL) was added Pd/C (10 mg) under hydrogen atmosphere, and the mixture was degassed with hydrogen 6 times, then stirred for 16 h at ambient temperature under hydrogen atmosphere. The solution was filtered and the filtrate was evaporated to the crude product as brown solid (215 mg, 60% for two steps). MS (ESI): m/z=474.1 $[M+H]^+$.

2-(4-phenoxyphenyl)-6-(piperidin-4-yl)nicotinamide (Example 2) (8)

To a solution of tert-butyl 4-(5-carbamoyl-6-(4-phenoxyphenyl)pyridin-2-yl)piperidine-1-carboxylate 7 (215 mg, 0.45 mmol) in dry dichloromethane (6 mL) was added TFA (2 mL), and the resulting mixture was stirred for 1 h at ambient temperature. The solvent was removed and the residue was partitioned between saturated aqueous sodium bicarbonate (30 mL) and ethyl acetate (20 mL). The organic phase was separated, dried over anhydrous sodium sulfate, filtered and concentrated. The crude residue was purified by flash chromatography, eluting with 5:1 DCM/MeOH to afford the title compound as a white solid (120 mg, 71%). MS (ESI): m/z=374.2 $[M+H]^+$.

Example 3

6-(1-acryloylpiperidin-4-yl)-2-(4-phenoxyphenyl) nicotinamide

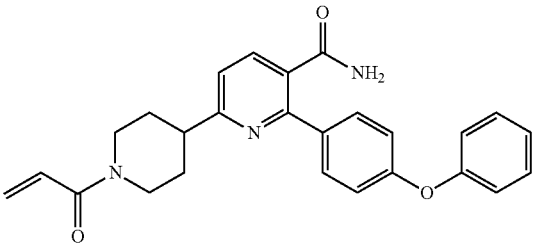 [SMILES: C=CC(=O)N1CCC(c2ccc(C(N)=O)c(-c3ccc(Oc4ccccc4)cc3)n2)CC1]

To a solution of 2-(4-phenoxyphenyl)-6-(piperidin-4-yl) nicotinamide 8 (26 mg, 0.07 mmol) in DCM (5 mL) was added TEA (0.05 mL, 0.4 mmol) and acryloyl chloride 9 (7 mg, 0.07 mmol) at 0° C. The mixture was stirred at 0° C. for 10 minutes. The solvent was removed and the residue was purified by Prep-TLC eluting with 25:1 DCM/MeOH to afford the title compound (13 mg, 44%) as white solid. $^1H$ NMR (400 MHz, CDCl₃) δ 7.90 (d, J=8.0 Hz, 1H), 7.71-7.62 (m, 2H), 7.42-7.31 (m, 2H), 7.21-7.11 (m, 2H), 7.10-7.01 (m, 4H), 6.60 (dd, J=16.8, 10.5 Hz, 1H), 6.26 (dd, J=16.8, 2.0 Hz, 1H), 5.84 (s, 1H), 5.68 (dd, J=10.5, 2.0 Hz, 1H), 5.54 (s, 1H), 4.79 (d, J=13.3 Hz, 1H), 4.13 (d, J=12.8 Hz, 1H), 3.17 (t, J=12.3 Hz, 1H), 3.39 (t, J=11.7 Hz, 1H), 2.76 (t, J=11.7 Hz, 1H), 2.03 (br, 2H), 1.80 (ddd, J=25.5, 12.5, 4.2 Hz, 2H). MS (ESI, method A): m/z=428.0 $[M+H]^+$, $t_R$=1.480 min. HPLC: 96.7% (214 nm), 99.3% (254 nm).

31

Scheme 3

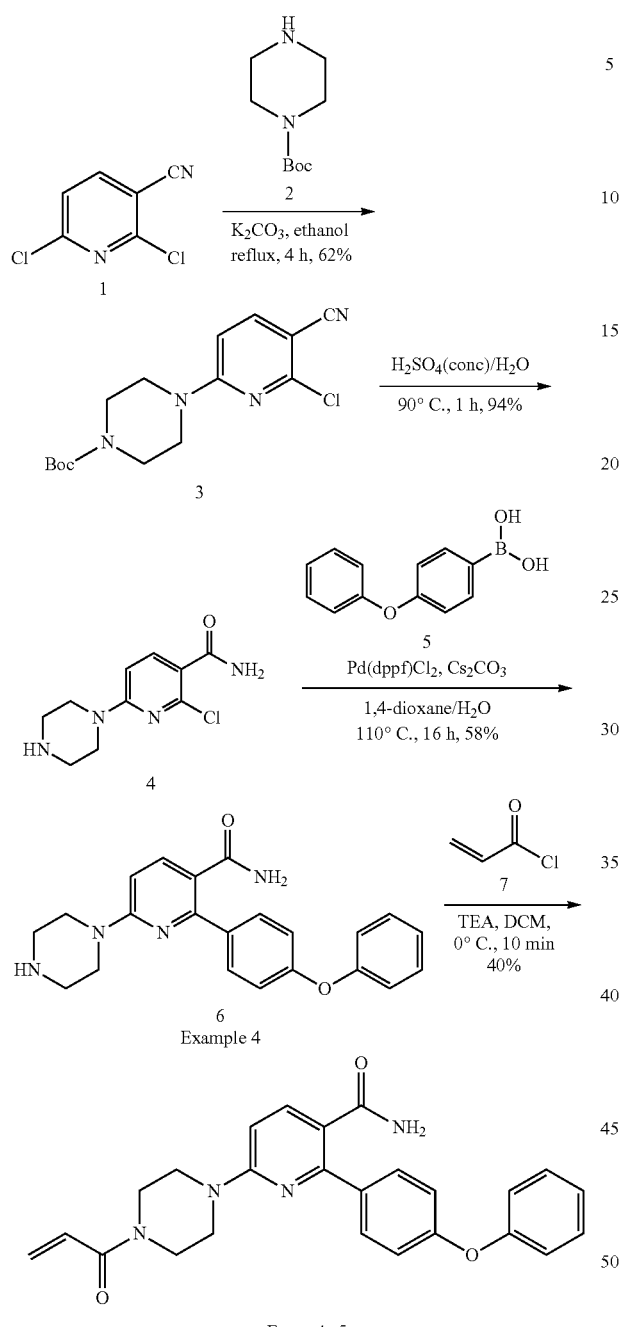

tert-butyl 4-(6-chloro-5-cyanopyridin-2-yl)pipera-
zine-1-carboxylate (3)

To a solution of 2,6-dichloronicotinonitrile 1 (519 mg, 3.0 mmol) and tert-butyl piperazine-1-carboxylate 2 (558 mg, 3.0 mmol) in ethanol (15 mL) was added $K_2CO_3$ (636 mg, 6.0 mmol), and the resulting solution was refluxed for 4 h. After cooling to room temperature, the solvent was evaporated and the crude product was purified by flash chromatography, eluting with 5:1 to 2:1 PE/EA to afford the title compound as a white solid (600 mg, 62%). MS (ESI): m/z=345.1 [M+Na]$^+$.

32

6-chloro-2-(4-phenoxyphenyl)nicotinamide (4)

To tert-butyl-(6-chloro-5-cyanopyridin-2-yl)piper azine-1-carboxylate 3 (600 mg, 10 mmol) was added $H_2SO_4$ (conc., 5 mL) and water (1 mL). The mixture was heated to 90° C. and stirred for 1 h. After cooling to room temperature, the solution was poured into ice-cold water, then adjusted to PH=8 with ammonia water. The precipitate was filtered, washed with water (20 mL) and dried under vacuum to afford the title compound as an off-white solid (420 mg, 94%). MS (ESI): m/z=241.0 [M+H]$^+$.

2-(4-phenoxyphenyl)-6-(piperazin-1-yl)nicotinamide
(Example 4) (6)

To a solution of 6-chloro-2-(4-phenoxyphenyl)nicotinamide 4 (420 mg, 1.75 mmol), $K_2CO_3$ (483 mg, 3.5 mmol) and 4-phenoxyphenylboronic acid 5 (374 mg, 1.75 mmol) in 1,4-dioxane (15 mL) and water (3 mL) was added Pd(PPh$_3$)$_4$ (231 mg, 0.20 mmol) under nitrogen atmosphere, and the mixture was degassed with nitrogen 6 times, then heated to 90° C. and stirred for 5 h under nitrogen atmosphere. After cooling to room temperature, the solvent was evaporated and the crude product was purified by flash chromatography eluting with 70:1 DCM/MeOH to afford the title compound as a white solid (260 mg, 58%). MS (ESI): m/z=375.0 [M+H]$^+$.

Example 5

6-(4-acryloylpiperazin-1-yl)-2-(4-phenoxyphenyl)
nicotinamide

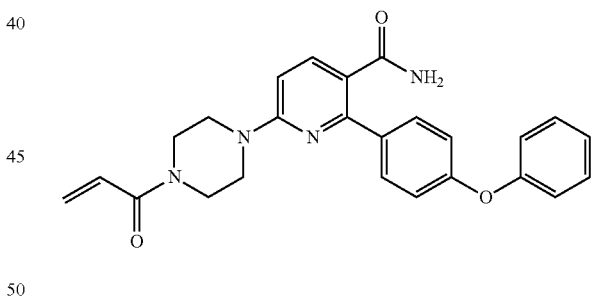

To a solution of 2-(4-phenoxyphenyl)-6-(piperazin-1-yl)nicotinamide 6 (59 mg, 0.16 mmol) in DCM (5 mL) was added TEA (0.05 mL, 0.4 mmol) and acryloyl chloride 7 (14 mg, 0.16 mmol) at 0° C. The mixture was stirred at 0° C. for 10 minutes. The solvent was removed and the residue was purified by Prep-TLC eluting with 25:1 DCM/MeOH to afford the title compound (27 mg, 40%) as light yellow solid. $^1$H NMR (400 MHz, CDCl$_3$) δ 8.04 (d, J=8.7 Hz, 1H), 7.64 (d, J=8.2 Hz, 2H), 7.40 (t, J=7.6 Hz, 2H), 7.18 (t, J=7.3 Hz, 1H), 7.08 (dd, J=12.0, 8.4 Hz, 4H), 6.66 (d, J=8.5 Hz, 1H), 6.64-6.56 (m, 1H), 6.37 (d, J=16.7 Hz, 1H), 5.77 (d, J=10.6 Hz, 1H), 5.57 (s, 1H), 5.33 (s, 1H), 3.81 (s, 4H), 3.73 (s, 4H). MS (ESI, method A): m/z=429.2 [M+H]$^+$, $t_R$=1.454 min., HPLC: 97.5% (214 nm), 98.0% (254 nm).

Scheme 4

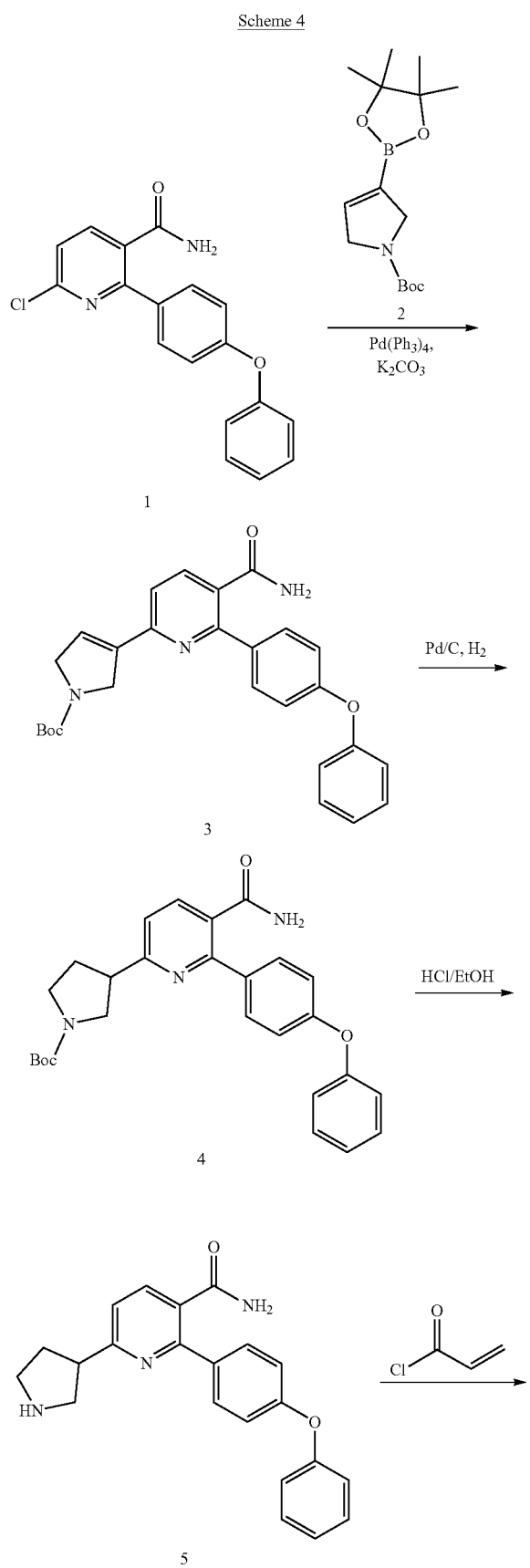

6-chloro-2-(4-phenoxyphenyl)nicotinamide (1)

6-chloro-2-(4-phenoxyphenyl)nicotinamide 1 was synthesized by using the same procedure above providing a yellow solid (611 mg, 53%). MS (ESI): m/z=325.0 [M+H]$^+$.

tert-butyl-3-(5-carbamoyl-6-(4-phenoxyphenyl)pyridin-2-yl)-2,5-dihydro-1H-pyrrole-1-carboxylate (3)

The title compound was synthesized using a procedure analogous to the procedure described in tert-butyl 4-(5-carbamoyl-6-(4-phenoxyphenyl)pyridin-2-yl)-5,6-dihydropyridine-1(2H)-carboxylate provided as white solid (300 mg, crude). MS (ESI): m/z=458.2 [M+H]$^+$.

tert-butyl-3-(5-carbamoyl-6-(4-phenoxyphenyl)pyridin-2-yl)pyrrolidine-1-carboxylate (4)

The title compound was synthesized using a procedure analogous to the procedure described in tert-butyl 4-(5-carbamoyl-6-(4-phenoxyphenyl)pyridin-2-yl)piperidine-1-carboxylate provided as white solid (240 mg, 45% for two steps). MS (ESI): m/z=460.1 [M+H]$^+$.

2-(4-phenoxyphenyl)-6-(pyrrolidin-3-yl)nicotinamide (5)

The title compound was synthesized using a procedure analogous to the procedure described in 2-(4-phenoxyphenyl)-6-(piperidin-4-yl)nicotinamide as white solid (190 mg, crude). MS (ESI): m/z=360.1 [M+H]$^+$.

Example 6

6-(1-acryloylpyrrolidin-3-yl)-2-(4-phenoxyphenyl)nicotinamide

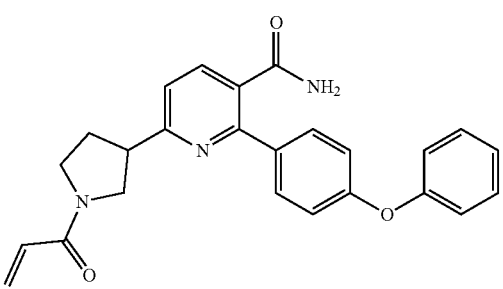 [SMILES: C=CC(=O)N1CCC(c2ccc(C(N)=O)c(-c3ccc(Oc4ccccc4)cc3)n2)C1]

Example 6

The title compound was synthesized using a procedure analogous to the procedure described in Example 3 as a white solid (18 mg, 29%). $^1$H NMR (300 MHz, CD$_3$OD) δ 7.85 (d, J=7.9 Hz, 1H), 7.72 (d, J=8.8 Hz, 2H), 7.37 (m, 3H), 7.15 (t, J=7.4 Hz, 1H), 7.02 (m, 4H), 6.65 (dd, J=16.7, 10.6 Hz, 1H), 6.28 (m, 1H), 5.74 (dd, J=9.5, 7.4 Hz, 1H), 3.98 (m, 2H), 3.69 (m, 3H), 2.34 (dtd, J=30.9, 12.6, 8.0 Hz, 2H). MS (ESI, method A): m/z=414.2 [M+H]$^+$, $t_R$=1.421 min. HPLC: 100% (214 nm), 100% (254 nm).

Scheme 5

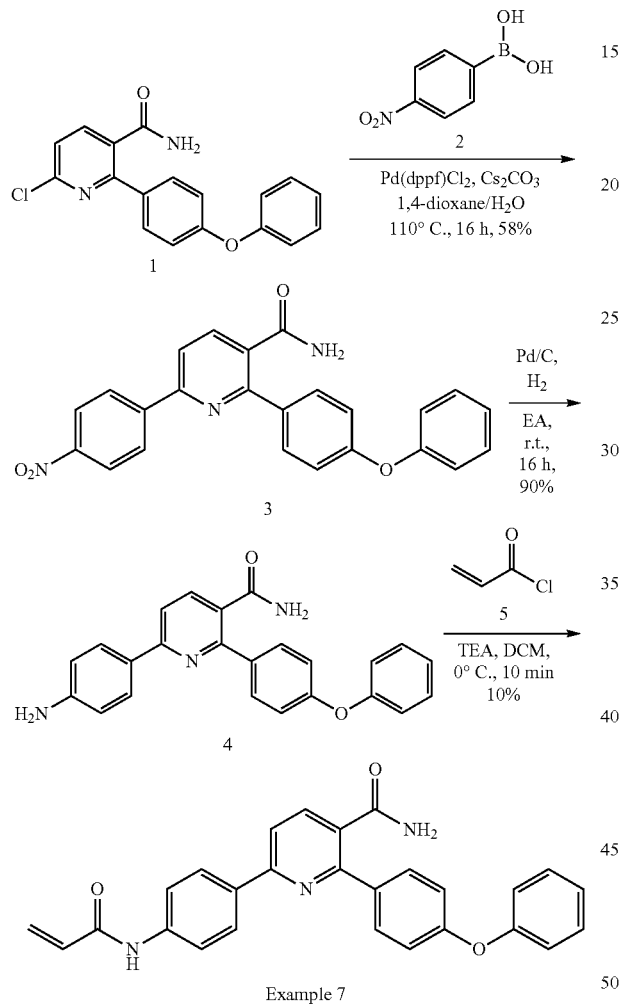

tert-butyl 4-(6-chloro-5-cyanopyridin-2-yl)piperazine-1-carboxylate (3)

To a solution of 6-chloro-2-(4-phenoxyphenyl)nicotinamide 1 (130 mg, 0.4 mmol) and 4-nitrophenylboronic acid 2 (67 mg, 0.4 mmol) in DME (10 mL)/water (3 mL), was added K$_2$CO$_3$ (110 mg, 0.8 mmol) and Pd(dppf)Cl$_2$ (33 mg, 0.04 mmol) under nitrogen atmosphere, and the mixture was degassed with nitrogen 6 times, then heated to 90° C. and stirred for 5 h under nitrogen atmosphere. After cooling to room temperature, the solvent was evaporated and the crude product was purified by flash chromatography eluting with 70:1 DCM/MeOH to afford the title compound as a white solid (60 mg, crude). MS (ESI): m/z=412.1 [M+H]$^+$.

6-(4-aminophenyl)-2-(4-phenoxyphenyl)nicotinamide (4)

To a solution of tert-butyl 4-(6-chloro-5-cyanopyridin-2-yl)piperazine-1-carboxylate 3 (60 mg, 0.15 mmol) in ethyl acetate (5 mL) was added Pd/C (6 mg) under hydrogen atmosphere, and the mixture was degassed with hydrogen 6 times, then stirred for 16 h at ambient temperature under hydrogen atmosphere. The solution was filtered and the filtrate was evaporated to the crude product as brown solid (42 mg, 90%). MS (ESI): m/z=382.0 [M+H]$^+$.

Example 7

6-(4-acrylamidophenyl)-2-(4-phenoxyphenyl)nicotinamide

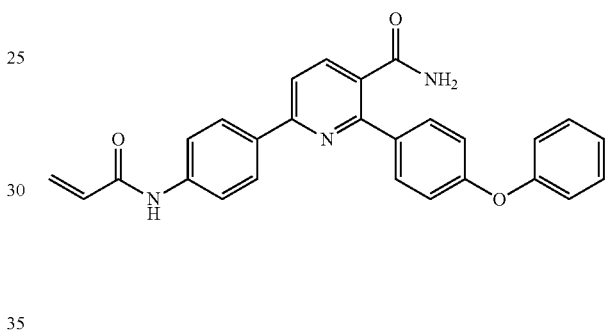

To a solution of 6-(4-aminophenyl)-2-(4-phenoxyphenyl)nicotinamide 4 (42 mg, 0.11 mmol) in DCM (5 mL) was added TEA (0.05 mL, 0.4 mmol) and acryloyl chloride 5 (10 mg, 0.11 mmol) at 0° C. The mixture was stirred at 0° C. for 10 minutes. The solvent was removed and the residue was purified by Prep-TLC eluting with 25:1 DCM/MeOH to afford the title compound (2.5 mg, 10%) as white solid. $^1$H NMR (300 MHz, CD$_3$OD) δ 8.17-8.11 (m, 1H), 7.98-7.92 (m, 1H), 7.90-7.84 (m, 1H), 7.81 (s, 3H), 7.69-7.60 (m, 2H), 7.58-7.52 (m, 1H), 7.42-7.34 (m, 2H), 7.18-7.12 (m, 1H), 7.10-7.00 (m, 3H), 6.47-6.38 (m, 2H), 5.82-5.76 (m, 1H). MS (ESI, method A): m/z=435.9 [M+H]$^+$, $t_R$=1.540 min., HPLC: 97.5% (214 nm), 98.7% (254 nm).

Scheme 6

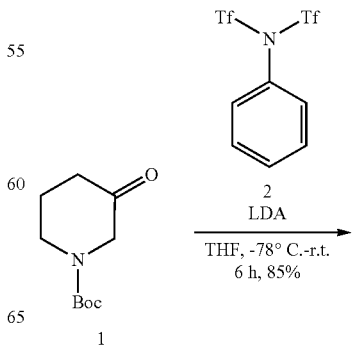

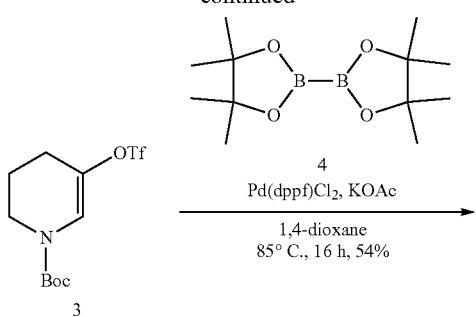
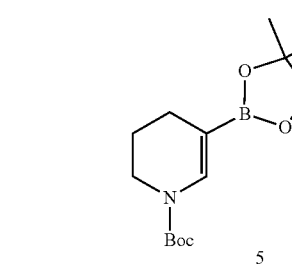
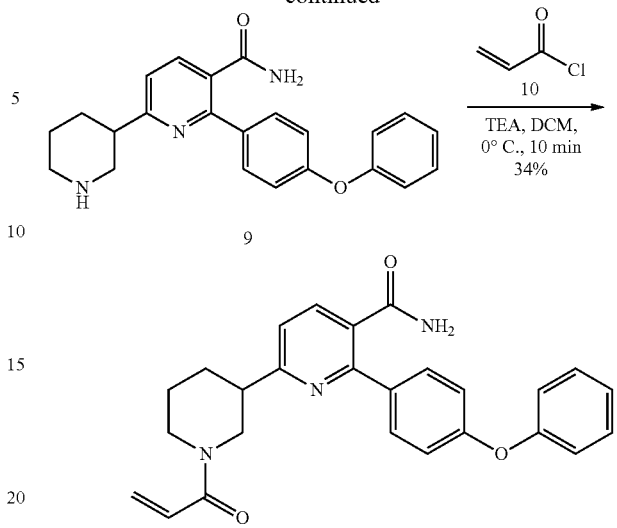

Example 8 tert-butyl 5-(trifluoromethylsulfonyloxy)-3,4-dihydropyridine-1(2H)-carboxylate (3)

To a solution of tert-butyl 3-oxopiperidine-1-carboxylate 1 (495 mg, 5.0 mmol) in tetrahydrofuran (10 mL) in a three-necked flask was added lithium diisopropylamide (2.0M, 2.5 mL, 5.0 mmol) at −78° C. After stirring for 2 h at −78° C., a solution of trifluoro-N-phenyl-N-(trifluoromethylsulfonyl)methanesulfonamide 2 (1.8 g, 5.0 mmol) in tetrahydrofuran (5 mL) was added, and the solution was stirred for another 30 min at this temperature, then warmed to room temperature and stirred for 3 h. Water (30 mL) was added to quench the reaction, and the solution was extracted with ethyl acetate (3×30 mL). The organic layers were combined, dried over anhydrous sodium sulfate, filtered and concentrated. The residue was purified by silica gel column chromatography eluting with petroleum ether to afford the title compound as brown oil (1.4 g, 85%).

tert-butyl-5-(4,4,5,5-tetramethyl-1,3,2-dioxaborolan-2-yl)-3,4-dihydropyridine-1(2H)-carboxylate (5)

To a solution of 4,4,4',4',5,5,5',5'-octamethyl-2,2'-bi(1,3,2-dioxaborolane) 4 (559 mg, 2.2 mmol), KOAc (588 mg, 6.0 mmol) and tert-butyl 5-(trifluoromethylsulfonyloxy)-3,4-dihydropyridine-1(2H)-carboxylate 3 (662 mg, 2.0 mmol) in dry 1,4-dioxane (10 mL) was added Pd(dppf)Cl₂·DCM (326 mg, 0.4 mmol) under nitrogen atmosphere, and the mixture was degassed with nitrogen 6 times, then heated to 85° C. and stirred overnight under nitrogen atmosphere. After cooling to room temperature, the solvent was evaporated and the crude product was purified by silica gel column chromatography, eluting with 100:1 to 20:1 PE/EA to afford the title compound as brown oil (336 mg, 54%).

tert-butyl-5-(5-carbamoyl-6-(4-phenoxyphenyl)pyridin-2-yl)-3,4-dihydropyridine-1(2H)-carboxylate (7)

To a solution of tert-butyl 5-(4,4,5,5-tetramethyl-1,3,2-dioxaborolan-2-yl)-3,4-dihydropyridine-1(2H)-carboxylate 5 (260 mg, 0.84 mmol), Cs₂CO₃ (456 mg, 1.4 mmol) and 6-chloro-2-(4-phenoxyphenyl)nicotinamide 6 (227 mg, 0.7 mmol) in 1,4-dioxane (10 mL) was added Pd(dppf)Cl$_2$·DCM (57 mg, 0.07 mmol) under nitrogen atmosphere, and the mixture was degassed with nitrogen 6 times, then heated to 90° C. and stirred overnight under nitrogen atmosphere. After cooling to room temperature, the solvent was evaporated and the crude product was purified by silica gel column chromatography eluting with 100:1 to 20:1 DCM/MeOH to afford the title compound as white solid (240 mg, 71%). MS (ESI): m/z=472.2 [M+H]$^+$.

tert-butyl 3-(5-carbamoyl-6-(4-phenoxyphenyl)pyridin-2-yl)piperidine-1-carboxylate (8)

To a solution of tert-butyl 5-(5-carbamoyl-6-(4-phenoxyphenyl)pyridin-2-yl)-3,4-dihydropyridine-1(2H)-carboxylate 7 (240 mg, 0.5 mmol) in ethyl acetate (5 mL) was added Pd/C (24 mg) under hydrogen atmosphere, and the mixture was degassed with hydrogen 6 times, then stirred for 16 h at ambient temperature under hydrogen atmosphere. The solution was filtered and the filtrate was evaporated to the crude product as brown solid (230 mg, crude). MS (ESI): m/z=474.2 [M+H]$^+$.

2-(4-phenoxyphenyl)-6-(piperidin-3-yl)nicotinamide (9)

To a solution of tert-butyl 3-(5-carbamoyl-6-(4-phenoxyphenyl)pyridin-2-yl)piperidine-1-carboxylate 8 (150 mg, 0.32 mmol) in dry dichloromethane (6 mL) was added TFA (2 mL), and the resulting mixture was stirred for 1 h at ambient temperature. The solvent was removed and the residue was partitioned between saturated aqueous sodium bicarbonate (30 mL) and ethyl acetate (20 mL). The organic phase was separated, dried over anhydrous sodium sulfate, filtered and concentrated. The crude residue was purified by silica gel column chromatography eluting with 5:1 DCM/MeOH to afford the title compound as a white solid (77 mg, 71%). MS (ESI): m/z=374.2 [M+H]$^+$.

Example 8

6-(1-acryloylpiperidin-3-yl)-2-(4-phenoxyphenyl)nicotinamide

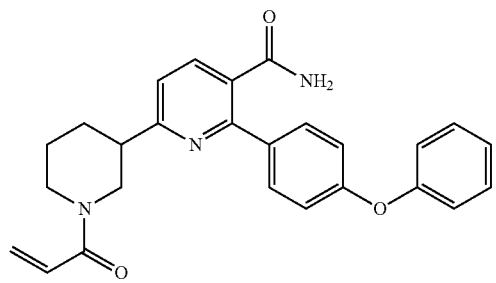 [SMILES: C=CC(=O)N1CCCC(c2ccc(C(N)=O)c(-c3ccc(Oc4ccccc4)cc3)n2)C1]

To a solution of 2-(4-phenoxyphenyl)-6-(piperidin-3-yl)nicotinamide 9 (19 mg, 0.05 mmol) in DCM (5 mL) was added TEA (0.05 mL, 0.4 mmol) and acryloyl chloride 10 (5 mg, 0.05 mmol) at 0° C. The mixture was stirred at 0° C. for 10 minutes. The solvent was removed and the residue was purified by Prep-TLC eluting with 25:1 DCM/MeOH to afford the title compound (7 mg, 34%) as white solid. $^1$H NMR (300 MHz, CDCl$_3$) δ 7.97 (d, J=8.9 Hz, 1H), 7.69 (d, J=8.1 Hz, 2H), 7.38 (t, J=7.8 Hz, 2H), 7.24-7.15 (m, 2H), 7.12-7.01 (m, 4H), 6.62 (dd, J=16.6, 10.6 Hz, 1H), 6.28 (d, J=16.4 Hz, 1H), 5.75-5.60 (m, 2H), 5.46 (s, 1H), 4.89-4.55 (m, 1H), 4.30-3.90 (m, 1H), 3.50 (t, J=12.2 Hz, 0.5H), 3.24-3.06 (m, 1H), 2.99 (d, J=10.7 Hz, 1H), 2.80 (t, J=12.2 Hz, 0.5H), 2.13 (s, 1H), 1.87 (d, J=13.4 Hz, 2H), 1.64 (s, 1H). MS (ESI, method A): m/z=428.0 [M+H]$^+$, $t_R$=1.526 min., HPLC: 93.3% (214 nm), 99.8% (254 nm).

Scheme 7

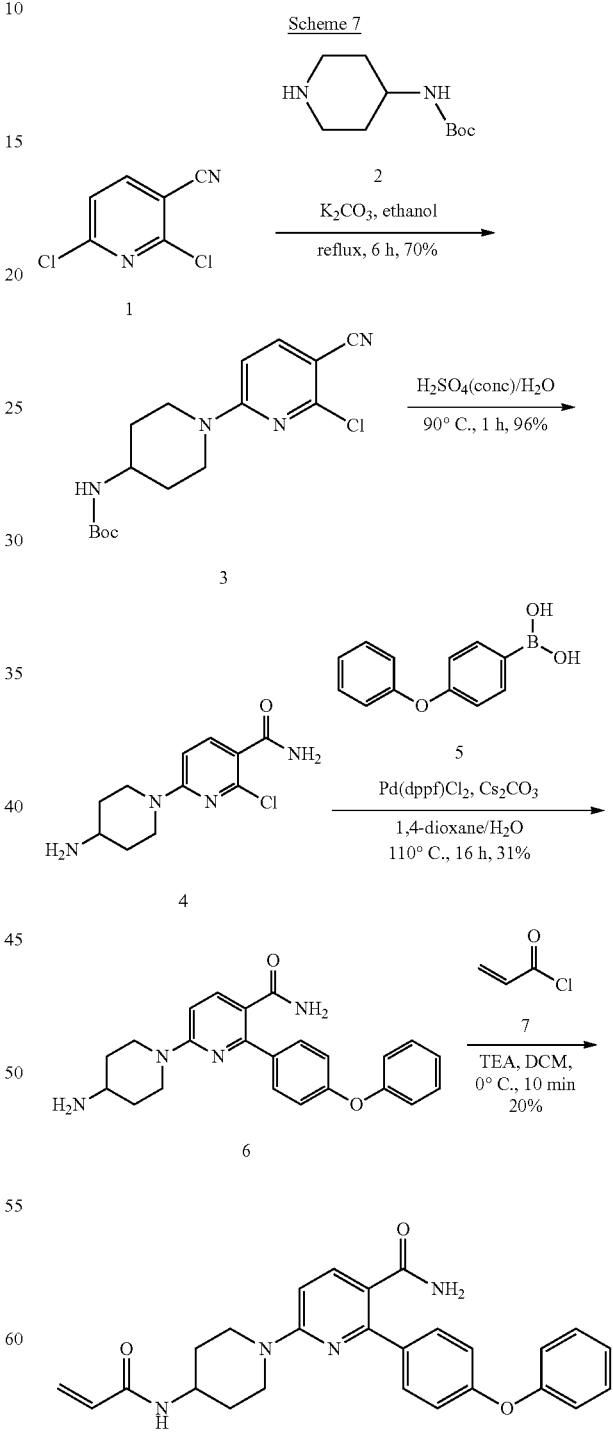

Example 9 tert-butyl 1-(6-chloro-5-cyanopyridin-2-yl)piperidin-4-ylcarbamate (3)

To a solution of 2,6-dichloronicotinonitrile 1 (346 mg, 2.0 mmol) in ethanol (10 mL) was added tert-butyl piperidin-4-ylcarbamate 2 (400 mg, 2.0 mmol) and K$_2$CO$_3$ (552 mg, 4.0 mmol). The mixture was heated to reflux stirred for 4 h. After cooling to room temperature, the solvent was evaporated and the crude product was purified by silica gel column chromatography eluting with 20:1 to 5:1 PE/EA to afford the title compound as a white solid (470 mg, 70%). MS (ESI, method A): m/z=337.2 [M+H].$^+$

6-(4-aminopiperidin-1-yl)-2-chloronicotinamide (4)

To tert-butyl 1-(6-chloro-5-cyanopyridin-2-yl) piperidin-4-ylcarbamate 3 (470 mg, 1.4 mmol) was added H$_2$SO$_4$ (conc., 5 mL) and water (1 mL). The mixture was heated to 90° C. and stirred for 1 h. After cooling to room temperature, the solution was poured into ice-cold water, then adjusted to PH=8 with ammonia water. The precipitate was filtered, washed with water (10 mL) and dried under vacuum to afford the title compound as a white solid (340 mg, 96%). MS (ESI): m/z=255.0 [M+H]$^+$.

6-(4-aminopiperidin-1-yl)-2-(4-phenoxyphenyl)nicotinamide (6)

To a solution of 6-(4-aminopiperidin-1-yl)-2-chloronicotinamide 4 (51 mg, 0.2 mmol), K$_2$CO$_3$ (55 mg, 0.4 mmol) and 4-phenoxyphenylboronic acid 5 (43 mg, 0.2 mmol) in 1,4-dioxane (15 mL) and water (3 mL) was added Pd(dppf)Cl$_2$ (18 mg, 0.02 mmol) under nitrogen atmosphere, and the mixture was degassed with nitrogen 6 times, then heated to 90° C. and stirred for 5 h under nitrogen atmosphere. After cooling to room temperature, the solvent was evaporated and the crude product was purified by silica gel column chromatography eluting with 70:1 DCM/MeOH to afford the title compound as a white solid (24 mg, 31%). MS (ESI): m/z=389.2 [M+H]$^+$.

Example 9

6-(4-acrylamidopiperidin-1-yl)-2-(4-phenoxyphenyl)nicotinamide

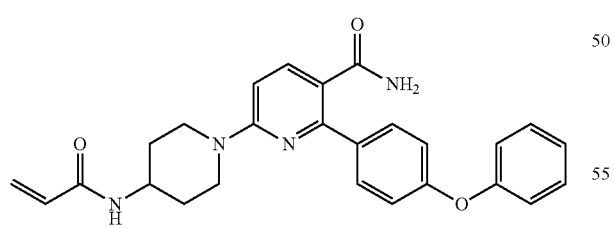

To a solution of 6-(4-aminopiperidin-1-yl)-2-(4-phenoxyphenyl)nicotinamide 6 (62 mg, 0.16 mmol) in DCM (5 mL) was added TEA (0.05 mL, 0.4 mmol) and acryloyl chloride 7 (15 mg, 0.16 mmol) at 0° C. The mixture was stirred at 0° C. for 10 minutes. The solvent was removed and the residue was purified by Prep-TLC eluting with 25:1 DCM/MeOH to afford the title compound (14 mg, 20%) as white solid. $^1$H NMR (300 MHz, CDCl$_3$) δ 7.98 (d, J=8.8 Hz, 1H), 7.62 (d, J=8.5 Hz, 2H), 7.38 (t, J=7.8 Hz, 2H), 7.16 (t, J=7.4 Hz, 1H), 7.12-7.00 (m, 4H), 6.65 (d, J=8.9 Hz, 1H), 6.31 (d, J=16.9 Hz, 1H), 6.07 (dd, J=16.9, 10.2 Hz, 1H), 5.66 (d, J=10.2 Hz, 1H), 5.52-5.48 (m, 1H), 5.28 (s, 1H), 4.44 (d, J=13.4 Hz, 2H), 4.24-4.08 (m, 1H), 3.08 (t, J=11.9 Hz, 2H), 2.08 (d, J=10.7 Hz, 2H), 1.62 (s, 1H), 1.47 (dt, J=11.3, 6.1 Hz, 2H). MS (ESI, method A): m/z=443.2 [M+H]$^+$, t$_R$=1.434 min., HPLC: 99.1% (214 nm), 99.3% (254 nm).

Scheme 8

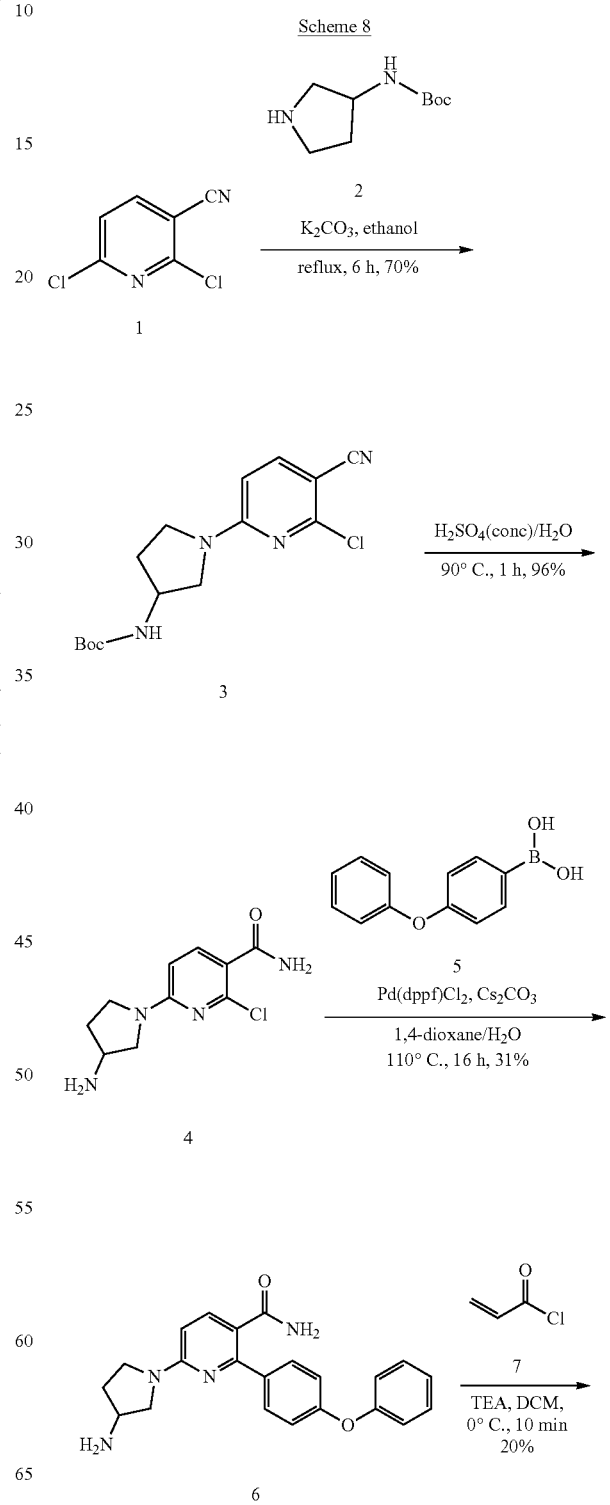

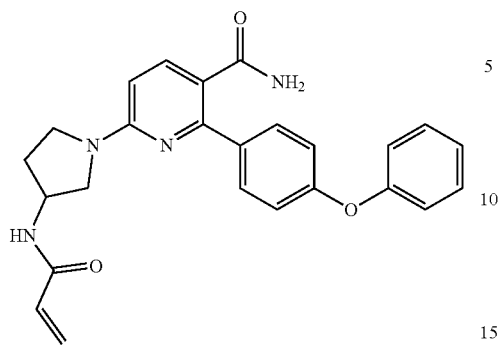

Example 10 tert-butyl 1-(6-chloro-5-cyanopyridin-2-yl)pyrrolidin-3-ylcarbamate (3)

To a solution of 2, 6-dichloronicotinonitrile 1 (346 mg, 2.0 mmol) in ethanol (10 mL) was added tert-butyl piperidin-4-ylcarbamate 2 (372 mg, 2.0 mmol) and $K_2CO_3$ (552 mg, 4.0 mmol). The mixture was heated to reflux and stirred for 4 h. After cooling to room temperature, the solvent was evaporated and the crude product was purified by silica gel column chromatography eluting with 20:1 to 5:1 PE/EA to afford the title compound as a white solid (365 mg, 57%). MS (ESI, method A): m/z=345.1 [M+Na]$^+$.

6-(4-aminopiperidin-1-yl)-2-chloronicotinamide (4)

To tert-butyl 1-(6-chloro-5-cyanopyridin-2-yl) pyrrolidin-3-ylcarbamate 3 (357 mg, 1.1 mmol) was added $H_2SO_4$ (conc., 5 mL) and water (1 mL). The mixture was heated to 90° C. and stirred for 1 h. After cooling to room temperature, the solution was poured into ice-cold water, then adjusted to PH=8 with ammonia water. The precipitate was filtered, washed with water (10 mL) and dried under vacuum to afford the title compound as brown solid (192 mg, 72%). MS (ESI, method A): m/z=241.0 [M+H]$^+$.

6-(3-aminopyrrolidin-1-yl)-2-(4-phenoxyphenyl) nicotinamide (6)

To a solution of 6-(4-aminopiperidin-1-yl)-2-chloronicotinamide 4 (192 mg, 0.79 mmol), $K_2CO_3$ (220 mg, 1.6 mmol) and 4-phenoxyphenylboronic acid 5 (171 mg, 0.8 mmol) in 1,4-dioxane (15 mL) and water (3 mL) was added Pd(dppf)Cl$_2$ (69 mg, 0.08 mmol) under nitrogen atmosphere, and the mixture was degassed with nitrogen 6 times, then heated to 90° C. and stirred for 5 h under nitrogen atmosphere. After cooling to room temperature, the solvent was evaporated and the crude product was purified by flash chromatography eluting with 70:1 DCM/MeOH to afford the title compound as a white solid (92 mg, 31%). MS (ESI): m/z=375.2 [M+H]$^+$.

Example 10

6-(3-acrylamidopyrrolidin-1-yl)-2-(4-phenoxyphenyl)nicotinamide

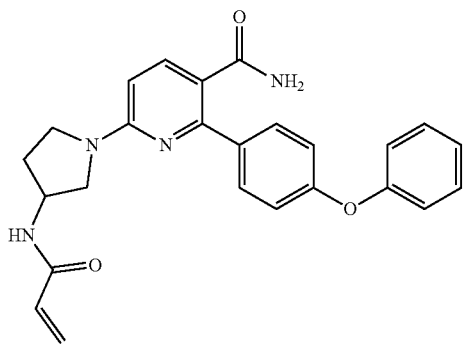 [SMILES: C=CC(=O)NC1CCN(c2ccc(C(N)=O)c(-c3ccc(Oc4ccccc4)cc3)n2)C1]

To a solution of 6-(3-aminopyrrolidin-1-yl)-2-(4-phenoxyphenyl)nicotinamide 6 (92 mg, 0.25 mmol) in DCM (5 mL) was added TEA (0.14 mL, 1.0 mmol) and acryloyl chloride 7 (23 mg, 0.25 mmol) at 0° C. The mixture was stirred at 0° C. for 10 minutes. The solvent was removed and the residue was purified by Prep-TLC eluting with 25:1 DCM/MeOH to afford the title compound (58 mg, 54%) as white solid. $^1$H NMR (300 MHz, CDCl$_3$) δ 7.95 (d, J=8.7 Hz, 1H), 7.62 (d, J=8.5 Hz, 2H), 7.38 (t, J=7.8 Hz, 2H), 7.16 (t, J=7.4 Hz, 1H), 7.05 (dd, J=12.6, 8.3 Hz, 4H), 6.40-625 (m, 1H), 6.10 (dd, J=16.8, 10.2 Hz, 2H), 5.67 (d, J=10.2 Hz, 1H), 5.48 (s, 1H), 5.31 (s, 1H), 4.71 (d, J=4.4 Hz, 1H), 3.85 (dd, J=11.2, 6.0 Hz, 1H), 3.75-340 (m, 4H), 2.40-2.25 (m, 1H), 2.10-1.90 (m, 1H). MS (ESI, method A): m/z=429.0 [M+H]$^+$, t$_R$=1.443 min., HPLC: 100% (214 nm), 100% (254 nm).

Example 11

1-(1-acryloylpiperidin-3-yl)-3-(4-phenoxyphenyl)-1H-pyrazole-4-carboxamide

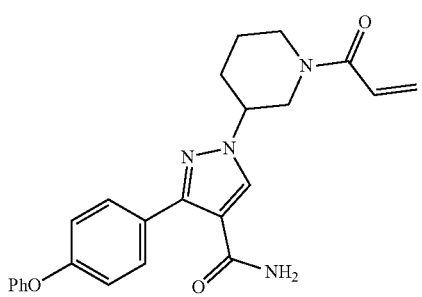 [SMILES: C=CC(=O)N1CCCC(n2cc(C(N)=O)c(-c3ccc(Oc4ccccc4)cc3)n2)C1]

Refer to Example 34 schemes and associated experimental procedures and data described below.

Example 12

1-(1-acryloylpiperidin-4-yl)-3-(4-phenoxyphenyl)-1H-pyrazole-4-carboxamide

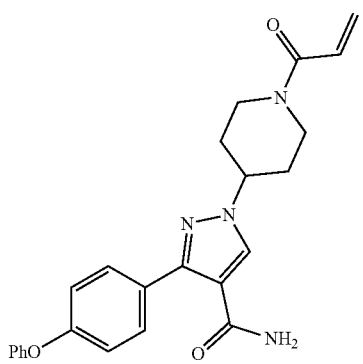 [SMILES: C=CC(=O)N1CCC(n2cc(C(N)=O)c(-c3ccc(Oc4ccccc4)cc3)n2)CC1]

Refer to Example 34 schemes and associated experimental procedures and data described below.

Example 13

1-(1-acryloylpyrrolidin-3-yl)-3-(4-phenoxyphenyl)-1H-pyrazole-4-carboxamide

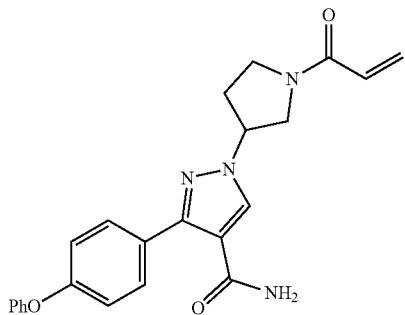 [SMILES: C=CC(=O)N1CCC(n2cc(C(N)=O)c(-c3ccc(Oc4ccccc4)cc3)n2)C1]

Refer to Example 34 schemes and associated experimental procedures and data described below.

Example 14

1-(azetidin-3-yl)-3-(4-phenoxyphenyl)-1H-pyrazole-4-carboxamide

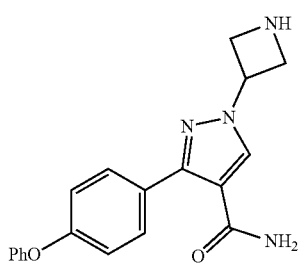 [SMILES: NC(=O)c1cn(C2CNC2)nc1-c1ccc(Oc2ccccc2)cc1]

Refer to Example 34 scheme and associated experimental procedures and data described below.

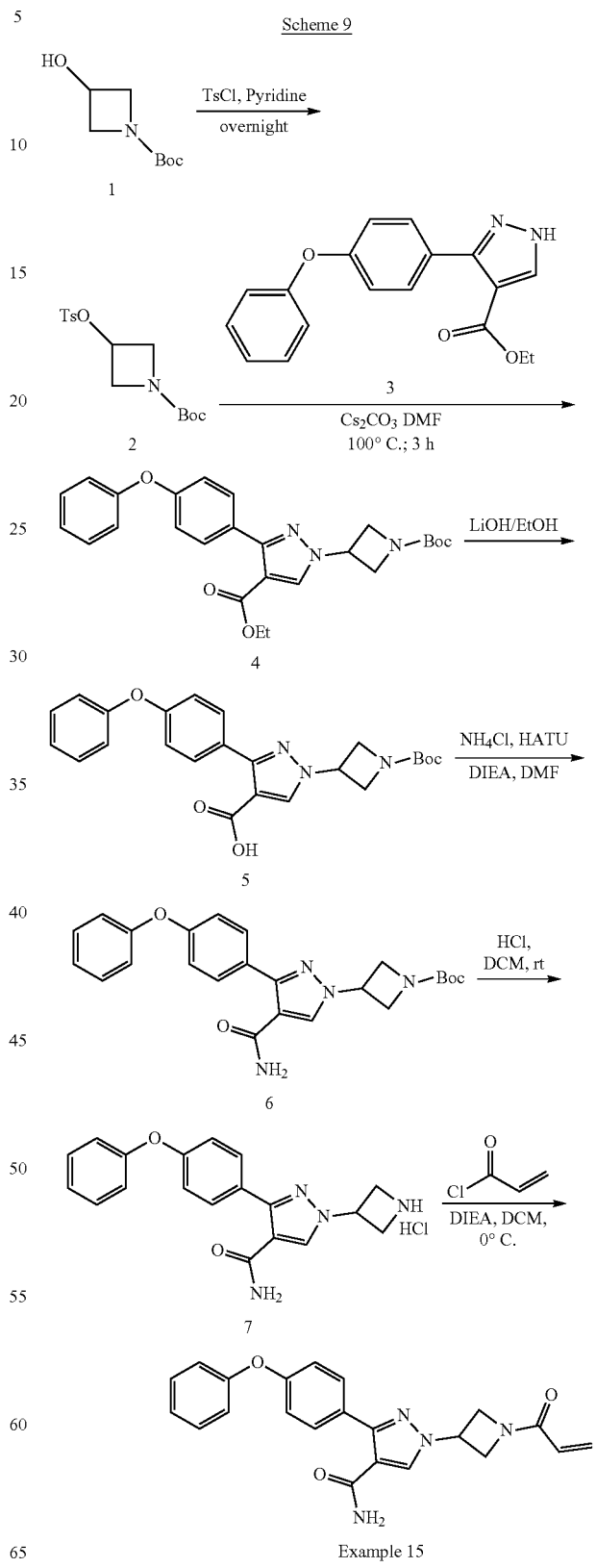

Scheme 9

Example 15 tert-butyl 3-(tosyloxy)azetidine-1-carboxylate (2)

To a solution of tert-butyl 3-hydroxyazetidine-1-carboxylate 1 (2.0 g, 11.5 mmol) in pyridine (25 mL) was added TsCl (2.64 g, 13.8 mmol), and the resulting solution was stirred for 16 h at rt. The solvent was evaporated and the crude residue was purified by silica gel column, eluting with 5:1 petroleum ether/ethyl acetate to afford the title compound (3.2 g, 85%) as colorless oil. MS (ESI): m/z=350.0 [M+Na]$^+$.

Ethyl-1-(1-(tert-butoxycarbonyl)azetidin-3-yl)-3-(4-phenoxyphenyl)-1H-pyrazole-4-carboxylate (4)

To a solution of tert-butyl 3-(tosyloxy)azetidine-1-carboxylate 2 (1.3 g, 3.88 mmol) and CsCO$_3$ (2.12 g, 6.48 mmol) in DMF (25 mL) was added ethyl 3-(4-phenoxyphenyl)-1H-pyrazole-4-carboxylate 3 (1.0 g, 3.24 mmol), and the resulting solution was stirred for 16 h at 100° C. The solvent was evaporated and the crude residue was purified by silica gel column eluting with 3:1 petroleum ether/ethyl acetate to afford the title compound (1.39 g, 93%) as white solid. MS (ESI): m/z=464.0 [M+H]$^+$.

1-(1-(tert-butoxycarbonyl)azetidin-3-yl)-3-(4-phenoxyphenyl)-1H-pyrazole-4-carboxylic acid (5)

To a solution of ethyl 1-(1-(tert-butoxycarbonyl)azetidin-3-yl)-3-(4-phenoxyphenyl)-1H-pyrazole-4-carboxylate 4 (1.39 g, 3.0 mmol) in EtOH (20 mL) and water (2 mL) was added LiOH (630 mg, 15.0 mmol), and the resulting solution was stirred for 16 h at rt. The solvent was evaporated, and the residue was dissolved in water (5 mL) and the resulting solution was acidified with 2 N hydrochloric acid to pH=6. The precipitate was filtered, washed with water (15 mL) and dried under vacuum to afford the title compound (1.2 g, 92%) as a white solid. MS (ESI): m/z=436.0 [M+H]$^+$.

tert-butyl-3-(4-carbamoyl-3-(4-phenoxyphenyl)-1H-pyrazol-1-yl)azetidine-1-carboxylate (6)

To a solution of 1-(1-(tert-butoxycarbonyl)azetidin-3-yl)-3-(4-phenoxyphenyl)-1H-pyrazole-4-carboxylic acid 5 (800 mg, 1.84 mmol), NH$_4$Cl (120 mg, 2.21 mmol) and HATU (1.04 mg, 2.76 mmol) in dry DMF (10 mL) was added DIPEA (957 mg, 7.36 mmol), and the resulting solution was stirred overnight at rt. After the reaction was completed, the solution was concentrated, diluted with ethyl acetate (30 mL) and washed with water (2×20 mL) and brine (2×20 mL). The organic layer was dried over anhydrous sodium sulfate, filtered and concentrated. The residue was purified by silica gel column eluting with 40:1 DCM/MeOH to afford the title compound (700 mg, 82%) as white solid. MS (ESI): m/z=435.0 [M+H]$^+$.

1-(azetidin-3-yl)-3-(4-phenoxyphenyl)-1H-pyrazole-4-carboxamide (7)

To a solution of 3-(4-carbamoyl-3-(4-phenoxyphenyl)-1H-pyrazol-1-yl)azetidine-1-carboxylate 6 (700 mg, 1.61 mmol) in DCM (20 mL) was added conc. HCl (5 mL) and the reaction mixture was stirred at rt for 1 h. After the reaction was completed, the solution was concentrated to afford the title compound (600 mg, 100%) as white solid. MS (ESI): m/z=335.0 [M+H]$^+$.

Example 15

1-(1-acryloylazetidin-3-yl)-3-(4-phenoxyphenyl)-1H-pyrazole-4-carboxamide

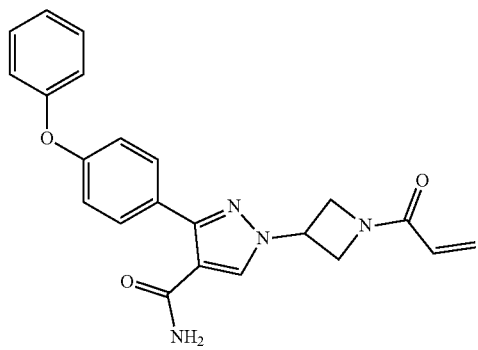 [SMILES: C=CC(=O)N1CC(n2cc(C(N)=O)c(-c3ccc(Oc4ccccc4)cc3)n2)C1]

To a solution of 1-(azetidin-3-yl)-3-(4-phenoxyphenyl)-1H-pyrazole-4-carboxamide 7 (300 mg, 0.81 mmol) in dry DCM (15 mL) were added DIEA (316 mg, 2.43 mmol) and acryloyl chloride (88 mg, 0.97 mmol) at 0° C., and the resulting solution was stirred at 0° C. for 10 min. Water (10 mL) was added to quench the reaction. The mixture was diluted with DCM (20 mL), and washed with water (2×20 mL) and brine (2×20 mL). The organic layer was dried over anhydrous sodium sulfate, filtered and concentrated. The residue was purified by Prep-HPLC (ACN—H$_2$O=20-70, 0.1% FA) to afford the title compound (160 mg, 51%) as a white solid. $^1$H NMR (400 MHz, DMSO) δ 8.38 (s, 1H), 7.81 (d, J=8.7 Hz, 2H), 7.47-7.38 (m, 3H), 7.20-7.14 (m, 1H), 7.11-6.99 (m, 5H), 6.43-6.34 (m, 1H), 6.20-6.12 (m, 1H), 5.76-5.70 (m, 1H), 5.38-5.29 (m, 1H), 4.78-4.68 (m, 1H), 4.59-4.49 (m, 1H), 4.48-4.40 (m, 1H), 4.32-4.22 (m, 1H). MS (ESI, Method A): m/z=389.1 [M+H]$^+$, $t_R$=1.374 min. HPLC: 99.7% (214 nm), 99.7% (254 nm).

Example 16

1-(4-acrylamidophenyl)-3-(4-phenoxyphenyl)-1H-pyrazole-4-carboxamide

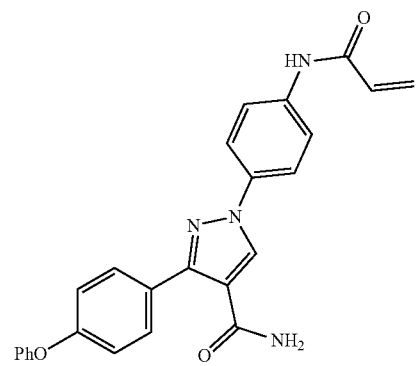 [SMILES: C=CC(=O)Nc1ccc(-n2cc(C(N)=O)c(-c3ccc(Oc4ccccc4)cc3)n2)cc1]

Refer to Example 34 schemes and associated experimental procedures and data described below.

Example 17

1-(3-aminophenyl)-3-(4-phenoxyphenyl)-1H-pyrazole-4-carboxamide

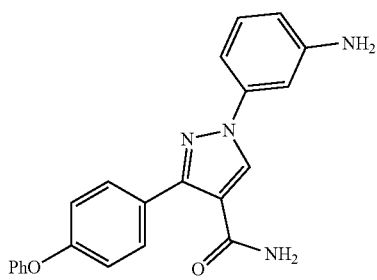 [SMILES: NC(=O)c1cn(-c2cccc(N)c2)nc1-c1ccc(Oc2ccccc2)cc1]

Refer to Example 34 schemes and associated experimental procedures and data described below.

Example 18

1-(3-acrylamidophenyl)-3-(4-phenoxyphenyl)-1H-pyrazole-4-carboxamide

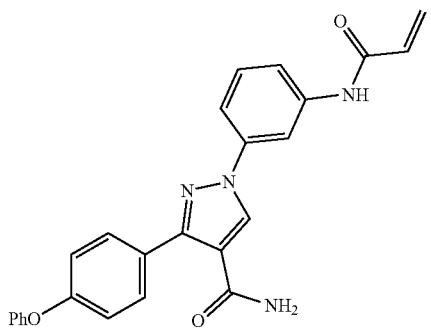 [SMILES: C=CC(=O)Nc1cccc(-n2cc(C(N)=O)c(-c3ccc(Oc4ccccc4)cc3)n2)c1]

Refer to Example 34 schemes and associated experimental procedures and data described below.

Example 19

(S)-1-(1-acryloylpyrrolidin-3-yl)-3-(4-phenoxyphenyl)-1H-pyrazole-4-carboxamide

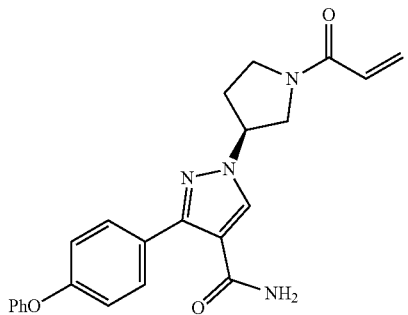 [SMILES: C=CC(=O)N1CC[C@H](n2cc(C(N)=O)c(-c3ccc(Oc4ccccc4)cc3)n2)C1]

Refer to Example 34 schemes and associated experimental procedures and data described below.

Example 20

(R)-1-(1-acryloylpyrrolidin-3-yl)-3-(4-phenoxyphenyl)-1H-pyrazole-4-carboxamide

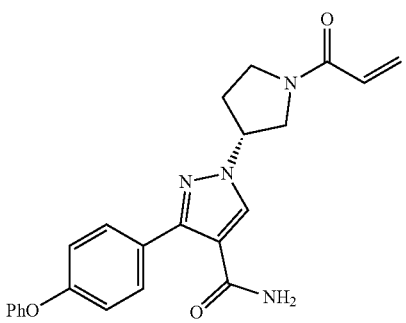

Refer to Example 34 schemes and associated experimental procedures and data described below.

Scheme 10

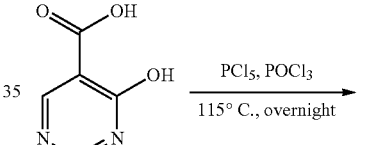

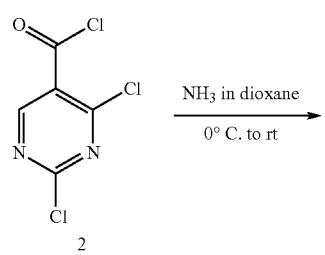

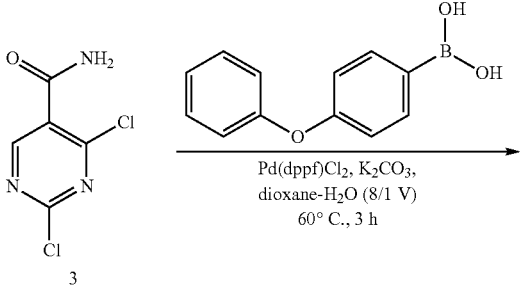

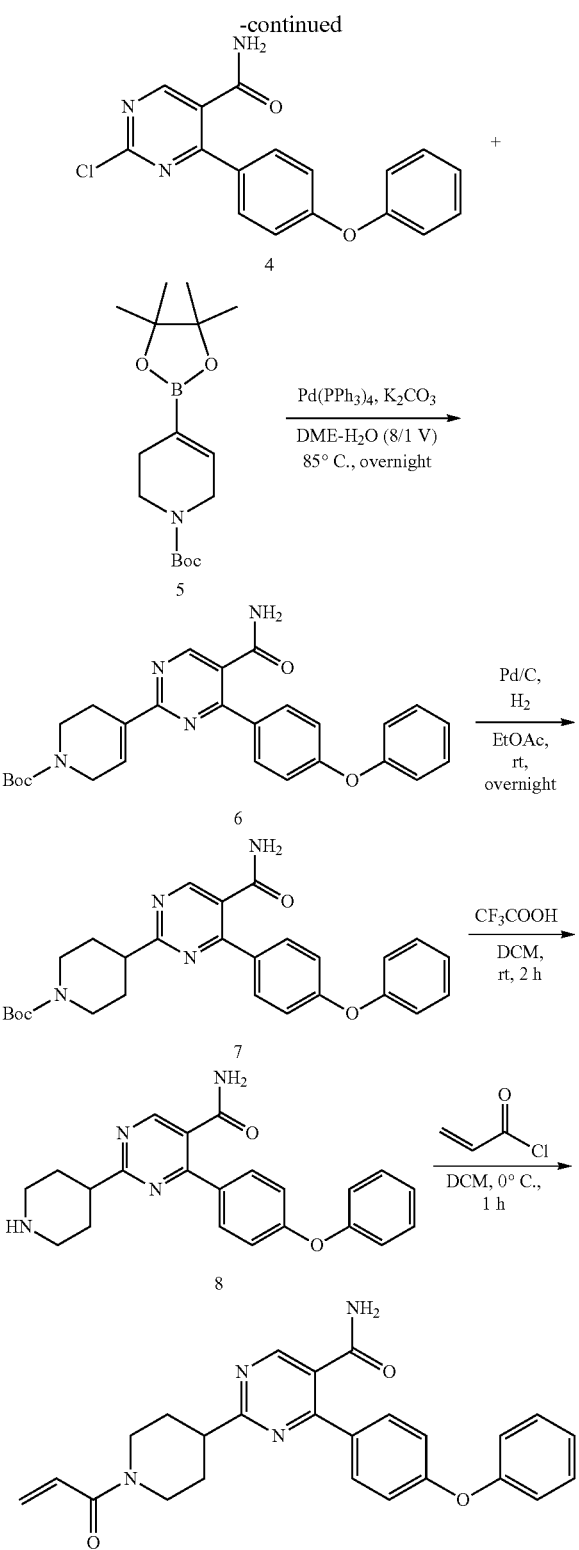

Example 21

2,4-dichloropyrimidine-5-carbonyl Chloride (2)

To a solution of 2,4-dihydroxypyrimidine-5-carboxylic acid (5.0 g, 32.0 mmol) in POCl$_3$ (50 mL) was added PCl$_5$ (23.9 g, 115.2 mmol), and the resulting solution was heated to 115° C. and stirred for 12 h. The solvent was evaporated and the crude residue was diluted with ethyl acetate (100 mL). The solid was filtered and the filtrate was concentrated to give the title compound as brown oil (6.2 g, 92%).

2,4-dichloropyrimidine-5-carboxamide (3)

To a solution of 2,4-dichloropyrimidine-5-carbonyl chloride (6.2 g, 29.3 mmol) in 1,4-dioxane (50 mL) was added ammonia (1.0 g, 58.3 mmol) in 1,4-dioxane (50 mL) dropwise at 0° C., and the resulting solution was stirred for 12 h at ambient temperature. The mixture was diluted with ethyl acetate (50 mL), and washed with water (2×80 mL) and brine (2×80 mL). The organic layer was dried over anhydrous sodium sulfate, filtered and concentrated to afford the title compound as a white solid (4.5 g, 80%). MS (ESI): m/z=191.8 [M+H]$^+$.

2-chloro-4-(4-phenoxyphenyl)pyrimidine-5-carboxamide (4)

To a solution of 4-phenoxyphenylboronic acid (1.0 g, 4.7 mmol), K$_2$CO$_3$ (1.4 g, 10.4 mmol) and 2,4-dichloropyrimidine-5-carboxamide (1.0 g, 5.2 mmol) in 1,4-dioxane (24 mL) and water (3 mL) was added Pd(dppf)Cl$_2$ (380 mg, 0.52 mmol) under nitrogen atmosphere, and the mixture was degassed with nitrogen 6 times, then heated to 60° C. and stirred for 3 h under nitrogen atmosphere. After cooling to room temperature, the solution was poured into water (50 mL), and then extracted with ethyl acetate (3×40 mL). The combined organic layers were dried over anhydrous sodium sulfate, filtered and concentrated. The crude product was purified by column chromatography, eluting with 100:1 dichloromethane/methanol to afford the title compound as a brown solid (410 mg, 24%). MS (ESI): m/z=325.9 [M+H]$^+$.

tert-butyl 4-(5-carbamoyl-4-(4-phenoxyphenyl)pyrimidin-2-yl)-5,6-dihydropyridine-1(2H)-carboxylate (6)

To a solution of 2-chloro-4-(4-phenoxyphenyl)pyrimidine-5-carboxamide 4 (410 mg, 1.26 mmol), K$_2$CO$_3$ (521.6 mg, 3.78 mmol) and tert-butyl 4-(4,4,5,5-tetramethyl-1,3,2-dioxaborolan-2-yl)-5,6-dihydropyridine-1(2H)-carboxylate 5 (583 mg, 1.89 mmol) in DME (30 mL) and water (5 mL) was added Pd(PPh$_3$)$_4$ (146 mg, 0.126 mmol) under nitrogen atmosphere, and the mixture was degassed with nitrogen 6 times, and then heated to 85° C. and stirred for 12 h under nitrogen atmosphere. After cooling to room temperature, the solvent was evaporated and the crude product was purified by flash chromatography eluting with 80:1 DCM/MeOH to afford the title compound as a brown solid (420 mg, 71%). MS (ESI): m/z=472.8 [M+H]$^+$.

tert-butyl 4-(5-carbamoyl-4-(4-phenoxyphenyl)pyrimidin-2-yl)piperidine-1-carboxylate (7)

To a solution of tert-butyl 4-(5-carbamoyl-4-(4-phenoxyphenyl)pyrimidin-2-yl)-5,6-dihydropyridine-1(2H)-carboxylate 6 (100 mg, 0.212 mmol) in ethyl acetate (5 mL) was added Pd/C (20 mg) under hydrogen atmosphere, and the mixture was degassed with hydrogen 6 times, then stirred for 16 h at ambient temperature under hydrogen atmosphere. The solution was filtered and the filtrate was evaporated to the crude product as brown solid (96 mg). MS (ESI): m/z=474.8 [M+H]$^+$.

53

4-(4-phenoxyphenyl)-2-(piperidin-4-yl)pyrimidine-5-carboxamide (8)

To a solution of tert-butyl 4-(5-carbamoyl-4-(4-phenoxyphenyl)pyrimidin-2-yl) piperidine-1-carboxylate 7 (96 mg, crude) in dry dichloromethane (2 mL) was added TFA (2 mL), and the resulting mixture was stirred for 1 h at ambient temperature. The solvent was removed and the residue was partitioned between saturated aqueous sodium bicarbonate (30 mL) and ethyl acetate (20 mL). The organic phase was separated, dried over anhydrous sodium sulfate, filtered and concentrated. The crude residue was purified by flash chromatography, eluting with 5:1 DCM/MeOH to afford the title compound as a white solid (70 mg, 88% for two steps). MS (ESI): m/z=374.9 [M+H]+.

Example 21

2-(1-acryloylpiperidin-4-yl)-4-(4-phenoxyphenyl)pyrimidine-5-carboxamide

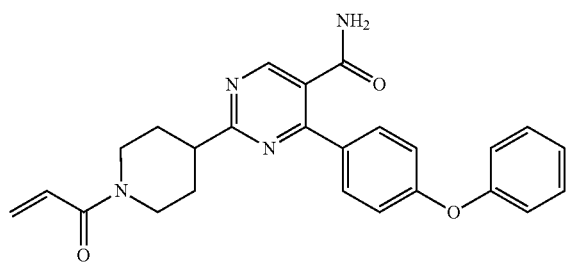 [SMILES: C=CC(=O)N1CCC(c2ncc(C(N)=O)c(-c3ccc(Oc4ccccc4)cc3)n2)CC1]

To a solution of 4-(4-phenoxyphenyl)-2-(piperidin-4-yl)pyrimidine-5-carboxamide 8 (70 mg, 0.187 mmol) in DCM (3 mL) was added TEA (56.7 mg, 0.56 mmol) and acryloyl chloride (25.3 mg, 0.28 mmol) at 0° C. The mixture was stirred at 0° C. for 10 min. The solvent was removed and the residue was purified by Prep-TLC eluting with 25:1 DCM/MeOH to afford the title compound (50 mg, 63%) as light yellow solid. $^1$H NMR (400 MHz, CDCl$_3$) δ 8.95 (s, 1H), 7.82 (d, J=8.8 Hz, 2H), 7.49-7.36 (m, 2H), 7.27-7.17 (m, 1H), 7.16-7.04 (m, 4H), 6.64 (dd, J=16.8, 10.6 Hz, 1H), 6.29 (dd, J=16.8, 1.9 Hz, 1H), 5.94 (s, 1H), 5.77 (s, 1H), 5.71 (dd, J=10.6, 1.9 Hz, 1H), 4.76 (d, J=12.5 Hz, 1H), 4.14 (d, J=14.1 Hz, 1H), 3.37-3.19 (m, 2H), 2.89 (t, J=11.5 Hz, 1H), 2.16 (d, J=11.0 Hz, 2H), 1.97 (d, J=9.9 Hz, 2H). MS (ESI, method F): m/z=428.8 [M+H]+, t$_R$=1.407 min., HPLC: 99.8% (214 nm), 99.6% (254 nm).

Scheme 11

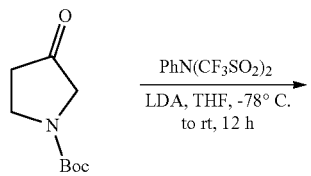

1

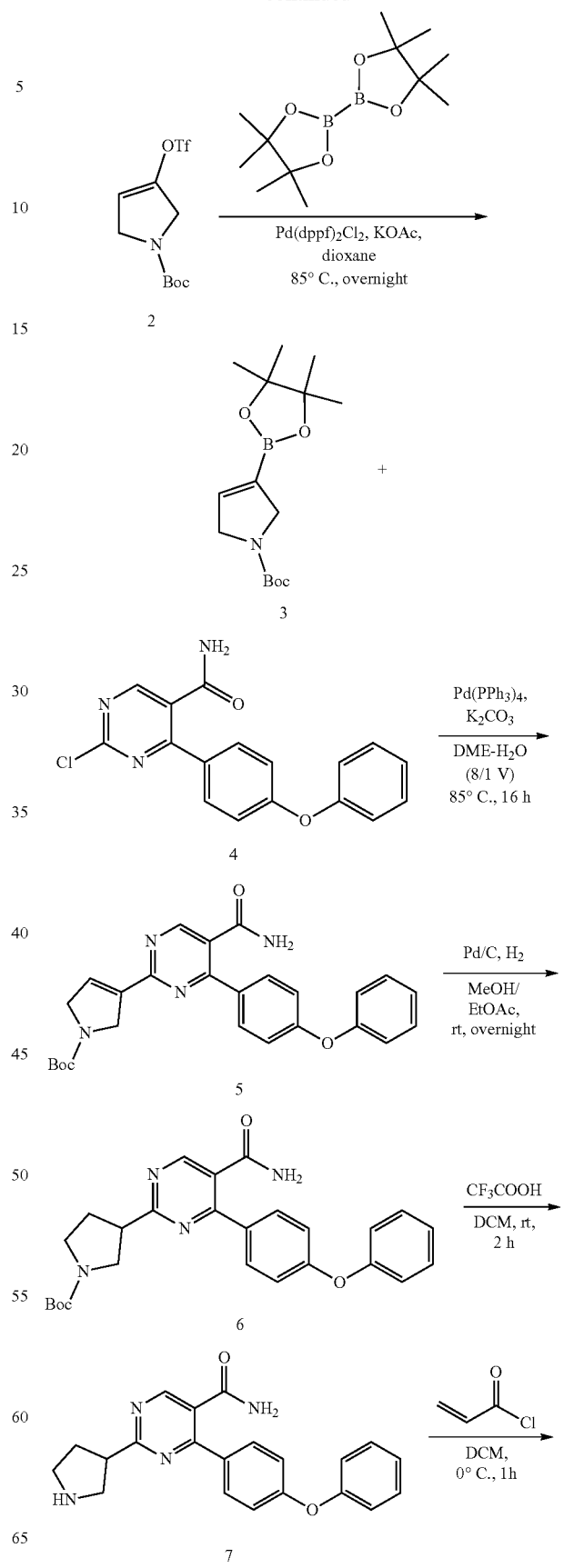

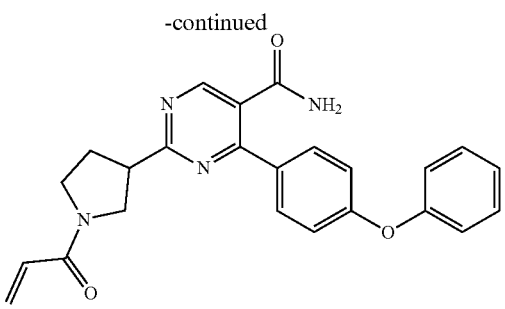

Example 22

1-(tert-butoxycarbonyl)-2,5-dihydro-1H-pyrrol-3-yl Trifluoromethanesulfonate (2)

To a solution of tert-butyl 3-oxopyrrolidine-1-carboxylate 1 (5.0 g, 27.0 mmol) in tetrahydrofuran (130 mL) in a three-necked flask was added lithium diisopropylamide (2.0M, 16.2 mL, 32.4 mmol) at −78° C. After stirring for 2 h at −78° C., a solution of trifluoro-N-phenyl-N-(trifluoromethylsulfonyl) methanesulfonamide (10.1 g, 28.4 mmol) in tetrahydrofuran (20 mL) was added, and the solution was stirred for another 30 min at this temperature, then warmed to room temperature and stirred for 3 h. Water (30 mL) was added to quench the reaction, and the solution was extracted with ethyl acetate (3×200 mL). The organic layers were combined, dried over anhydrous sodium sulfate, filtered and concentrated. The residue was purified by silica gel column chromatography, eluting with petroleum ether to afford the title compound as a brown oil (4.2 g, 49%). MS (ESI): m/z=318.1 [M+H]+.

tert-butyl-(4,4,5,5-tetramethyl-1,3,2-dioxaborolan-2-yl)-2H-pyrrole-1(5H)-carboxylate (3)

To a solution of bis(pinacolato)diborone (4.0 g, 15.9 mmol), KOAc (2.59 g, 26.4 mmol) and 1-(tert-butoxycarbonyl)-2,5-dihydro-1H-pyrrol-3-yl trifluoromethanesulfonate 2 (4.2 g, 13.2 mmol) in dry 1,4-dioxane (10 mL) was added Pd(dppf)Cl$_2$ (965 mg, 1.32 mmol) under nitrogen atmosphere, and the mixture was degassed with nitrogen 6 times, then heated to 85° C. and stirred overnight under nitrogen atmosphere. After cooling to room temperature, the solvent was evaporated and the crude product was purified by silica gel column chromatography, eluting from 100:1 to 20:1 petroleum ether/ethyl acetate to afford the title compound as brown oil (1.2 g, 31%). MS (ESI): m/z=296.1 [M+H]+.

tert-butyl-3-(5-carbamoyl-4-(4-phenoxyphenyl)pyrimidin-2-yl)-2H-pyrrole-1(5H)-carboxylate (5)

To a solution of tert-butyl 3-(4,4,5,5-tetramethyl-1,3,2-dioxaborolan-2-yl)-2H-pyrrole-1(5H)-carboxylate 3 (136 mg, 0.46 mmol), K$_2$CO$_3$ (127 mg, 0.92 mmol) and 2-chloro-4-(4-phenoxyphenyl)pyrimidine-5-carboxamide 4 (100 mg, 0.31 mmol) in 1,4-dioxane (15 mL) and water (3 mL) was added Pd(PPh$_3$)$_4$ (35.5 mg, 0.031 mmol) under nitrogen atmosphere. The mixture was degassed with nitrogen 6 times, then heated to 90° C. and stirred for 12 h under nitrogen atmosphere. After cooling to room temperature, the solvent was evaporated and the crude product was purified by flash chromatography eluting with 70:1 DCM/MeOH to afford the title compound as a white solid (90 mg, 64%). MS (ESI): m/z=458.8 [M+H]+.

tert-butyl-3-(5-carbamoyl-4-(4-phenoxyphenyl)pyrimidin-2-yl)pyrrolidine-1-carboxylate (6)

To a solution of tert-butyl 3-(5-carbamoyl-4-(4-phenoxyphenyl)pyrimidin-2-yl)-2H-pyrrole-1(5H)-carboxylate 5 (90 mg, 0.20 mmol) in ethyl acetate (3 mL) and MeOH (3 mL) was added Pd/C (20 mg) under hydrogen atmosphere, and the mixture was degassed with hydrogen 6 times, then stirred for 16 h at ambient temperature under hydrogen atmosphere. The solution was filtered and the filtrate was evaporated to the crude product as brown solid (80 mg, 88%). MS (ESI): m/z=461.1 [M+H]+.

4-(4-phenoxyphenyl)-2-(pyrrolidin-3-yl)pyrimidine-5-carboxamide (7)

To a solution of tert-butyl 3-(5-carbamoyl-4-(4-phenoxyphenyl)pyrimidin-2-yl)pyrrolidine-1-carboxylate 6 (80 mg, 0.174 mmol) in dry dichloromethane (2 mL) was added TFA (2 mL), and the resulting mixture was stirred for 1 h at ambient temperature. The solvent was removed and the residue was partitioned between saturated aqueous sodium bicarbonate (30 mL) and ethyl acetate (20 mL). The organic phase was separated, dried over anhydrous sodium sulfate, filtered and concentrated to afford the title compound as a white solid (70 mg, crude). MS (ESI): m/z=360.8 [M+H]+.

Example 22

2-(1-acryloylpyrrolidin-3-yl)-4-(4-phenoxyphenyl)pyrimidine-5-carboxamide

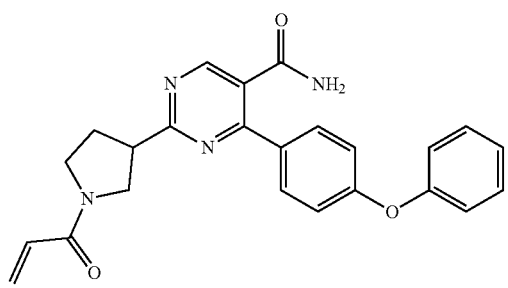

To a solution of 4-(4-phenoxyphenyl)-2-(pyrrolidin-3-yl)pyrimidine-5-carboxamide 7 (70 mg, crude) in DCM (5 mL) was added TEA (59 mg, 0.58 mmol) and acryloyl chloride (26 mg, 0.29 mmol) at 0° C. The mixture was stirred at 0° C. for 10 min. The solvent was removed and the residue was purified by Prep-TLC eluting with 25:1 DCM/MeOH to afford the title compound (20 mg, 25%) as a white solid. $^1$H NMR (400 MHz, CDCl$_3$) δ 8.95 (d, J=6.2 Hz, 1H), 7.82 (d, J=6.6 Hz, 2H), 7.42 (t, J=7.8 Hz, 2H), 7.22 (t, J=7.4 Hz, 1H), 7.10 (t, J=7.9 Hz, 4H), 6.55-6.47 (m, 1H), 6.39 (d, J=16.8, Hz, 1H), 5.84 (s, 2H), 5.71 (d, J=10.1 Hz, 1H), 4.14-3.96 (m, 2H), 3.94-3.78 (m, 2H), 3.76-3.62 (m, 1H), 2.55-2.36 (m, 2H). MS (ESI, method F): m/z=414.8 [M+H]+, $t_R$=1.382 min., HPLC: 99.0% (214 nm), 98.4% (254 nm).

Scheme 12

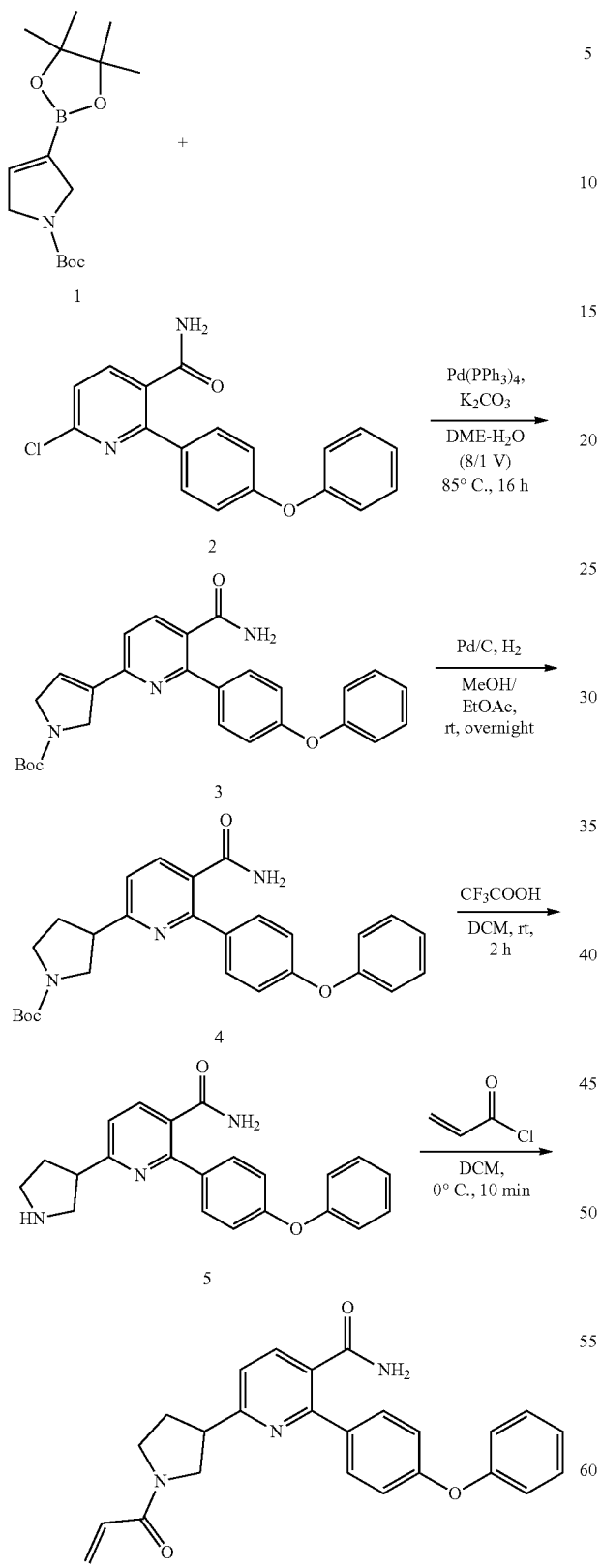

tert-butyl-3-(5-carbamoyl-6-(4-phenoxyphenyl)pyridin-2-yl)-2H-pyrrole-1(5H)-carboxylate (3)

To a solution of tert-butyl 3-(4,4,5,5-tetramethyl-1,3,2-dioxaborolan-2-yl)-2H-pyrrole-1(5H)-carboxylate 1 (136 mg, 0.0.46 mmol), $K_2CO_3$ (127.5 mg, 0.92 mmol) and 6-chloro-2-(4-phenoxyphenyl) nicotinamide 2 (100 mg, 0.31 mmol) in 1,2-dimethoxyethane (5 mL) and water (1 mL) was added $Pd(PPh_3)_4$ (35.6 mg, 0.031 mmol) under nitrogen atmosphere, and the mixture was degassed with nitrogen 6 times, then heated to 85° C. and stirred for 12 h under nitrogen atmosphere. After cooling to room temperature, the solvent was evaporated and the crude product was purified by flash chromatography, eluting with 50:1 DCM/MeOH to afford the title compound as a white solid (84 mg, 60%). MS (ESI): m/z=458.1 $[M+H]^+$.

tert-butyl 3-(5-carbamoyl-6-(4-phenoxyphenyl)pyridin-2-yl)pyrrolidine-1-carboxylate (4)

To a solution of tert-butyl 3-(5-carbamoyl-6-(4-phenoxyphenyl)pyridin-2-yl)-2H-pyrrole-1(5H)-carboxylate 3 (84 mg, 0.18 mmol) in ethyl acetate (5 mL) and MeOH (5 mL) was added Pd/C (40 mg) under hydrogen atmosphere, and the mixture was degassed with hydrogen 6 times, then stirred for 12 h at ambient temperature under hydrogen atmosphere. The solution was filtered and the filtrate was evaporated to the crude product as brown solid (80 mg, 95%). MS (ESI): m/z=459.8 $[M+H]^+$.

2-(4-phenoxyphenyl)-6-(pyrrolidin-3-yl)pyridine-3-carboxamide (5)

To a solution of tert-butyl 3-(5-carbamoyl-6-(4-phenoxyphenyl)pyridin-2-yl)pyrrolidine-1-carboxylate 4 (80 mg, 0.17 mmol) in dry dichloromethane (2 mL) was added TFA (2 mL), and the resulting mixture was stirred for 1 h at ambient temperature. The solvent was removed and the residue was partitioned between saturated aqueous sodium bicarbonate (30 mL) and ethyl acetate (20 mL). The organic phase was separated, dried over anhydrous sodium sulfate, filtered and concentrated to afford the title compound as a white solid (70 mg, crude). MS (ESI): m/z=359.9 $[M+H]^+$.

Example 23

6-(1-acryloylpyrrolidin-3-yl)-2-(4-phenoxyphenyl)pyridine-3-carboxamide

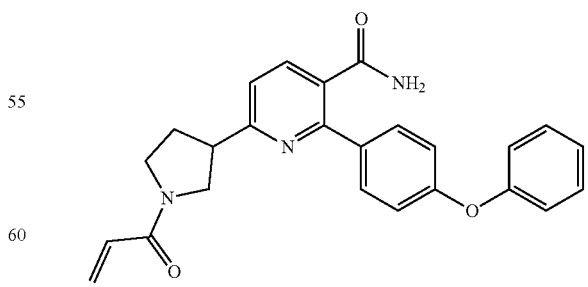

To a solution of 2-(4-phenoxyphenyl)-6-(pyrrolidin-3-yl)pyridine-3-carboxamide 5 (70 mg, crude) in DCM (5 mL) was added TEA (59 mg, 0.58 mmol) and acryloyl chloride (26.4 mg, 0.29 mmol) at 0° C. The mixture was stirred at 0°

C. for 10 min. The solvent was removed and the residue was purified by Prep-TLC eluting with 25:1 DCM/MeOH to afford the title compound (18 mg, 25% for two steps) as white solid. $^1$H NMR (400 MHz, CDCl$_3$) δ 8.06 (s, 1H), 7.72 (s, 2H), 7.41 (t, J=7.8 Hz, 2H), 7.28-7.24 (m, 1H), 7.19 (t, J=7.4 Hz, 1H), 7.11-7.09 (m, 4H), 6.55-6.47 (m, 1H), 6.41 (d, J=16.8, Hz, 1H), 5.71 (d, J=10.1 Hz, 1H), 5.65 (br, 1H), 5.45 (br, 1H), 4.14-3.96 (m, 1H), 3.94-3.78 (m, 2H), 3.76-3.62 (m, 2H), 2.55-2.36 (m, 2H). MS (ESI, method F): m/z=413.8 [M+H]$^+$, t$_R$=1.393 min., HPLC: 97.3% (214 nm), 99.5% (254 nm).

Scheme 13

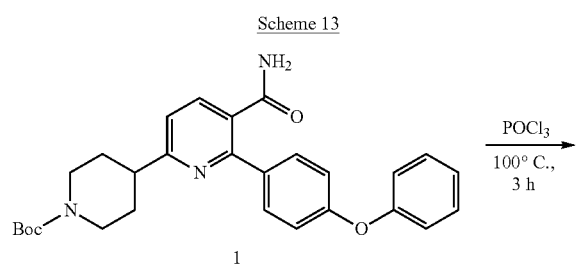

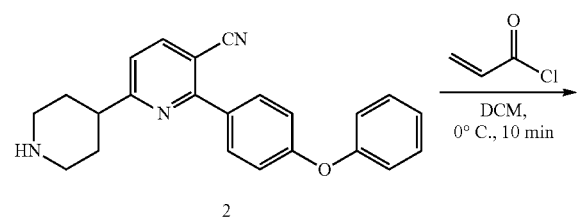

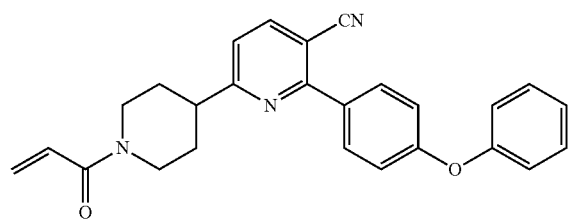 [SMILES: C=CC(=O)N1CCC(c2ccc(C#N)c(-c3ccc(Oc4ccccc4)cc3)n2)CC1]

Example 24

2-(4-phenoxyphenyl)-6-(piperidin-4-yl)pyridine-3-carbonitrile (2)

A solution of tert-butyl 4-(5-carbamoyl-4-(4-phenoxyphenyl)pyrimidin-2-yl)piperidine-1-carboxylate (100 mg, 0.21 mmol) in POCl$_3$ (3 mL) was heated to 100° C. and stirred for 3 h. After cooling to room temperature, the reaction mixture was poured into water (3 mL), and basified by saturate aqueous NaHCO$_3$ to PH=10. Then the solution was extracted with ethyl acetate (3×60 mL). The organic layers were combined, dried over anhydrous sodium sulfate, filtered and concentrated. The crude residue was purified by preparative TLC eluting with 8:1 DCM/MeOH to afford the title compound as brown oil (10 mg, 13%). MS (ESI): m/z=356.1 [M+H]$^+$.

Example 24

6-(1-acryloylpiperidin-4-yl)-2-(4-phenoxyphenyl)pyridine-3-carbonitrile

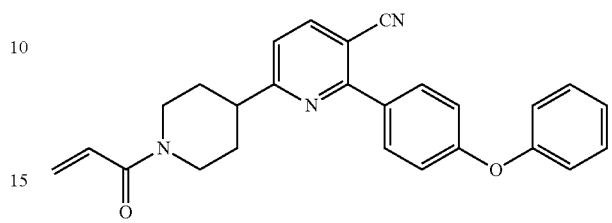

To a solution of 2-(4-phenoxyphenyl)-6-(piperidin-4-yl)pyridine-3-carbonitrile 2 (10 mg, 0.028 mmol) in DCM (2 mL) was added TEA (8.5 mg, 0.084 mmol) and acryloyl chloride (3.8 mg, 0.042 mmol) at 0° C. The mixture was stirred at 0° C. for 10 min. The solvent was removed and the residue was purified by Prep-TLC eluting with 25:1 DCM/MeOH to afford the title compound (13 mg, 44%) as white solid. $^1$H NMR (400 MHz, CDCl$_3$) δ 8.01 (d, J=8.1 Hz, 1H), 7.97 (dd, J=9.2, 2.3 Hz, 2H), 7.41 (t, J=7.9 Hz, 2H), 7.24-7.17 (m, 2H), 7.16-7.09 (m, 4H), 6.64 (dd, J=16.8, 10.6 Hz, 1H), 6.32 (dd, J=16.8, 1.8 Hz, 1H), 5.73 (dd, J=10.6, 1.9 Hz, 1H), 4.85-4.79 (m, 1H), 4.21-4.16 (m, 1H), 3.25-4.18 (m, 1H), 3.12 (tt, J=12.0, 3.8 Hz, 1H), 2.84-2.78 (m, 1H), 2.09-2.06 (m, 2H), 1.93-1.82 (m, 2H). MS (ESI, method F): m/z=409.8 [M+H]$^+$, t$_R$=1.669 min., HPLC: 98.7% (214 nm), 98.8% (254 nm).

Scheme 14

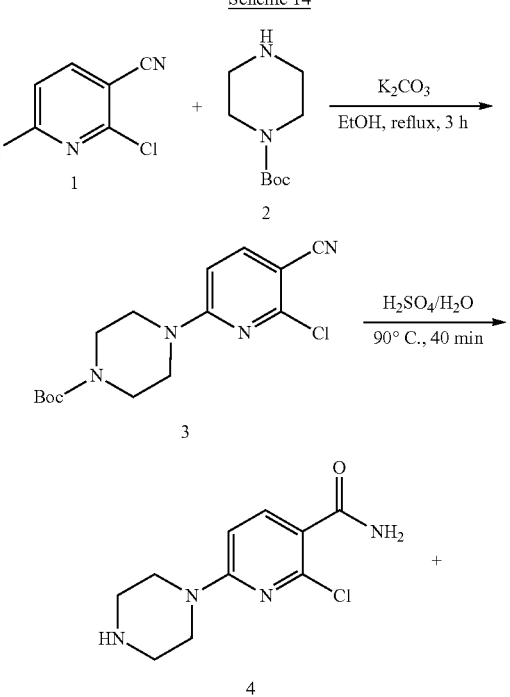

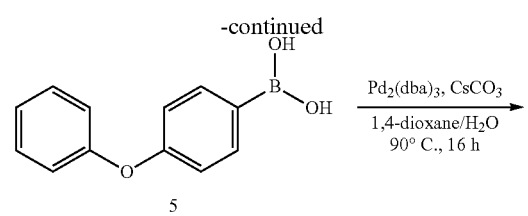

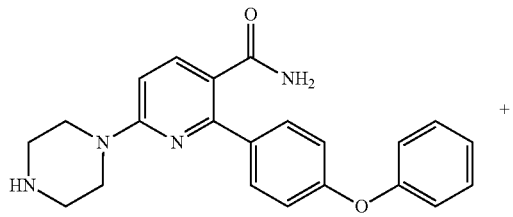

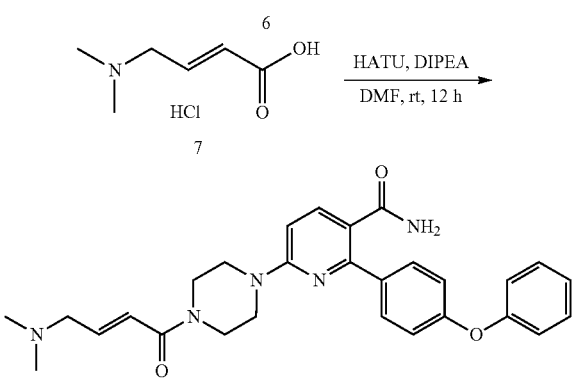

Example 25 tert-butyl 4-(6-chloro-5-cyanopyridin-2-yl)piperazine-1-carboxylate (3)

To a solution of 2,6-dichloronicotinonitrile 1 (1.0 g, 5.78 mmol) and tert-butyl piperazine-1-carboxylate 2 (1.08 g, 5.78 mmol) in ethanol (20 mL) was added $K_2CO_3$ (636 mg, 6.0 mmol). The resulting solution was refluxed for 3 h. After cooling to room temperature, the solvent was evaporated and the crude product was purified by flash chromatography eluting from 5:1 to 2:1 PE/EA to afford the title compound as a white solid (800 mg, 43%). MS (ESI): m/z=345.1 $[M+Na]^+$.

6-chloro-2-(4-phenoxyphenyl)nicotinamide (4)

To tert-butyl-(6-chloro-5-cyanopyridin-2-yl)piper azine-1-carboxylate 3 (800 mg, 2.5 mmol) was added conc. $H_2SO_4$ (5 mL) and water (1 mL). The mixture was heated to 90° C. and stirred for 40 min. After cooling to room temperature, the solution was poured into ice-cold water, then adjusted to PH=8 by ammonia water. The precipitate was filtered, washed with water (20 mL) and dried under vacuum to afford the title compound as an off-white solid (580 mg, 96%). MS (ESI): m/z=241.1 $[M+H]^+$.

2-(4-phenoxyphenyl)-6-(piperazin-1-yl)nicotinamide (6)

To a solution of 6-chloro-2-(4-phenoxyphenyl)nicotinamide 4 (580 mg, 2.41 mmol), $Cs_2CO_3$ (2.35 g, 7.23 mmol) and 4-phenoxyphenylboronic acid 5 (619 mg, 2.89 mmol) in 1,4-dioxane (15 mL) and water (3 mL) was added $Pd_2(dba)_3$ (220 mg, 0.24 mmol) under nitrogen atmosphere, and the mixture was degassed with nitrogen 6 times, then heated to 90° C. and stirred for 12 h under nitrogen atmosphere. After cooling to room temperature, the solvent was evaporated and the crude product was purified by flash chromatography eluting with 10:1 DCM/MeOH to afford the title compound as a white solid (480 mg, 52%). MS (ESI): m/z=375.1 $[M+H]^+$.

Example 25

(E)-6-(4-(4-(dimethylamino)but-2-enoyl)piperazin-1-yl)-2-(4-phenoxyphenyl)nicotinamide

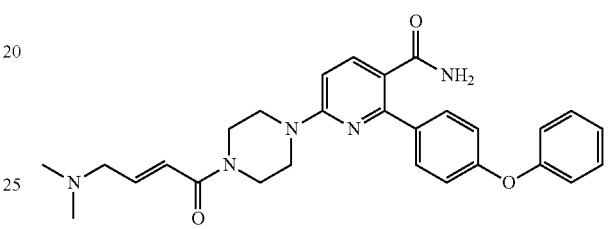

A mixture of 2-(4-phenoxyphenyl)-6-(piperazin-1-yl) nicotinamide 6 (100 mg, 0.27 mmol), (E)-4-(dimethylamino)but-2-enoic acid hydrochloride 7 (53 mg, 0.32 mmol), HATU (152 mg, 0.4 mmol), and DIPEA (172.5 mg, 1.34 mmol) in DMF (10 mL) was stirred at rt for 12 h. The solution was poured into water (50 mL), and then extracted with ethyl acetate (3×50 mL). The combined organic layers were dried over anhydrous sodium sulfate, filtered and concentrated. The residue was purified by Prep-TLC eluting with 10:1 DCM/MeOH to afford the title compound (30 mg, 23%) as a white solid. $^1$H NMR (400 MHz, MeOD) δ 7.78 (d, J=8.7 Hz, 1H), 7.69 (d, J=8.6 Hz, 2H), 7.40 (t, J=7.9 Hz, 2H), 7.17 (d, J=7.4 Hz, 1H), 7.04 (dd, J=15.3, 8.3 Hz, 4H), 6.93 (d, J=15.3 Hz, 1H), 6.82 (d, J=8.7 Hz, 1H), 6.77 (m, 1H), 3.89-3.68 (m, 10H), 2.76 (s, 6H). MS (ESI, method F): m/z=485.9 $[M+H]^+$, $t_R$=1.249 min., HPLC: 93.3% (214 nm), 93.0% (254 nm).

Scheme 15

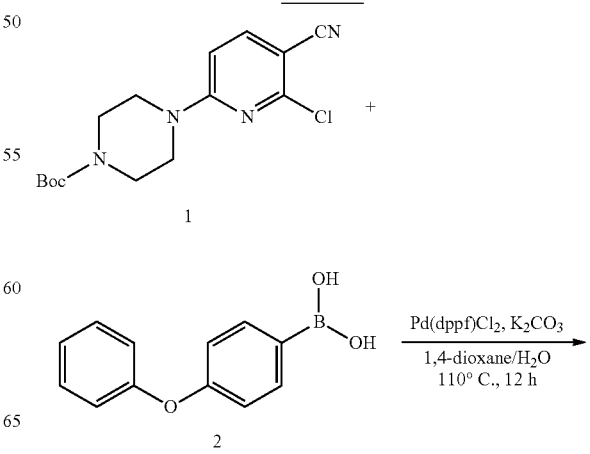

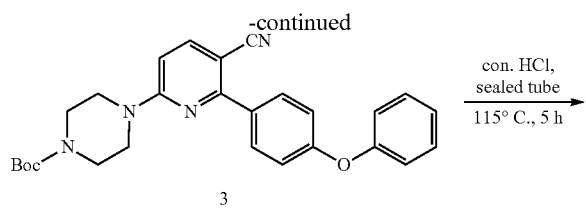

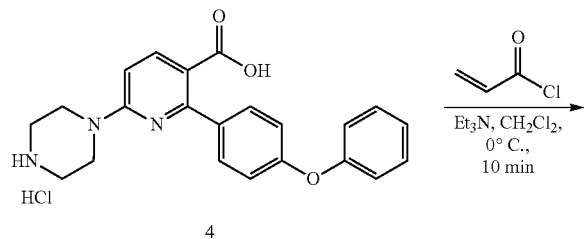

Example 26

2-(4-phenoxyphenyl)-6-(piperazin-1-yl)nicotinamide (3)

To a solution of tert-butyl 4-(6-chloro-5-cyanopyridin-2-yl)piperazine-1-carboxylate 1 (300 mg, 0.93 mmol), K$_2$CO$_3$ (385 mg, 2.79 mmol) and 4-phenoxyphenylboronic acid 2 (297 mg, 1.39 mmol) in 1,4-dioxane (12 mL) and water (2 mL) was added Pd(dppf)Cl$_2$ (68 mg, 0.093 mmol) under nitrogen atmosphere. The mixture was degassed with nitrogen 6 times, then heated to 90° C. and stirred for 12 h under nitrogen atmosphere. After cooling to room temperature, the solvent was evaporated and the crude product was purified by flash chromatography eluting with 20:1 DCM/MeOH to afford the title compound as a white solid (260 mg, 58%). MS (ESI): m/z=457.1 [M+H]$^+$.

2-(4-phenoxyphenyl)-6-(piperazin-1-yl)nicotinic acid hydrochloride (4)

In a 20 mL sealed tube, was placed a solution of 2-(4-phenoxyphenyl)-6-(piperazin-1-yl)nicotinamide 3 (140 mg, 0.31 mmol) in conc. HCl (5 mL). The mixture was heated to 115° C. and stirred for 4 h. After cooling to room temperature, the solution was concentrated under vacuum to afford the title compound as an off-white solid (120 mg, 95%). MS (ESI): m/z=376.1 [M+H]$^+$.

Example 26

6-(4-acryloylpiperazin-1-yl)-2-(4-phenoxyphenyl)pyridine-3-carboxylic acid

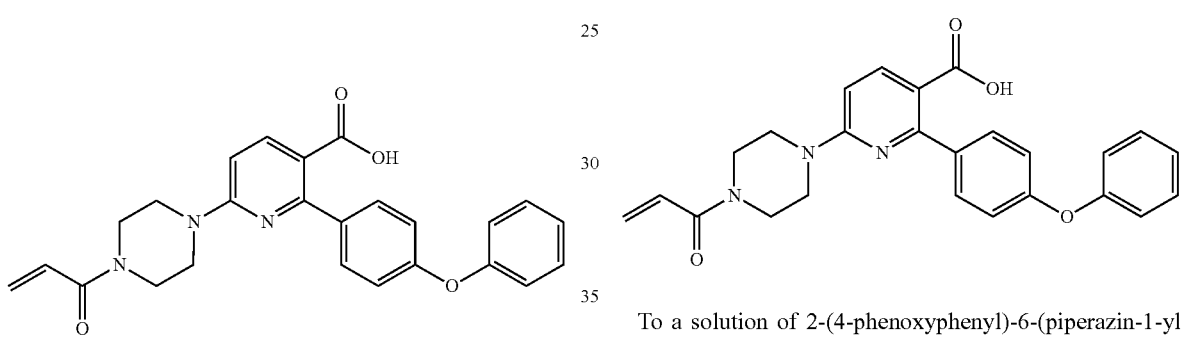

To a solution of 2-(4-phenoxyphenyl)-6-(piperazin-1-yl)nicotinic acid hydrochloride 4 (120 mg, 0.32 mmol) in DCM (5 mL) was added TEA (162 mg, 1.6 mmol) and acryloyl chloride (35 mg, 0.38 mmol) at 0° C. The mixture was stirred at 0° C. for 10 minutes. The solvent was removed and the residue was purified by Prep-TLC eluting with 20:1 DCM/MeOH to afford the title compound (15 mg, 11%) as a white solid. $^1$H NMR (400 MHz, CDCl$_3$) δ 8.17 (d, J=8.9 Hz, 1H), 7.55 (d, J=8.3 Hz, 2H), 7.38 (t, J=7.7 Hz, 2H), 7.16 (t, J=7.4 Hz, 1H), 7.11 (d, J=8.0 Hz, 2H), 7.03 (d, J=8.3 Hz, 2H), 6.65-6.55 (m, 2H), 6.38 (d, J=16.7 Hz, 1H), 5.78 (d, J=10.6 Hz, 1H), 3.86-375 (m, 8H). MS (ESI, method F): m/z=429.8 [M+H]$^+$, t$_R$=1.477 min., HPLC: 93.5% (214 nm), 93.0% (254 nm).

Scheme 16

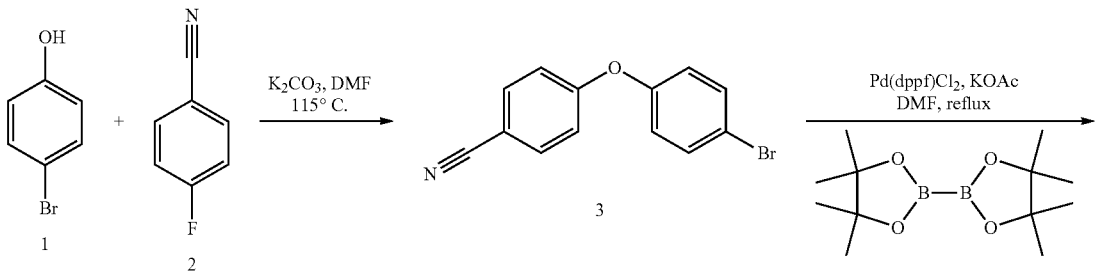

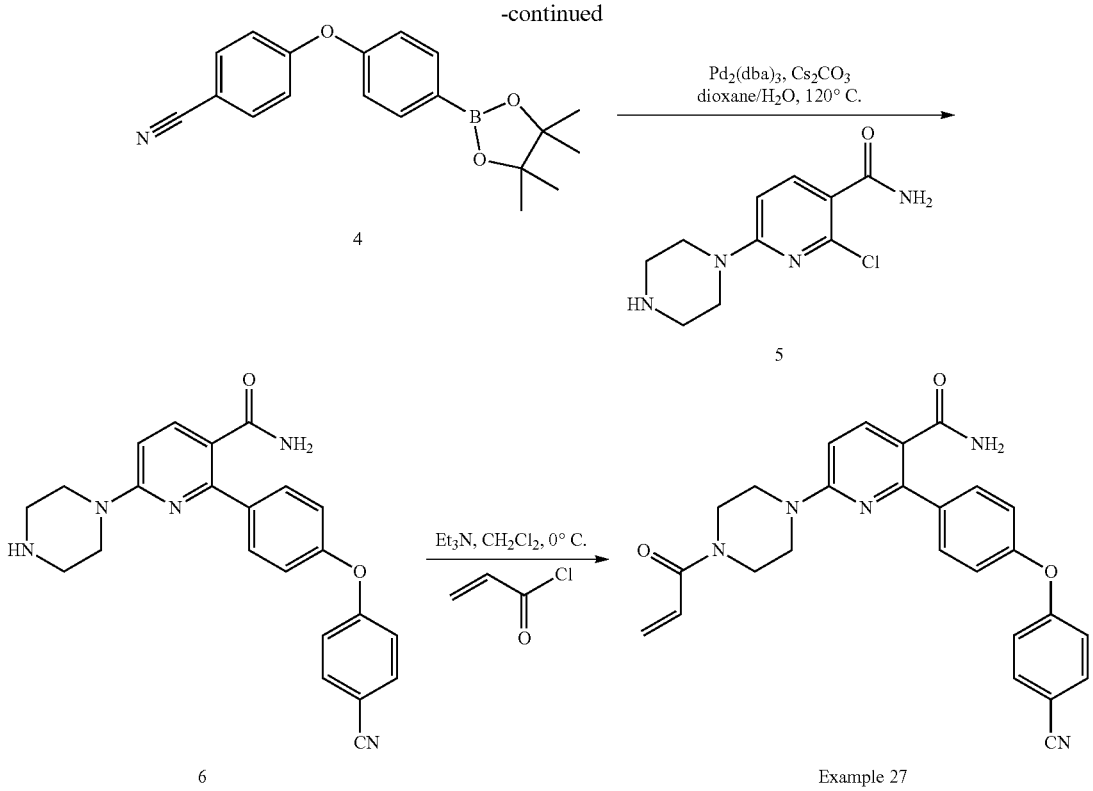

4-(4-bromophenoxy)benzonitrile (3)

The mixture of 4-bromophenol 1 (0.50 g, 2.9 mmol), 4-fluorobenzonitrile 2 (0.28 g, 2.31 mmol), $K_2CO_3$ (0.80 g, 5.8 mmol) and DMF (4 mL) was stirred at 115° C. for 16 h. After cooled to rt, the mixture was concentrated in vacuo. The residue was purified by silica gel chromatography eluting with 100:1 petroleum ether/EtOAc to afford the title compound (0.59 g, 74%) as white solid. $^1$H NMR (400 MHz, DMSO-d6) δ 7.86 (d, J=8.7 Hz, 2H), 7.64 (d, J=6.0 Hz, 2H), 7.13 (dd, J=5.1, 4.7 Hz, 4H).

4-(4-(4,4,5,5-tetramethyl-1,3,2-dioxaborolan-2-yl)phenoxy)benzonitrile (4)

The mixture of 4-(4-bromophenoxy)benzonitrile 3 (0.59 g, 2.15 mmol), bispinacolato diboron (1.09 g, 4.3 mmol), KOAc (0.63 g, 6.45 mmol), Pd(dppf)Cl$_2$ (0.157 g, 0.215 mmol) and DMF (3.5 mL) was degassed with N$_2$ 6 times and then stirred under reflux for 16 h. After cooled to rt, the mixture was concentrated in vacuo. The residue was purified by silica gel chromatography eluting with 50:1 petroleum ether/EtOAc to afford the title compound (0.55 g, 79%) as white solid.

2-(4-(4-cyanophenoxy)phenyl)-6-(piperazin-1-yl)nicotinamide (6)

The title compound was obtained using a procedure analogous to the procedure described in 2-(4-(hydroxy(phenyl)methyl)phenyl)-6-(piperidin-4-yl)nicotinamide (see Scheme 48) as yellow solid (0.15 g, 37%). MS (ESI): m/z=400.1 [M+H]$^+$.

Example 27

6-(4-acryloylpiperazin-1-yl)-2-(4-(4-cyanophenoxy)phenyl)nicotinamide

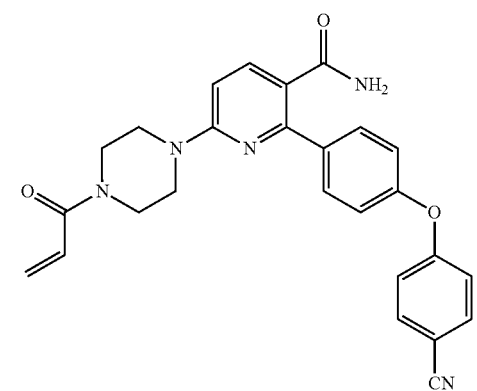

The title compound was obtained using a procedure analogous to the procedure described in Example 1 as white solid (40 mg, 23%). $^1$H NMR (400 MHz, DMSO-d6) δ 7.88 (d, J=8.7 Hz, 2H), 7.73 (d, J=8.6 Hz, 2H), 7.68 (d, J=8.7 Hz, 1H), 7.59 (s, 1H), 7.26 (s, 1H), 7.21-7.14 (m, 4H), 6.86 (dd, J=17.8, 9.3 Hz, 2H), 6.16 (dd, J=16.7, 2.2 Hz, 1H), 5.73 (dd, J=10.4, 2.2 Hz, 1H), 3.66-3.67 (m, 8H). MS (ESI, method A): m/z=454.1 [M+H]$^+$, $t_R$=1.685 (min). HPLC: 97.1% (214 nm), 99.7% (254 nm).

Scheme 17

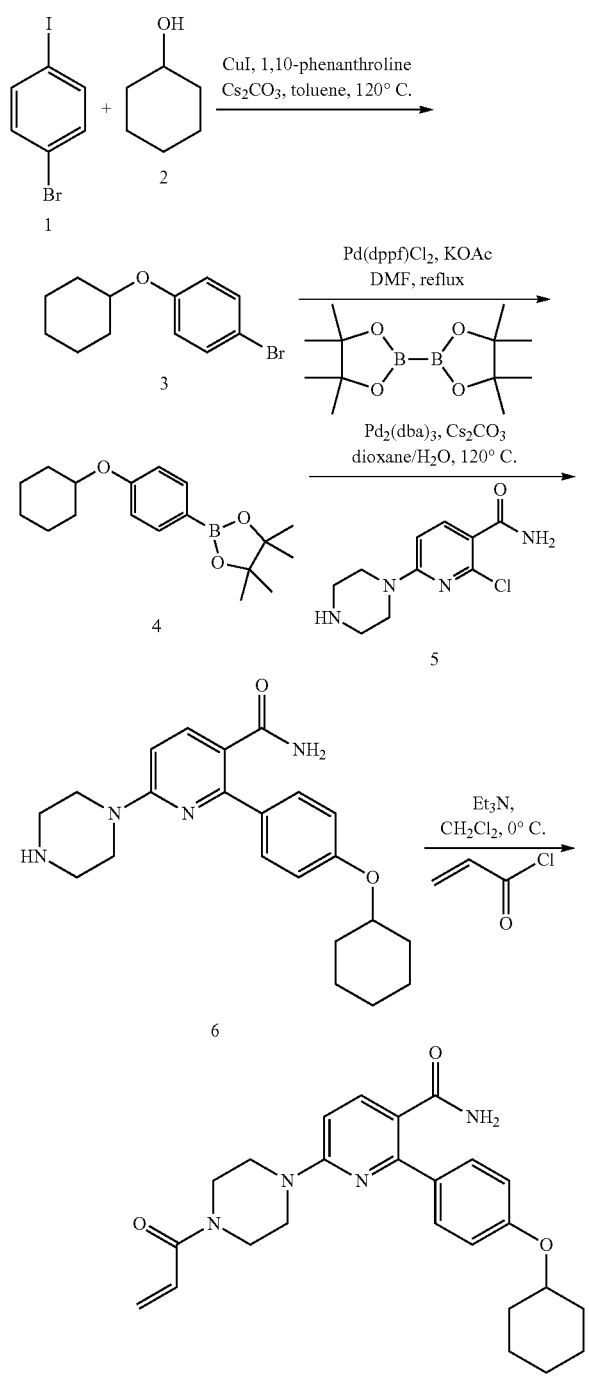

Example 28 chromatography eluting with 20:1 petroleum ether/EtOAc to afford the title compound (1.17 g, 46%) as colorless oil. $^1$H NMR (400 MHz, CDCl$_3$) δ 7.40-7.33 (m, 2H), 6.83-6.77 (m, 2H), 4.26-4.16 (m, 1H), 2.04-1.92 (m, 2H), 1.87-1.75 (m, 2H), 1.65-1.47 (m, 3H), 1.45-1.25 (m, 3H).

2-(4-(cyclohexyloxy)phenyl)-4,4,5,5-tetramethyl-1,3,2-dioxaborolane (4)

The title compound was obtained using a procedure analogous to the procedure described in 4-(4-(4,4,5,5-tetramethyl-1,3,2-dioxaborolan-2-yl)phenoxy)benzonitrile (see Scheme 16) as brown oil (1.04 g, 75%). $^1$H NMR (400 MHz, CDCl$_3$) δ 7.75 (d, J=8.5 Hz, 2H), 6.91 (d, J=8.5 Hz, 2H), 4.40-4.25 (m, 1H), 2.09-1.94 (m, 2H), 1.89-1.76 (m, 2H), 1.66-1.49 (m, 4H), 1.48-1.23 (m, 14H).

2-(4-(cyclohexyloxy)phenyl)-6-(piperazin-1-yl)nicotinamide (6)

The title compound was obtained using a procedure analogous to the procedure described in 6-(3-nitrophenyl)-2-(4-phenoxyphenyl)nicotinamide (see Scheme 1) as brown gum (0.157 g, 41%). MS (ESI): m/z=381.1 [M+H]$^+$.

Example 28

6-(4-acryloylpiperazin-1-yl)-2-(4-(cyclohexyloxy)phenyl)nicotinamide

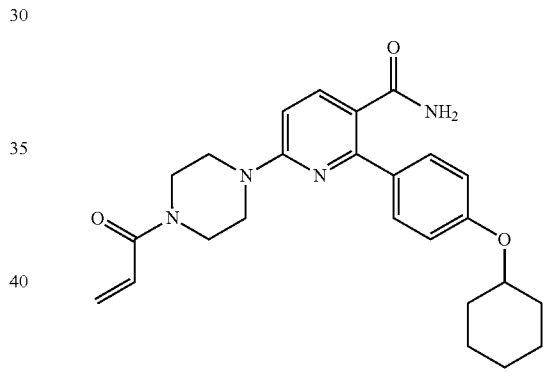

The title compound was obtained using a procedure analogous to the procedure described in Example 1 as white solid (61 mg, 34%). $^1$H NMR (400 MHz, CD$_3$OD) δ 7.76 (d, J=8.7 Hz, 1H), 7.63 (d, J=8.7 Hz, 2H), 6.96 (d, J=8.7 Hz, 2H), 6.87-6.76 (m, 2H), 6.27 (dd, J=16.8, 1.8 Hz, 1H), 5.80 (dd, J=10.6, 1.8 Hz, 1H), 4.43-4.35 (m, 1H), 3.79-3.75 (m, 8H), 2.07-1.96 (m, 2H), 1.89-1.78 (m, 2H), 1.63-1.34 (m, 6H). MS (ESI, method A): m/z=435.2 [M+H]$^+$, $t_R$=1.800 (min). HPLC: 98.2% (214 nm), 98.5% (254 nm).

Scheme 18

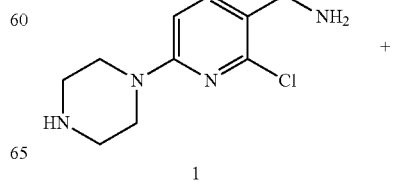

1-bromo-4-(cyclohexyloxy)benzene (3)

The mixture of 1-bromo-4-iodobenzene 1 (2.83 g, 10 mmol), cyclohexanol 2 (5.0 g, 50 mmol), CuI (0.381 g, 2.0 mmol), 1,10-phenanthroline (0.793 g, 4.0 mmol), Cs$_2$CO$_3$ (8.15 g, 25 mmol) and toluene (5 mL) was stirred at 120° C. in a sealed tube under N$_2$ for 16 h. After cooled to rt, the mixture was filtered over celite. The filtrate was dried over Na$_2$SO$_4$, concentrated in vacuo and purified by silica gel

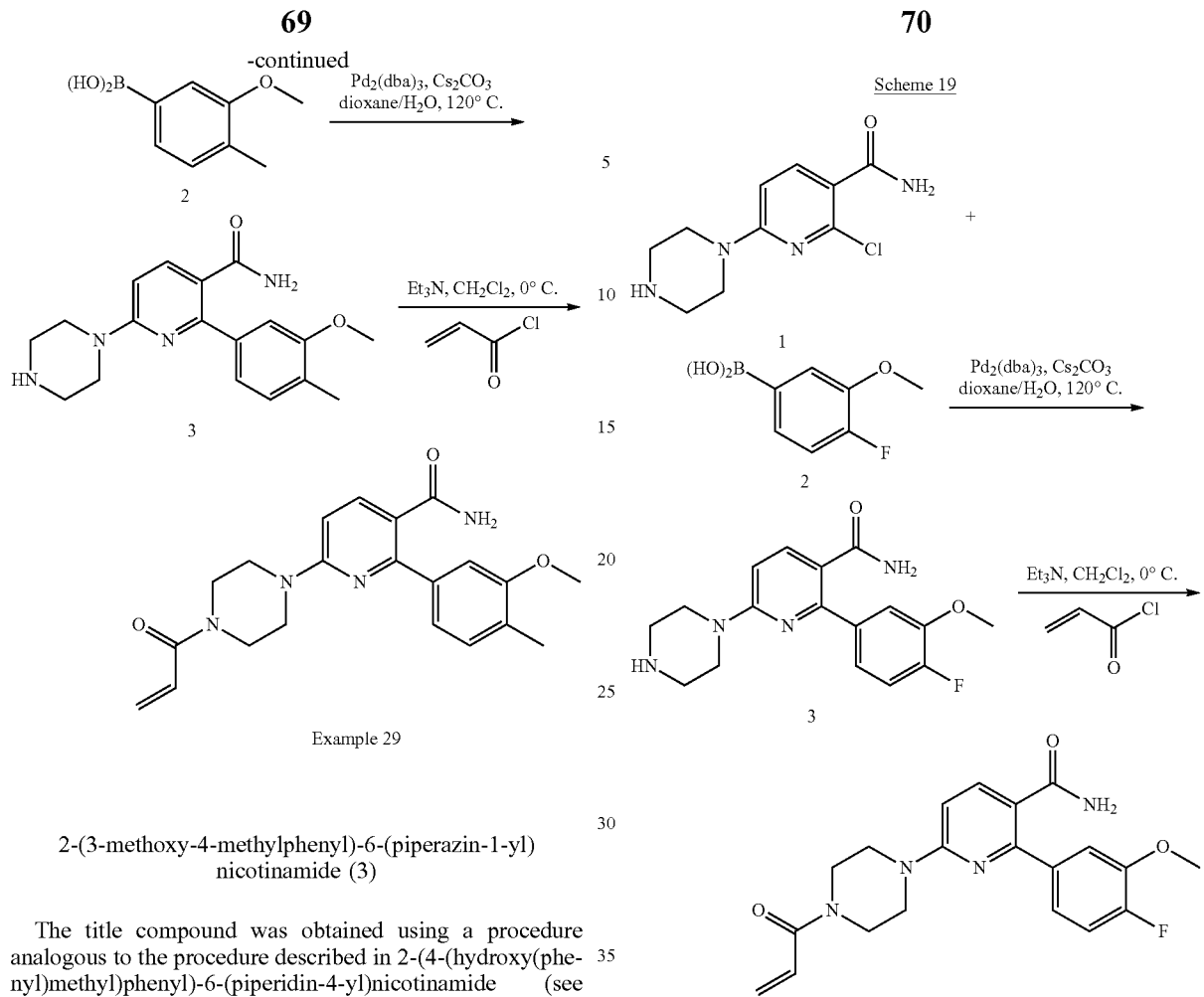

2-(3-methoxy-4-methylphenyl)-6-(piperazin-1-yl) nicotinamide (3)

The title compound was obtained using a procedure analogous to the procedure described in 2-(4-(hydroxy(phenyl)methyl)phenyl)-6-(piperidin-4-yl)nicotinamide (see Scheme 48) as brown solid (0.238 g, 58%). MS (ESI): m/z=327.1 [M+H]$^+$.

Example 29

6-(4-acryloylpiperazin-1-yl)-2-(3-methoxy-4-methylphenyl)nicotinamide

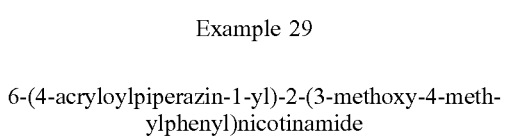

The title compound was obtained using a procedure analogous to the procedure described in Example 1 as white solid (115 mg, 43%). $^1$H NMR (400 MHz, CDCl$_3$) δ 7.77 (d, J=8.7 Hz, 1H), 7.23 (s, 1H), 7.21-7.15 (m, 2H), 6.88-6.78 (m, 2H), 6.26 (dd, J=16.8, 1.9 Hz, 1H), 5.80 (dd, J=10.6, 1.9 Hz, 1H), 3.88 (s, 3H), 3.75-3.78 (m, 8H), 2.24 (s, 3H). MS (ESI, method A): m/z=381.1 [M+H]$^+$, t$_R$=1.513 (min). HPLC: 95.9% (214 nm), 98.7% (254 nm).

2-(4-fluoro-3-methoxyphenyl)-6-(piperazin-1-yl) nicotinamide (3)

The title compound was obtained using a procedure analogous to the procedure described in 6-(3-nitrophenyl)-2-(4-phenoxyphenyl)nicotinamide (see Scheme 1) as brown gum (0.264 g, 72%). MS (ESI): m/z=331.1 [M+H]$^+$.

Example 30

6-(4-acryloylpiperazin-1-yl)-2-(4-fluoro-3-methoxyphenyl)nicotinamide

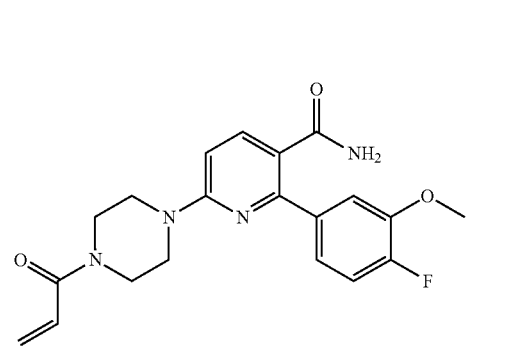 [SMILES: C=CC(=O)N1CCN(c2ccc(C(N)=O)c(-c3ccc(F)c(OC)c3)n2)CC1]

The title compound was obtained using a procedure analogous to the procedure described in Example 1 as white solid (45 mg, 15%). $^1$H NMR (400 MHz, CD$_3$OD) δ 7.78 (d, J=8.7 Hz, 1H), 7.41 (dd, J=8.3, 2.0 Hz, 1H), 7.28-7.22 (m, 1H), 7.16-7.12 (m, =1H), 6.88-6.77 (m, 2H), 6.27 (dd, J=16.8, 1.9 Hz, 1H), 5.80 (dd, J=10.6, 1.9 Hz, 1H), 3.93 (s, 3H), 3.87-3.71 (m, 8H). MS (ESI, method A): m/z=385.1 [M+H]$^+$, $t_R$=1.527 (min). HPLC: 99.6% (214 nm), 99.7% (254 nm).

Scheme 20

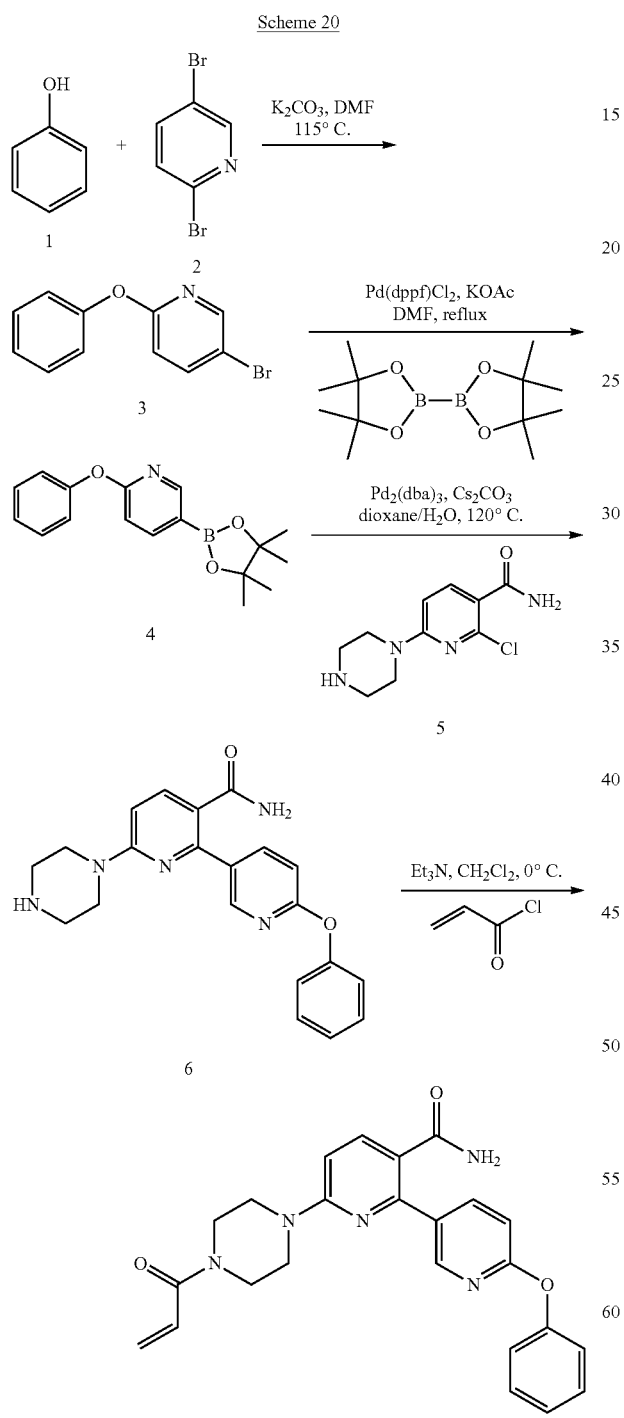

5-bromo-2-phenoxypyridine (3)

The title compound was obtained using a procedure analogous to the procedure described in 4-(4-bromophenoxy)benzonitrile (see Scheme 16) as yellow solid (3.85 g, 81%).

2-phenoxy-5-(4,4,5,5-tetramethyl-1,3,2-dioxaborolan-2-yl)pyridine (4)

The title compound was obtained using a procedure analogous to the procedure described in 4-(4-(4,4,5,5-tetramethyl-1,3,2-dioxaborolan-2-yl)phenoxy)benzonitrile (see Scheme 16) as yellow solid (0.536 g, 90%).

6'-phenoxy-6-(piperazin-1-yl)-2,3'-bipyridine-3-carboxamide (6)

The title compound was obtained using a procedure analogous to the procedure described in 6-(3-nitrophenyl)-2-(4-phenoxyphenyl)nicotinamide (see Scheme 1) as brown gum (0.14 g, 55%). MS (ESI): m/z=376.1 [M+H]$^+$.

Example 31

6-(4-acryloylpiperazin-1-yl)-6'-phenoxy-2,3'-bipyridine-3-carboxamide

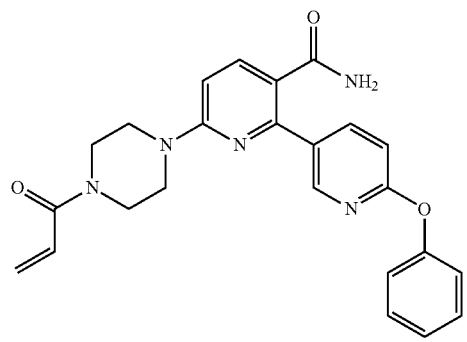 [SMILES: C=CC(=O)N1CCN(c2ccc(C(N)=O)c(-c3ccc(Oc4ccccc4)nc3)n2)CC1]

The title compound was obtained using a procedure analogous to the procedure described in Example 1 as white solid (50 mg, 31%). $^1$H NMR (400 MHz, CD$_3$OD) δ 8.43 (d, J=2.4 Hz, 1H), 8.10 (dd, J=8.6, 2.4 Hz, 1H), 7.80 (d, J=8.7 Hz, 1H), 7.49-7.41 (m, 2H), 7.29-7.22 (m, 1H), 7.16 (d, J=7.9 Hz, 2H), 6.97 (d, J=8.6 Hz, 1H), 6.88-6.77 (m, 2H), 6.27 (dd, J=16.8, 1.8 Hz, 1H), 5.80 (dd, J=10.6, 1.8 Hz, 1H), 3.87-3.69 (m, 8H). MS (ESI, method A): m/z=430.1 [M+H]$^+$, $t_R$=1.620 (min). HPLC: 95.1% (214 nm), 96.2% (254 nm).

Scheme 21

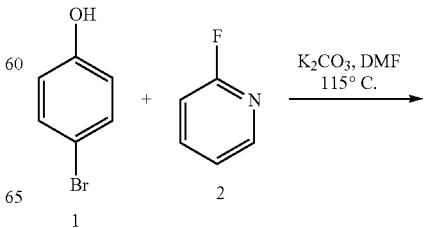

-continued

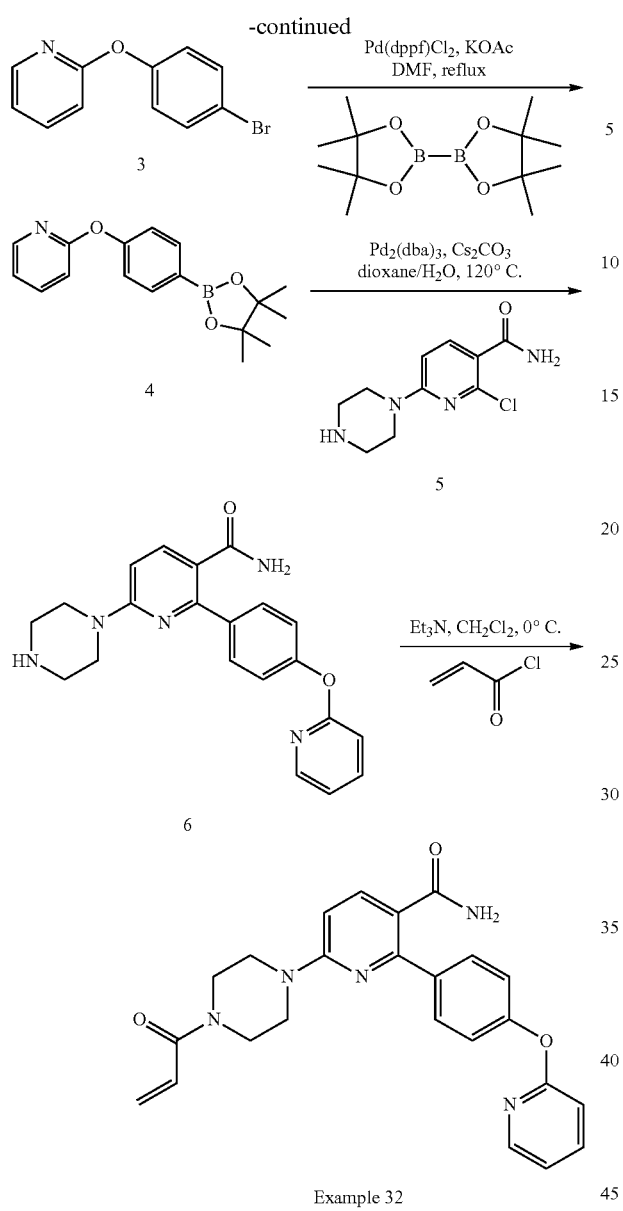

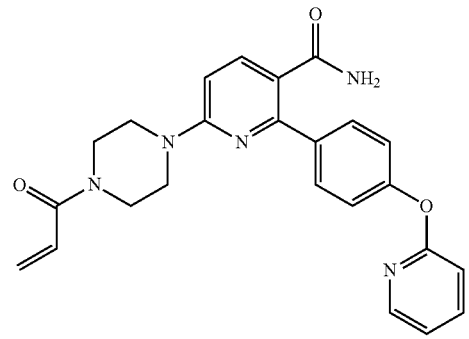 [SMILES: C=CC(=O)N1CCN(c2ccc(C(N)=O)c(-c3ccc(Oc4ccccn4)cc3)n2)CC1]

nyl)methyl)phenyl)-6-(piperidin-4-yl)nicotinamide (see Scheme 48) as brown gum (0.198 g, 53%). MS (ESI): m/z=376.0 [M+H]⁺.

Example 32

6-(4-acryloylpiperazin-1-yl)-2-(4-(pyridin-2-yloxy)phenyl)nicotinamide

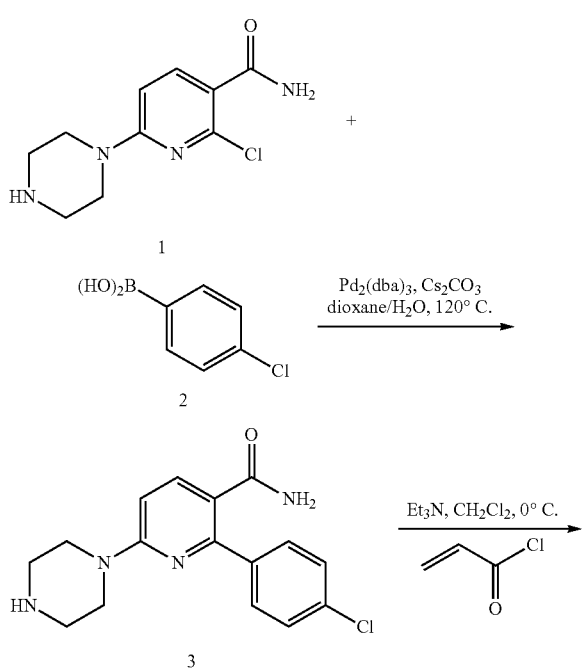

The title compound was obtained using a procedure analogous to the procedure described in Example 1 as white solid (41 mg, 18%). $^1$H NMR (400 MHz, CD$_3$OD) δ 8.18 (dd, J=5.0, 1.4 Hz, 1H), 7.86 (ddd, J=8.4, 7.3, 2.0 Hz, 1H), 7.82-7.74 (m, 3H), 7.20-7.14 (m, 3H), 7.01 (d, J=8.3 Hz, 1H), 6.88-6.79 (m, 2H), 6.27 (dd, J=16.8, 1.9 Hz, 1H), 5.80 (dd, J=10.6, 1.9 Hz, 1H), 3.86-3.71 (m, 8H). MS (ESI, method A): m/z=430.1 [M+H]⁺, $t_R$=1.560 (min). HPLC: 100% (214 nm), 100% (254 nm).

Scheme 22

2-(4-bromophenoxy)pyridine (3)

The title compound was obtained using a procedure analogous to the procedure described in 4-(4-bromophenoxy)benzonitrile (see Scheme 16) as yellow solid (2.83 g, 57%). MS (ESI): m/z=250.1 [M+H]⁺.

2-(4-(4,4,5,5-tetramethyl-1,3,2-dioxaborolan-2-yl)phenoxy)pyridine (4)

The title compound was obtained using a procedure analogous to the procedure described in 4-(4-(4,4,5,5-tetramethyl-1,3,2-dioxaborolan-2-yl)phenoxy)benzonitrile (see Scheme 16) as brown solid (0.882 g, 74%). MS (ESI): m/z=298.1 [M+H]⁺.

6-(piperazin-1-yl)-2-(4-(pyridin-2-yloxy)phenyl)nicotinamide (6)

The title compound was obtained using a procedure analogous to the procedure described in 2-(4-(hydroxy(phe-

75

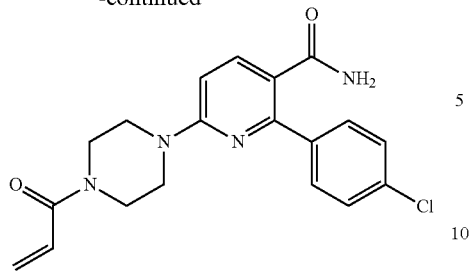

Example 33

2-(4-chlorophenyl)-6-(piperazin-1-yl)nicotinamide
(3)

The title compound was obtained using a procedure analogous to the procedure described in 2-(4-(hydroxy(phenyl)methyl)phenyl)-6-(piperidin-4-yl)nicotinamide (see Scheme 48) as brown gum (0.23 g, 72%).

Example 33

6-(4-acryloylpiperazin-1-yl)-2-(4-chlorophenyl)nicotinamide

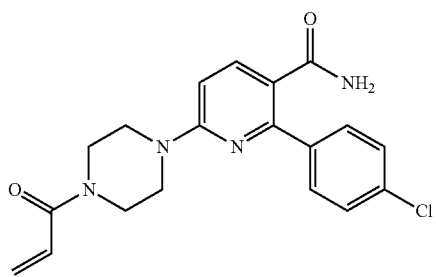 [SMILES: C=CC(=O)N1CCN(c2ccc(C(N)=O)c(-c3ccc(Cl)cc3)n2)CC1]

The title compound was obtained using a procedure analogous to the procedure described in Example 1 as white solid (50 mg, 18%). $^1$H NMR (400 MHz, CD$_3$OD) δ 7.78 (d, J=8.7 Hz, 1H), 7.72-7.64 (m, 2H), 7.45-7.39 (m, 2H), 6.88-6.76 (m, 2H), 6.27 (dd, J=16.8, 1.9 Hz, 1H), 5.80 (dd, J=10.6, 1.9 Hz, 1H), 3.87-3.69 (m, 8H). MS (ESI, method A): m/z=371.0 [M+H]$^+$, $t_R$=1.645 (min). HPLC: 95.1% (214 nm), 95.3% (254 nm).

Scheme 23

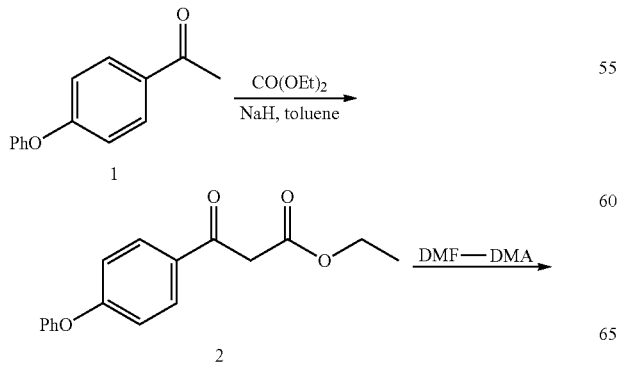

76

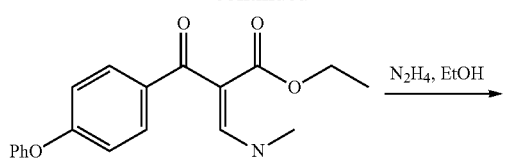

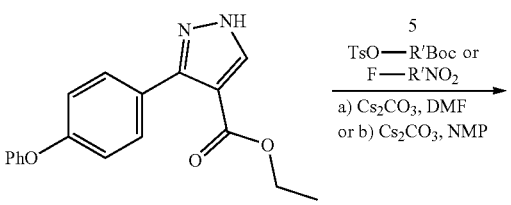

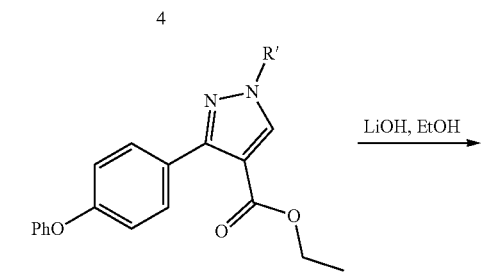

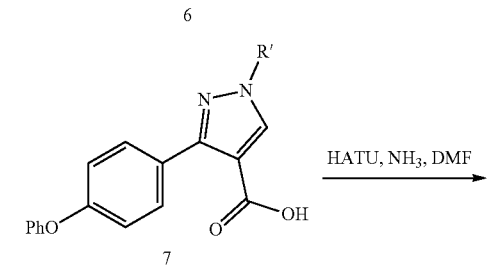

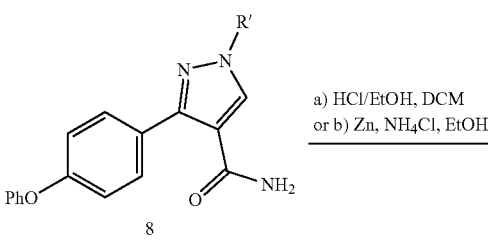

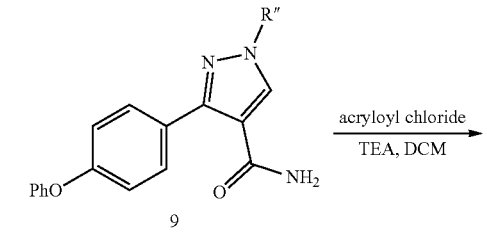

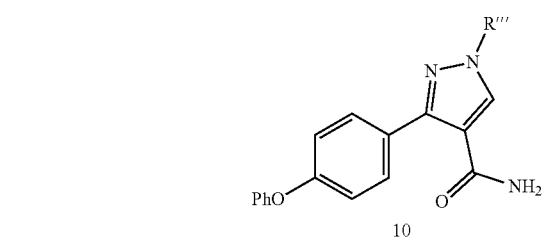

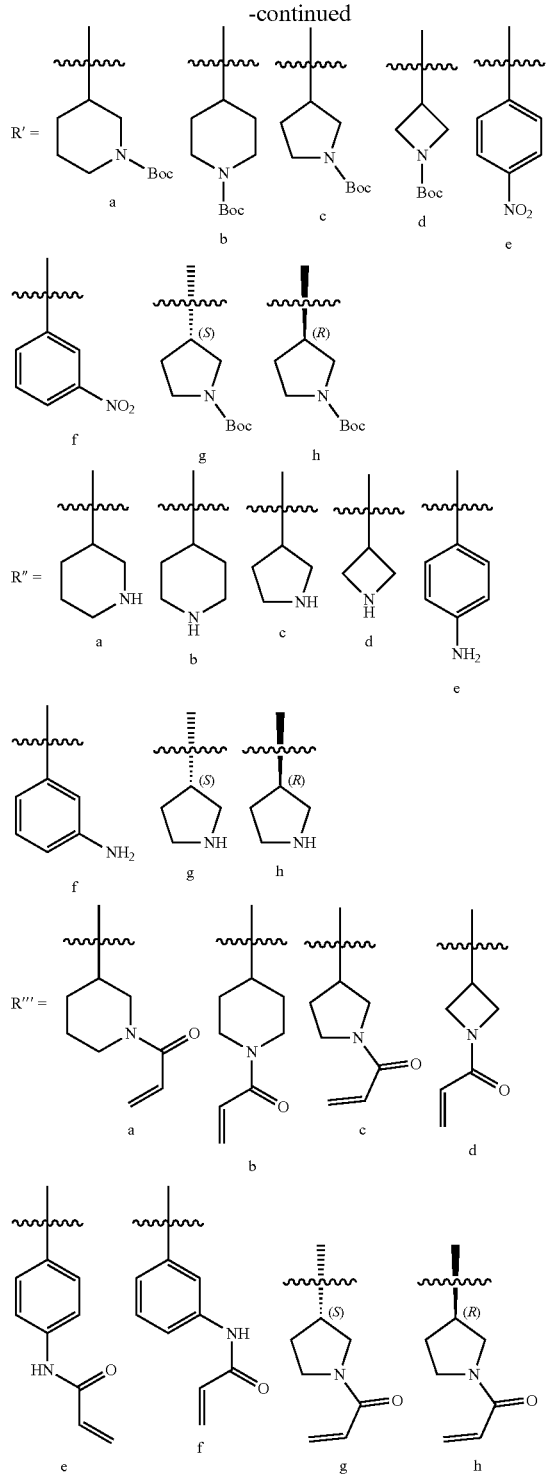

Ethyl 3-oxo-3-(4-phenoxyphenyl)propanoate (2)

To a solution of diethyl carbonate (14 g, 120 mmol) in toluene (100 mL) was added NaH (60%, 4.7 g, 12 mmol) at 0° C., and the resulting solution was heated to 90° C., then a solution of 1-(4-phenoxyphenyl)ethanone 1 (10 g, 47 mmol) in toluene (50 mL) was added drop-wise over 30 min, and the solution was refluxed for 20 min. After cooling to room temperature, AcOH/H$_2$O (55 mL/275 mL) was added. Toluene was removed under vacuum, and the crude residue was diluted with water (500 mL). Then the mixture was extracted with dichloromethane (4×800 mL). The organic layers were combined, dried over anhydrous sodium sulfate, filtered and concentrated. The residue was purified by silica gel column chromatography eluting with 9:1 PE/EA to get the title compound as brown oil (11.5 g, 79%). MS (ESI): m/z=285.0 [M+H]$^+$.

Ethyl 3-(dimethylamino)-2-(4-phenoxybenzoyl)acrylate (3)

A solution of ethyl 3-oxo-3-(4-phenoxyphenyl)propanoate 2 (9.6 g, 34 mmol) in DMA-DMF (100 mL) was stirred at 100° C. for 1 h. The resulting solution was concentrated in high vacuum to get the title compound (12 g, 100%) as brown thick oil. MS (ESI): m/z=340.1 [M+H]$^+$.

Ethyl 3-(4-phenoxyphenyl)-1H-pyrazole-4-carboxylate (4)

To a solution of ethyl 3-(dimethylamino)-2-(4-phenoxybenzoyl)acrylate 3 (6 g, 17 mmol) in ethanol (30 mL) was added hydrazine hydrate (875 mg, 17 mmol), and the resulting solution was heated to 85° C. and stirred for 3 h. The solvent was evaporated and the crude residue was purified by silica gel column chromatography eluting with 4:1 PE/EA to get the title compound as brown oil (4.3 g, 78%). MS (ESI): m/z=309.0 [M+H]$^+$.

Ethyl-1-(1-(tert-butoxycarbonyl)pyrrolidin-3-yl)-3-(4-phenoxyphenyl)-1H-pyrazole-4-carboxylate (6c)

Cs$_2$CO$_3$ (1.08 g, 3.3 mmol) was added to a solution of ethyl 3-(4-phenoxyphenyl)-1H-pyrazole-4-carboxylate 4 (500 mg, 1.6 mmol) and tert-butyl 3-(tosyloxy)pyrrolidine-1-carboxylate 5c (1.1 g, 3.2 mmol) in DMF (20 mL) and the resulting mixture was stirred at 100° C. for 16 h. The reaction mixture was concentrated in high vacuum and the crude residue was purified by silica gel column chromatography eluting with 20:1 DCM/EA to get the title compound (780 mg, 100%) as colorless thick oil. MS (ESI): m/z=478.1 [M+H]$^+$.

Similar procedures were used to prepare the following compounds: 6a, 6b, 6d, 6g, 6h.

tert-butyl-3-(4-(ethoxycarbonyl)-3-(4-phenoxyphenyl)-1H-pyrazol-1-yl)piperidine-1-carboxylate (6a), thick colorless oil, 340 mg, 36%. MS (ESI): m/z=492.1 [M+H]$^+$.

tert-butyl-4-(4-(ethoxycarbonyl)-3-(4-phenoxyphenyl)-1H-pyrazol-1-yl)piperidine-1-carboxylate (6b), thick oil, 557 mg, 71%. MS (ESI): m/z=492.1 [M+H]$^+$.

Ethyl-1-(1-(tert-butoxycarbonyl)azetidin-3-yl)-3-(4-phenoxyphenyl)-1H-pyrazole-4-carboxylate (6d), white solid, 1.7 g, 61%. MS (ESI): m/z=464.1 [M+H]$^+$.

(S)-ethyl-1-(1-(tert-butoxycarbonyl)pyrrolidin-3-yl)-3-(4-phenoxyphenyl)-1H-pyrazole-4-carboxylate (6g), colorless oil, 1.5 g, 99%. MS (ESI): m/z=478.1 [M+H]$^+$.

(R)-ethyl-1-(1-(tert-butoxycarbonyl)pyrrolidin-3-yl)-3-(4-phenoxyphenyl)-1H-pyrazole-4-carboxylate (6h), yellow oil, 2 g, 100%. MS (ESI): m/z=478.1 [M+H]$^+$.

Ethyl 1-(4-nitrophenyl)-3-(4-phenoxyphenyl)-1H-pyrazole-4-carboxylate (6e)

To a solution of ethyl 3-(4-phenoxyphenyl)-1H-pyrazole-4-carboxylate 4 (300 mg, 1.0 mmol) and 1-fluoro-4-nitrobenzene 5e (140 mg, 1.0 mmol) in 1-methyl-2-pyrrolidone (8 mL) was added cesium carbonate (950 mg, 3.0 mmol), and the resulting solution was heated to 130° C. and stirred for 3 h. After cooling to ambient temperature, the solvent was evaporated and the crude residue was purified by silica gel column chromatography eluting with 4:1 PE/EA to get the title compound as a yellow solid (290 mg, 68%). MS (ESI): m/z=430.1 [M+H]$^+$.

Similar procedures were used to prepare compound of 6f:
ethyl 1-(3-nitrophenyl)-3-(4-phenoxyphenyl)-1H-pyrazole-4-carboxylate (6f), yellow solid, 290 mg, 40%. MS (ESI): m/z=430.1 [M+H]$^+$.

1-(1-(tert-butoxycarbonyl)pyrrolidin-3-yl)-3-(4-phenoxyphenyl)-1H-pyrazole-4-carboxylic acid (7c)

To a solution of ethyl 1-(1-(tert-butoxycarbonyl)pyrrolidin-3-yl)-3-(4-phenoxyphenyl)-1H-pyrazole-4-carboxylate 6c (390 mg, 0.8 mmol) in EtOH (8 mL) was added 1N LiOH/H$_2$O (4 mL). the reaction mixture was stirred at 75° C. for 1 h. Then to the solution was added 1N HCl/H$_2$O to pH=4-5, concentrated to give title compound (690 mg, crude) as white solid contented LiCl salt. MS (ESI): m/z=450.1 [M+H]$^+$.

Similar procedures were used to prepare the following compounds: 7a, 7b, 7d, 7e, 7f, 7g, 7h.
1-(1-(tert-butoxycarbonyl)piperidin-3-yl)-3-(4-phenoxyphenyl)-1H-pyrazole-4-carboxylic acid (7a), white solid, 310 mg, 100%. MS (ESI): m/z=464.1 [M+H]$^+$.
1-(1-(tert-butoxycarbonyl)piperidin-4-yl)-3-(4-phenoxyphenyl)-1H-pyrazole-4-carboxylic acid (7b), yellow solid, 525 mg, 99%. MS (ESI): m/z=464.1 [M+H]$^+$.
1-(1-(tert-butoxycarbonyl)azetidin-3-yl)-3-(4-phenoxyphenyl)-1H-pyrazole-4-carboxylic acid (7d), yellow solid, 300 mg, 80%. MS (ESI): m/z=436.1 [M+H]$^+$.
1-(4-nitrophenyl)-3-(4-phenoxyphenyl)-1H-pyrazole-4-carboxylic acid (7e), white solid, 280 mg, 99%. MS (ESI): m/z=402.1 [M+H]$^+$.
1-(3-nitrophenyl)-3-(4-pheonxyphenyl)-1H-pyrazole-4-carboxylic acid (7f), yellow oil, 260 mg, 100%. MS (ESI): m/z=402.1 [M+H]$^+$.
(S)-1-(1-(tert-butoxycarbonyl)pyrrolidin-3-yl)-3-(4-phenoxyphenyl)-1H-pyrazole-4-carboxylic acid (7g), yellow foam, 1.2 g, 99%. MS (ESI): m/z=450.1 [M+H]$^+$.
(R)-1-(1-(tert-butoxycarbonyl)pyrrolidin-3-yl)-3-(4-phenoxyphenyl)-1H-pyrazole-4-carboxylic acid (7h), yellow oil, 1.2 g, 99%. MS (ESI): m/z=450.1 [M+H]$^+$.

Tert-butyl-3-(4-carbamoyl-3-(4-phenoxyphenyl)-1H-pyrazol-1-yl)pyrrolidine-1-carboxylate (8c)

To a solution of 1-(1-(tert-butoxycarbonyl)pyrrolidin-3-yl)-3-(4-phenoxyphenyl)-1H-pyrazole-4-carboxylic acid 7c (630 mg, crude, 0.67 mmol) in DMF (20 mL) was added HATU (510 mg, 1.33 mmol) and stirred at rt for 30 minutes, the resulting solution was bubbled with NH$_3$ gas for 10 minutes. After stirring at rt for 1 h, the solution was concentrated in high vacuum and the crude residue was diluted with DCM (50 mL), washed with water (3×20 mL), dried over Na$_2$SO$_4$, concentrated to give a residue which was purified by silica gel column chromatography eluting with 100:1 DCM/MeOH to get the title compound (120 mg, 33%) as colorless foam. MS (ESI): m/z=471.2 [M+Na]$^+$.

Similar procedures were used to prepare the following compounds: 8a, 8b, 8d, 8e, 8f, 8g, 8h tert-butyl-3-(4-carbamoyl-3-(4-phenoxyphenyl)-1H-pyrazol-1-yl)piperidine-1-carboxylate (8a), colorless oil, 310 mg, 100%. MS (ESI): m/z=463.1 [M+H]$^+$.
tert-butyl-4-(4-carbamoyl-3-(4-phenoxyphenyl)-1H-pyrazol-1-yl)piperidine-1-carboxylate (8b), yellow solid, 320 mg, 63%. MS (ESI): m/z=463.1 [M+H]$^+$.
tert-butyl-3-(4-carbamoyl-3-(4-phenoxyphenyl)-1H-pyrazol-1-yl)azetidine-1-carboxylate (8d), yellow solid, 300 mg, 99%. MS (ESI): m/z=435.1 [M+H]$^+$.
1-(4-nitrophenyl)-3-(4-phenoxyphenyl)-1H-pyrazole-4-carboxamide (8e), yellow solid, 230 mg, 99%. MS (ESI): m/z=401.1 [M+H]$^+$.
1-(3-nitrophenyl)-3-(4-phenoxyphenyl)-1H-pyrazole-4-carboxamide (8f), yellow solid, 260 mg, 100%. MS (ESI): m/z=401.0 [M+H]$^+$.
(S)-tert-butyl-3-(4-carbamoyl-3-(4-phenoxyphenyl)-1H-pyrazol-1-yl)pyrrolidine-1-carboxylate (8g), white solid, 1.2 g, 100%. MS (ESI): m/z=449.0 [M+H]$^+$.
(R)-tert-butyl-3-(4-carbamoyl-3-(4-phenoxyphenyl)-1H-pyrazol-1-yl)pyrrolidine-1-carboxylate (8h), white solid, 960 mg, 80%. MS (ESI): m/z=449.0 [M+H]$^+$.

3-(4-phenoxyphenyl)-1-(pyrrolidin-3-yl)-1H-pyrazole-4-carboxamide

To a solution of tert-butyl 3-(4-carbamoyl-3-(4-phenoxyphenyl)-1H-pyrazol-1-yl)pyrrolidine-1-carboxylate 8c (120 mg, 0.27 mmol) in DCM (10 mL) was added 6 N HCl/EtOH (5 mL, 30 mmol), stirred at rt for 1 h, the resulting solution was concentrated in high vacuum and the crude residue was purified by Prep-HPLC to give title compound (86 mg, 91%) as white solid. $^1$H NMR (400 MHz, CD$_3$OD): δ 8.20 (s, 1H), 7.75 (d, J=8.6 Hz, 2H), 7.43-7.36 (m, 2H), 7.20-7.13 (m, 1H), 7.08-7.00 (m, 4H), 5.32-5.27 (m, 1H), 3.87-3.72 (m, 3H), 3.59-3.50 (m, 1H), 2.67-2.56 (m, 1H), 2.52-2.43 (m, 1H). MS (ESI, Method A): m/z=349.1 [M+H]$^+$, t$_R$=1.242 min. HPLC: 99.3% (214 nm), 99.5% (254 nm).

Similar procedures were used to prepare the following compounds: 9a, 9b, 9d, 9g, 9e, and 9f.
3-(4-phenoxyphenyl)-1-(piperidin-3-yl)-1H-pyrazole-4-carboxamide (9a), white solid, 240 mg, 99%. $^1$H NMR (400 MHz, CD$_3$OD): δ 8.23 (s, 1H), 7.73 (d, J=8.6 Hz, 2H), 7.48-7.31 (m, 2H), 7.21-7.12 (m, 1H), 7.12-6.97 (m, 4H), 4.76-4.65 (m, 1H), 3.74-3.57 (m, 2H), 3.43-3.36 (m, 1H), 3.28-3.15 (m, 1H), 2.39-2.02 (m, 3H), 2.01-1.84 (m, 1H). MS (ESI, Method A): m/z=363.2 [M+H]$^+$, t$_R$=1.255 min. HPLC: 100% (214 nm), 100% (254 nm).
3-(4-phenoxyphenyl)-1-(piperidin-4-yl)-1H-pyrazole-4-carboxamide (9b), light yellow solid, 3.1 mg, 40%. $^1$H NMR (300 MHz, CD$_3$OD): δ 8.18 (s, 1H), 7.67 (d, J=8.7 Hz, 2H), 7.43-7.31 (m, 2H), 7.19-7.09 (m, 1H), 7.07-6.95 (m, 4H), 4.65-4.55 (m, 1H), 3.64-3.54 (m, 2H), 3.29-3.17 (m, 2H), 2.42-2.23 (m, 4H). MS (ESI, Method A): m/z=363.0 [M+H]$^+$, t$_R$=1.288 min. HPLC: 100% (214 nm), 100% (254 nm).
1-(azetidin-3-yl)-3-(4-phenoxyphenyl)-1H-pyrazole-4-carboxamide (Example 14) (9d), yellow solid, 300 mg, 100%. $^1$H NMR (300 MHz, CD$_3$OD): δ 8.20-8.14 (m, 1H), 7.82-7.66 (m, 2H), 7.44-7.30 (m, 2H), 7.18-7.11 (m, 1H), 7.07-6.96 (m, 4H), 5.52-5.40 (m, 1H), 4.64-4.55 (m, 4H). MS (ESI, Method A): m/z=335.1 [M+H]$^+$, t$_R$=1.235-1.255 min. HPLC: 100% (214 nm), 100% (254 nm).
(S)-3-(4-phenoxyphenyl)-1-(pyrrolidin-3-yl)-1H-pyrazole-4-carboxamide (9g), white solid, 90 mg, 83%. $^1$H NMR (400 MHz, CD$_3$OD): δ 8.25 (s, 1H), 7.80-7.68 (m, 2H), 7.45-7.33 (m, 2H), 7.20-7.11 (m, 1H), 7.11-6.98 (m, 4H), 5.38-5.25 (m, 1H), 3.88-3.69 (m, 3H), 3.62-3.49 (m, 1H), 2.68-2.54 (m, 1H), 2.54-2.40 (m, 1H). MS (ESI, Method A): m/z=349.1 [M+H]$^+$, t$_R$=1.219 min. HPLC: 100% (214 nm), 100% (254 nm).

(R)-3-(4-phenoxyphenyl)-1-(pyrrolidin-3-yl)-1H-pyrazole-4-carboxamide (9h), yellow oil, 100 mg, 100%. MS (ESI, Method A): m/z=349.1 [M+H]$^+$.

1-(4-aminophenyl)-3-(4-phenoxyphenyl)-1H-pyrazole-4-carboxamide (9e)

To a solution of 1-(4-nitrophenyl)-3-(4-phenoxyphenyl)-1H-pyrazole-4-carboxamide 8e (200 mg, 0.50 mmol) in ethanol (8 mL) was added saturated aqueous NH$_4$Cl (4 mL), followed by the addition of zinc powder (260 mg, 4.0 mmol) in portion over 5 min, then the resulting solution was stirred for 10 h at ambient temperature. The mixture was filtered and the filtrate was diluted with ethyl acetate (30 mL), and washed with water (2×20 mL) and brine (2×20 mL). The organic layer was dried over anhydrous sodium sulfate, filtered and concentrated to give the title compound as a yellow solid (150 mg, 81%). $^1$H NMR (400 MHz, CD$_3$OD): δ 8.47 (s, 1H), 7.78 (d, J=8.7 Hz, 2H), 7.51 (d, J=8.7 Hz, 2H), 7.44-7.36 (m, 2H), 7.16 (s, 1H), 7.19-7.13 (m, 4H), 6.83 (d, J=8.7 Hz, 2H). MS (ESI, Method A): m/z=371.1 [M+H]$^+$, t$_R$=1.468 min. HPLC: 97.8% (214 nm), 98.0% (254 nm).

Similar procedures were used to prepare compound 8f.

1-(3-aminophenyl)-3-(4-phenoxyphenyl)-1H-pyrazole-4-carboxamide (8f), white solid, 105 mg, 47%. $^1$H NMR (400 MHz, CD$_3$OD): δ 8.60 (s, 1H), 7.81 (d, J=8.6 Hz, 2H), 7.44-7.36 (m, 2H), 7.28-7.03 (m, 8H), 6.75 (d, J=7.9 Hz, 1H). MS (ESI, Method A): m/z=371.1 [M+H]$^+$, t$_R$=1.507 min. HPLC: 96.9% (214 nm), 98.2% (254 nm).

1-(1-acryloylpyrrolidin-3-yl)-3-(4-phenoxyphenyl)-1H-pyrazole-4-carboxamide (Example 13) (10c)

To a solution of 3-(4-phenoxyphenyl)-1-(pyrrolidin-3-yl)-1H-pyrazole-4-carboxamide 9c (43 mg, 0.12 mmol) and TEA (50 mg, 0.5 mmol) in DCM (10 mL) was added acryloyl chloride (22 mg, 0.24 mmol) and stirred at 75° C. for 1 h, the resulting was concentrated and purified by Prep-TLC eluting with 10:1 DCM/MeOH to get the title compound (17 mg, 35%) as white solid. $^1$H NMR (400 MHz, CD$_3$OD): δ 8.18 (d, J=8.7 Hz, 1H), 7.70 (d, J=8.6 Hz, 2H), 7.43-7.34 (m, 2H), 7.18-7.08 (m, 1H), 7.03 (dd, J=15.5, 8.3 Hz, 4H), 6.72-6.58 (m, 1H), 6.32 (dd, J=15.9, 4.0 Hz, 1H), 5.83-5.73 (m, 1H), 5.18-5.04 (m, 1H), 4.21-3.65 (m, 4H), 2.63-2.45 (m, 2H). MS (ESI, Method A): m/z=403.1 [M+H]$^+$, t$_R$=1.414 min. HPLC: 95.3% (214 nm), 95.3% (254 nm).

Similar procedures were used to prepare the following compounds: 10a, 10b, 10d, 10e, 10f, 10g and 10h.

1-(1-acryloylpiperidin-3-yl)-3-(4-phenoxyphenyl)-1H-pyrazole-4-carboxamide (Example 11) (10a). White solid, 39 mg, 23%. $^1$H NMR (400 MHz, CD$_3$OD) δ 8.20 (d, J=5.4 Hz, 1H), 7.71 (d, J=8.3 Hz, 2H), 7.44-7.35 (m, 2H), 7.19-7.12 (m, 1H), 7.04 (dd, J=12.3, 8.4 Hz, 4H), 6.89-6.73 (m, 1H), 6.3-6.12 (m, 1H), 5.76 (dd, J=25.5, 10.7 Hz, 1H), 4.71 (d, J=11.5 Hz, 0.5H), 4.45-4.17 (m, 2H), 4.08 (d, J=14.3 Hz, 0.5H), 3.85-3.73 (m, 0.5H), 3.45-3.34 (m, 1H), 3.27-3.14 (m, 0.5H), 2.39-2.18 (m, 2H), 2.06-1.92 (m, 1H), 1.71-1.61 (m, 1H). MS (ESI, Method A): m/z=417.2 [M+H]$^+$, t$_R$=1.468 min. HPLC: 97.7% (214 nm), 98.7% (254 nm).

1-(1-acryloylpiperidin-4-yl)-3-(4-phenoxyphenyl)-1H-pyrazole-4-carboxamide (Example 12) (10b). White solid, 4.7 mg, 20.8%. $^1$H NMR (400 MHz, CD$_3$OD) δ 8.19 (s, 1H), 7.69 (d, J=8.5 Hz, 2H), 7.45-7.33 (m, 2H), 7.25-7.12 (m, 1H), 7.04 (dd, J=12.2, 8.5 Hz, 4H), 6.84 (dd, J=16.8, 10.7 Hz, 1H), 6.24 (dd, J=16.8, 1.5 Hz, 1H), 5.79 (dd, J=10.7, 1.5 Hz, 1H), 4.77-4.64 (m, 1H), 4.61-4.46 (m, 1H), 4.35-4.23 (m, 1H), 3.38 (d, J=13.0 Hz, 1H), 3.03-2.92 (m, 1H), 2.34-2.17 (m, 2H), 2.12-1.96 (m, 2H). MS (ESI, Method A): m/z=417.1 [M+H]$^+$, t$_R$=1.421 min. HPLC: 97.5% (214 nm), 97.8% (254 nm).

1-(1-acryloylazetidin-3-yl)-3-(4-phenoxyphenyl)-1H-pyrazole-4-carboxamide (10d). White solid, 19 mg, 18%. $^1$H NMR (300 MHz, CD$_3$OD) δ 8.21 (s, 1H), 7.71 (d, J=9.1 Hz, 2H), 7.42-7.31 (m, 2H), 7.20-7.09 (m, 1H), 7.06-6.94 (m, 4H), 6.46-6.22 (m, 2H), 5.78 (dd, J=9.9, 2.3 Hz, 1H), 5.33 (td, J=8.0, 4.0 Hz, 1H), 4.83-4.65 (m, 2H), 4.62-4.41 (m, 2H). MS (ESI, Method A): m/z=389.1 [M+H]$^+$, t$_R$=1.388-1.401 min. HPLC: 95.1% (214 nm), 96.1% (254 nm).

1-(4-acrylamidophenyl)-3-(4-phenoxyphenyl)-1H-pyrazole-4-carboxamide (Example 16) (10e). White solid, 52 mg, 46%. $^1$H NMR (400 MHz, CD$_3$OD) δ 8.67 (s, 1H), 7.89-7.78 (m, 6H), 7.44-7.36 (m, 2H), 7.20-7.12 (m, 1H), 7.11-7.02 (m, 4H), 6.52-6.37 (m, 2H), 5.82 (dd, J=9.4, 2.4 Hz, 1H). MS (ESI, Method A): m/z=425.2 [M+H]$^+$, t$_R$=1.521 min. HPLC: 97.3% (214 nm), 97.0% (254 nm).

1-(3-acrylamidophenyl)-3-(4-phenoxyphenyl)-1H-pyrazole-4-carboxamide (Example 18) (10f). White solid, 24 mg, 24%. $^1$H NMR (400 MHz, CD$_3$OD) δ 8.70 (s, 1H), 8.35 (s, 1H), 7.84 (d, J=8.7 Hz, 2H), 7.60 (d, J=8.1 Hz, 2H), 7.54-7.48 (m, 1H), 7.44-7.36 (m, 2H), 7.11-7.03 (m, 1H), 7.20-7.13 (m, 4H), 6.53-6.38 (m, 2H), 5.83 (dd, J=9.2, 2.6 Hz, 1H). MS (ESI, Method A): m/z=425.1 [M+H]$^+$, t$_R$=1.547 (min). HPLC: 97.6% (214 nm), 98.6% (254 nm).

(S)-1-(1-acryloylpyrrolidin-3-yl)-3-(4-phenoxyphenyl)-1H-pyrazole-4-carboxamide (Example 20) (10g). Gray solid, 120 mg, 27%. $^1$H NMR (400 MHz, CD$_3$OD): δ 8.21 (d, J=6.6 Hz, 1H), 7.73-7.64 (m, 2H), 7.43-7.34 (m, 2H), 7.20-7.10 (m, 1H), 7.10-6.96 (m, 4H), 6.75-6.55 (m, 1H), 6.32 (ddd, J=16.8, 4.8, 1.9 Hz, 1H), 5.86-5.72 (m, 1H), 5.21-5.03 (m, 1H), 4.22-4.07 (m, 1H), 4.05-3.67 (m, 3H), 2.64-2.43 (m, 2H). MS (ESI, Method A): m/z=403.2 [M+H]$^+$, t$_R$=1.421 min. HPLC: 99.0% (214 nm), 99.0% (254 nm).

(R)-1-(1-acryloylpyrrolidin-3-yl)-3-(4-phenoxyphenyl)-1H-pyrazole-4-carboxamide (Example 19) (10h). White solid, 20 mg, 6%. $^1$H NMR (300 MHz, CD$_3$OD): δ 8.16 (d, J=5.9 Hz, 1H), 7.67 (d, J=8.7 Hz, 2H), 7.42-7.30 (m, 2H), 7.17-6.92 (m, 5H), 6.71-6.56 (m, 1H), 6.34-6.25 (m, 1H), 5.80-5.72 (m, 1H), 5.18-5.02 (m, 1H), 4.20-4.05 (m, 1H), 4.02-3.65 (m, 3H), 2.62-2.45 (m, 2H). MS (ESI, Method A): m/z=403.1 [M+H]$^+$, t$_R$=1.409 min. HPLC: 95.0% (214 nm), 97.0% (254 nm).

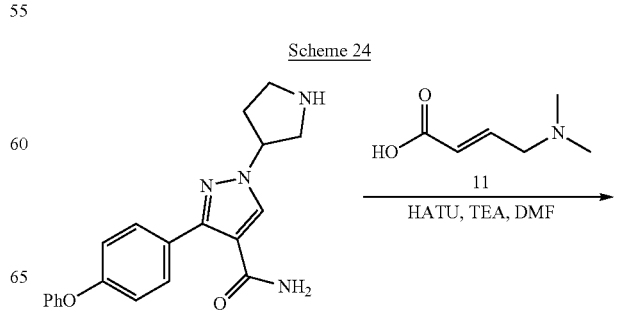

Scheme 24

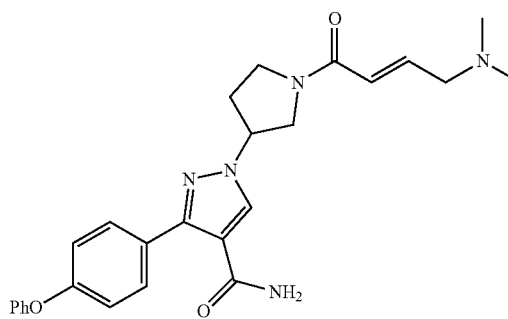

Example 34

Example 34

1-(1-(4-(dimethylamino)but-2-enoyl)pyrrolidin-3-yl)-3-(4-phenoxyphenyl)-1H-pyrazole-4-carboxamide

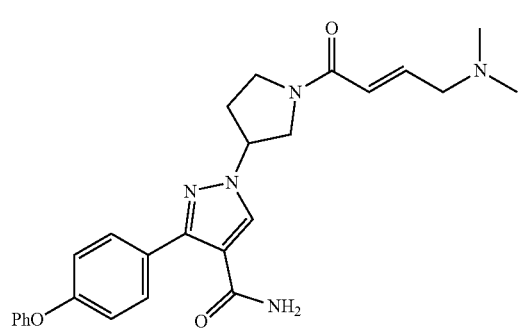 [SMILES: CN(C)C/C=C/C(=O)N1CCC(n2cc(C(N)=O)c(-c3ccc(Oc4ccccc4)cc3)n2)C1]

To a solution of 4-(dimethylamino)but-2-enoic acid 11 (22 mg, 0.17 mmol) and HATU (98 mg, 0.26 mmol) in DMF (10 mL) was added 3-(4-phenoxyphenyl)-1-(pyrrolidin-3-yl)-1H-pyrazole-4-carboxamide 9c (Scheme 23) (60 mg, 0.17 mmol) and DIPEA (22 mg, 0.5 mmol). The reaction mixture was stirred at rt for 1 h. The solution was concentrated in high vacuum and the residue was diluted in DCM (10 mL), washed with water (3×10 mL), dried over $Na_2SO_4$, concentrated to give a residue which was purified by Prep-TLC eluting with 10:1 DCM/MeOH to get the title compound (26 mg, 37%) as brown solid. $^1$H NMR (300 MHz, $CD_3OD$): δ 8.20 (d, J=9.0 Hz, 1H), 7.73-7.56 (m, 2H), 7.41-7.27 (m, 2H), 7.11 (t, J=7.4 Hz, 1H), 7.05-6.91 (m, 4H), 6.88-6.66 (m, 2H), 5.22-5.02 (m, 1H), 4.24-4.06 (m, 1H), 4.05-3.76 (m, 4.5H), 3.76-3.61 (m, 0.5H), 2.86 (d, J=6.1 Hz, 6H), 2.66-2.39 (m, 2H). MS (ESI, Method A): m/z=459.8 $[M+H]^+$, $t_R$=1.244 min. HPLC: 97.5% (214 nm), 98.2% (254 nm).

Scheme 25

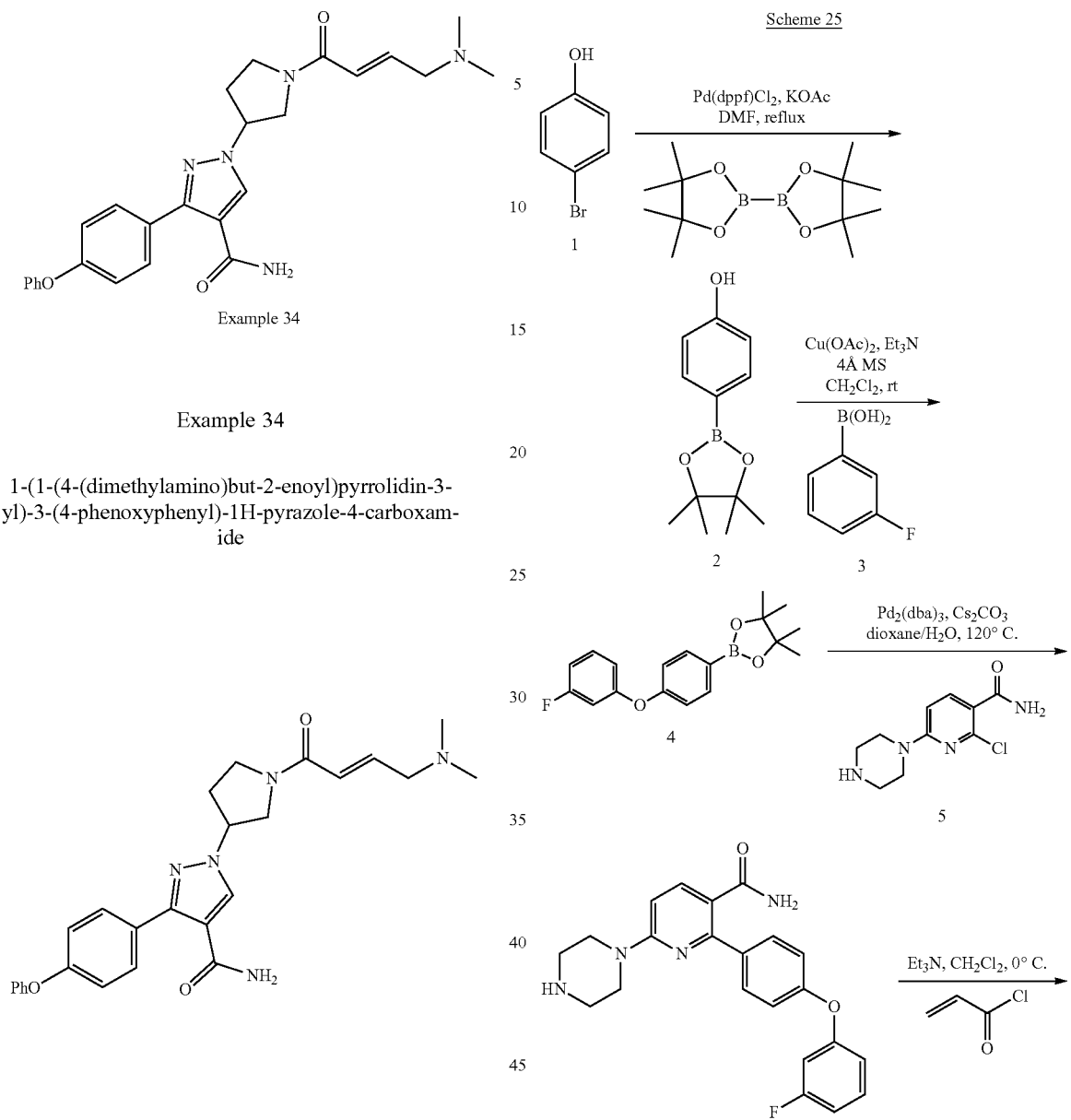

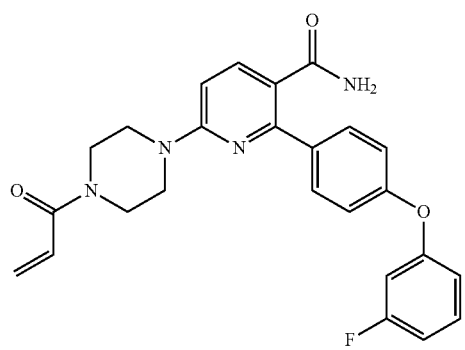 [SMILES: C=CC(=O)N1CCN(c2ccc(C(N)=O)c(-c3ccc(Oc4cccc(F)c4)cc3)n2)CC1]

Example 35

4-(4,4,5,5-tetramethyl-1,3,2-dioxaborolan-2-yl)phenol (2)

The title compound was obtained using a procedure analogous to the procedure described in 4-(4-(4,4,5,5-tetramethyl-1,3,2-dioxaborolan-2-yl)phenoxy)benzonitrile (see Scheme 16) as white solid (10.2 g, 80%).

2-(4-(3-fluorophenoxy)phenyl)-4,4,5,5-tetramethyl-1,3,2-dioxaborolane (4)

The mixture of 4-(4,4,5,5-tetramethyl-1,3,2-dioxaborolan-2-yl)phenol 2 (1.0 g, 4.5 mmol), 3-fluorophenylboronic acid 3 (0.70 g, 5.0 mmol), Cu(OAc)$_2$ (1.0 g, 5.0 mmol), Et$_3$N (2.75 g, 27.3 mmol), 4 A molecular sieves (1 g) and CH$_2$Cl$_2$ (15 mL) was stirred at rt for 16 h. Then the mixture was concentrated in vacuo and the residue was purified by silica gel chromatography eluting with 20:1 petroleum ether/EtOAc to afford the title compound (0.45 g, 32%) as white solid.

2-(4-(3-fluorophenoxy)phenyl)-6-(piperazin-1-yl)nicotinamide (6)

The title compound was obtained using a procedure analogous to the procedure described in 6-(3-nitrophenyl)-2-(4-phenoxyphenyl)nicotinamide (see Scheme 1) as white solid (0.15 g, 41%). MS (ESI): m/z=393.1 [M+H]$^+$.

Example 35

6-(4-acryloylpiperazin-1-yl)-2-(4-(3-fluorophenoxy)phenyl)nicotinamide

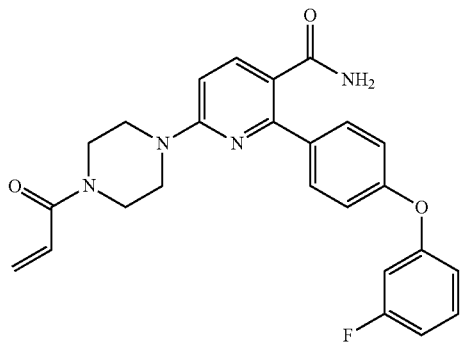

The title compound was obtained using a procedure analogous to the procedure described in Example 1 as white solid (50 mg, 27%). $^1$H NMR (400 MHz, CD$_3$OD) δ 7.79 (d, J=8.7 Hz, 1H), 7.77-7.70 (m, 2H), 7.42-7.33 (m, 1H), 7.13-7.06 (m, 2H), 6.93-6.75 (m, 5H), 6.27 (dd, J=16.8, 1.9 Hz, 1H), 5.80 (dd, J=10.6, 1.9 Hz, 1H), 3.84-3.72 (m, 8H). MS (ESI, method A): m/z=447.1 [M+H]$^+$, t$_R$=1.746 (min). HPLC: 95.9% (214 nm), 96.4% (254 nm).

Scheme 26

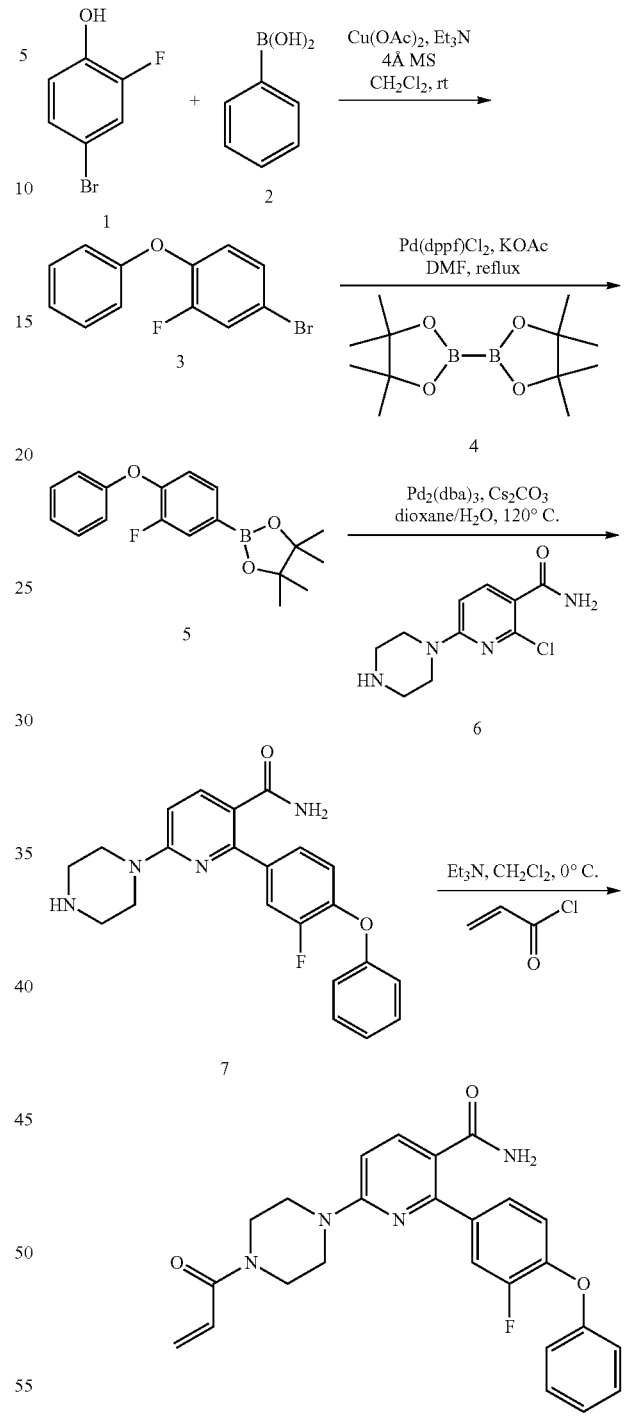

Example 36

4-bromo-2-fluoro-1-phenoxybenzene (3)

The title compound was obtained using a procedure analogous to the procedure described in 2-(4-(3-fluorophenoxy)phenyl)-4,4,5,5-tetramethyl-1,3,2-dioxaborolane (see Scheme 25) as yellow oil (1.5 g, 21%). MS (ESI): m/z=267.1 [M+H]$^+$.

2-(3-fluoro-4-phenoxyphenyl)-4,4,5,5-tetramethyl-1,3,2-dioxaborolane (5)

The title compound was obtained using a procedure analogous to the procedure described in 4-(4-(4,4,5,5-tetramethyl-1,3,2-dioxaborolan-2-yl)phenoxy)benzonitrile (see Scheme 16) as yellow oil (1.04 g, 73%).

2-(3-fluoro-4-phenoxyphenyl)-6-(piperazin-1-yl)nicotinamide (7)

The title compound was obtained using a procedure analogous to the procedure described in 6-(3-nitrophenyl)-2-(4-phenoxyphenyl)nicotinamide (see Scheme 1) as brown gum (0.194 g, 49%). MS (ESI): m/z=393.1 [M+H]$^+$.

Example 36

6-(4-acryloylpiperazin-1-yl)-2-(3-fluoro-4-phenoxyphenyl)nicotinamide

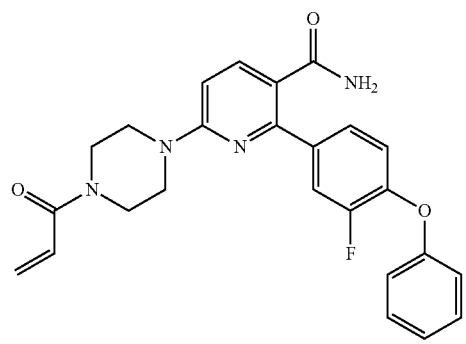 [SMILES: C=CC(=O)N1CCN(c2ccc(C(N)=O)c(-c3ccc(Oc4ccccc4)c(F)c3)n2)CC1]

The title compound was obtained using a procedure analogous to the procedure described in Example 1 as white solid (38 mg, 17%). $^1$H NMR (400 MHz, DMSO-d6) δ (m, 2H), 7.59 (d, J=11.4 Hz, 1H), 7.48 (d, J=8.2 Hz, 1H), 7.42 (t, J=7.7 Hz, 2H), 7.35-7.28 (m, 1H), 7.24-7.15 (m, 2H), 7.04 (d, J=7.9 Hz, 2H), 6.95-6.81 (m, 2H), 6.16 (d, J=16.6 Hz, 1H), 5.73 (d, J=10.2 Hz, 1H), 3.79-3.50 (m, 8H). MS (ESI, method A): m/z=447.1 [M+H]$^+$, $t_R$=1.753 (min). HPLC: 98.6% (214 nm), 98.4% (254 nm).

Scheme 27

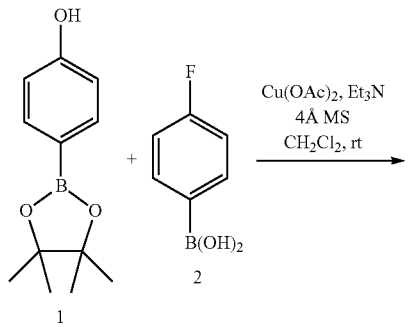

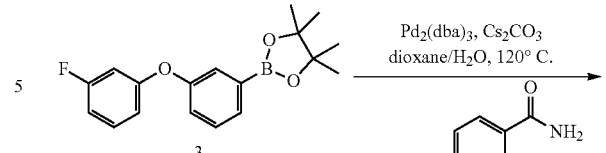

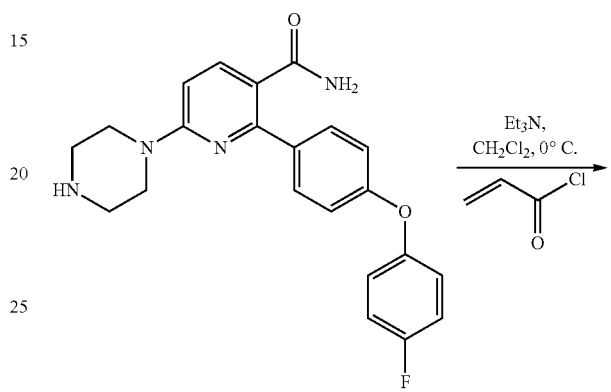

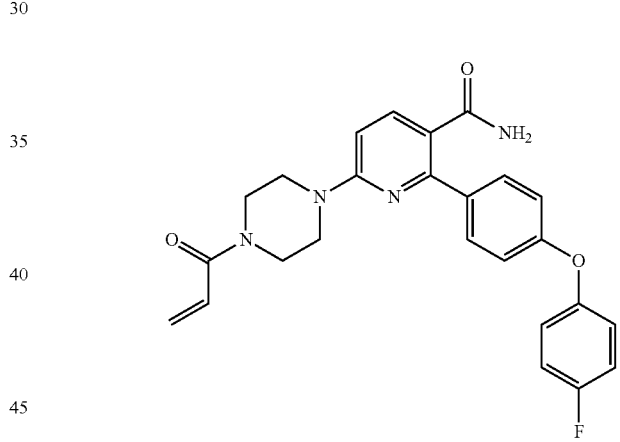

Example 37

2-(4-(4-fluorophenoxy)phenyl)-4,4,5,5-tetramethyl-1,3,2-dioxaborolane (3)

The title compound was obtained using a procedure analogous to the procedure described in 2-(4-(3-fluorophenoxy)phenyl)-4,4,5,5-tetramethyl-1,3,2-dioxaborolane (see Scheme 25) as white solid (0.45 g, 32%).

2-(4-(4-fluorophenoxy)phenyl)-6-(piperazin-1-yl)nicotinamide (5)

The title compound was obtained using a procedure analogous to the procedure described in 6-(3-nitrophenyl)-2-(4-phenoxyphenyl)nicotinamide (see Scheme 1) as brown gum (0.18 g, 41%).

Example 37

6-(4-acryloylpiperazin-1-yl)-2-(4-(4-fluorophenoxy)phenyl)nicotinamide

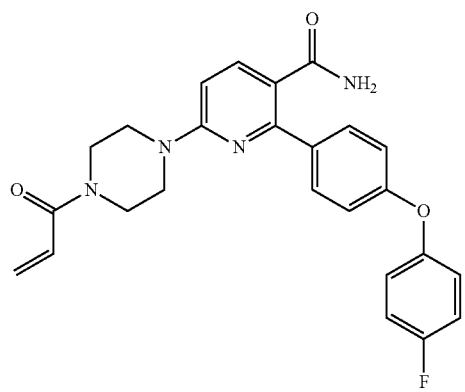 [SMILES: C=CC(=O)N1CCN(c2ccc(C(N)=O)c(-c3ccc(Oc4ccc(F)cc4)cc3)n2)CC1]

The title compound was obtained using a procedure analogous to the procedure described in Example 1 as white solid (80 mg, 44%). $^1$H NMR (400 MHz, CD$_3$OD) δ 7.77 (d, J=8.7 Hz, 1H), 7.69 (d, J=8.7 Hz, 2H), 7.17-7.05 (m, 4H), 7.00 (d, J=8.7 Hz, 2H), 6.87-6.76 (m, 2H), 6.26 (dd, J=16.8, 1.8 Hz, 1H), 5.80 (dd, J=10.6, 1.8 Hz, 1H), 3.87-3.71 (m, 8H). MS (ESI, method A): m/z=447.0 [M+H]$^+$, $t_R$=1.739 (min). HPLC: 99.8% (214 nm), 100% (254 nm).

Scheme 28

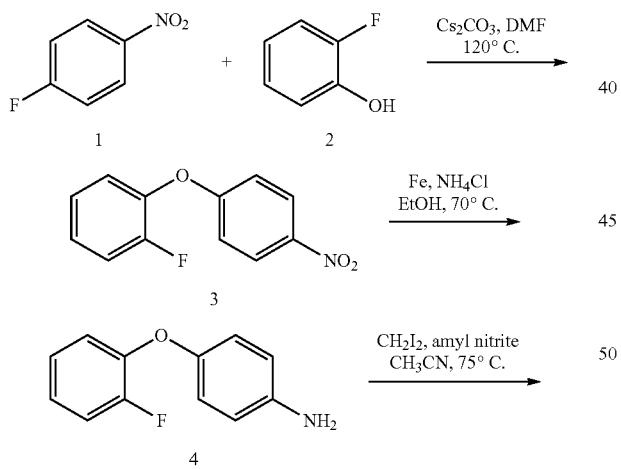

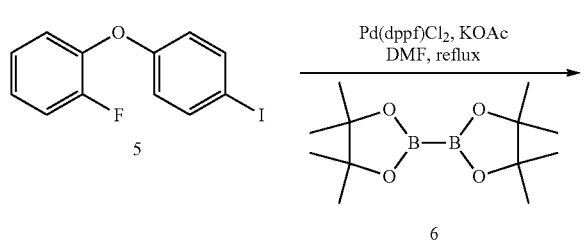

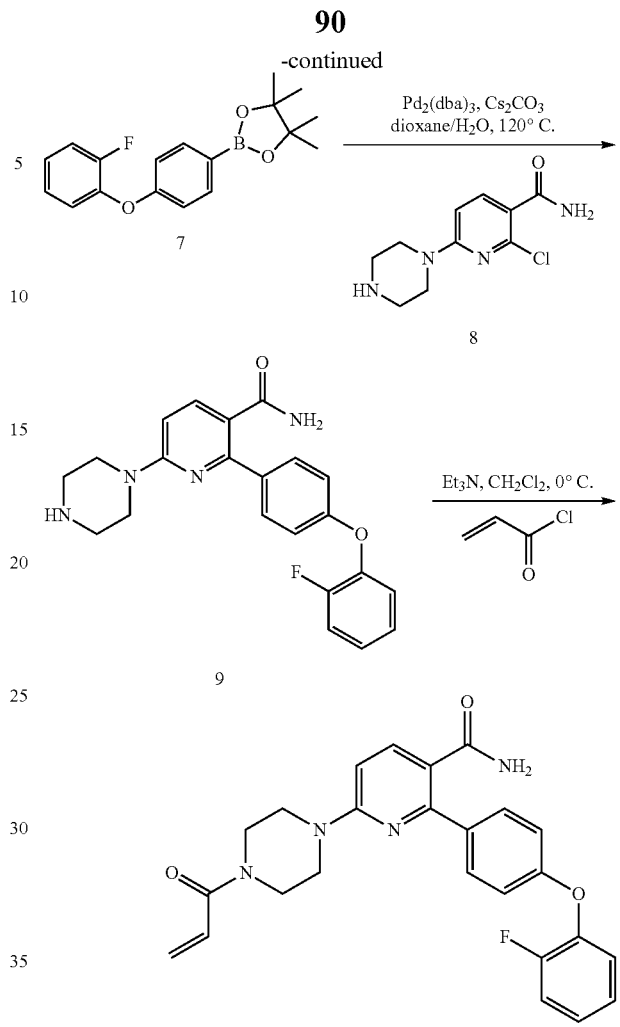

Example 38

1-fluoro-2-(4-nitrophenoxy)benzene (3)

The mixture of 1-fluoro-4-nitrobenzene 1 (10.0 g, 70.8 mmol), 2-fluorophenol 2 (9.54 g, 85.0 mmol), Cs$_2$CO$_3$ (34.6 g, 106 mmol) and DMF (80 mL) was heated to 120° C. and stirred for 2 h. After being cooled to rt, the mixture was diluted with water (150 mL) and extracted with EtOAc (200 mL×2). The combined organic phase was washed with brine (100 mL×3), dried over Na$_2$SO$_4$ and filtered. The filtrate was concentrated in vacuo. The residue was recrystallized from MeOH (20 mL×2) to afford the title compound as light yellow solid (14.6 g, 88%).

4-(2-fluorophenoxy)benzenamine (4)

To the mixture of 1-fluoro-2-(4-nitrophenoxy)benzene 3 (16.2 g, 69.3 mmol), saturated aqueous NH$_4$Cl solution (30 mL) and EtOH (150 mL) was added iron powder (19.4 g, 347 mmol) slowly and then the resulting mixture was heated to 70° C. for 3.5 h. After being cooled to rt, the mixture was filtered. The filtrate was concentrated in vacuo. The residue was dissolved in EtOAc (160 mL) and washed successively with water (100 mL×2) and brine (100 mL×2). The organic phase was dried over Na$_2$SO$_4$, filtered and concentrated in vacuo to afford the title compound (13.6 g, 96%) as yellow solid. $^1$H NMR (400 MHz, DMSO-d6) δ 7.35-7.28 (m, 1H), 7.14-7.00 (m, 2H), 6.93-6.85 (m, 1H), 6.80-6.73 (m, 2H), 6.64-6.56 (m, 2H), 4.99 (brs, 2H).

1-fluoro-2-(4-iodophenoxy)benzene (5)

The mixture of 4-(2-fluorophenoxy)benzenamine 4 (7.94 g, 39.1 mmol), $CH_2I_2$ (29.0 g, 136.8 mmol) and $CH_3CN$ (120 mL) was heated to 55° C. and then amyl nitrite (11.6 g, 97.7 mmol) was added. The resulting mixture was heated to 75° C. for 3.5 h. After being cooled to rt, the mixture was diluted with EtOAc and then washed successively with 10% $Na_2S_2O_3$ and brine. The organic phase was dried over $Na_2SO_4$, filtered, concentrated in vacuo and purified by silica gel chromatography eluting with petroleum ether to afford the title compound (4.12 g, 51%) as light yellow oil. $^1$H NMR (400 MHz, DMSO) δ 7.78-7.63 (m, 2H), 7.44-7.37 (m, 1H), 7.34-7.14 (m, 3H), 6.87-6.74 (m, 2H).

2-(4-(2-fluorophenoxy)phenyl)-4,4,5,5-tetramethyl-1,3,2-dioxaborolane (7)

The title compound was obtained using a procedure analogous to the procedure described in 4-(4-(4,4,5,5-tetramethyl-1,3,2-dioxaborolan-2-yl)phenoxy)benzonitrile (see Scheme 16) as yellow oil (0.40 g, 13%).

2-(4-(2-fluorophenoxy)phenyl)-6-(piperazin-1-yl)nicotinamide (9)

The title compound was obtained using a procedure analogous to the procedure described in 6-(3-nitrophenyl)-2-(4-phenoxyphenyl)nicotinamide (see Scheme 1) as white solid (0.16 g, 31%). MS (ESI): m/z=393.1 [M+H]$^+$.

Example 38

6-(4-acryloylpiperazin-1-yl)-2-(4-(2-fluorophenoxy)phenyl)nicotinamide

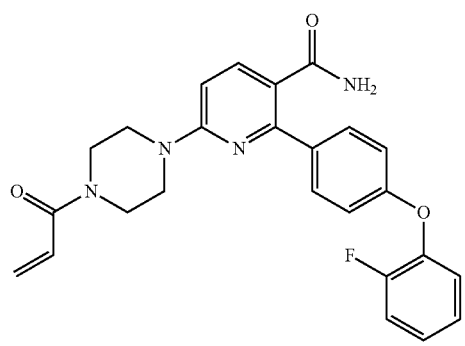 [SMILES: C=CC(=O)N1CCN(c2ccc(C(N)=O)c(-c3ccc(Oc4ccccc4F)cc3)n2)CC1]

The title compound was obtained using a procedure analogous to the procedure described in Example 1 as white solid (28 mg, 24%). $^1$H NMR (400 MHz, CD$_3$OD) δ 7.77 (d, J=8.7 Hz, 1H), 7.71-7.68 (m, 2H), 7.34-7.13 (m, 4H), 6.99 (d, J=8.7 Hz, 2H), 6.88-6.79 (m, 2H), 6.26 (dd, J=16.8, 1.9 Hz, 1H), 5.80 (dd, J=10.6, 1.9 Hz, 1H), 3.89-3.71 (m, 8H). MS (ESI, method A): m/z=447.1 [M+H]$^+$, $t_R$=1.723 (min). HPLC: 98.6% (214 nm), 98.8% (254 nm).

Scheme 29

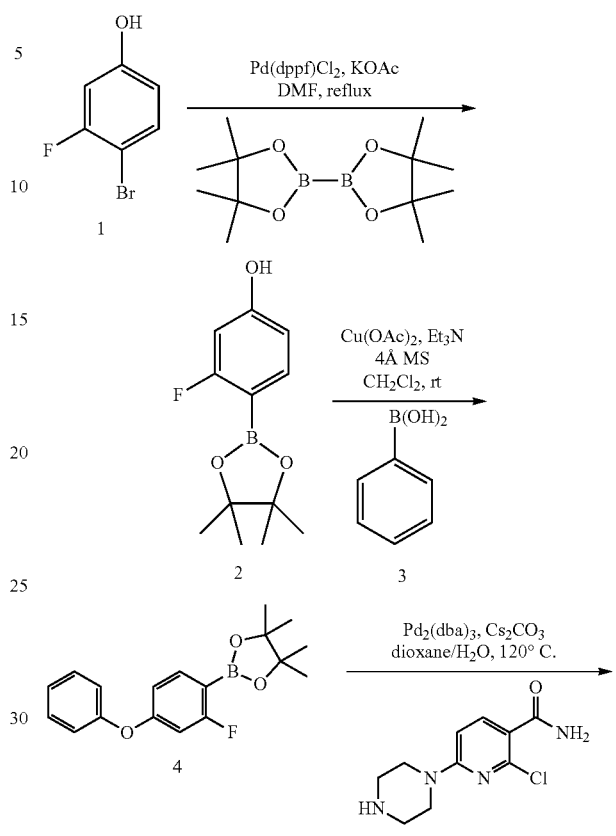

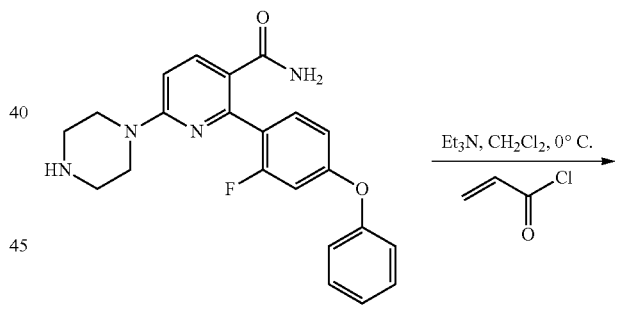

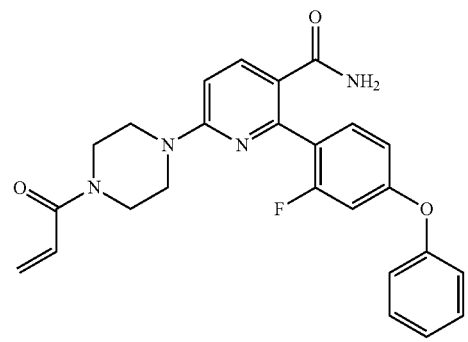 [SMILES: C=CC(=O)N1CCN(c2ccc(C(N)=O)c(-c3ccc(Oc4ccccc4)cc3F)n2)CC1]

Example 39

3-fluoro-4-(4,4,5,5-tetramethyl-1,3,2-dioxaborolan-2-yl)phenol (2)

The title compound was obtained using a procedure analogous to the procedure described in 4-(4,4,5,5-tetramethyl-1,3,2-dioxaborolan-2-yl)phenol (see Scheme 25) as white solid (4.1 g, 66%). MS (ESI): m/z=239.2 [M+H]$^+$.

2-(2-fluoro-4-phenoxyphenyl)-4,4,5,5-tetramethyl-1,3,2-dioxaborolane (4)

The title compound was obtained using a procedure analogous to the procedure described in 2-(4-(3-fluorophenoxy)phenyl)-4,4,5,5-tetramethyl-1,3,2-dioxaborolane (see Scheme 25) as white solid (2.1 g, 39%).

2-(2-fluoro-4-phenoxyphenyl)-6-(piperazin-1-yl)nicotinamide (6)

the title compound was obtained using a procedure analogous to the procedure described in 6-(3-nitrophenyl)-2-(4-phenoxyphenyl)nicotinamide (see Scheme 1) as brown solid (0.105 g, 21%). MS (ESI): m/z=393.1 [M+H]$^+$.

Example 39

6-(4-acryloylpiperazin-1-yl)-2-(2-fluoro-4-phenoxyphenyl)nicotinamide

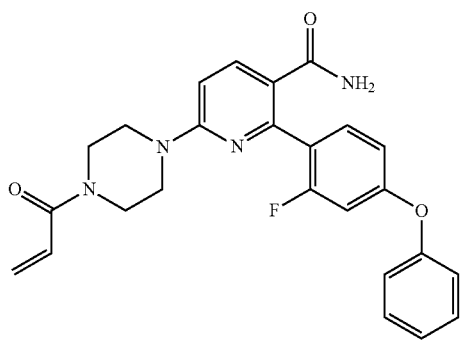

The title compound was obtained using a procedure analogous to the procedure described in Example 1 as white solid (78 mg, 65%). $^1$H NMR (400 MHz, MeOD) δ 7.78 (d, J=8.7 Hz, 1H), 7.59 (dd, J=11.8, 2.0 Hz, 1H), 7.48 (d, J=9.2 Hz, 1H), 7.44-7.33 (m, 2H), 7.17-7.06 (m, 2H), 7.05-6.99 (m, 2H), 6.90-6.79 (m, 2H), 6.27 (dd, J=16.8, 1.8 Hz, 1H), 5.80 (dd, J=10.6, 1.8 Hz, 1H), 3.86-3.70 (m, 8H). MS (ESI, method A): m/z=447.0 [M+H]$^+$, $t_R$=1.770 (min). HPLC: 96.5% (214 nm), 96.9% (254 nm).

Scheme 30

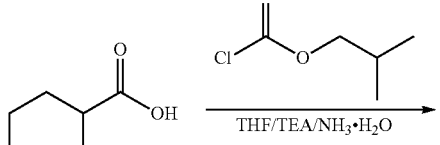

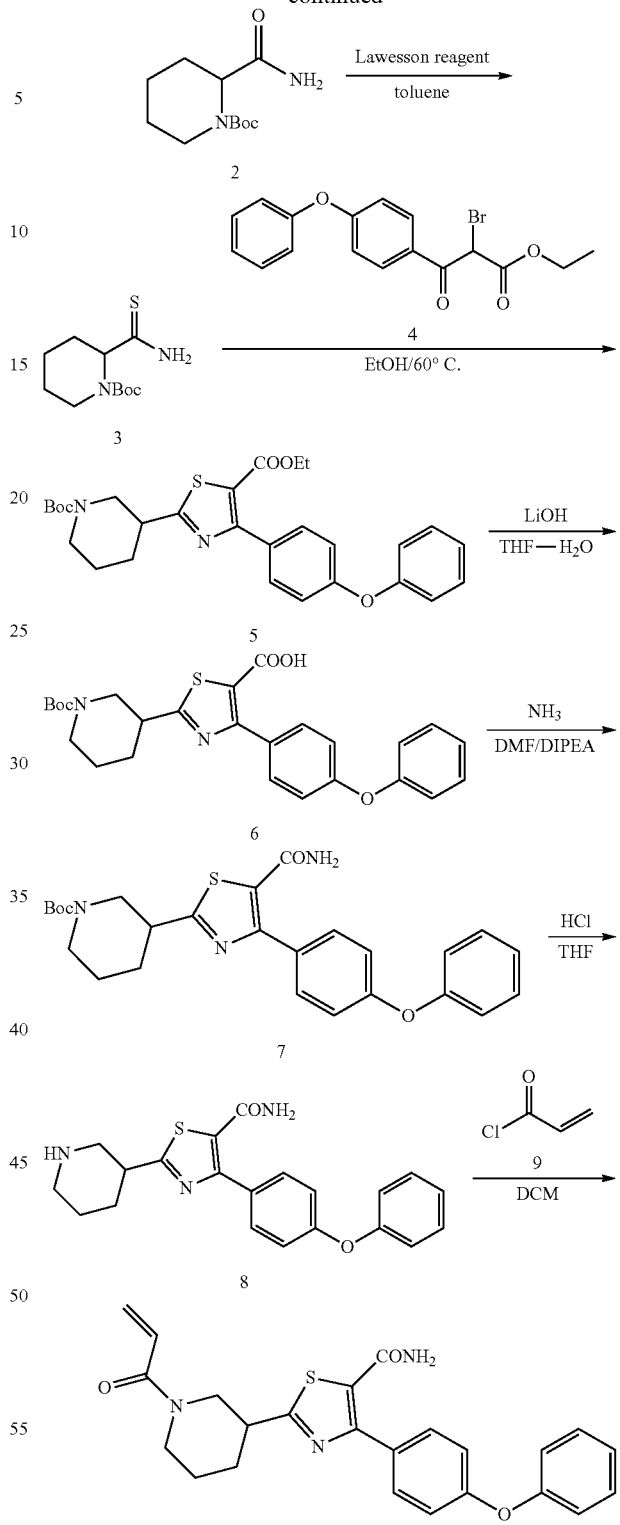

tert-butyl 2-carbamoylpiperidine-1-carboxylate (2)

To a solution of 1-(tert-butoxycarbonyl)piperidine-2-carboxylic acid 1 (5.0 g, 21.8 mmol) in dry THF (100 mL) was added TEA (3.30 g, 32.7 mmol), isobutyl carbonochloridate (3.27 g, 23.99 mmol) at 0° C. and the resulting solution was stirred for 20 min. $NH_3$—$H_2O$ was added and stirred at rt for 2 h. The mixture was diluted with ethyl acetate (30 mL), and washed with sat. aq. $Na_2CO_3$ (2×20 mL) and sat. aq. citric acid (2×20 mL). The organic layer was dried over anhydrous sodium sulfate, filtered and concentrated to give crude product (3.6 g, 72%) as white solid. MS (ESI): m/z=173.0 [M−55]$^+$.

tert-butyl 2-carbamothioylpiperidine-1-carboxylate (3)

To a solution of tert-butyl 2-carbamoylpiperidine-1-carboxylate 2 (2.0 g, 8.77 mmol) in dry toluene (20 mL) was added Lawesson's reagent (2.13 g, 5.26 mmol) at $N_2$ atmosphere. The resulting solution was stirred at 80° C. for 16 h. The mixture was diluted with ethyl acetate (30 mL), and washed with saturated aqueous (sat. aq.) $Na_2CO_3$ (2×20 mL) and brine (2×20 mL). The organic layer was dried over anhydrous sodium sulfate, filtered and concentrated to give crude product which was purified by silica gel column chromatography eluting with 4:1 PE/EA to get the title compound (330 mg, 15%) as white solid. MS (ESI): m/z=245.2 [M+H]$^+$.

ethyl-2-(1-(tert-butoxycarbonyl)piperidin-3-yl)-4-(4-phenoxyphenyl)thiazole-5-carboxylate (5)

A solution of tert-butyl 2-carbamothioylpiperidine-1-carboxylate 3 (60 mg, 0.239 mmol) and ethyl 2-bromo-3-oxo-3-(4-phenoxyphenyl)propanoate 4 (250 mg, 0.7 mmol) in EtOH (10 mL) was stirred for 2 h at 60° C. The mixture was diluted with ethyl acetate (30 mL), and washed with water (2×20 mL) and brine (2×20 mL). The organic layer was dried over anhydrous sodium sulfate, filtered and concentrated. The residue was purified by silica gel column chromatography eluting with 40:1 PE/EA to get the title compound (120 mg, 34%) as colorless oil. MS (ESI): m/z=509.3 [M+H]$^+$.

2-(1-(tert-butoxycarbonyl)piperidin-3-yl)-4-(4-phenoxyphenyl)thiazole-5-carboxylic Acid (6)

A solution of ethyl 2-(1-(tert-butoxycarbonyl)piperidin-3-yl)-4-(4-phenoxyphenyl)thiazole-5-carboxylate 5 (120 mg, 0.263 mmol) in THF-$H_2O$ (1/1, 20 mL) and added LiOH (30 mg, 0.71 mmol) was stirred at rt for 13 h. The mixture was evaporated and diluted with water (5 mL), and the solution was acidified with 2 N hydrochloric acid to pH=4. The residue was extracted with Ethyl Acetate (EA) (3×30 mL). Dried and concentrated to get crude compound (110 mg, 100%) as light red liquid. MS (ESI): m/z=481.0 [M+H]$^+$.

tert-butyl 3-(5-carbamoyl-4-(4-phenoxyphenyl)thiazol-2-yl)piperidine-1-carboxylate (7)

The mixture of 2-(1-(tert-butoxycarbonyl)piperidin-3-yl)-4-(4-phenoxyphenyl)thiazole-5-carboxylic acid 6 (110 mg, 0.229 mmol), HATU (113 mg, 0.297 mmol), DIPEA (88 mg, 0.687 mmol) and dry DMF (10 mL) was bubbled with $NH_3$ for 20 min, and the resulting solution was stirred for 3 h at ambient temperature. The mixture was diluted with ethyl acetate (30 mL), and washed with water (2×20 mL) and brine (2×20 mL). The organic layer was dried over anhydrous sodium sulfate, filtered and concentrated. The residue was purified by Prep-TLC with 3:2 PE/EA to get the title compound (100 mg, 75%) as colorless oil. MS (ESI): m/z=480.1 [M+H]$^+$.

4-(4-phenoxyphenyl)-2-(piperidin-3-yl)thiazole-5-carboxamide (8)

To a solution of tert-butyl 3-(5-carbamoyl-4-(4-phenoxyphenyl)thiazol-2-yl)piperidine-1-carboxylate 7 (100 mg, 0.21 mmol) in DCM (5 mL) was added TFA (2.5 mL) at ambient temperature. The mixture was stirred for 3 h. The mixture was diluted with water (2×150 mL) and extracted with ethyl acetate (2×20 mL) and washed with brine (2×150 mL). The organic layer was dried over anhydrous sodium sulfate, filtered and concentrated to give the title compound (60 mg, 76%) as brown oil. MS (ESI): m/z=380.0 [M+H]$^+$.

Example 40

2-(1-acryloylpiperidin-3-yl)-4-(4-phenoxyphenyl)thiazole-5-carboxamide

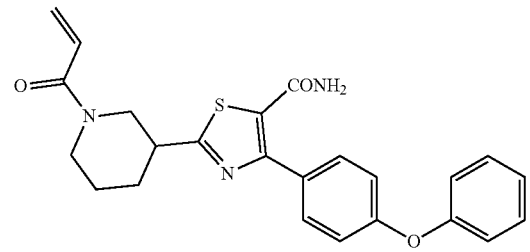 [SMILES: C=CC(=O)N1CCCC(c2nc(-c3ccc(Oc4ccccc4)cc3)c(C(N)=O)s2)C1]

To a solution of 4-(4-phenoxyphenyl)-2-(piperidin-3-yl)thiazole-5-carboxamide 8 (60 mg, 0.155 mmol) in dry dichloromethane (10 mL) were added TEA (19 mg, 0.21 mmol) and acryloyl chloride 9 (32 mg, 0.316 mmol), and the resulting solution was stirred at rt for 1 h. Water (10 mL) was added to quench the reaction. The mixture was diluted with ethyl acetate (30 mL), washed with brine (2×20 mL). The organic layer was dried over $Na_2SO_4$, filtered and concentrated to get the residue which was purified by Prep-TLC with 17:1 DCM/MeOH to get the title compound (33 mg, 50%) as a white solid. $^1$H NMR (400 MHz, DMSO) δ 7.76 (d, J=8.5 Hz, 2H), 7.76 (brs, 1H), 7.70 (brs, 1H), 7.44 (t, J=8.0 Hz, 2H), 7.19 (t, J=7.4 Hz, 1H), 7.08 (t, J=8.6 Hz, 4H), 6.92-6.82 (m, 1H), 6.14-6.04 (m, 1H), 5.73-5.64 (m, 1H), 4.65-4.62 (m, 0.5H), 4.15-4.04 (m, 0.5H), 4.02-4.00 (m, 1H), 3.59-3.56 (m, 0.5H), 3.26-3.14 (m, 1.5H), 3.09-2.98 (m, 1H), 2.22-2.16 (m, 1H), 1.90-1.74 (m, 2H), 1.58-1.48 (m, 1H). MS (ESI, method A): m/z=433.8 [M+H]$^+$, $t_R$=1.488 min. HPLC: 99.1% (214 nm), 99.2% (254 nm).

Scheme 31

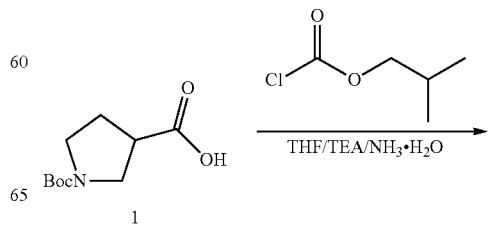

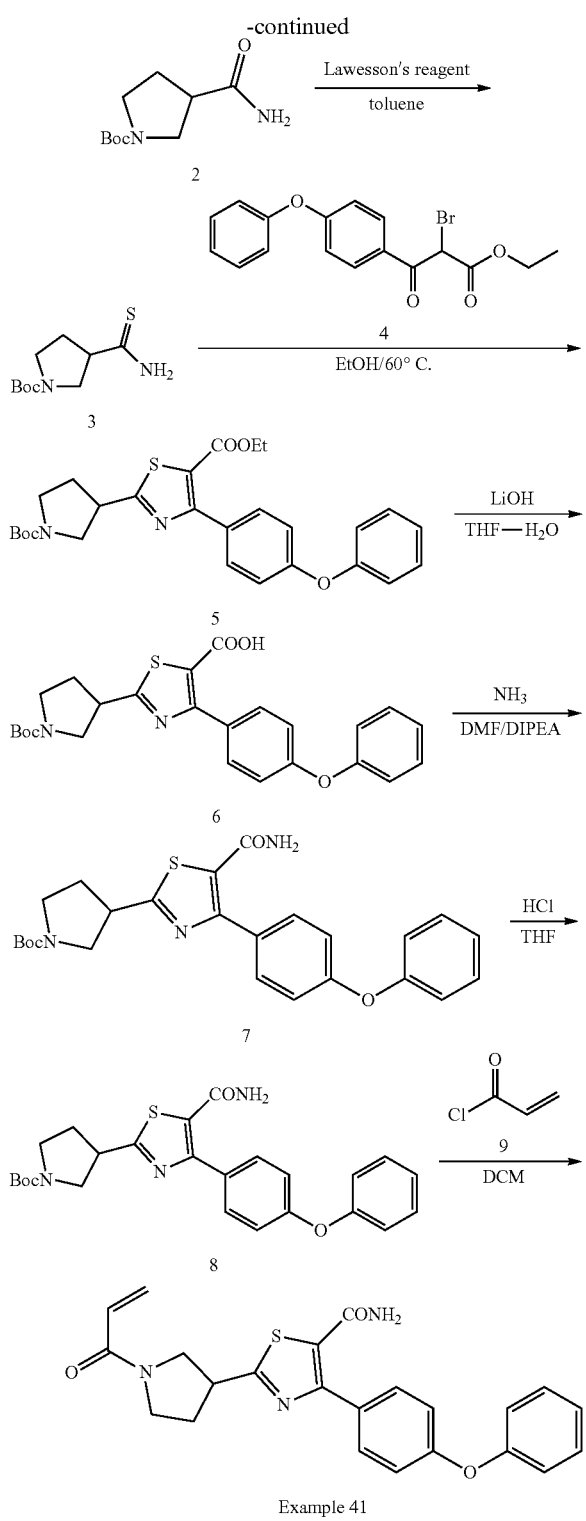

Example 41 tert-butyl 3-carbamoylpyrrolidine-1-carboxylate (2)

To a solution of 1-(tert-butoxycarbonyl)pyrrolidine-3-carboxylic acid 1 (5 g, 23.23 mmol) in dry THF (100 mL) was added TEA (4.69 g, 46.46 mmol), isobutyl carbonochloridate (3.8 g, 27.87 mmol) at 0° C. and the resulting solution was stirred for 20 min. NH$_3$—H$_2$O added and stirred at rt for 2 h. The mixture was diluted with ethyl acetate (30 mL), and washed with saturated (sat.) Na$_2$CO$_3$ (2×20 mL) and sat. citric acid (2×20 mL). The organic layer was dried over anhydrous sodium sulfate, filtered and concentrated to give crude product (2.39 g, 49%) as yellow solid. MS (ESI): m/z=159.0 [M+H]$^+$.

tert-butyl 3-carbamothioylpyrrolidine-1-carboxylate (3)

To a solution of tert-butyl 3-carbamoylpyrrolidine-1-carboxylate 2 (0.76 g, 3.55 mmol) in dry toluene (20 mL) was added Lawesson's regent (0.71 g, 1.77 mmol) at N$_2$ atmosphere. The resulting solution was stirred at 80° C. for 16 h. The mixture was diluted with ethyl acetate (30 mL), and washed with sat. Na$_2$CO$_3$ (2×20 mL) and brine (2×20 mL). The organic layer was dried over anhydrous sodium sulfate, filtered and concentrated to give crude product which was purified by silica gel column chromatography eluting with 6:1 PE/EA to get the title compound (230 mg, 28%) as brown oil. MS (ESI): m/z=175.2 [M+H]$^+$.

ethyl 2-(1-(tert-butoxycarbonyl)pyrrolidin-3-yl)-4-(4-phenoxyphenyl)thiazole-5-carboxylate (5)

A solution of tert-butyl 3-carbamothioylpyrrolidine-1-carboxylate 3 (360 mg, 0.1 mmol) and ethyl 2-bromo-3-oxo-3-(4-phenoxyphenyl)propanoate 4 (230 mg, 0.1 mmol) in EtOH (10 mL) was stirred for 2 h at 60° C. The mixture was diluted with ethyl acetate (30 mL), and washed with water (2×20 mL) and brine (2×20 mL). The organic layer was dried over anhydrous sodium sulfate, filtered and concentrated. The residue was purified by silica gel column chromatography eluting with 30:1 PE/EA to get the title compound (100 mg, 20%) as colorless oil. MS (ESI): m/z=495.3[M+H]$^+$.

2-(1-(tert-butoxycarbonyl)pyrrolidin-3-yl)-4-(4-phenoxyphenyl)thiazole-5-carboxylic Acid (6)

A solution of ethyl 2-(1-(tert-butoxycarbonyl)pyrrolidin-3-yl)-4-(4-phenoxyphenyl)thiazole-5-carboxylate 5 (100 mg, 0.2 mmol) in THF-H$_2$O (1/1, 20 mL) and added LiOH (84 mg, 2 mmol) was stirred at rt for 13 h. The mixture was evaporated and diluted with water (5 mL), and the solution was acidified with 2 N hydrochloric acid to pH=4. The residue was extracted with EA (3×30 mL). Dried and evaporated to get crude compound (95 mg, 100%) as red oil. MS (ESI): m/z=411.0 [M+H]$^+$.

tert-butyl 3-(5-carbamoyl-4-(4-phenoxyphenyl)thiazol-2-yl)pyrrolidine-1-carboxylate (7)

The mixture of 2-(1-(tert-butoxycarbonyl)pyrrolidin-3-yl)-4-(4-phenoxyphenyl)thiazole-5-carboxylic acid 6 (950 mg, 0.2 mmol), HATU (116 mg, 0.3 mmol), DIPEA (103 mg, 0.8 mmol) and dry DMF (10 mL) was bubbled with NH$_3$ for 20 min, and the resulting solution was stirred for 3 h at ambient temperature. The mixture was diluted with ethyl acetate (30 mL), and washed with water (2×20 mL) and brine (2×20 mL). The organic layer was dried over anhydrous sodium sulfate, filtered and concentrated. The residue was purified by Prep-TLC with 2:1 PE/EA to get the title compound (70 mg, 75%) as colorless oil. MS (ESI): m/z=466.1 [M+H]$^+$.

tert-butyl 3-(5-carbamoyl-4-(4-phenoxyphenyl)thiazol-2-yl)pyrrolidine-1-carboxylate (8)

To a solution of tert-butyl 3-(5-carbamoyl-4-(4-phenoxyphenyl)thiazol-2-yl)pyrrolidine-1-carboxylate 7 (70 mg, 0.15 mmol) in DCM (5 mL) was added TFA (2.5 mL) at ambient temperature. The mixture was stirred for 3 h. The mixture was diluted with water (2×150 mL) and extracted with ethyl acetate (2×20 mL) and washed with brine (2×150 mL). The organic layer was dried over anhydrous sodium sulfate, filtered and concentrated to give the title compound (65 mg, 100%) as brown oil. MS (ESI): m/z=366.1 [M+H]$^+$.

Example 41

2-(1-acryloylpyrrolidin-3-yl)-4-(4-phenoxyphenyl)thiazole-5-carboxamide

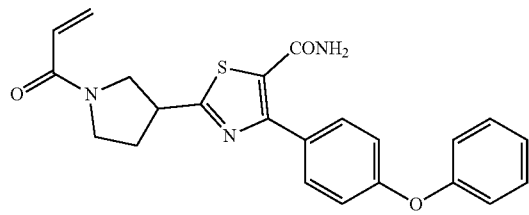 [SMILES: C=CC(=O)N1CCC(c2nc(-c3ccc(Oc4ccccc4)cc3)c(C(N)=O)s2)C1]

To a tert-butyl 3-(5-carbamoyl-4-(4-phenoxyphenyl)thiazol-2-yl)pyrrolidine-1-carboxylate 8 (65 mg, 0.15 mmol) in dry dichloromethane (10 mL) were added TEA (50 mg, 0.45 mmol) and acryloyl chloride 9 (20.4 mg, 0.225 mmol), and the resulting solution was stirred at rt for 1 h. Water (10 mL) was added to quench the reaction. The mixture was diluted with ethyl acetate (30 mL), washed with brine (2×20 mL). The organic layer was dried over Na$_2$SO$_4$, filtered and concentrated to get the residue which was purified by Prep-TLC with 1:1 PE/EA to get the title compound (22 mg, 35%) as a white solid. $^1$H NMR (400 MHz, DMSO) δ 7.76 (d, J=8.0 Hz, 2H), 7.76 (brs, 1H), 7.70 (brs, 1H), 7.44 (t, J=8.0 Hz, 2H), 7.19 (t, J=7.4 Hz, 1H), 7.07 (t, J=8.6 Hz, 4H), 6.65-6.59 (m, 1H), 6.19-6.15 (m, 1H), 5.72-5.68 (m, 1H), 4.11-4.07 (m, 0.5H), 3.99-3.95 (m, 0.5H), 3.91-3.78 (m, 2H), 3.70-3.62 (m, 1.5H), 3.50-3.47 (m, 0.5H), 2.44-2.36 (m, 1H), 2.28-2.25 (m, 0.5H), 2.18-2.13 (m, 0.5H). MS (ESI, method A): m/z=419.8 [M+H]$^+$, $t_R$=1.429 min. HPLC: 97.2% (214 nm), 97.5% (254 nm).

Scheme 32

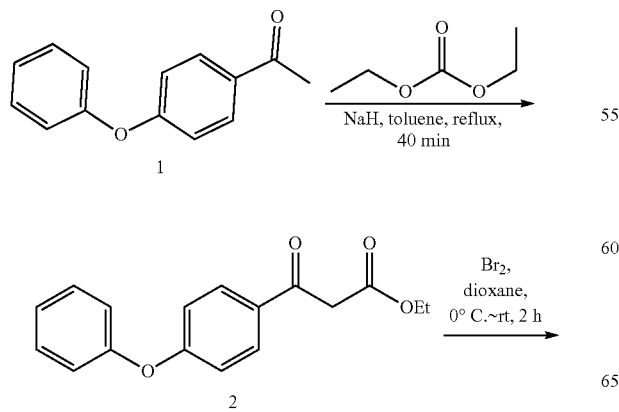

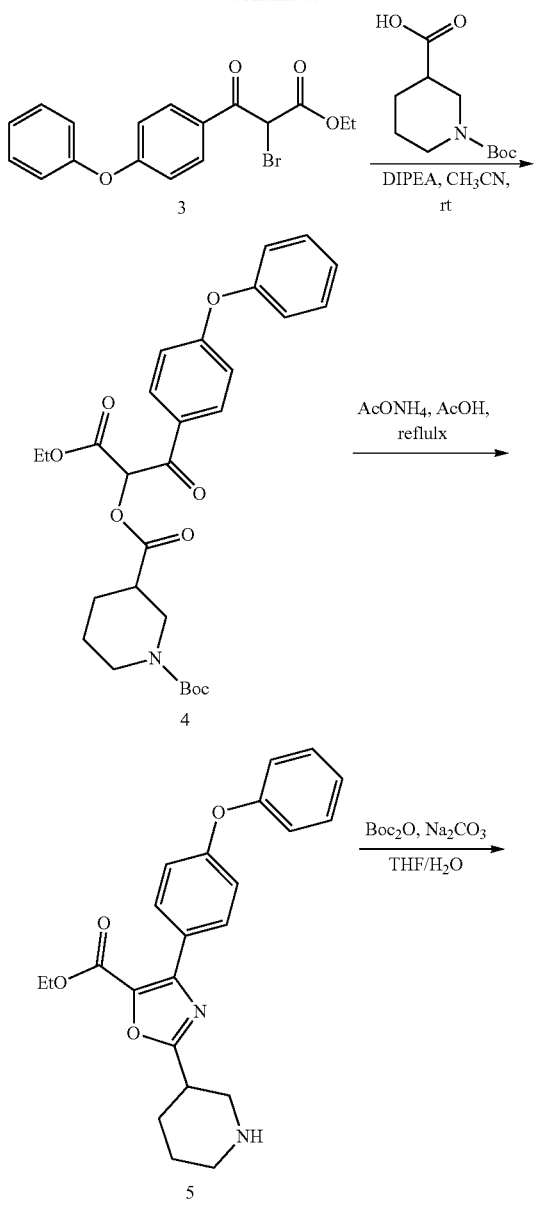

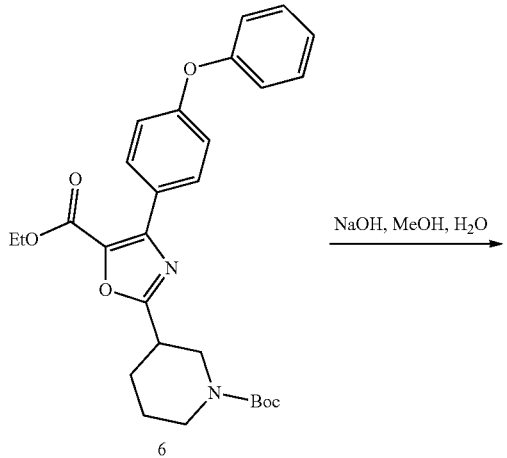

101
-continued

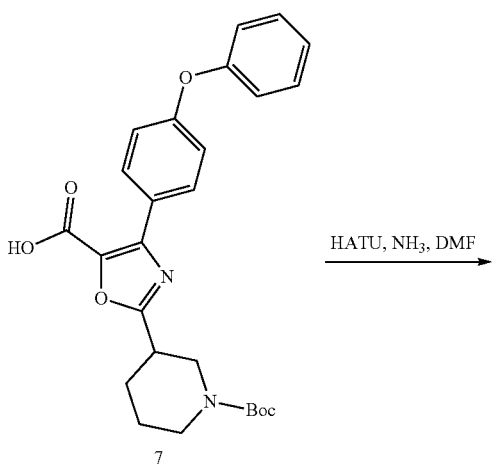

7

HATU, NH₃, DMF →

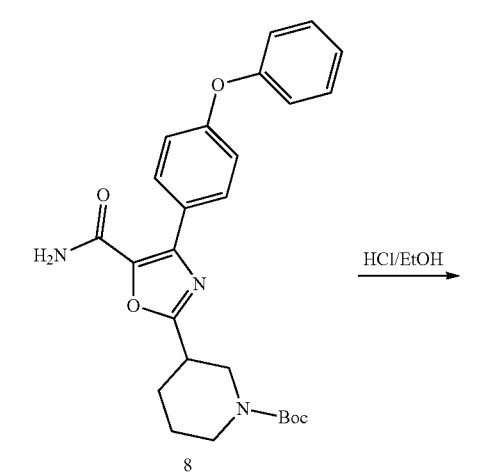

8

HCl/EtOH →

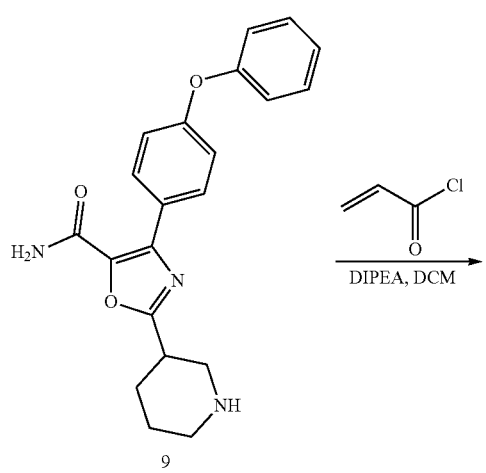

9

102
-continued

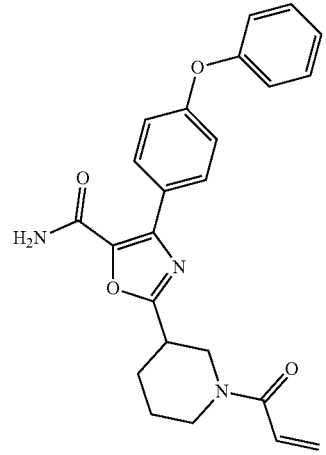

Example 42 ethyl 3-oxo-3-(4-phenoxyphenyl)propanoate (2)

To a mixture of diethyl carbonate (14 g, 120 mmol) and NaH (4.8 g, 120 mmol) in toluene (100 mL) was added 1-(4-phenoxyphenyl)ethanone 1 (10 g, 47 mmol) dropwise for 20 min. The resulting mixture was refluxed for 40 min. When it cooled to rt, which was quenched with AcOH/H₂O (6 mL/30 mL), then diluted with EA (100 mL). The organic layer was separated, washed with brine, dried over sodium sulfate, filtered and concentrated. The residue was applied onto silica gel column eluting with 20:1 PE/EA to get the title compound (7.5 g, 56%) as yellow oil. MS (ESI): m/z=285.1 [M+H]⁺.

ethyl 2-bromo-3-oxo-3-(4-phenoxyphenyl)propanoate (3)

To a mixture of ethyl 3-oxo-3-(4-phenoxyphenyl)propanoate 2 (6.55 g, 23.1 mmol) in dioxane (100 mL) was added Br₂ (3.69 g, 23.1 mmol) dropwise at 0° C. under N₂. The resulting mixture was stirred at rt for 3 h. The volatile phase was removed under reduced pressure. This resulted in crude title compound (9.5 g, overweight) as yellow oil. MS (ESI): m/z=363.0/365.0 [M+H]⁺.

1-tert-butyl 3-(1-ethoxy-1,3-dioxo-3-(4-phenoxyphenyl)propan-2-yl) piperidine-1,3-dicarboxylate (4)

To a mixture of ethyl 2-bromo-3-oxo-3-(4-phenoxyphenyl)propanoate 3 (1.0 g, 2.75 mmol) in CH₃CN (20 mL) was added DIEA (0.39 g, 3.0 mmol) dropwise. The resulting mixture was stirred at rt overnight. The volatile phase was removed under reduced pressure. The residue was applied onto silica gel column eluting with 3:1 PE/EA to get the title compound (1.15 g, 82%) as yellow oil. MS (ESI): m/z=412.1 [M+H-Boc]⁺.

ethyl 4-(4-phenoxyphenyl)-2-(piperidin-3-yl)oxazole-5-carboxylate (5)

A mixture of 1-tert-butyl 3-(1-ethoxy-1,3-dioxo-3-(4-phenoxyphenyl)propan-2-yl) piperidine-1,3-dicarboxylate 4 (1.15 g, 2.25 mmol) and AcONH₄ (0.86 g, 11.23 mmol) in AcOH (20 mL) was stirred at 120° C. for 2 h. The volatile phase was removed under reduced pressure. The residue was dissolved in EA (50 mL), which was washed with sat. NaHCO₃, brine, dried over sodium sulfate, filtered and concentrated. This resulted in crude title compound (0.85 g, crude) as yellow oil. MS (ESI): m/z=393.1 [M+H]⁺.

Ethyl-2-(1-(tert-butoxycarbonyl)piperidin-3-yl)-4-(4-phenoxyphenyl)oxazole-5-carboxylate (6)

The title compound was obtained using a procedure analogous to the procedure described in ethyl 2-(4-(tert-butoxycarbonyl)piperazin-1-yl)-4-(4-phenoxyphenyl)thiazole-5-carboxylate (see Scheme 37) as pale yellow oil (0.35 g, 33%, two steps). MS (ESI): m/z=437.0 [M+H−56]⁺.

2-(1-(tert-butoxycarbonyl)piperidin-3-yl)-4-(4-phenoxyphenyl)oxazole-5-carboxylic Acid (7)

The title compound was obtained using a procedure analogous to the procedure described in 5-(1-(tert-butoxycarbonyl)piperidin-4-yl)-4'-phenoxybiphenyl-2-carboxylic acid (see Scheme 45) as yellow oil (350 mg, overweight). MS (ESI): m/z=465.1 [M+H]⁺.

tert-butyl 3-(5-carbamoyl-4-(4-phenoxyphenyl)oxazol-2-yl)piperidine-1-carboxylate (8)

The title compound was obtained using a procedure analogous to the procedure described in tert-butyl-3-(4-carbamoyl-3-(4-phenoxyphenyl)-1H-pyrazol-1-yl)pyrrolidine-1-carboxylate (see Scheme 23) as pale yellow solid (250 mg, overweight). MS (ESI): m/z=408.0 [M+H−56]⁺.

4-(4-phenoxyphenyl)-2-(piperidin-3-yl)oxazole-5-carboxamide hydrochloride (9)

The title compound was obtained using a procedure analogous to the procedure described in 1-(4-phenoxyphenyl)-5-(piperidin-4-yl)-1H-pyrazole-3-carboxamide hydrochloride (see Scheme 46) as white solid (150 mg, overweight). MS (ESI): m/z=364.1 [M+H]⁺.

Example 42

2-(1-acryloylpiperidin-3-yl)-4-(4-phenoxyphenyl)oxazole-5-carboxamide

The title compound was obtained using a procedure analogous to the procedure described below in Example 43 as white solid (60 mg, 45%, four steps). ¹H NMR (300 MHz, DMSO) δ 8.26 (d, J=9.0 Hz, 2H), 7.92 (s, 1H), 7.67 (s, 1H), 7.53-7.29 (m, 2H), 7.25-7.13 (m, 1H), 7.11-6.99 (m, 4H), 6.85 (dd, J=16.7, 10.5 Hz, 1H), 6.11 (dd, J=16.7, 2.4 Hz, 1H), 5.68 (dd, J=10.4, 2.4 Hz, 1H), 4.39-4.31 (m, 1H), 4.12-4.04 (m, 1H), 3.33-3.14 (m, 2H), 3.02-2.89 (m, 1H), 2.14-2.06 (m, 2H), 1.90-1.65 (m, 2H). MS (ESI, method A): m/z=418.1 [M+H]⁺, t_R=1.488 min. HPLC: 97% (214 nm), 97% (254 nm).

Scheme 33

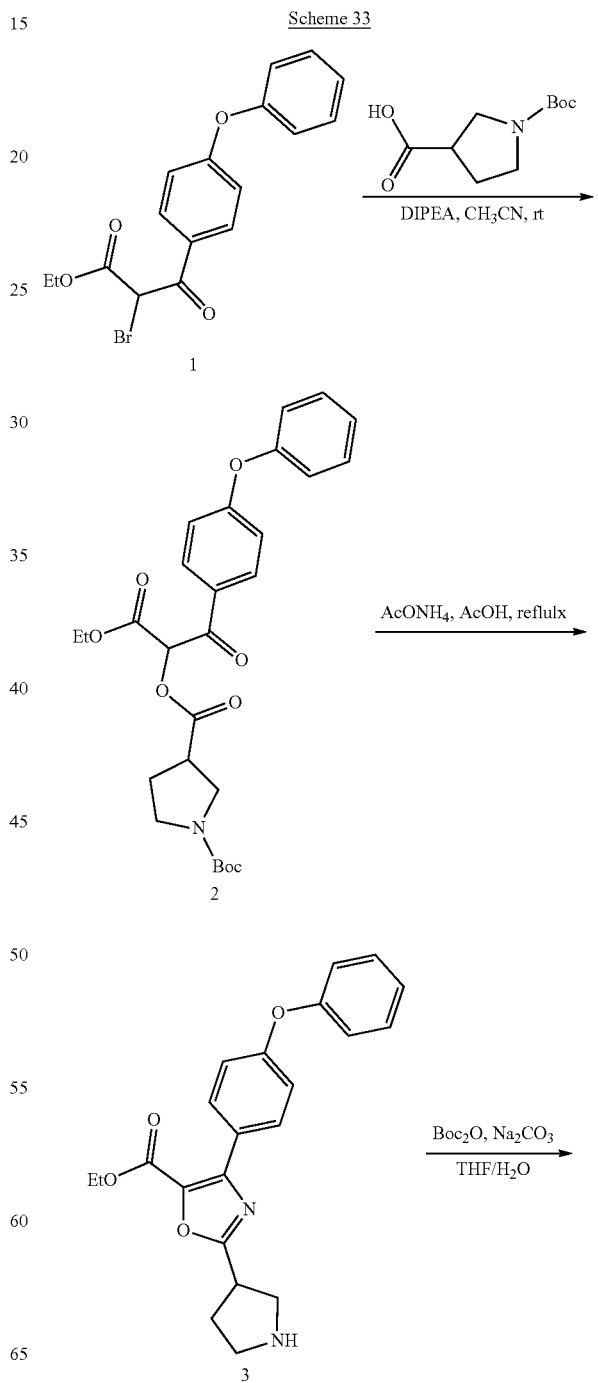

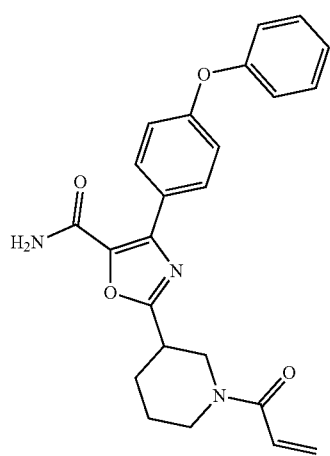 [SMILES: C=CC(=O)N1CCCC(c2nc(-c3ccc(Oc4ccccc4)cc3)c(C(N)=O)o2)C1]

105

-continued

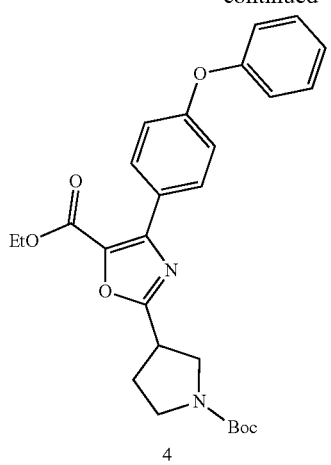
4

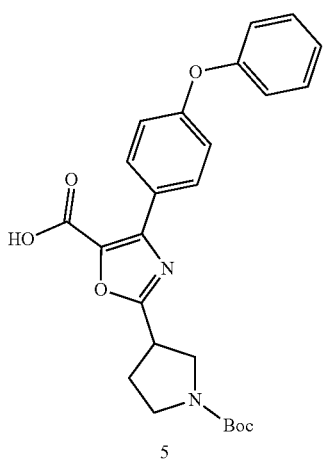
5

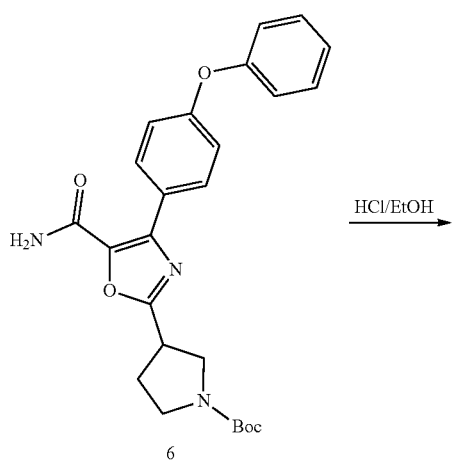
6

NaOH, MeOH, H₂O →

HATU, NH₃, DMF →

HCl/EtOH →

106

-continued

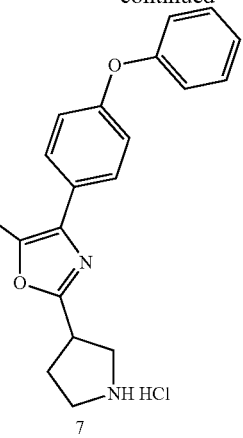
7

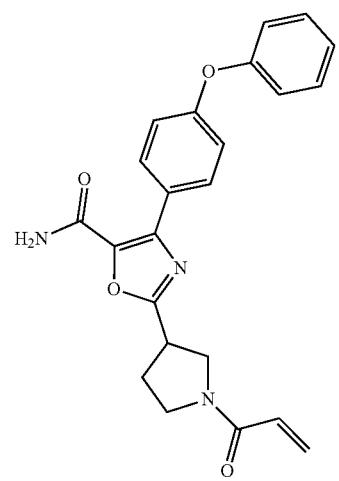
Example 43

Acryloyl chloride, DIPEA, DCM →

1-tert-butyl 3-(1-ethoxy-1,3-dioxo-3-(4-phenoxyphenyl)propan-2-yl) pyrrolidine-1,3-dicarboxylate (2)

The title compound was obtained using a procedure analogous to the procedure described in 1-tert-butyl 3-(1-ethoxy-1,3-dioxo-3-(4-phenoxyphenyl)propan-2-yl) piperidine-1,3-dicarboxylate (see Scheme 32) as pale yellow oil (1.1 g, 80%). MS (ESI): m/z=441.8 [M+H−56]⁺.

ethyl 4-(4-phenoxyphenyl)-2-(pyrrolidin-3-yl)oxazole-5-carboxylate (3)

The title compound was obtained using a procedure analogous to the procedure described in ethyl 4-(4-phenoxyphenyl)-2-(piperidin-3-yl)oxazole-5-carboxylate (see Scheme 32) as yellow oil (0.80 g, crude). MS (ESI): m/z=420.1 [M+H+41]⁺.

ethyl 2-(1-(tert-butoxycarbonyl)pyrrolidin-3-yl)-4-(4-phenoxyphenyl)oxazole-5-carboxylate (4)

The title compound was obtained using a procedure analogous to the procedure described in ethyl 2-(4-(tert-butoxycarbonyl)piperazin-1-yl)-4-(4-phenoxyphenyl)thiazole-5-carboxylate (see Scheme 37) as pale yellow oil (0.35 g, 33%, two steps). MS (ESI): m/z=423.1 [M+H−56]⁺.

2-(1-(tert-butoxycarbonyl)pyrrolidin-3-yl)-4-(4-phenoxyphenyl)oxazole-5-carboxylic Acid (5)

The title compound was obtained using a procedure analogous to the procedure described in 5-(1-(tert-butoxycarbonyl)piperidin-4-yl)-4'-phenoxybiphenyl-2-carboxylic acid (see Scheme 45) as yellow oil (350 mg, overweight). MS (ESI): m/z=395.0 [M+H−56]$^+$.

tert-butyl 3-(5-carbamoyl-4-(4-phenoxyphenyl)oxazol-2-yl)pyrrolidine-1-carboxylate (6)

The title compound was obtained using a procedure analogous to the procedure described in tert-butyl-3-(4-carbamoyl-3-(4-phenoxyphenyl)-1H-pyrazol-1-yl)pyrrolidine-1-carboxylate (see Scheme 23) as pale yellow solid (250 mg, overweight). MS (ESI): m/z=394.1 [M+H−56]$^+$.

4-(4-phenoxyphenyl)-2-(pyrrolidin-3-yl)oxazole-5-carboxamide hydrochloride (7)

The title compound was obtained using a procedure analogous to the procedure described in 1-(4-phenoxyphenyl)-5-(piperidin-4-yl)-1H-pyrazole-3-carboxamide hydrochloride (see Scheme 46) as white solid (150 mg, overweight). MS (ESI): m/z=350.1 [M+H]$^+$.

Example 43

2-(1-acryloylpyrrolidin-3-yl)-4-(4-phenoxyphenyl)oxazole-5-carboxamide

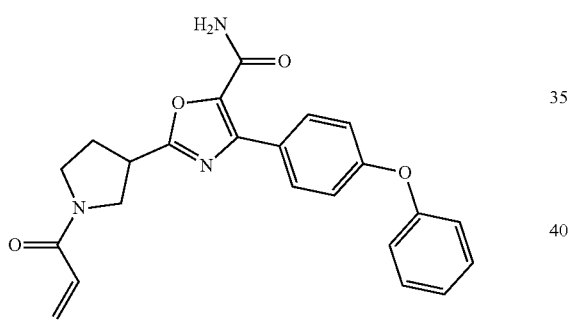

The title compound was obtained using a procedure analogous to the procedure described in Example 15 as white solid (45 mg, 34%, four steps). $^1$H NMR (400 MHz, DMSO) δ 8.27 (d, J=8.8 Hz, 2H), 7.94 (d, J=8.0 Hz, 1H), 7.70 (d, J=8.0 Hz, 1H), 7.43 (t, J=7.9 Hz, 2H), 7.19 (t, J=7.9 Hz, 1H), 7.11-7.02 (m, 4H), 6.69-6.55 (m, 1H), 6.19 (d, J=18.0 Hz, 1H), 5.70 (d, J=10.4 Hz, 1H), 4.08-3.96 (m, 1H), 3.90-3.65 (m, 3H), 3.64-3.55 (m, 0.5H), 3.53-3.45 (m, 0.5H), 2.45-2.37 (m, 1H), 2.36-2.27 (m, 1H). MS (ESI, method A): m/z=404.1 [M+H]$^+$, $t_R$=1.542 min. HPLC: 98% (214 nm), 98% (254 nm).

Scheme 34

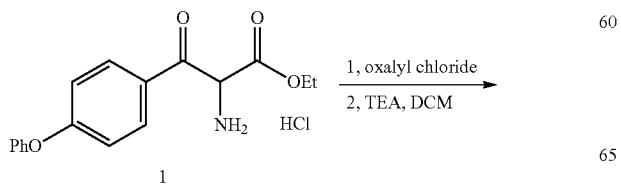

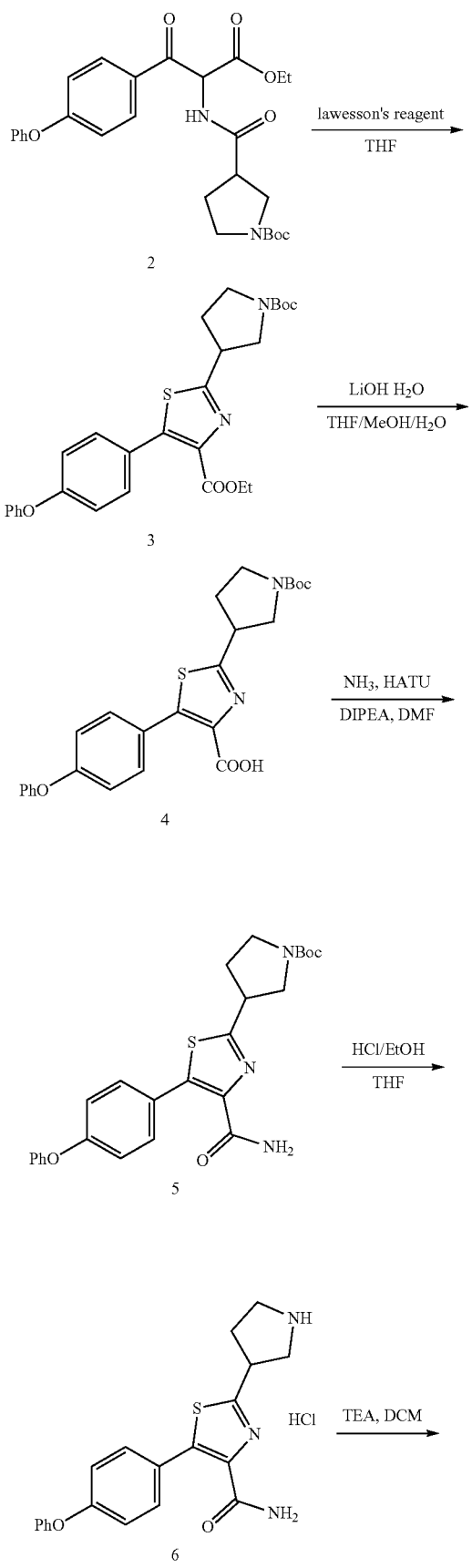

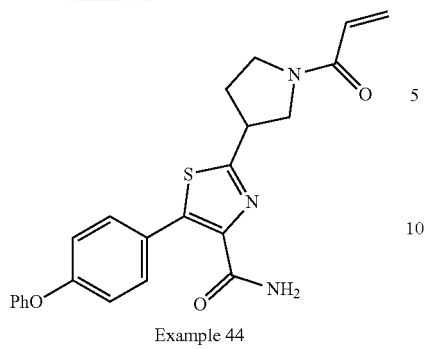

Example 44 tert-butyl 3-(1-ethoxy-1,3-dioxo-3-(4-phenoxyphenyl)propan-2-ylcarbamoyl)pyrrolidine-1-carboxylate (2)

The title compound was obtained using a procedure analogous to the procedure described in tert-butyl 3-(1-ethoxy-1,3-dioxo-3-(4-phenoxyphenyl)propan-2-ylcarbamoyl)piperidine-1-carboxylate (see Scheme 35) as yellow oil (0.35 g, 30%). MS (ESI): m/z=440.7 [M−55]⁺.

ethyl 2-(1-(tert-butoxycarbonyl)pyrrolidin-3-yl)-5-(4-phenoxyphenyl)thiazole-4-carboxylate (3)

The title compound was obtained using a procedure analogous to the procedure described in ethyl 2-(1-(tert-butoxycarbonyl)piperidin-3-yl)-5-(4-phenoxyphenyl)thiazole-4-carboxylate (see Scheme 35) as yellow oil (0.12 g, 61%). MS (ESI): m/z=494.7 [M+H]⁺.

2-(1-(tert-butoxycarbonyl)pyrrolidin-3-yl)-5-(4-phenoxyphenyl)thiazole-4-carboxylic Acid (4)

The title compound was obtained using a procedure analogous to the procedure described in 5-(1-(tert-butoxycarbonyl)piperidin-4-yl)-1-(4-phenoxyphenyl)-1H-pyrazole-3-carboxylic acid (see Scheme 46) as colorless oil (110 mg, 97%). MS (ESI): m/z=488.7 [M+Na]⁺.

tert-butyl 3-(4-carbamoyl-5-(4-phenoxyphenyl)thiazol-2-yl)pyrrolidine-1-carboxylate (5)

The title compound was obtained using a procedure analogous to the procedure described in tert-butyl 4-carbamoylpiperidine-1-carboxylate (see Scheme 42) as colorless oil (95 mg, 87%). MS (ESI): m/z=487.7 [M+Na]⁺.

5-(4-phenoxyphenyl)-2-(pyrrolidin-3-yl)thiazole-4-carboxamide hydrochloride (6)

The title compound was obtained using a procedure analogous to the procedure described in 1-(4-phenoxyphenyl)-5-(piperidin-4-yl)-1H-pyrazole-3-carboxamide hydrochloride (see Scheme 46) as colorless oil (90 mg, 100%). MS (ESI): m/z=365.8 [M+H]⁺.

Example 44

2-(1-acryloylpyrrolidin-3-yl)-5-(4-phenoxyphenyl)thiazole-4-carboxamide

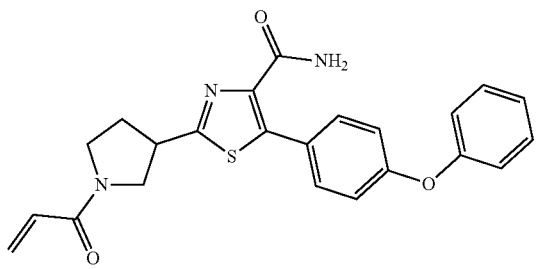 [SMILES: C=CC(=O)N1CCC(c2nc(C(N)=O)c(-c3ccc(Oc4ccccc4)cc3)s2)C1]

The title compound was obtained using a procedure analogous to the procedure described in Example 3 as a white solid (30 mg, 30%). ¹H NMR (300 MHz, CD₃OD) δ 7.52 (d, J=9.0 Hz, 2H), 7.37 (d, J=9.0 Hz, 2H), 7.15 (t, J=7.4 Hz, 1H), 7.06-7.02 (m, 2H), 6.99-6.94 (m, 2H), 6.64 (ddd, J=16.9, 10.4, 7.2 Hz, 1H), 6.29 (dt, J=16.8, 1.9 Hz, 1H), 5.76 (dt, J=10.4, 1.7 Hz, 1H), 4.19-4.05 (m, 0.5H), 4.03-3.82 (m, 3H), 3.83-3.71 (m, 1H), 3.65-3.55 (m, 0.5H), 2.61-2.23 (m, 2H). MS (ESI, method F): m/z=419.7 [M+H]⁺, $t_R$=1.487 min. HPLC: 99.3% (214 nm), 98.7% (254 nm).

Scheme 35

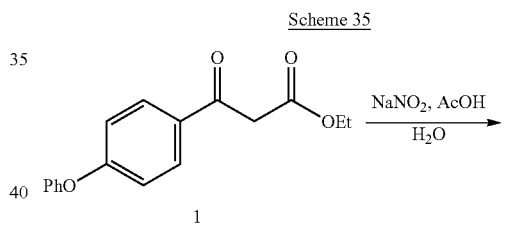

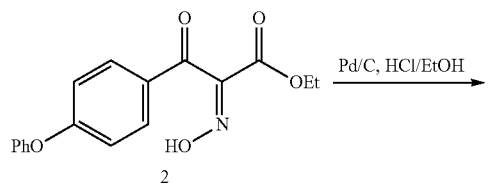

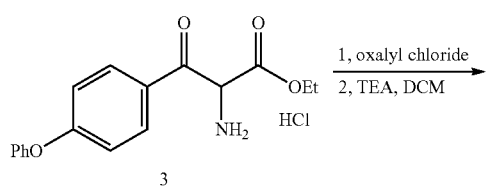

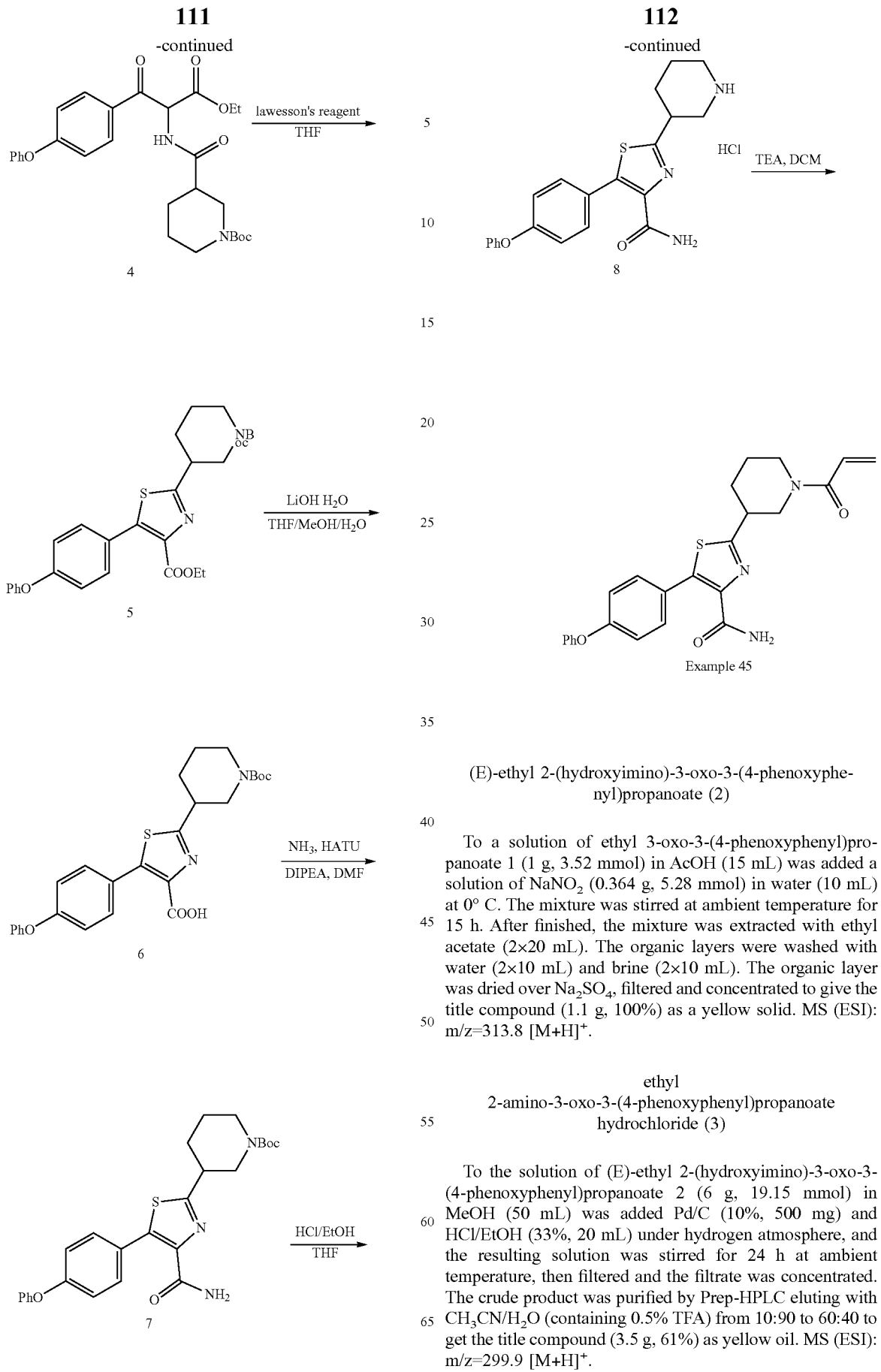

(E)-ethyl 2-(hydroxyimino)-3-oxo-3-(4-phenoxyphenyl)propanoate (2)

To a solution of ethyl 3-oxo-3-(4-phenoxyphenyl)propanoate 1 (1 g, 3.52 mmol) in AcOH (15 mL) was added a solution of NaNO$_2$ (0.364 g, 5.28 mmol) in water (10 mL) at 0° C. The mixture was stirred at ambient temperature for 15 h. After finished, the mixture was extracted with ethyl acetate (2×20 mL). The organic layers were washed with water (2×10 mL) and brine (2×10 mL). The organic layer was dried over Na$_2$SO$_4$, filtered and concentrated to give the title compound (1.1 g, 100%) as a yellow solid. MS (ESI): m/z=313.8 [M+H]$^+$.

ethyl 2-amino-3-oxo-3-(4-phenoxyphenyl)propanoate hydrochloride (3)

To the solution of (E)-ethyl 2-(hydroxyimino)-3-oxo-3-(4-phenoxyphenyl)propanoate 2 (6 g, 19.15 mmol) in MeOH (50 mL) was added Pd/C (10%, 500 mg) and HCl/EtOH (33%, 20 mL) under hydrogen atmosphere, and the resulting solution was stirred for 24 h at ambient temperature, then filtered and the filtrate was concentrated. The crude product was purified by Prep-HPLC eluting with CH$_3$CN/H$_2$O (containing 0.5% TFA) from 10:90 to 60:40 to get the title compound (3.5 g, 61%) as yellow oil. MS (ESI): m/z=299.9 [M+H]$^+$.

tert-butyl 3-(1-ethoxy-1,3-dioxo-3-(4-phenoxyphenyl)propan-2-ylcarbamoyl)piperidine-1-carboxylate (4)

To the solution of 1-(tert-butoxycarbonyl)piperidine-3-carboxylic acid (0.5 g, 2.18 mmol) in DCM (10 mL) was added oxalyl chloride (0.415 g, 3.27 mmol) and 5 drops of DMF. The mixture was stirred at rt for 2 h, concentrated to give the crude mixture. To the solution of ethyl 2-amino-3-oxo-3-(4-phenoxyphenyl)propanoate hydrochloride 3 (0.73 g, 2.18 mmol) in DCM (20 mL) was added TEA (0.66 g, 6.54 mmol) and a solution of above mixture in DCM (10 mL). The resulting solution was stirred at rt for 2 h. The reaction mixture was washed with brine (2×10 mL), dried over $Na_2SO_4$, filtered and concentrated to get a residue which was purified by silica gel column chromatography eluting with 1:1 PE/EA to get the title compound (0.16 g, 14%) as a yellow oil. MS (ESI): m/z=454.7 [M−55]$^+$.

ethyl 2-(1-(tert-butoxycarbonyl)piperidin-3-yl)-5-(4-phenoxyphenyl)thiazole-4-carboxylate (5)

To a solution of tert-butyl 3-(1-ethoxy-1,3-dioxo-3-(4-phenoxyphenyl)propan-2-ylcarbamoyl)piperidine-1-carboxylate 4 (0.16 g, 0.31 mmol) in THF (20 mL) was added lawesson's reagent (0.127 g, 0.31 mmol). The mixture was degassed with $N_2$ for 3 times, then heated to reflux and stirred for 2 h. When finished, the mixture was extracted with ethyl acetate (2×20 mL). The organic layers were washed with sat. $NaHCO_3$ (2×20 mL) and brine (2×20 mL). The organic layer was dried over $Na_2SO_4$, filtered and concentrated to get a residue which was purified by silica gel column chromatography eluting with 2:1 PE/EA to get the title compound (90 mg, 57%) as a yellow oil. MS (ESI): m/z=508.8 [M+H]$^+$.

2-(1-(tert-butoxycarbonyl)piperidin-3-yl)-5-(4-phenoxyphenyl)thiazole-4-carboxylic Acid (6)

The title compound was obtained using a procedure analogous to the procedure described in 5-(1-(tert-butoxycarbonyl)piperidin-4-yl)-1-(4-phenoxyphenyl)-1H-pyrazole-3-carboxylic acid (see Scheme 46) as a white solid (80 mg, 94%). MS (ESI): m/z=480.8 [M+H]$^+$.

tert-butyl 3-(4-carbamoyl-5-(4-phenoxyphenyl)thiazol-2-yl)piperidine-1-carboxylate (7)

The title compound was obtained using a procedure analogous to the procedure described in tert-butyl 4-carbamoylpiperidine-1-carboxylate (see Scheme 42) as colorless oil as colorless oil (40 mg, 50%). MS (ESI): m/z=479.7[M+H]$^+$.

5-(4-phenoxyphenyl)-2-(piperidin-3-yl)thiazole-4-carboxamide hydrochloride (8)

The title compound was obtained using a procedure analogous to the procedure described in 1-(4-phenoxyphenyl)-5-(piperidin-4-yl)-1H-pyrazole-3-carboxamide hydrochloride (see Scheme 46) as yellow oil (35 mg, 100%). MS (ESI): m/z=379.8[M+H]$^+$.

Example 45

2-(1-acryloylpiperidin-3-yl)-5-(4-phenoxyphenyl)thiazole-4-carboxamide

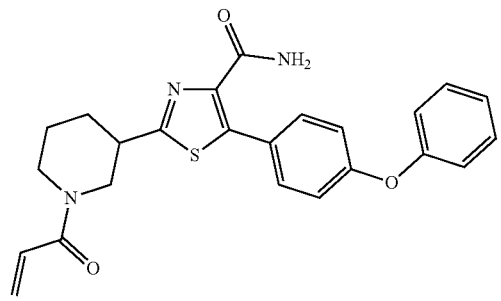 [SMILES: C=CC(=O)N1CCCC(c2nc(C(N)=O)c(-c3ccc(Oc4ccccc4)cc3)s2)C1]

The title compound was obtained using a procedure analogous to the procedure described in Example 3 as a white solid (10 mg, 27%). $^1$H NMR (300 MHz, CD$_3$OD) δ 7.56-7.48 (m, 2H), 7.44-7.32 (m, 2H), 7.15 (t, J=7.4 Hz, 1H), 7.03 (d, J=0.9 Hz, 2H), 6.99-6.94 (m, 2H), 6.84 (ddd, J=23.2, 16.7, 10.6 Hz, 1H), 6.21 (dd, J=16.8, 1.9 Hz, 1H), 5.75 (d, J=10.7 Hz, 1H), 4.62 (d, J=11.6 Hz, 0.5H), 4.27 (d, J=13.2 Hz, 0.5H), 4.15 (d, J=12.8 Hz, 0.5H), 4.00 (d, J=13.6 Hz, 0.5H), 3.72 (dd, J=13.5, 8.9 Hz, 0.5H), 3.42-3.33 (m, 1H), 3.29-3.15 (m, 1.5H), 2.35-2.23 (m, 1H), 2.08-1.85 (m, 2H), 1.75-1.55 (m, 1H). MS (ESI, method F): m/z=433.8 [M+H]$^+$, $t_R$=1.557 min. HPLC: 96.7% (214 nm), 98.0% (254 nm).

Scheme 36

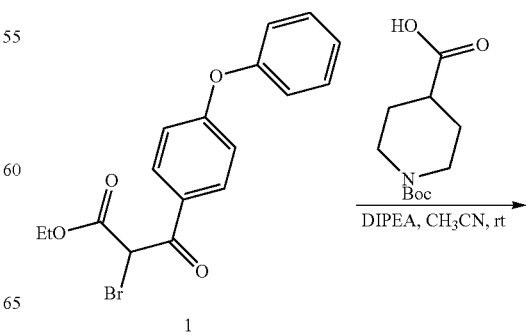

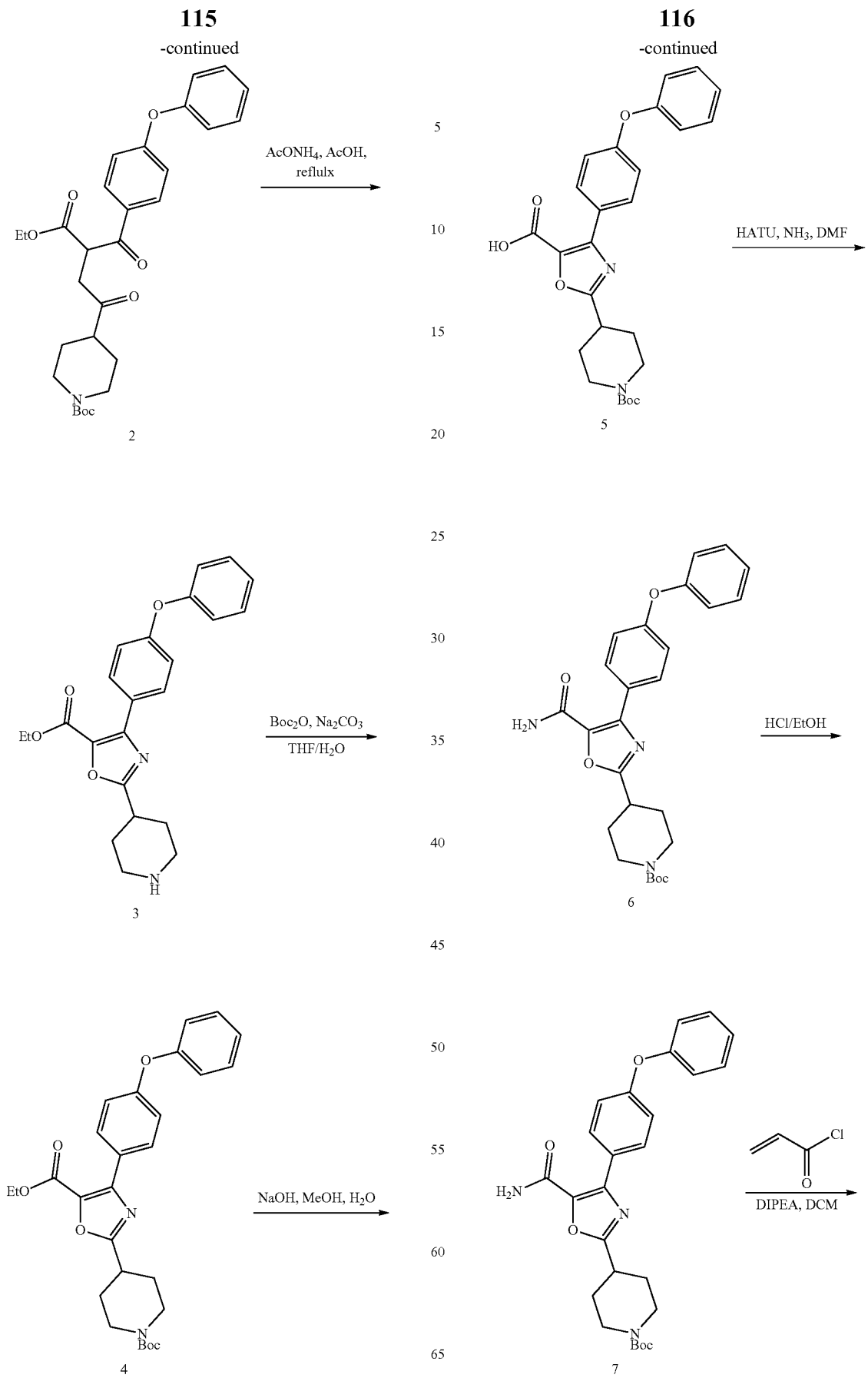

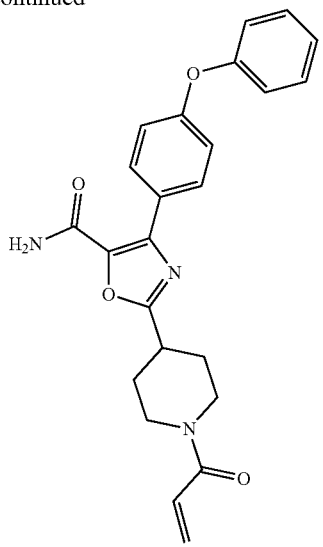

Example 46

1-tert-butyl 4-(1-ethoxy-1,3-dioxo-3-(4-phenoxyphenyl)propan-2-yl) piperidine-1,4-dicarboxylate (2)

The title compound was obtained using a procedure analogous to the procedure described in 1-tert-butyl 3-(1-ethoxy-1,3-dioxo-3-(4-phenoxyphenyl)propan-2-yl) piperidine-1,3-dicarboxylate (see Scheme 32) as pale yellow oil (0.85 g, 60%). MS (ESI): m/z=456.1 [M+H−56]$^+$.

ethyl 4-(4-phenoxyphenyl)-2-(piperidin-4-yl)oxazole-5-carboxylate (3)

The title compound was obtained using a procedure analogous to the procedure described in ethyl 4-(4-phenoxyphenyl)-2-(piperidin-3-yl)oxazole-5-carboxylate (see Scheme 32) as yellow oil (0.80 g, crude). MS (ESI): m/z=393.2 [M+H]$^+$.

Ethyl-2-(1-(tert-butoxycarbonyl)piperidin-4-yl)-4-(4-phenoxyphenyl)oxazole-5-carboxylate (4)

The title compound was obtained using a procedure analogous to the procedure described in ethyl 2-(4-(tert-butoxycarbonyl)piperazin-1-yl)-4-(4-phenoxyphenyl)thiazole-5-carboxylate (see Scheme 37) as pale yellow oil (0.85 g, 68%, two steps). MS (ESI): m/z=437.2 [M+H−56]$^+$.

2-(1-(tert-butoxycarbonyl)piperidin-4-yl)-4-(4-phenoxyphenyl)oxazole-5-carboxylic Acid (5)

The title compound was obtained using a procedure analogous to the procedure described in 5-(1-(tert-butoxycarbonyl)piperidin-4-yl)-4'-phenoxybiphenyl-2-carboxylic acid (see Scheme 45) as yellow oil (0.8 g, 99%). MS (ESI): m/z=409.1 [M+H−56]$^+$.

tert-butyl 4-(5-carbamoyl-4-(4-phenoxyphenyl)oxazol-2-yl)piperidine-1-carboxylate (6)

The title compound was obtained using a procedure analogous to the procedure described in tert-butyl-3-(4-carbamoyl-3-(4-phenoxyphenyl)-1H-pyrazol-1-yl)pyrrolidine-1-carboxylate (see Scheme 23) as pale yellow solid (390 mg, overweight). MS (ESI): m/z=408.0 [M+H−56]$^+$.

4-(4-phenoxyphenyl)-2-(piperidin-4-yl)oxazole-5-carboxamide hydrochloride (7)

The title compound was obtained using a procedure analogous to the procedure described in 1-(4-phenoxyphenyl)-5-(piperidin-4-yl)-1H-pyrazole-3-carboxamide hydrochloride (see Scheme 46) as white solid (400 mg, overweight). MS (ESI): m/z=364.1 [M+H]$^+$.

Example 46

2-(1-acryloylpiperidin-4-yl)-4-(4-phenoxyphenyl)oxazole-5-carboxamide

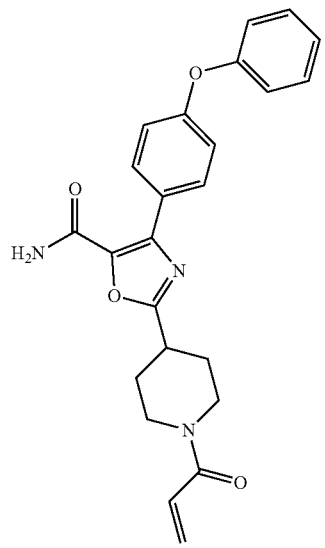 [SMILES: C=CC(=O)N1CCC(c2nc(-c3ccc(Oc4ccccc4)cc3)c(C(N)=O)o2)CC1]

The title compound was obtained using a procedure analogous to the procedure described in Example 15 as white solid (45 mg, 34%, three steps). $^1$H NMR (300 MHz, DMSO) δ 8.26 (d, J=9.0 Hz, 2H), 7.92 (s, 1H), 7.674 (s, 1H), 7.53-7.29 (m, 2H), 7.25-7.13 (m, 1H), 7.11-6.99 (m, 4H), 6.85 (dd, J=16.7, 10.5 Hz, 1H), 6.11 (dd, J=16.7, 2.4 Hz, 1H), 5.68 (dd, J=10.4, 2.4 Hz, 1H), 4.39-4.31 (m, 1H), 4.12-4.04 (m, 1H), 3.33-3.14 (m, 2H), 3.02-2.89 (m, 1H), 2.14-2.06 (m, 2H), 1.90-1.65 (m, 2H). MS (ESI, method A): m/z=418.1 [M+H]$^+$, $t_R$=1.489 min. HPLC: 97% (214 nm), 97% (254 nm).

Scheme 37
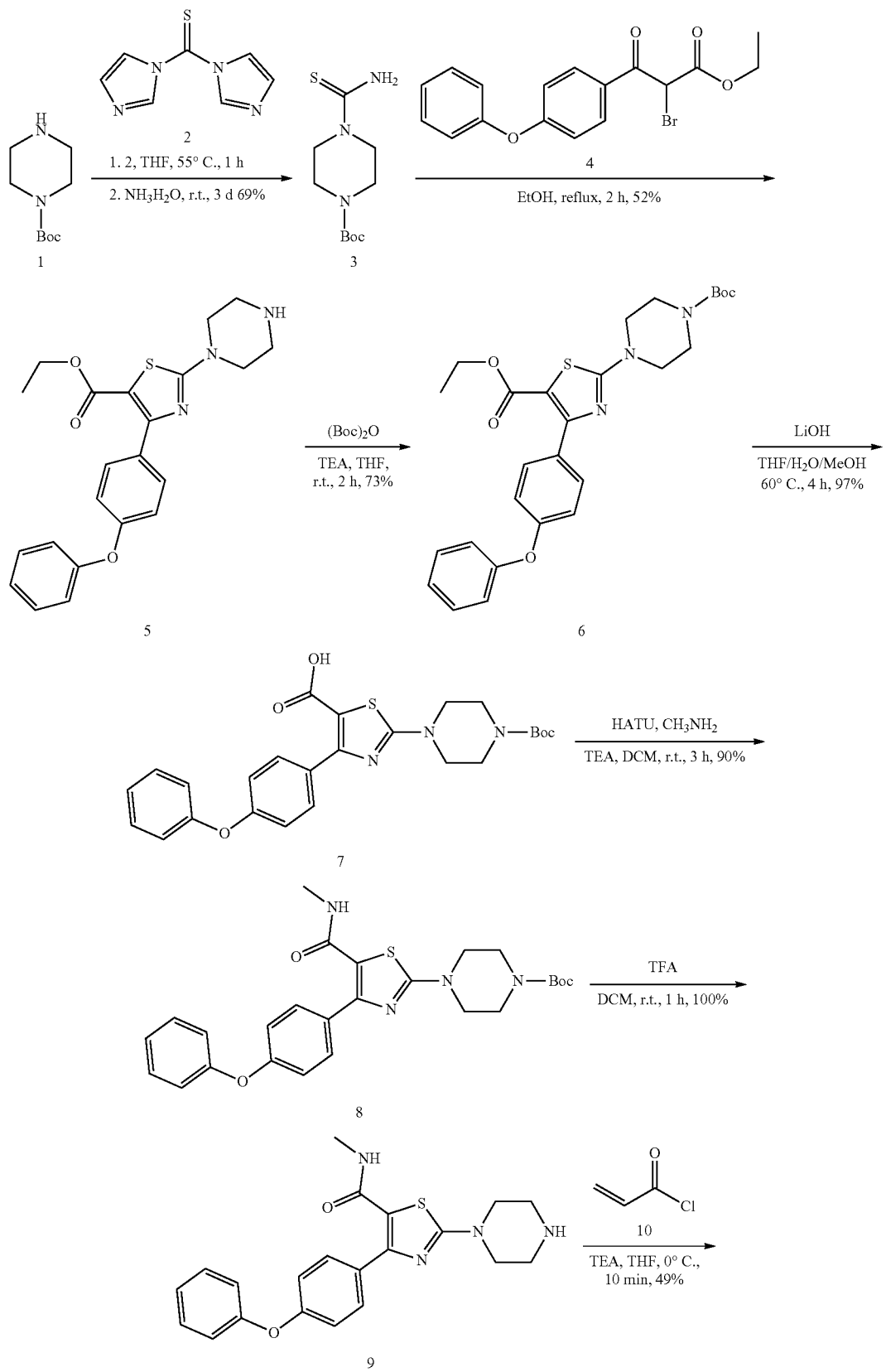

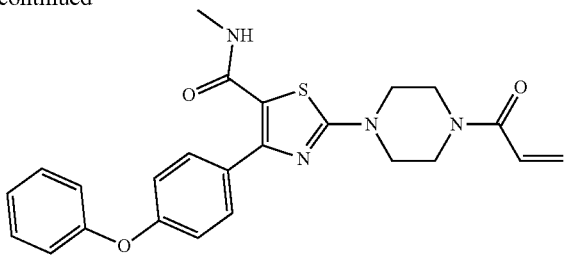

Example 47 tert-butyl 4-carbamothioylpiperazine-1-carboxylate (3)

To a solution of di(1H-imidazol-1-yl)methanethione 2 (2.14 g, 12 mmol) in anhydrous THF (30 mL) was added tert-butyl piperazine-1-carboxylate 1 (1.86 g, 10 mmol) at ambient temperature. The mixture was allowed to stir at ambient temperature for 2 h, then the mixture was heated at 55° C. for 1 h. The mixture was concentrated under vacuum to about half the volume. To the remaining reaction mixture was added 2 M solution of ammonia in methanol (20 mL) and allowed to stir at ambient temperature for 3 days. The solvent was removed and the residue was purified by chromatography eluting with 50:1 DCM/MeOH to afford the title compound (1.7 g, 69%) as white solid. MS (ESI): m/z=246.1 [M+H]+.

ethyl 4-(4-phenoxyphenyl)-2-(piperazin-1-yl)thiazole-5-carboxylate (5)

To a solution of ethyl 2-bromo-3-oxo-3-(4-phenoxyphenyl)propanoate 4 (362 mg, 1 mmol) in ethanol (10 mL) was added tert-butyl 4-carbamothioylpiperazine-1-carboxylate 3 (245 mg, 1 mmol) at ambient temperature. The mixture was then heated to reflux and stirred for 2 h. After cooling to ambient temperature, the solvent was removed and the residue was purified by silica gel column chromatography eluting with 40:1 to 20:1 DCM/MeOH to afford the title compound (214 mg, 52%) as brown solid. MS (ESI): m/z=410.1 [M+H]+.

ethyl 2-(4-(tert-butoxycarbonyl)piperazin-1-yl)-4-(4-phenoxyphenyl)thiazole-5-carboxylate (6)

To the compound of ethyl 4-(4-phenoxyphenyl)-2-(piperazin-1-yl)thiazole-5-carboxylate 5 (214 mg, 0.51 mmol) were added di-tert-butyl dicarbonate (134 mg, 0.6 mmol) and TEA (0.2 mL, 1.5 mmol) at ambient temperature. The mixture was then stirred at ambient temperature for 2 h. The solvent was removed and the residue was purified by silica gel column chromatography eluting with 50:1 DCM/MeOH to afford the title compound (190 mg, 73%) as brown solid. MS (ESI): m/z=510.1 [M+H]+.

2-(4-(tert-butoxycarbonyl)piperazin-1-yl)-4-(4-phenoxyphenyl)thiazole-5-carboxylic Acid (7)

To a solution of ethyl 2-(4-(tert-butoxycarbonyl)piperazin-1-yl)-4-(4-phenoxyphenyl)thiazole-5-carboxylate 6 (190 mg, 0.37 mmol) in THF (50 mL)/H2O (1 mL)/MeOH (3 mL) was added lithium hydroxide (30 mg, 0.74 mmol) at ambient temperature. The mixture was then heated to 60° C. and stirred for 2 h. After cooling to ambient temperature, the solvent was removed and the residue was purified by chromatography eluting with 10:1 DCM/MeOH to afford the title compound (173 mg, 97%) as white solid. MS (ESI): m/z=482.0 [M+H]+.

tert-butyl 4-(5-(methylcarbamoyl)-4-(4-phenoxyphenyl)thiazol-2-yl)piperazine-1-carboxylate (8)

To a solution of 2-(4-(tert-butoxycarbonyl)piperazin-1-yl)-4-(4-phenoxyphenyl)thiazole-5-carboxylic acid 7 (124 mg, 0.26 mmol) in DCM (10 mL) was added HATU (117 mg, 0.3 mmol) and methanamine (0.26 ml, 0.26 mmol) at ambient temperature. The mixture was stirred at ambient temperature for 3 h. The solvent was removed and the residue was purified by silica gel column chromatography eluting with 1:5 EA/PE to afford the title compound (115 mg, 90%) as colorless oil. MS (ESI): m/z=495.2 [M+H]+.

N-methyl-4-(4-phenoxyphenyl)-2-(piperazin-1-yl) thiazole-5-carboxamide (9)

To a solution of tert-butyl 4-(5-(methylcarbamoyl)-4-(4-phenoxyphenyl)thiazol-2-yl)piperazine-1-Carboxylate 8 (115 mg, 0.23 mmol) in DCM (5 mL) was added TFA (1 mL) at ambient temperature. The mixture was stirred for 1 h at ambient temperature. The solvent was removed and the residue was purified by silica gel column chromatography eluting with 10:1 DCM/MeOH to afford the title compound (117 mg, 100%) as colorless oil.

Example 47

2-(4-acryloylpiperazin-1-yl)-N-methyl-4-(4-phenoxyphenyl)thiazole-5-carboxamide

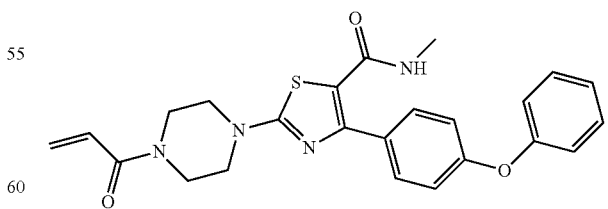

To a solution of N-methyl-4-(4-phenoxyphenyl)-2-(piperazin-1-yl)thiazole-5-carboxamide 9 (117 mg, 0.23 mmol) in DCM (5 mL) were added TEA (0.1 mL, 0.7 mmol) and acryloyl chloride 10 (0.21 mg, 0.23 mmol) at 0° C. The mixture was stirred at 0° C. for 10 minutes. The solvent was removed and the residue was purified by Prep-TLC eluting with 50:1 to 20:1 DCM/MeOH to afford the title compound (50 mg, 49%) as white solid. $^1$H NMR (400 MHz, CDCl$_3$) δ 7.57 (d, J=8.6 Hz, 2H), 7.40 (t, J=7.9 Hz, 2H), 7.19 (t, J=7.4 Hz, 1H), 7.09 (d, J=8.4 Hz, 4H), 6.60 (dd, J=16.8, 10.5 Hz, 1H), 6.37 (d, J=16.7 Hz, 1H), 5.79 (d, J=11.8 Hz, 1H), 5.59 (d, J=4.1 Hz, 1H), 3.78 (d, J=48.5 Hz, 4H), 3.62 (s, 4H), 2.80 (d, J=4.8 Hz, 3H), MS (ESI, method A): m/z=449.1 [M+H]$^+$, $t_R$=1.528 min. HPLC: 96.9% (214 nm), 96.9% (254 nm).

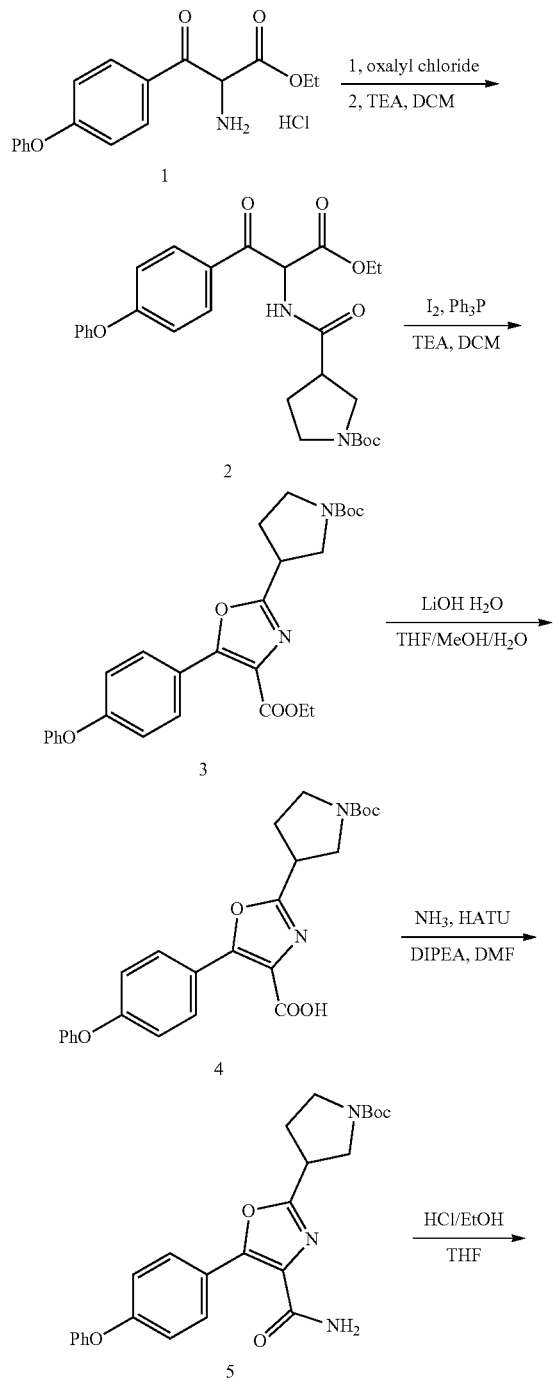

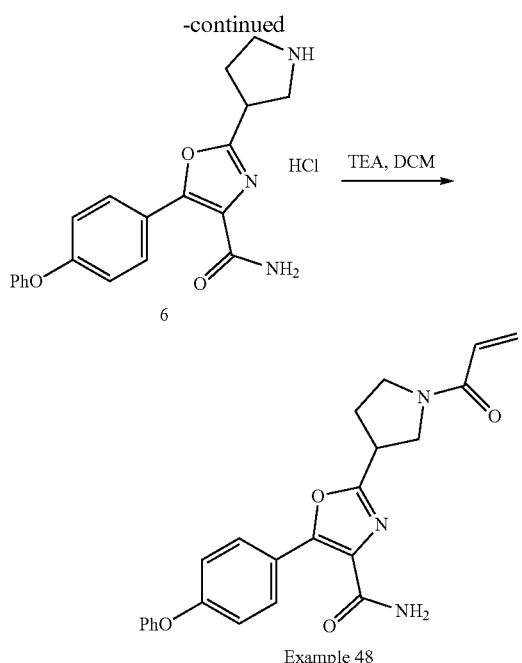

tert-butyl-3-(1-ethoxy-1,3-dioxo-3-(4-phenoxyphenyl)propan-2-ylcarbamoyl)pyrrolidine-1-carboxylate (2)

The title compound was obtained using a procedure analogous to the procedures described in the General Scheme and Example 15 as yellow oil (0.35 g, 30%). MS (ESI): m/z=440.7 [M−55]$^+$.

Ethyl-2-(1-(tert-butoxycarbonyl)pyrrolidin-3-yl)-5-(4-phenoxyphenyl)oxazole-4-carboxylate (3)

To a solution of Ph$_3$P (159 mg, 0.604 mmol) in DCM (20 mL) was added 12 (153 mg, 0.604 mmol). The resulting mixture was degassed with N$_2$ 3 times and stirred at ambient temperature for 2 h. TEA (122 mg, 1.208 mmol) was added and stirred for 10 min, then a solution of tert-butyl 3-(1-ethoxy-1,3-dioxo-3-(4-phenoxyphenyl)propan-2-ylcarbamoyl)pyrrolidine-1-carboxylate 2 (150 mg, 0.302 mmol) was added and stirred for 15 h. The mixture was diluted with ethyl acetate (50 mL), and washed with sat. Na$_2$S$_2$O$_3$ (20 mL), brine (3×20 mL). The organic layer was dried over Na$_2$SO$_4$, filtered and concentrated to get a residue which was purified by silica gel column chromatography eluting with 1:1 PE/EA to get the title compound (0.11 g, 76%) as a colorless oil. MS (ESI): m/z=422.8 [M−55]$^+$.

2-(1-(tert-butoxycarbonyl)pyrrolidin-3-yl)-5-(4-phenoxyphenyl)oxazole-4-carboxylic Acid (4)

The title compound was obtained using a procedure analogous to the procedure described in 5-(1-(tert-butoxycarbonyl)piperidin-4-yl)-1-(4-phenoxyphenyl)-1H-pyrazole-3-carboxylic acid (see Scheme 46) as yellow oil (110 mg, 100%). MS (ESI): m/z=394.8 [M−55]+ tert-butyl 3-(4-carbamoyl-5-(4-phenoxyphenyl)oxazol-2-yl)pyrrolidine-1-carboxylate (5)

The title compound was obtained using a procedure analogous to the procedure described in tert-butyl 4-carbamoylpiperidine-1-carboxylate (see Scheme 42) as colorless oil (95 mg, 92%). MS (ESI): m/z=393.8 [M−55]+.

5-(4-phenoxyphenyl)-2-(pyrrolidin-3-yl)oxazole-4-carboxamide hydrochloride (6)

The title compound was obtained using a procedure analogous to the procedure described in 1-(4-phenoxyphenyl)-5-(piperidin-4-yl)-1H-pyrazole-3-carboxamide hydrochloride (see Scheme 46) as a white solid (75 mg, 92%). MS (ESI): m/z=349.9 [M+H]+.

Example 48

2-(1-acryloylpyrrolidin-3-yl)-5-(4-phenoxyphenyl)oxazole-4-carboxamide

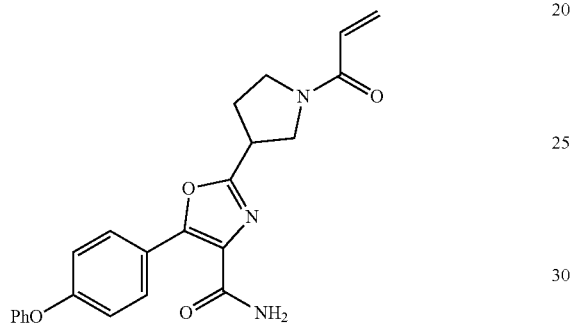

The title compound was obtained using a procedure analogous to the procedure described in Example 1 as an off white solid (50 mg, 64%). 1H NMR (400 MHz, DMSO) δ 8.27-8.22 (m, 2H), 7.61 (s, 1H), 7.58 (s, 1H), 7.45 (t, J=7.9 Hz, 2H), 7.21 (t, J=7.3 Hz, 1H), 7.14-7.06 (m, 4H), 6.67-6.58 (m, 1H), 6.16 (d, J=16.7 Hz, 1H), 5.70 (d, J=10.4 Hz, 1H), 4.05-4.01 (m, 0.5H), 3.97-3.92 (m, 0.5H), 3.90-3.59 (m, 3.5H), 3.53-3.45 (m, 0.5H), 2.45-2.21 (m, 2H). MS (ESI, method A): m/z=404.1 [M+H]+, $t_R$=1.484 min. HPLC: 99.5% (214 nm), 99.3% (254 nm)

Scheme 39

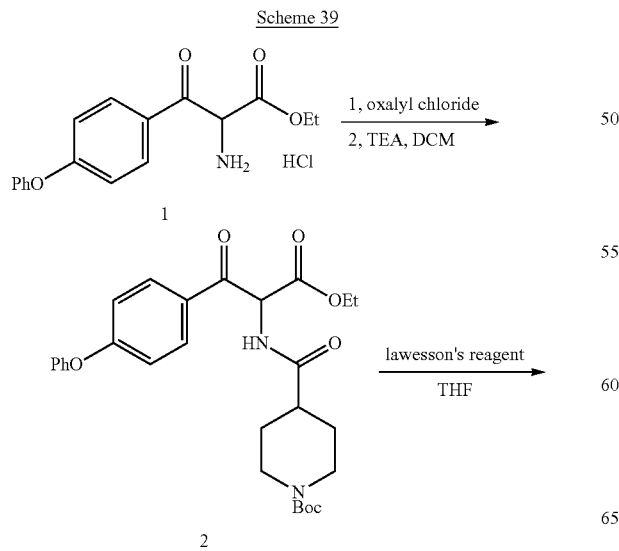

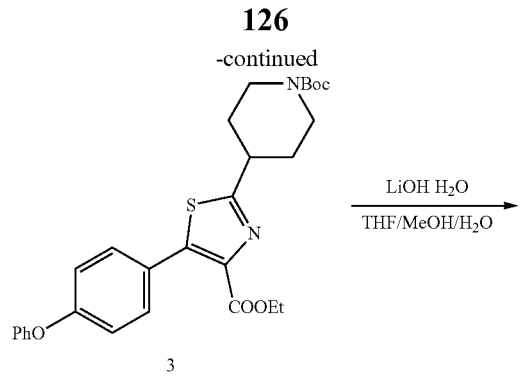

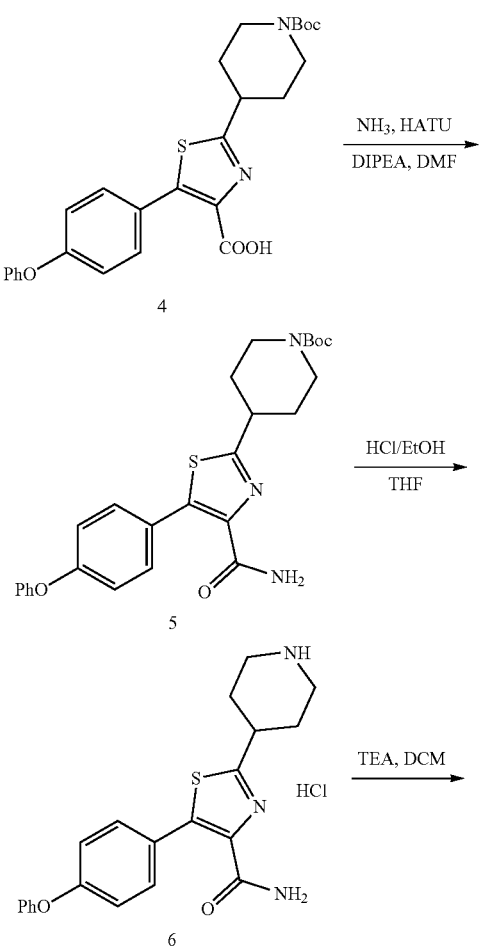

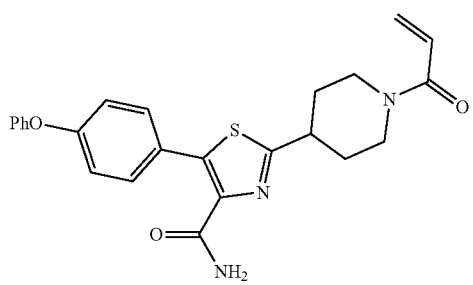

Example 49 tert-butyl-4-(1-ethoxy-1,3-dioxo-3-(4-phenoxyphenyl)propan-2-ylcarbamoyl)piperidine-1-carboxylate (2)

The title compound was obtained using a procedure analogous to the procedures described in the General Scheme and Example 15 as colorless oil (0.18 g, 16%). MS (ESI): m/z=454.8[M−55]⁺ ethyl 2-(1-(tert-butoxycarbonyl)piperidin-4-yl)-5-(4-phenoxyphenyl)thiazole-4-carboxylate (3)

The title compound was obtained using a procedure analogous to the procedure described in tert-butyl 2-carbamothioylpiperidine-1-carboxylate (see Scheme 30) as colorless oil (0.12 g, 67%). MS (ESI): m/z=508.8 [M+H]⁺.

2-(1-(tert-butoxycarbonyl)piperidin-4-yl)-5-(4-phenoxyphenyl)thiazole-4-carboxylic Acid (4)

The title compound was obtained using a procedure analogous to the procedure described in 5-(1-(tert-butoxycarbonyl)piperidin-4-yl)-1-(4-phenoxyphenyl)-1H-pyrazole-3-carboxylic acid (see Scheme 46) as yellow oil (120 mg, 100%). MS (ESI): m/z=480.8 [M+H]⁺.

tert-butyl 4-(4-carbamoyl-5-(4-phenoxyphenyl)thiazol-2-yl)piperidine-1-carboxylate (5)

The title compound was obtained using a procedure analogous to the procedure described in tert-butyl 3-(5-carbamoyl-4-(4-phenoxyphenyl)thiazol-2-yl)piperidine-1-carboxylate (see Scheme 30) as colorless oil (100 mg, 88%). MS (ESI): m/z=479.8[M+H]⁺.

5-(4-phenoxyphenyl)-2-(piperidin-4-yl)thiazole-4-carboxamide hydrochloride (6)

The title compound was obtained using a procedure analogous to the procedure described in 1-(4-phenoxyphenyl)-5-(piperidin-4-yl)-1H-pyrazole-3-carboxamide hydrochloride (see Scheme 46) as a white solid (80 mg, 92%). MS (ESI): m/z=379.8[M+H]⁺.

Example 49

2-(1-acryloylpiperidin-4-yl)-5-(4-phenoxyphenyl)thiazole-4-carboxamide

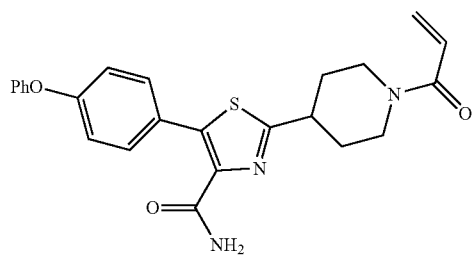 [SMILES: C=CC(=O)N1CCC(c2nc(C(N)=O)c(-c3ccc(Oc4ccccc4)cc3)s2)CC1]

The title compound was obtained using a procedure analogous to the procedure described in Example 51 as an off white solid (20 mg, 24%). ¹H NMR (400 MHz, DMSO) δ 7.68 (s, 1H), 7.56 (d, J=8.7 Hz, 2H), 7.50 (s, 1H), 7.47-7.42 (m, 2H), 7.21 (t, J=7.4 Hz, 1H), 7.10 (d, J=7.7 Hz, 2H), 7.00 (d, J=8.7 Hz, 2H), 6.85 (dd, J=16.7, 10.5 Hz, 1H), 6.12 (dd, J=16.7, 2.4 Hz, 1H), 5.69 (dd, J=10.5, 2.4 Hz, 1H), 4.49 (d, J=12.8 Hz, 1H), 4.15 (d, J=12.8 Hz, 1H), 3.33-3.19 (m, 2H), 2.88 (d, J=11.5 Hz, 1H), 2.12 (d, J=12.8 Hz, 2H), 1.73-1.55 (m, 2H). MS (ESI, method A): m/z=434.0 [M+H]⁺, t_R=1.606 min. HPLC: 95.0% (214 nm), 96.6% (254 nm)

Scheme 40

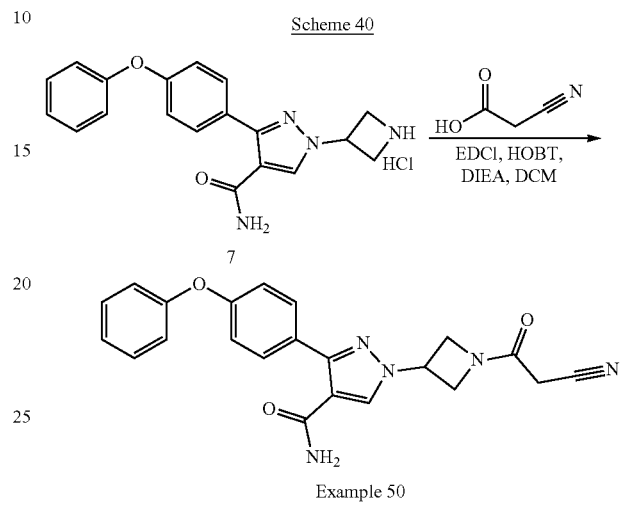

Example 50

Example 50

1-(1-(2-cyanoacetyl)azetidin-3-yl)-3-(4-phenoxyphenyl)-1H-pyrazole-4-carboxamide

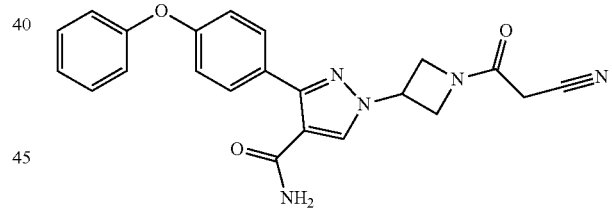

To a solution of 1-(azetidin-3-yl)-3-(4-phenoxyphenyl)-1H-pyrazole-4-carboxamide 7 (See Example 15 scheme, associated data and procedures) (900 mg, 2.4 mmol), 2-cyanoacetic acid (178 mg, 2.1 mmol), EDCI (534 mg, 2.8 mmol) and HOBT (64 mg, 0.48 mmol) in dry DCM (20 mL) was added DIPEA (936 mg, 7.2 mmol) at 0° C. Then the solution was allowed to warm to rt slowly and stirred at rt for 3 h. After the reaction was completed, the solution was washed with water (2×20 mL) and brine (2×20 mL). The organic layer was dried over anhydrous sodium sulfate, filtered and concentrated. The residue was purified by silica gel column eluting with 30:1 DCM/MeOH to afford the title compound (250 mg, 26%) as white solid. ¹H NMR (400 MHz, CDCl₃) δ 8.18 (s, 1H), 7.61-7.50 (m, 2H), 7.43-7.32 (m, 2H), 7.20-7.13 (m, 1H), 7.12-7.03 (m, 4H), 5.65 (s, 2H), 5.24-5.14 (m, 1H), 4.87-4.73 (m, 2H), 4.62-4.49 (m, 21H), 3.35 (s, 2H). MS (ESI, Method A): m/z=402.1 [M+H]⁺, t_R=1.361 min. HPLC: 98.0% (214 nm), 98.6% (254 nm).

Scheme 41

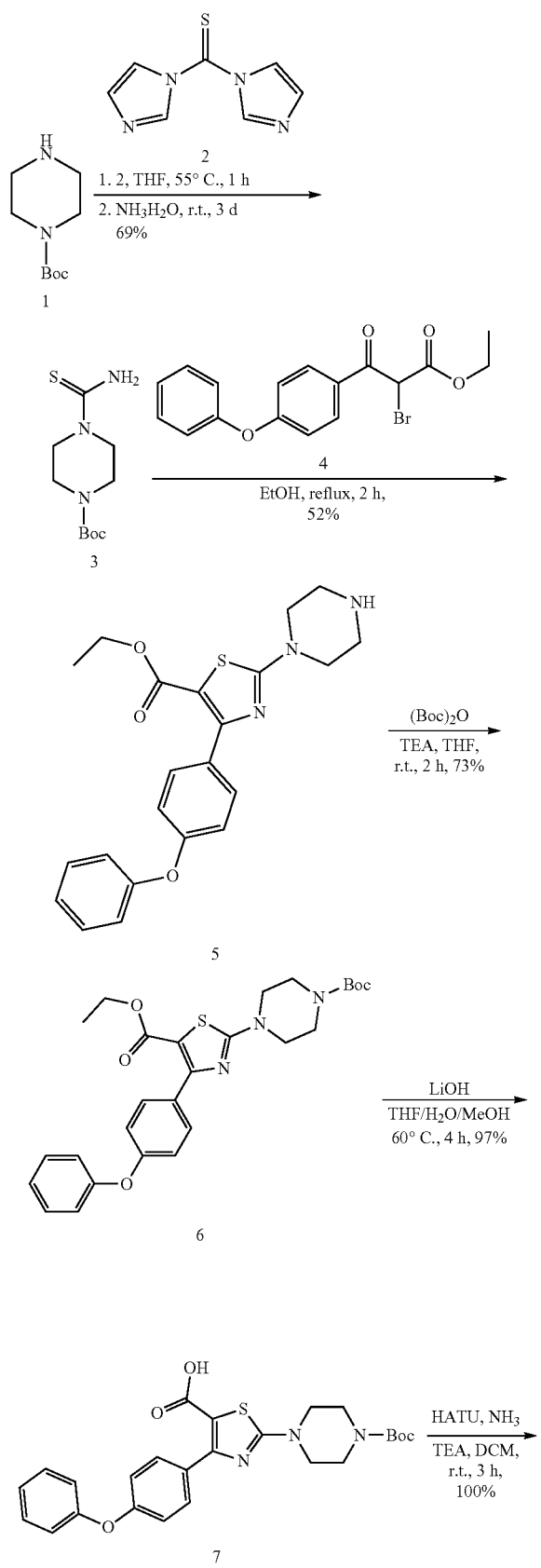

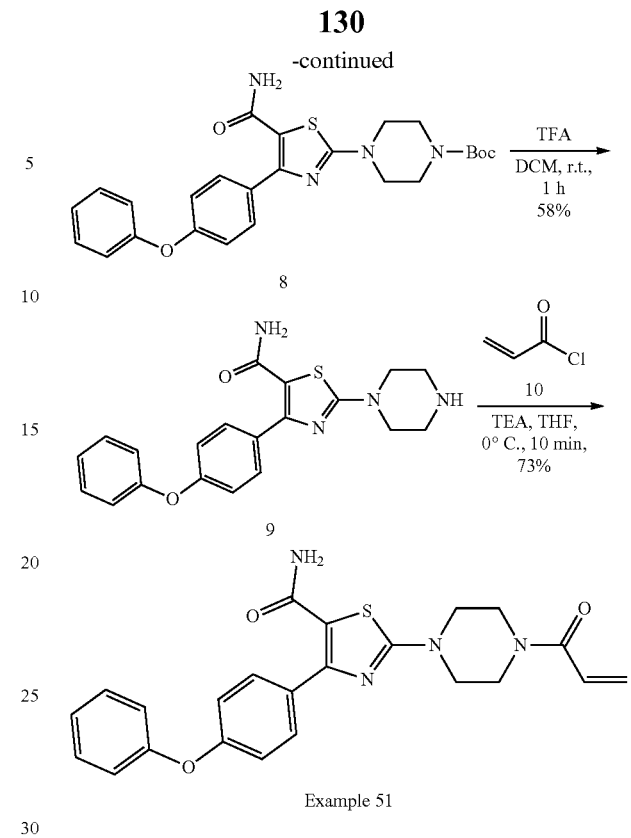

Example 51 tert-butyl 4-carbamothioylpiperazine-1-carboxylate (3)

To a solution of di(1H-imidazol-1-yl)methanethione 2 (2.14 g, 12 mmol) in anhydrous THF (30 mL) was added tert-butyl piperazine-1-carboxylate 1 (1.86 g, 10 mmol) at ambient temperature. The mixture was allowed to stir at ambient temperature for 2 h, and then the mixture was heated to 55° C. for 1 h. The mixture was concentrated in vacuum to about half the volume. To the remaining reaction mixture was added a 2 M ammonia in methanol (20 mL) and was allowed to stir at ambient temperature for 3 days. The solvent was removed and the residue was purified by silica gel column chromatography eluting with 50:1 DCM/MeOH to afford the title compound (1.7 g, 69%) as white solid. MS (ESI): m/z=246.1 [M+H]$^+$.

ethyl 4-(4-phenoxyphenyl)-2-(piperazin-1-yl)thiazole-5-carboxylate (5)

To a solution of ethyl 2-bromo-3-oxo-3-(4-phenoxyphenyl)propanoate 4 (362 mg, 1 mmol) in ethanol (10 mL) was added tert-butyl 4-carbamothioylpiperazine-1-carboxylate 3 (245 mg, 1 mmol) at ambient temperature. The mixture was then heated to reflux and stirred for 2 h. After cooling to ambient temperature, the solvent was removed and the residue was purified by silica gel column chromatography eluting with 40:1 to 20:1 DCM/MeOH to afford the title compound (214 mg, 52%) as brown solid. MS (ESI): m/z=410.1 [M+H]$^+$.

Ethyl-2-(4-(tert-butoxycarbonyl)piperazin-1-yl)-4-(4-phenoxyphenyl)thiazole-5-carboxylate (6)

To the compound of ethyl 4-(4-phenoxyphenyl)-2-(piperazin-1-yl)thiazole-5-carboxylate 5 (214 mg, 0.51 mmol) was added di-tert-butyl dicarbonate (134 mg, 0.6 mmol) and TEA (0.2 mL, 1.5 mmol) at ambient temperature. The mixture was then stirred at ambient temperature for 2 h. The solvent was removed and the residue was purified by silica gel column chromatography eluting with 50:1 DCM/MeOH to afford the title compound (190 mg, 73%) as brown solid. MS (ESI): m/z=510.1 [M+H]$^+$.

2-(4-(tert-butoxycarbonyl)piperazin-1-yl)-4-(4-phenoxyphenyl)thiazole-5-carboxylic Acid (7)

To a solution of ethyl 2-(4-(tert-butoxycarbonyl)piperazin-1-yl)-4-(4-phenoxyphenyl)thiazole-5-carboxylate 6 (190 mg, 0.37 mmol) in THF (50 mL)/H$_2$O(1 mL)/MeOH (3 mL) was added lithium hydroxide (30 mg, 0.74 mmol) at ambient temperature. The mixture was then heated to 60° C. and stirred for 2 h. After cooling to ambient temperature, the solvent was removed and the residue was purified by silica gel column chromatography eluting with 10:1 DCM/MeOH to afford the title compound (173 mg, 97%) as white solid. MS (ESI): m/z=482.0 [M+H]$^+$.

tert-butyl 4-(5-carbamoyl-4-(4-phenoxyphenyl)thiazol-2-yl)piperazine-1-carboxylate (8)

To a solution of 2-(4-(tert-butoxycarbonyl)piperazin-1-yl)-4-(4-phenoxyphenyl)thiazole-5-carboxylic acid 7 (173 mg, 4.6 mmol) in DCM (10 mL) was added HATU (164 mg, 0.43 mmol) at ambient temperature. The mixture was degassed three times with ammonia gas and stirred at ambient temperature under ammonia atmosphere for 6 h. The solvent was removed and the residue was purified by silica gel column chromatography eluting with 30:1 DCM/MeOH to afford the title compound (170 mg, 100%) as white solid. MS (ESI): m/z=481.1 [M+H]$^+$.

4-(4-phenoxyphenyl)-2-(piperazin-1-yl)thiazole-5-carboxamide (9)

A solution of tert-butyl 4-(5-carbamoyl-4-(4-phenoxyphenyl)thiazol-2-yl)piperazine-1-carboxylate 8 (170 mg, 0.35 mmol) in DCM (5 mL) and TFA (1 mL) at ambient temperature was stirred for 1 h. The solvent was removed and the residue was purified by silica gel column chromatography eluting with 20:1 to 10:1 DCM/MeOH to afford the title compound (110 mg, 58%) as white solid.

Example 51

2-(4-acryloylpiperazin-1-yl)-4-(4-phenoxyphenyl)thiazole-5-carboxamide

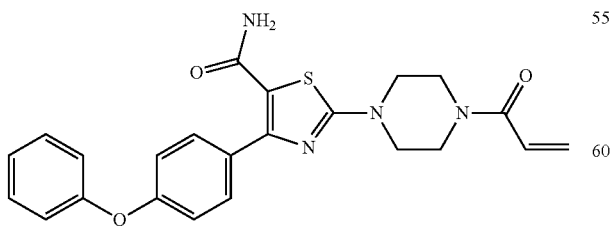

To a solution of 4-(4-phenoxyphenyl)-2-(piperazin-1-yl)thiazole-5-carboxamide 9 (110 mg, 0.22 mmol) in DCM (5 mL) was added TEA (0.1 mL, 0.66 mmol) and acryloyl chloride 10 (0.20 mg, 0.22 mmol) at 0° C. The mixture was stirred at 0° C. for 10 minutes. The solvent was removed and the residue was purified by Prep-TLC eluting with 25:1 DCM/MeOH to afford the title compound (70 mg, 73%) as white solid. $^1$H NMR (400 MHz, MeOD) δ 7.66-7.61 (m, 2H), 7.37-7.43 (m, 2H), 7.18 (t, J=7.4 Hz, 1H), 7.10-7.04 (m, 4H), 6.83 (dd, J=16.8, 10.6 Hz, 1H), 6.27 (dd, J=16.8, 1.8 Hz, 1H), 5.81 (dd, J=10.6, 1.9 Hz, 1H), 3.87-3.78 (m, 4H), 3.69-3.61 (m, 4H). MS (ESI, method A): m/z=435.0 [M+H]$^+$, t$_R$=1.539 min., HPLC: 95.5% (214 nm), 96.4% (254 nm).

Scheme 42

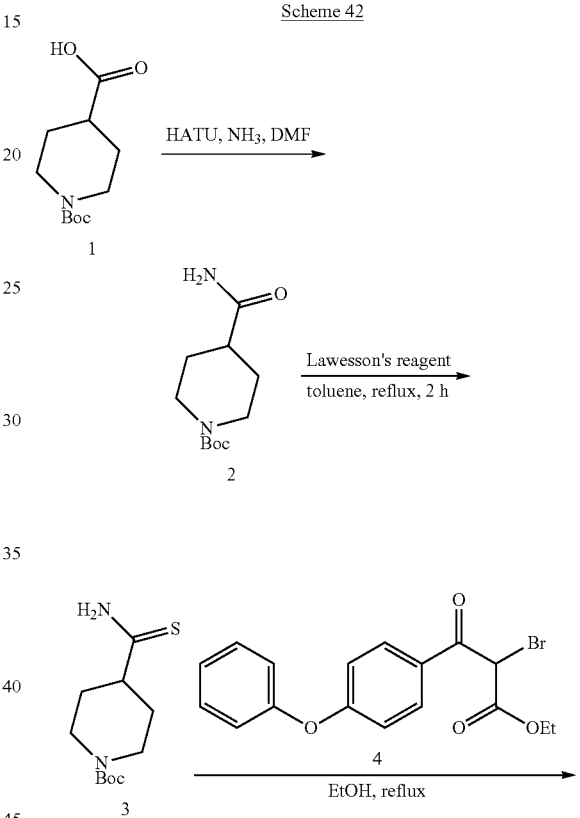

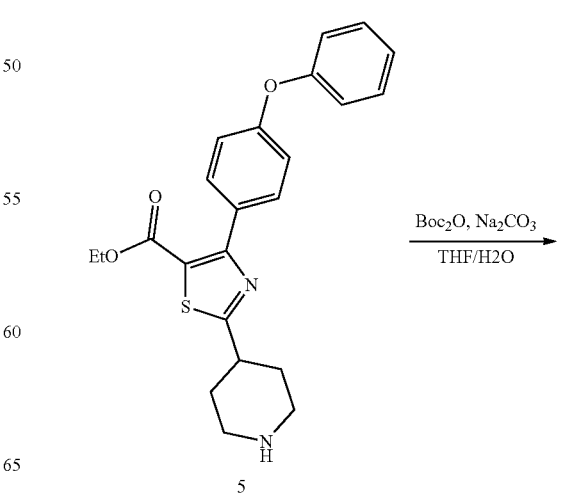

133

-continued

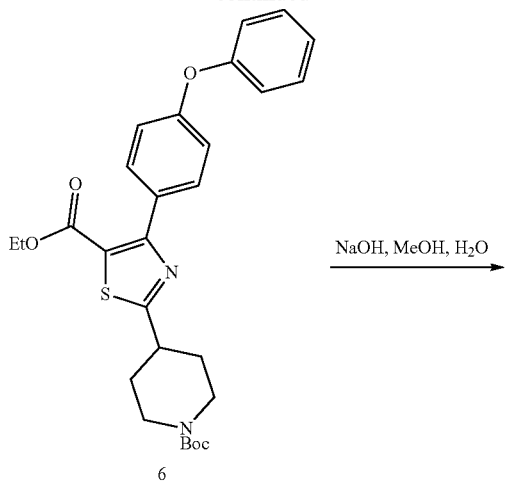

6

NaOH, MeOH, H₂O →

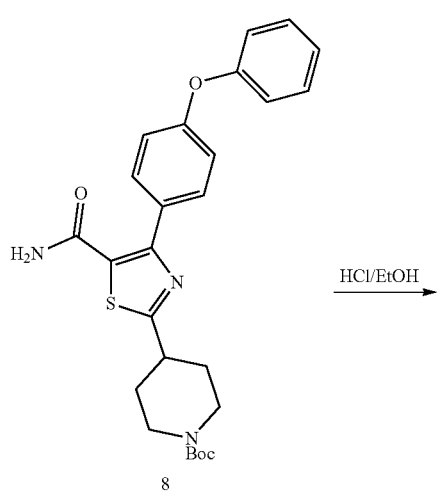

7

NH₃, HATU, DMF →

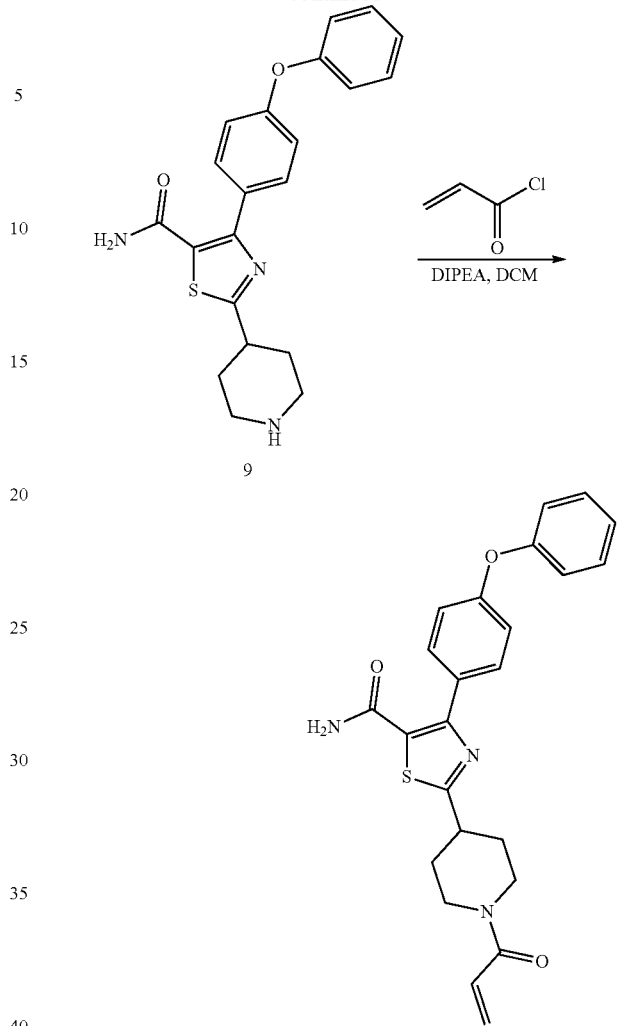

Example 52 tert-butyl 4-carbamoylpiperidine-1-carboxylate (2)

To a mixture of 1-(tert-butoxycarbonyl)piperidine-4-carboxylic acid 1 (2.29 g, 10 mmol), DIEA (3.87 g, 30 mmol) and HATU (4.18 g, 11 mmol) in DMF (50 mL) was added NH₃ by bubbling for 20 min. The resulting mixture was stirred at rt overnight. The mixture was diluted with water (200 mL) and extracted with EA (2×50 mL). The organic layers were combined, washed with brine, dried over sodium sulfate, filtered and concentrated. The residue was applied onto silica gel column eluting with EA to get the title compound (1.3 g, 56%) as white solid. MS (ESI): m/z=173.2 [M+H−56]⁺.

tert-butyl 4-carbamothioylpiperidine-1-carboxylate (3)

The title compound was obtained using a procedure analogous to the procedure described in cyclopentanecarbothioamide (see Scheme 30) as pale yellow solid (0.35 g, 29%). MS (ESI): m/z=245.2 [M+H]⁺.

ethyl 4-(4-phenoxyphenyl)-2-(piperidin-4-yl)thiaz-
ole-5-carboxylate (5)

The crude of the title compound was obtained using a procedure analogous to the procedure described in ethyl 2-cyclopentyl-4-(4-phenoxyphenyl)thiazole-5-carboxylate (see Scheme A-2) as yellow oil (0.90 g, overweight). MS (ESI): m/z=408.8 [M+H]+.

ethyl 4-(4-phenoxyphenyl)-2-(piperidin-4-yl)thiaz-
ole-5-carboxylate (6)

The title compound was obtained using a procedure analogous to the procedure described in ethyl 2-(4-(tert-butoxycarbonyl)piperazin-1-yl)-4-(4-phenoxyphenyl)thiazole-5-carboxylate (see Scheme 37) as yellow solid (0.30 g, 30%, two steps). MS (ESI): m/z=509.1 [M+H]+.

2-(1-(tert-butoxycarbonyl)piperidin-4-yl)-4-(4-phe-
noxyphenyl)thiazole-5-carboxylic Acid (7)

The title compound was obtained using a procedure analogous to the procedure described in 5-(1-(tert-butoxycarbonyl)piperidin-4-yl)-4'-phenoxybiphenyl-2-carboxylic acid (see Scheme 45) as yellow oil (250 mg, overweight). MS (ESI): m/z=481.0 [M+H]+.

tert-butyl 4-(5-carbamoyl-4-(4-phenoxyphenyl)thi-
azol-2-yl)piperidine-1-carboxylate (8)

The title compound was obtained using a procedure analogous to the procedure described in tert-butyl-3-(4-carbamoyl-3-(4-phenoxyphenyl)-1H-pyrazol-1-yl)pyrrolidine-1-carboxylate (see Scheme 23) as pale yellow solid (250 mg, overweight). MS (ESI): m/z=480.1 [M+H]+.

4-(4-phenoxyphenyl)-2-(piperidin-4-yl)thiazole-5-
carboxamide (9)

The title compound was obtained using a procedure analogous to the procedure described in 1-(4-phenoxyphenyl)-5-(piperidin-4-yl)-1H-pyrazole-3-carboxamide hydrochloride (see Scheme 46) as white solid (300 mg, overweight). MS (ESI): m/z=380.1 [M+H]+.

Example 52

2-(1-acryloylpiperidin-4-yl)-4-(4-phenoxyphenyl)
thiazole-5-carboxamide

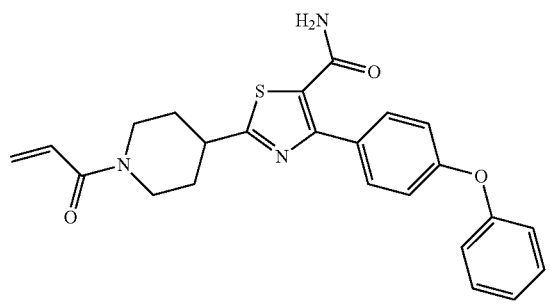 [SMILES: C=CC(=O)N1CCC(c2nc(-c3ccc(Oc4ccccc4)cc3)c(C(N)=O)s2)CC1]

The title compound was obtained using a procedure analogous to the procedure described in Example 15 as white solid (50 mg, 23%, four steps). 1H NMR (300 MHz, DMSO) δ 7.76-7.69 (m, 4H), 7.42 (t, J=7.4 Hz, 2H), 7.19 (t, J=7.4 Hz, 1H), 7.09-7.00 (m, 4H), 6.84 (dd, J=16.7, 10.4 Hz, 1H), 6.10 (dd, J=16.7, 2.4 Hz, 1H), 5.68 (dd, J=10.4, 2.4 Hz, 1H), 4.52-4.41 (m, 1H), 4.19-4.08 (m, 1H), 3.32-3.15 (m, 2H), 2.90-2.78 (m, 1H), 2.14-2.06 (m, 2H), 1.73-1.46 (m, 2H). MS (ESI, method A): m/z=434.0 [M+H]+, $t_R$=1.540 min. HPLC: 96% (214 nm), 96% (254 nm)

Scheme 43

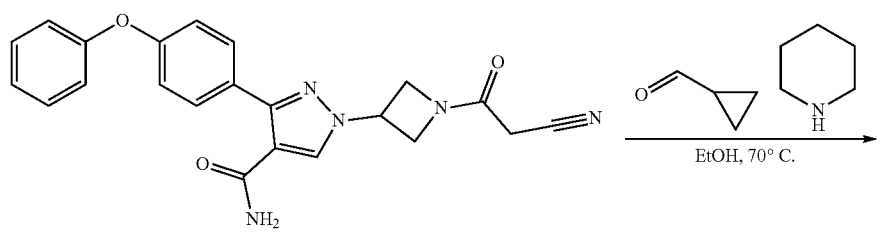

Example 50

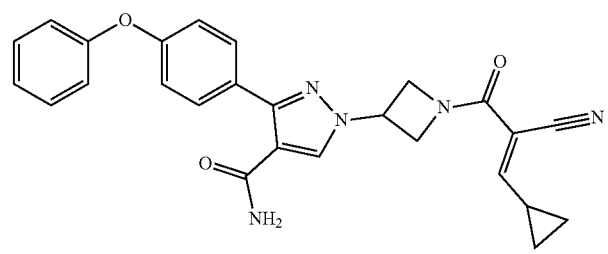

Example 53

Example 53

(E)-1-(1-(2-cyano-3-cyclopropylacryloyl)azetidin-3-yl)-3-(4-phenoxyphenyl)-1H-pyrazole-4-carboxamide

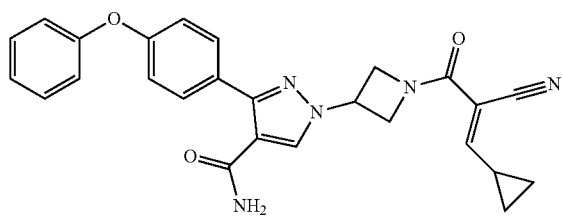 [SMILES: N#C/C(=C\C1CC1)C(=O)N1CC(n2cc(C(N)=O)c(-c3ccc(Oc4ccccc4)cc3)n2)C1]

To a solution of 1-(1-(2-cyanoacetyl)azetidin-3-yl)-3-(4-phenoxyphenyl)-1H-pyrazole-4-carboxamide (100 mg, 0.25 mmol) and piperidine (2 drops) in EtOH (10 mL) was added cyclopropanecarbaldehyde (70 mg, 1.0 mmol). Then the solution was stirred at 70° C. for 1 h. After the reaction was completed, the solution was concentrated and purified by Prep-TLC with 10:1 DCM/MeOH to give the crude product (70 mg) and then purified by Prep-HPLC (ACN/H$_2$O=42%, 0.1% FA) to afford the title compound (15 mg, 13%) as a white solid. $^1$H NMR (400 MHz, CDCl$_3$) δ 8.16 (s, 1H), 7.64-7.57 (m, 2H), 7.45-7.37 (m, 2H), 7.22-7.16 (m, 1H), 7.15-7.03 (m, 5H), 5.60 (s, 2H), 5.23-5.13 (m, 1H), 5.11-4.95 (m, 2H), 4.68-4.54 (m, 2H), 2.16-2.05 (m, 1H), 1.33-1.29 (m, 2H), 1.02-0.95 (m, 2H). MS (ESI, Method A): m/z=454.1 [M+H]$^+$, t$_R$=1.485 min. HPLC: 100% (214 nm), 100% (254 nm).

Scheme 44

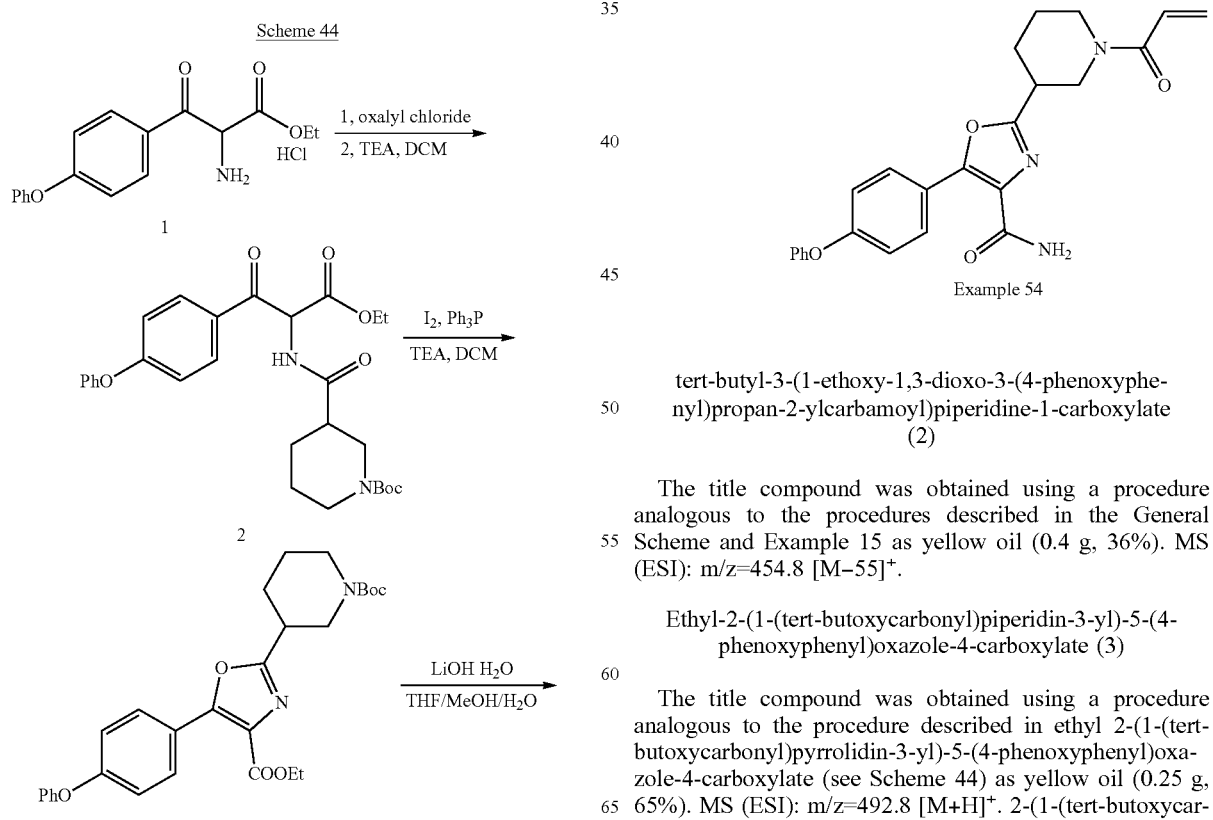

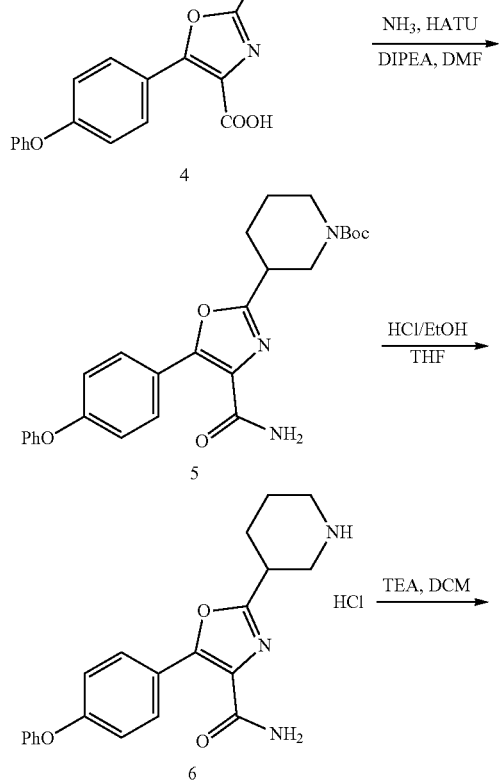

Example 54 tert-butyl-3-(1-ethoxy-1,3-dioxo-3-(4-phenoxyphenyl)propan-2-ylcarbamoyl)piperidine-1-carboxylate (2)

The title compound was obtained using a procedure analogous to the procedures described in the General Scheme and Example 15 as yellow oil (0.4 g, 36%). MS (ESI): m/z=454.8 [M−55]$^+$.

Ethyl-2-(1-(tert-butoxycarbonyl)piperidin-3-yl)-5-(4-phenoxyphenyl)oxazole-4-carboxylate (3)

The title compound was obtained using a procedure analogous to the procedure described in ethyl 2-(1-(tert-butoxycarbonyl)pyrrolidin-3-yl)-5-(4-phenoxyphenyl)oxazole-4-carboxylate (see Scheme 44) as yellow oil (0.25 g, 65%). MS (ESI): m/z=492.8 [M+H]$^+$. 2-(1-(tert-butoxycarbonyl)piperidin-3-yl)-5-(4-phenoxyphenyl)oxazole-4-carboxylic acid (4). The title compound was obtained using a procedure analogous to the procedure described in 5-(1-(tert-butoxycarbonyl)piperidin-4-yl)-1-(4-phenoxyphenyl)-1H-pyrazole-3-carboxylic acid (see Scheme 46) as yellow oil (0.25 g, 100%). MS (ESI): m/z=464.8 [M+H]$^+$.

tert-butyl 3-(4-carbamoyl-5-(4-phenoxyphenyl)oxazol-2-yl)piperidine-1-carboxylate (5)

The title compound was obtained using a procedure analogous to the procedure described in tert-butyl 3-(5-carbamoyl-4-(4-phenoxyphenyl)thiazol-2-yl)piperidine-1-carboxylate (see Scheme 30) as yellow oil (0.2 g, 84%). MS (ESI): m/z=407.8 [M−55]$^+$.

5-(4-phenoxyphenyl)-2-(piperidin-3-yl)oxazole-4-carboxamide hydrochloride (6)

The title compound was obtained using a procedure analogous to the procedure described in 1-(4-phenoxyphenyl)-5-(piperidin-4-yl)-1H-pyrazole-3-carboxamide hydrochloride (see Scheme 46) as brown oil (180 mg, 100%). MS (ESI): m/z=363.8[M+H]$^+$.

Example 54

2-(1-acryloylpiperidin-3-yl)-5-(4-phenoxyphenyl)oxazole-4-carboxamide

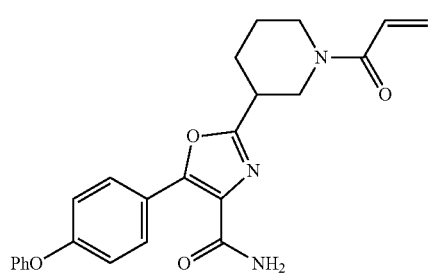 [SMILES: C=CC(=O)N1CCCC(c2nc(C(N)=O)c(-c3ccc(Oc4ccccc4)cc3)o2)C1]

The title compound was obtained using a procedure analogous to the procedure described in Example 1 as a yellow solid (70 mg, 37%). $^1$H NMR (400 MHz, DMSO) δ 8.24 (d, J=7.2 Hz, 2H), 7.57 (s, 1.5H), 7.50 (s, 0.5H), 7.45 (t, J=7.9 Hz, 2H), 7.21 (t, J=7.4 Hz, 1H), 7.11 (d, J=3.1 Hz, 2H), 7.08 (d, J=4.2 Hz, 2H), 6.96-6.78 (m, 1H), 6.13 (t, J=18 Hz, 1H), 5.75-5.57 (m, 1H), 4.51 (d, J=11.6 Hz, 0.5H), 4.08 (d, J=12 Hz, 0.5H), 3.93 (d, J=13.2 Hz, 0.5H), 3.85-3.73 (m, 0.8H), 3.34-3.20 (m, 2H), 3.10-2.97 (m, 0.7H), 2.27-2.09 (m, 1H), 2.07-1.64 (m, 2H), 1.60-1.43 (m, 1H). MS (ESI, method F): m/z=418.1 [M+H]$^+$, $t_R$=1.679 (min). HPLC: 100% (214 nm), 100% (254 nm).

Scheme 45

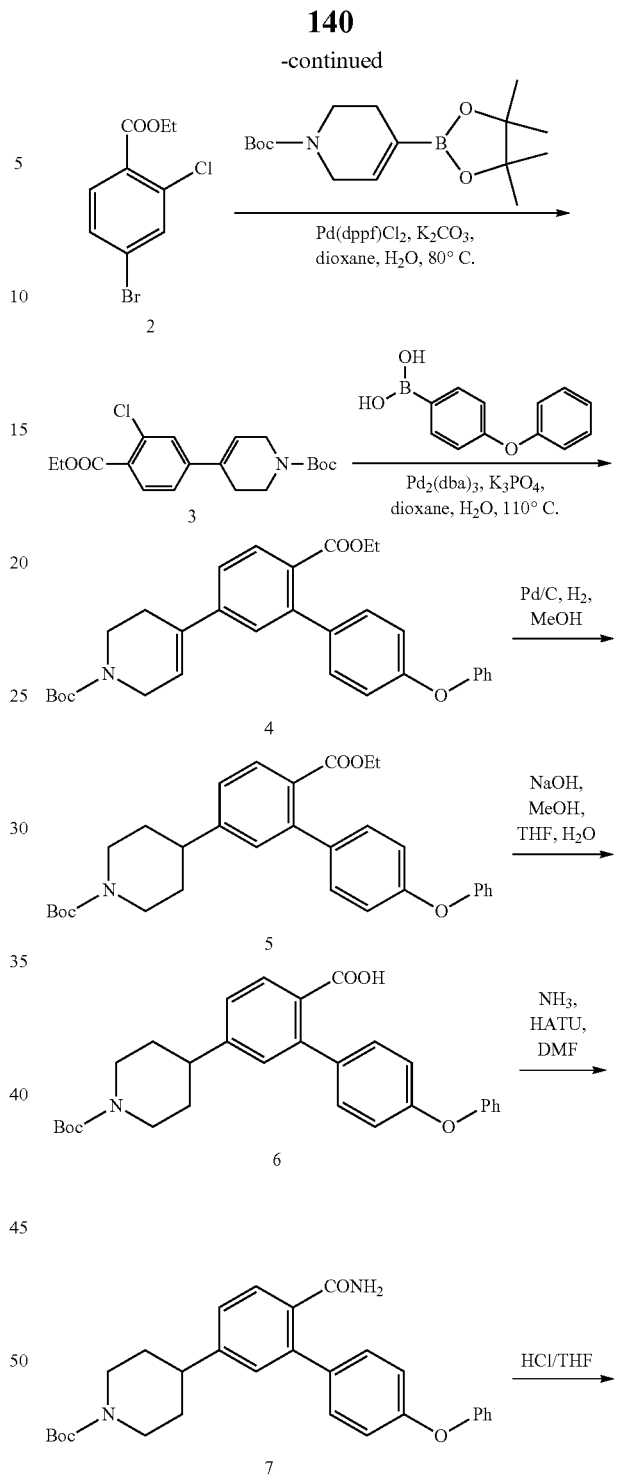

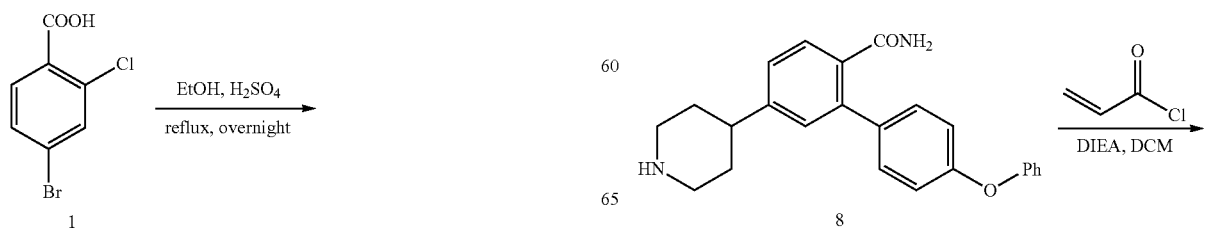

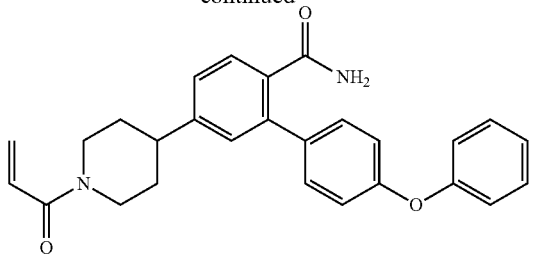

Example 55 ethyl 4-bromo-2-chlorobenzoate (2)

To a mixture of 4-bromo-2-chlorobenzoic acid 1 (1.9 g, 8.1 mmol) in EtOH (50 mL) was added $H_2SO_4$ (5 mL) dropwise carefully at 0° C. The resulting mixture was refluxed overnight. The volatile phase removed under reduced pressure. The residue was diluted with EA (100 mL), which was washed with water (2×50 mL) and brine, dried over sodium sulfate, filtered and concentrated. This resulted in the title compound (2.0 g, 95%) as brown oil. MS (ESI): m/z=263.0/265.0 [M+H]$^+$.

tert-butyl 4-(3-chloro-4-(ethoxycarbonyl)phenyl)-5,6-dihydropyridine-1(2H)-carboxylate (3)

A mixture of ethyl 4-bromo-2-chlorobenzoate 2 (0.53 g, 2.0 mmol), tert-butyl 4-(4,4,5,5-tetramethyl-1,3,2-dioxaborolan-2-yl)-5,6-dihydropyridine-1(2H)-carboxylate (0.74 g, 2.4 mmol), potassium carbonate (0.83 g, 6.0 mmol) and Pd(dppf)Cl$_2$ (0.15 g, 0.2 mmol) in dioxane/$H_2O$ (20 mL/5 mL) was stirred at 80° C. for 4 h under $N_2$ atmosphere. The volatile phase was removed under reduced pressure. The residue was applied onto silica gel column eluting with 6:1 PE/EA to get the title compound (0.7 g, 96%) as yellow oil. MS (ESI): m/z=310.1 [M+H−56]$^+$.

tert-butyl 4-(6-(ethoxycarbonyl)-4'-phenoxybiphenyl-3-yl)-5,6-dihydropyridine-1(2H)-carboxylate (4)

A mixture of tert-butyl 4-(3-chloro-4-(ethoxycarbonyl) phenyl)-5,6-dihydropyridine-1(2H)-carboxylate 3 (200 mg, 0.66 mmol), 4-phenoxyphenylboronic acid (172 mg, 0.80 mmol), $K_3PO_4$ (414 mg, 2.0 mmol), tricyclohexylphosphine (40 mg, 0.14 mmol) and Pd$_2$(dba)$_3$ (64 mg, 0.07 mmol) in dioxane/$H_2O$ (15 mL/3 mL) was stirred at 110° C. overnight under $N_2$ atmosphere. The volatile phase was removed under reduced pressure. The residue was applied onto silica gel column eluting with 6:1 PE/EA to get the title compound (200 mg, 61%) as yellow oil. MS (ESI): m/z=500.0 [M+H]$^+$.

tert-butyl 4-(6-(ethoxycarbonyl)-4'-phenoxybiphenyl-3-yl)piperidine-1-carboxylate (5)

A mixture of 4-(6-(ethoxycarbonyl)-4'-phenoxybiphenyl-3-yl)-5,6-dihydropyridine-1(2H)-carboxylate 4 (180 mg, 0.36 mmol) and Pd/C (wet 10%, 18 mg) in MeOH (10 mL) was stirred at rt under $H_2$ atmosphere for 5 h. The solid was filtered off and the filtrate was concentrated under reduced pressure. This resulted in the title compound (180 mg, 99%) as colorless oil, which was used directly for the next step. MS (ESI): m/z=524.0 [M+Na]$^+$.

5-(1-(tert-butoxycarbonyl)piperidin-4-yl)-4'-phenoxybiphenyl-2-carboxylic acid (6)

A mixture of tert-butyl 4-(6-(ethoxycarbonyl)-4'-phenoxybiphenyl-3-yl)piperidine-1-carboxylate 5 (180 mg, 0.36 mmol) and NaOH (72 mg, 1.8 mmol) in THF/MeOH/$H_2O$ (5 mL/5 mL/5 mL) was stirred at rt overnight. The volatile phase was removed under reduced pressure. The PH of which was adjusted to 3 by HCl (1 N), which was extracted with EA (2×30 mL). The organic layers were combined, washed with brine, dried over sodium sulfate, filtered and concentrated. This resulted in the title compound (180 mg, overweight) in colorless oil, which was used directly for the next step. MS (ESI): m/z=374.1 [M+H−Boc]$^+$.

tert-butyl 4-(6-carbamoyl-4'-phenoxybiphenyl-3-yl) piperidine-1-carboxylate (7)

The title compound was obtained using a procedure analogous to the procedure described in tert-butyl-3-(4-carbamoyl-3-(4-phenoxyphenyl)-1H-pyrazol-1-yl)pyrrolidine-1-carboxylate (see Scheme 23) as pale yellow solid (200 mg, overweight). MS (ESI): m/z=416.8 [M+H−56]$^+$.

tert-butyl 4-(6-carbamoyl-4'-phenoxybiphenyl-3-yl) piperidine-1-carboxylate (8)

The title compound was obtained using a procedure analogous to the procedure described in 1-(4-phenoxyphenyl)-5-(piperidin-4-yl)-1H-pyrazole-3-carboxamide hydrochloride (see Scheme 46) as white solid (200 mg, overweight). MS (ESI): m/z=373.1 [M+H]$^+$.

Example 55

5-(1-acryloylpiperidin-4-yl)-4'-phenoxybiphenyl-2-carboxamide

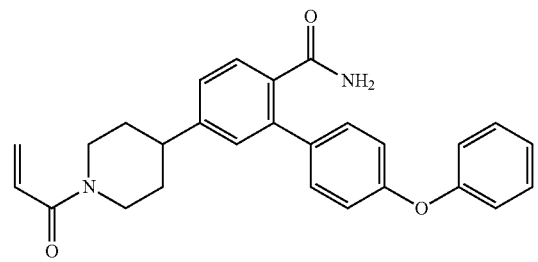 [SMILES: C=CC(=O)N1CCC(c2ccc(C(N)=O)c(-c3ccc(Oc4ccccc4)cc3)c2)CC1]

The title compound was obtained using a procedure analogous to the procedure described in Example 61 as white solid (70 mg, 20%). $^1$H NMR (300 MHz, CDCl$_3$) δ 7.75 (d, J=7.9 Hz, 1H), 7.44-7.32 (m, 4H), 7.23-7.28 (m, 1H), 7.20-7.12 (m, 2H), 7.11-6.99 (m, 4H), 6.62 (dd, J=16.5 Hz, 10.5 Hz, 1H), 6.31 (dd, J=16.5 Hz, 1.8 Hz, 1H), 5.73 (brs, 1H), 5.71 (dd, J=10.5 Hz, 1.8 Hz, 1H), 5.35 (brs, 1H), 4.99-4.74 (m, 1H), 4.24-4.03 (m, 1H), 3.30-3.05 (m, 1H), 2.97-2.58 (m, 2H), 2.04-1.88 (m, 2H), 1.83-1.58 (m, 2H). MS (ESI, method A): m/z=427.1 [M+H]$^+$, $t_R$=1.563 min. HPLC: 99% (214 nm), 99% (254 nm).

Scheme 46
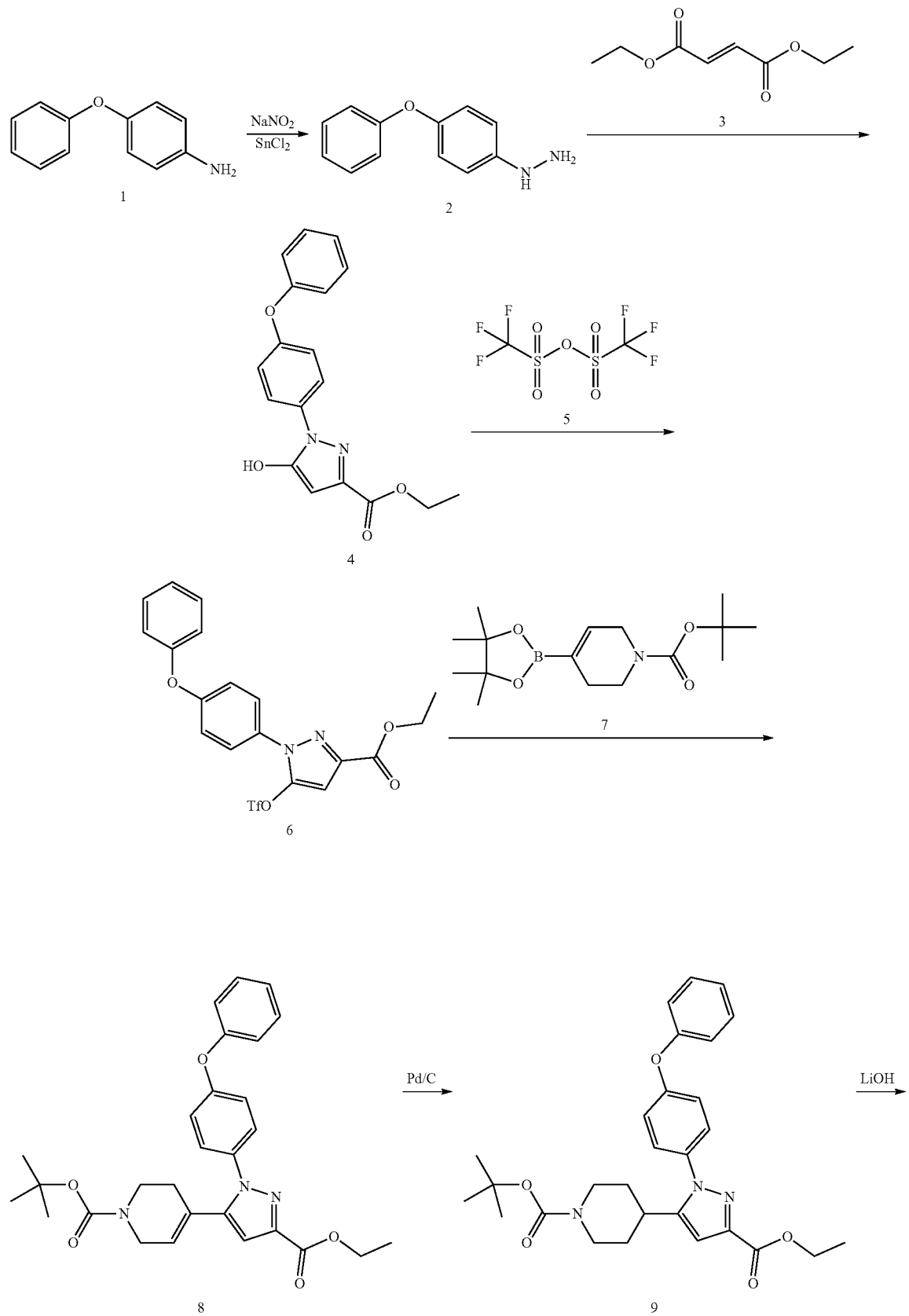

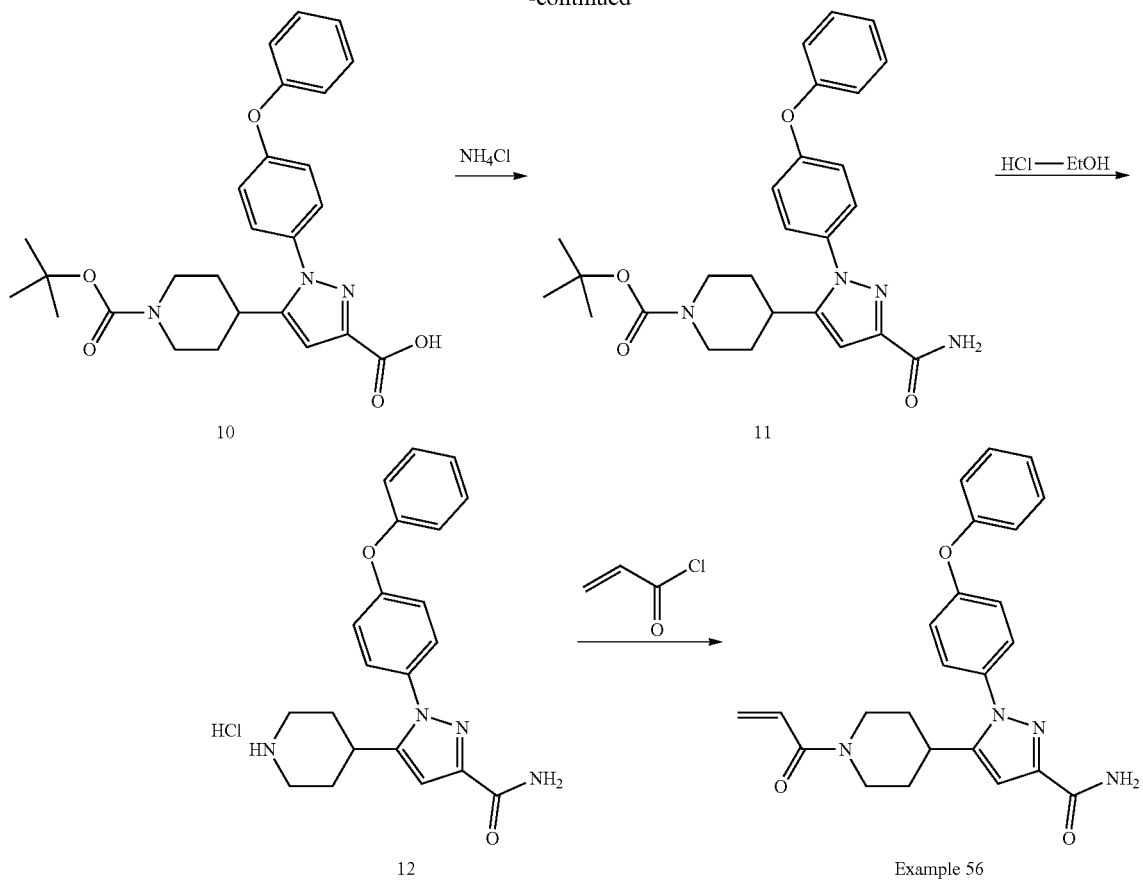

(4-phenoxyphenyl)hydrazine (2)

To a solution of 4-phenoxybenzenamine 1 (1.0 g, 5.4 mmol) in HCl (100 mL) was added NaNO$_2$ (700 mg, 10.1 mmol) at 0° C. Then the mixture was stirred at 0° C. for 1 h. A solution of SnCl$_2$ (5.0 g, 22.1 mmol) in HCl (100 mL) was added to the mixture, and the resulting mixture was stirred at rt for 3 h. Aqueous NaOH (3N) was added to adjust pH to 10, and the mixture was extracted with EA (3×50 mL), the combined organic phase was washed with brine (20 mL), dried over Na$_2$SO$_4$. The solvent was removed under reduced pressure to give a crude title compound (567 mg, 56%) as a yellow solid, which was used to next step without further purification. MS (ESI): m/z=201.0 [M+H]$^+$.

ethyl 5-hydroxy-1-(4-phenoxyphenyl)-1H-pyrazole-3-carboxylate (4)

To the solution of diethyl fumarate 3 (260 mg, 1.5 mmol) in EtOH (25 mL) was added (4-phenoxyphenyl)hydrazine 2 (254 mg, 1.3 mmol), and the resulting solution was stirred overnight at 80° C. The solvent was evaporated under vacuum and the crude residue was diluted with water (30 mL). The solution was extracted with ethyl acetate (3×30 mL). The organic layers were combined, dried over anhydrous sodium sulfate, filtered and concentrated. The residue was purified by silica gel column chromatography eluting with 20:1 DCM/MeOH to afford the title compound (174 mg, 42%) as a yellow solid. MS (ESI): m/z=325.1 [M+H]$^+$.

ethyl 1-(4-phenoxyphenyl)-5-(trifluoromethylsulfonyloxy)-1H-pyrazole-3-carboxylate (6)

To a solution of ethyl 5-hydroxy-1-(4-phenoxyphenyl)-1H-pyrazole-3-carboxylate 4 (170 mg, 0.5 mmol) in DCM (20 mL) was added trifluoromethanesulfonic anhydride 5 (295 mg, 1.0 mmol) and stirred for 1 h at −30° C. under N$_2$ atmosphere. The mixture was poured into water (60 mL), and the solution was extracted with ethyl acetate (3×30 mL). The organic layers were combined, dried over anhydrous sodium sulfate, filtered and concentrated. The residue was purified by silica gel column chromatography eluting with 5:1 PE/EA to afford the title compound (210 mg, 92%) as a yellow solid. MS (ESI): m/z=457.0 [M+H]$^+$.

tert-butyl-4-(3-(ethoxycarbonyl)-1-(4-phenoxyphenyl)-1H-pyrazol-5-yl)-5,6-dihydropyridine-1(2H)-carboxylate (8)

To a solution of ethyl 1-(4-phenoxyphenyl)-5-(trifluoromethylsulfonyloxy)-1H-pyrazole-3-carboxylate 6 (210 mg, 0.5 mmol), K$_2$CO$_3$ (552 mg, 4.0 mmol) and tert-butyl 4-(4,4,5,5-tetramethyl-1,3,2-dioxaborolan-2-yl)-5,6-dihydropyridine-1(2H)-carboxylate 7 (201 mg, 0.6 mmol) in dioxane/H$_2$O (10:1, 20 mL) was added Pd(dppf)Cl$_2$ (327 mg, 0.2 mmol) under nitrogen atmosphere, and the mixture was degassed with nitrogen 6 times, then heated to 90° C. and stirred overnight under nitrogen atmosphere. After cooling to room temperature, the solvent was evaporated and the crude product was purified by silica gel column chromatography eluting with 20:1 DCM/MeOH to afford the title compound (95 mg, 42%) as a yellow solid. MS (ESI): m/z=490.2[M+H]+.

tert-butyl-4-(3-(ethoxycarbonyl)-1-(4-phenoxyphenyl)-1H-pyrazol-5-yl)piperidine-1-carboxylate (9)

The mixture of tert-butyl 4-(3-(ethoxycarbonyl)-1-(4-phenoxyphenyl)-1H-pyrazol-5-yl)-5,6-dihydropyridine-1 (2H)-carboxylate 8 (95 mg, 0.2 mmol), Pd/C (10% palladium on carbon, 56.5% water, 48 mg) and MeOH (20 mL) was degassed with $H_2$ 6 times and then stirred under $H_2$ at rt for 1 h. Then the mixture was filtered and the filtrate was concentrated in vacuo to give the title compound (56 mg, 58%) as colorless oil. MS (ESI): m/z=492.2 [M+H]+.

5-(1-(tert-butoxycarbonyl)piperidin-4-yl)-1-(4-phenoxyphenyl)-1H-pyrazole-3-carboxylic acid (10)

To the solution of tert-butyl 4-(3-(ethoxycarbonyl)-1-(4-phenoxyphenyl)-1H-pyrazol-5-yl)piperidine-1-carboxylate 9 (166 mg, 0.3 mmol) in THF/MeOH/$H_2O$ (20:20:10 mL) was added LiOH (60 mg, 1.4 mmol), and the resulting solution was stirred for 15 h at ambient temperature. The mixture was concentrated, the residue was diluted with water (10 mL), and the solution was acidified with citric acid to pH=4, extracted with ethyl acetate (3×20 mL), washed with brine (20 mL), dried over $Na_2SO_4$, filtered and concentrated to get the title compound (120 mg, 76%) as a brown solid. MS (ESI): m/z=464.2 [M+H]+ tert-butyl-4-(3-carbamoyl-1-(4-phenoxyphenyl)-1H-pyrazol-5-yl)piperidine-1-carboxylate (11)

To a solution of 5-(1-(tert-butoxycarbonyl)piperidin-4-yl)-1-(4-phenoxyphenyl)-1H-pyrazole-3-carboxylic acid 10 (250 mg, 0.59 mmol) and HATU (147 mg, 0.38 mmol) in dry N,N-dimethyl formamide (25 mL) was added DIPEA (67 mg, 0.51 mmol), and the resulting solution was stirred for 20 min at ambient temperature, then $NH_4Cl$ (28 mg, 0.51 mmol) was added and stirred overnight. The mixture was diluted with ethyl acetate (50 mL), and washed with water (2×20 mL) and brine (2×20 mL). The organic layer was dried over $Na_2SO_4$, filtered and concentrated to get a residue which was purified by silica gel column chromatography eluting with 20:1 DCM/MeOH to afford the title compound (100 mg, 84%) as a yellow solid. MS (ESI): m/z=463.2 [M+H]+.

1-(4-phenoxyphenyl)-5-(piperidin-4-yl)-1H-pyrazole-3-carboxamide hydrochloride (12)

To a solution of tert-butyl 4-(3-carbamoyl-1-(4-phenoxyphenyl)-1H-pyrazol-5-yl)piperidine-1-carboxylate 11 (100 mg, 0.21 mmol) in EtOH (20 mL) was added HCl/EtOH (33%, 2 mL) at ambient temperature. The mixture was stirred for 12 h at room temperature. The mixture concentrated to give the title compound (70 mg, 89%) as yellow oil. MS (ESI): m/z=363.1 [M+H]+.

Example 56

5-(1-acryloylpiperidin-4-yl)-1-(4-phenoxyphenyl)-1H-pyrazole-3-carboxamide

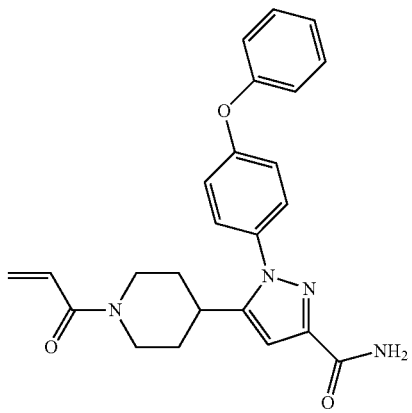 [SMILES: C=CC(=O)N1CCC(c2cc(C(N)=O)nn2-c2ccc(Oc3ccccc3)cc2)CC1]

To the solution of 1-(4-phenoxyphenyl)-5-(piperidin-4-yl)-1H-pyrazole-3-carboxamide hydrochloride 12 (110 mg, 0.3 mmol), DIPEA (117 mg, 0.9 mmol) and $CH_2Cl_2$ (10 mL) was added acryloyl chloride (28 mg, 0.3 mmol) dropwise and then the reaction mixture was stirred at 0° C. for 1 h. The mixture was diluted with $CH_2Cl_2$ (20 mL) and washed with saturated aqueous $NaHCO_3$ solution (20 mL). The aqueous phase was reextracted with EtOAc (20 mL). The combined organic phase was dried over $Na_2SO_4$, concentrated in vacuo and purified by Prep-TLC developing with 20:1 $CH_2Cl_2$/MeOH to give the title compound (66 mg, 52%) as yellow oil. $^1H$ NMR (300 MHz, $CD_3OD$) δ 7.52-7.37 (m, 4H), 7.24-7.06 (m, 5H), 6.84-6.68 (m, 2H), 6.21 (d, J=2.0 Hz, 0.5H), 6.15 (d, J=2.0 Hz, 0.5H), 5.73 (dd, J=10.6, 2.0 Hz, 1H), 4.61 (d, J=12.8 Hz, 1H), 4.15 (d, J=14.0 Hz, 1H), 3.04 (tt, J=8.0, 7.5 Hz, 2H), 2.77-2.59 (m, 1H), 2.03-1.81 (m, 2H), 1.72-1.46 (m, 2H). MS (ESI, method A): m/z=417.1 [M+H]+, $t_R$=1.547 min. HPLC: 98.2% (214 nm), 98.8% (254 nm).

Scheme 47

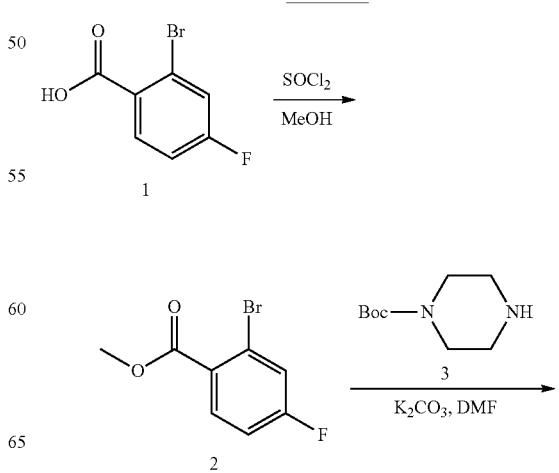

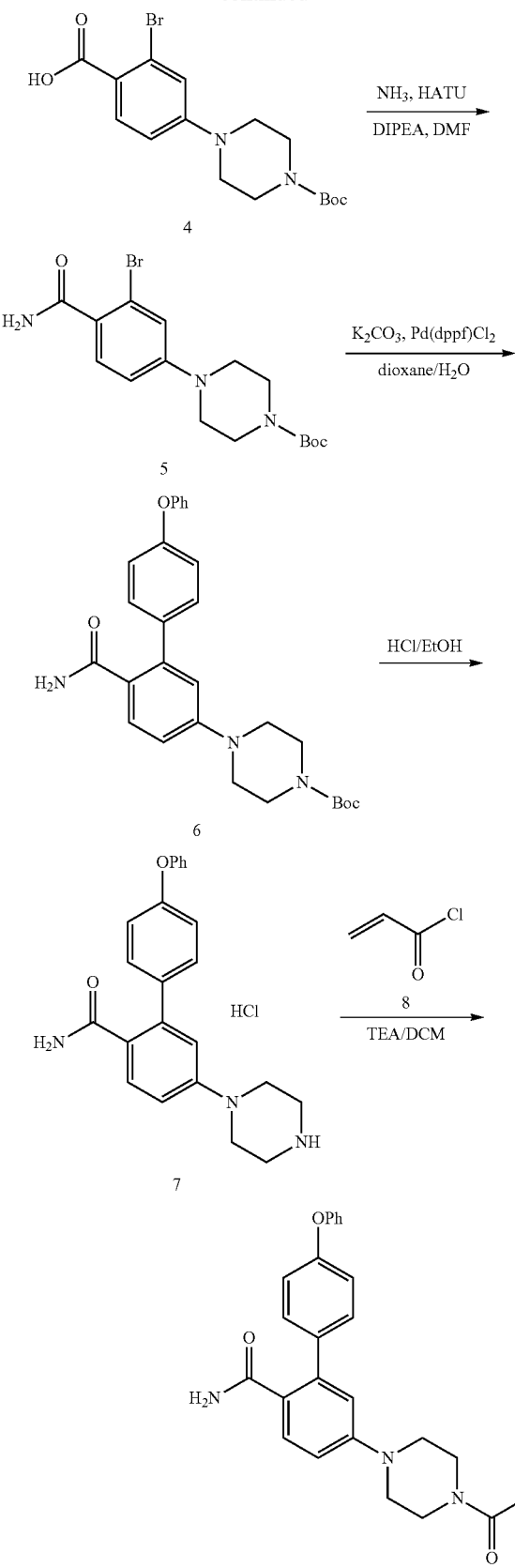

methyl 2-bromo-4-fluorobenzoate (2)

To a mixture of 2-bromo-4-fluorobenzoic acid 1 (2.19 g, 10 mmol) in MeOH (20 mL) was added $SOCl_2$ (0.5 mL) dropwise at rt. The resulting mixture was stirred at 60° C. for 10 h. The mixture was concentrated to give the title compound (2 g, 86%) as brown oil. MS (ESI): m/z=232.8 $[M+H]^+$.

2-bromo-4-(4-(tert-butoxycarbonyl)piperazin-1-yl) benzoic acid (4)

To a solution of methyl 2-bromo-4-fluorobenzoate 2 (1.8 g, 7.72 mmol) in DMSO (30 mL) was added tert-butyl piperazine-1-carboxylate 3 (1.726 g, 9.27 mmol) and $K_2CO_3$ (4.26 g, 30.9 mmol). The mixture was stirred at 120° C. for 5 h. When finished, the mixture was extracted with ethyl acetate (2×50 mL), and washed with water (50 mL) and brine (2×50 mL). The organic layer was dried over $Na_2SO_4$, filtered and concentrated to get a residue which was purified by silica gel column chromatography eluting with 10:1 PE/EA to get the title compound (1.1 g, 36%) as a yellow oil. MS (ESI): m/z=328.7 $[M-55]^+$.

tert-butyl 4-(3-bromo-4-carbamoylphenyl)piperazine-1-carboxylate (5)

The title compound was obtained using a procedure analogous to the procedure described in tert-butyl 3-(5-carbamoyl-4-(4-phenoxyphenyl)thiazol-2-yl)pyrrolidine-1-carboxylate (see Scheme 31) as a yellow solid (0.8 g, 73%). MS (ESI): m/z=327.7 $[M-55]^+$.

tert-butyl 4-(6-carbamoyl-4'-phenoxybiphenyl-3-yl) piperazine-1-carboxylate (6)

To a mixture of tert-butyl 4-(3-bromo-4-carbamoylphenyl)piperazine-1-carboxylate 5 (192 mg, 0.5 mmol), 4-phenoxyphenylboronic acid (102 mg, 0.5 mmol) and $K_2CO_3$ (207 mg, 1.5 mmol) in dioxane/water (20/4 mL) were added $Pd(dppf)_2Cl_2$ (36.55 mg, 0.05 mmol). The mixture was degassed with $N_2$ 3 times, then heated to 100° C. and stirred for 16 h. After cooling to room temperature, the mixture was added to ethyl acetate (30 mL), washed with water (2×20 mL) and brine (2×20 mL). The organic layer was dried over $Na_2SO_4$, filtered and concentrated to get a residue which was purified by silica gel column chromatography eluting with 30:1 DCM/MeOH to get the title compound (50 mg, 21%) as a yellow solid. MS (ESI): m/z=473.8 $[M+H]^+$ 4'-phenoxy-5-(piperazin-1-yl)biphenyl-2-carboxamide hydrochloride (7). The title compound was obtained using a procedure analogous to the procedure described in 1-(4-phenoxyphenyl)-5-(piperidin-4-yl)-1H-pyrazole-3-carboxamide hydrochloride (see Scheme 46) as a yellow solid (40 mg, 92%). MS (ESI): m/z=374.1$[M+H]^+$.

Example 57

5-(4-acryloylpiperazin-1-yl)-4'-phenoxybiphenyl-2-carboxamide

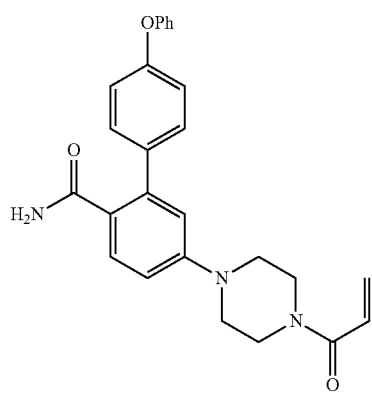 [SMILES: C=CC(=O)N1CCN(c2ccc(C(N)=O)c(-c3ccc(Oc4ccccc4)cc3)c2)CC1]

The title compound was obtained using a procedure analogous to the procedure described in Example 1 as an off white solid (15 mg, 36%). $^1$H NMR (400 MHz, DMSO) δ 7.52-7.30 (m, 6H), 7.25-6.93 (m, 7H), 6.91-6.82 (m, 2H), 6.15 (d, J=16.7 Hz, 1H), 5.73 (d, J=9.9 Hz, 1H), 3.70 (d, J=12.0 Hz, 4H), 3.27 (s, 4H). MS (ESI, method A): m/z=428.1 [M+H]$^+$, $t_R$=1.525 min. HPLC: 96.4% (214 nm), 99.3% (254 nm)

Scheme 48

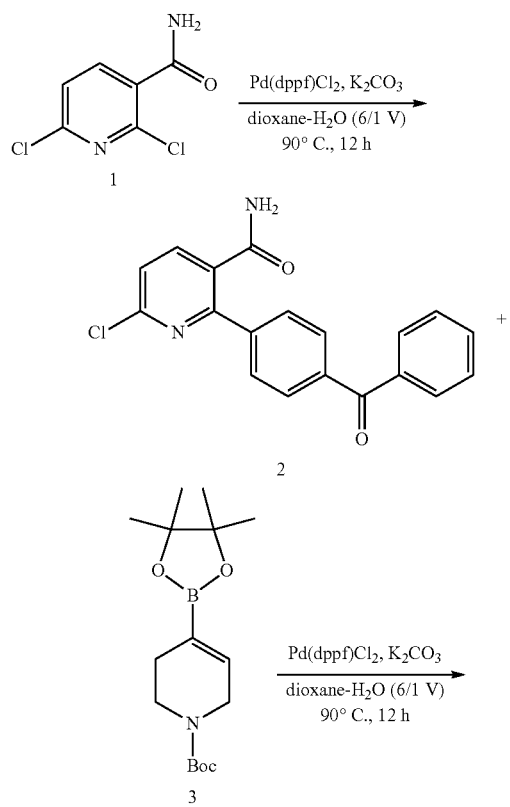

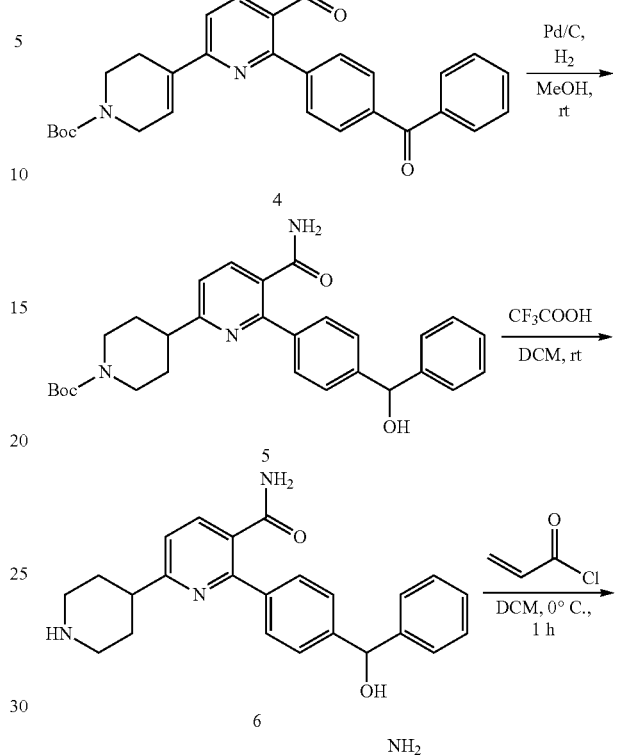

Example 58

2-(4-benzoylphenyl)-6-chloronicotinamide (2)

To a solution of 4-phenoxyphenylboronic acid (650 mg, 2.88 mmol), K$_2$CO$_3$ (1.08 g, 7.86 mmol) and 2,6-dichloronicotinamide (500 mg, 2.62 mmol) in 1,4-dioxane (25 mL) and water (4 mL) was added Pd(dppf)Cl$_2$ (192 mg, 0.262 mmol) under nitrogen atmosphere, and the mixture was degassed with nitrogen 6 times, then heated to 60° C. and stirred for 12 h under nitrogen atmosphere. After cooling to room temperature, the solution was poured into water (50 mL), and then extracted with ethyl acetate (2×50 mL). The combined organic layers were dried over anhydrous sodium sulfate, filtered and concentrated. The crude product was purified by column chromatography, eluting with 80:1 dichloromethane/methanol to afford the title compound as a brown oil (868 mg, 98%). MS (ESI): m/z=336.9 [M+H]$^+$.

tert-butyl 4-(6-(4-benzoylphenyl)-5-carbamoylpyridin-2-yl)-5,6-dihydropyridine-1(2H)-carboxylate (4)

To a solution of tert-butyl 4-(4,4,5,5-tetramethyl-1,3,2-dioxaborolan-2-yl)-5,6-dihydropyridine-1(2H)-carboxylate (1.2 g, 3.87 mmol), K$_2$CO$_3$ (1.07 g, 7.74 mmol) and 2-(4- benzoylphenyl)-6-chloronicotinamide 2 (868 mg, 2.58 mmol) in 1,4-dioxane (24 mL) and water (3 mL) was added Pd(dppf)Cl$_2$ (188 mg, 0.258 mmol) under nitrogen atmosphere, and the mixture was degassed with nitrogen 6 times, then heated to 90° C. and stirred for 12 h under nitrogen atmosphere. After cooling to room temperature, the solution was poured into water (50 mL), and then extracted with ethyl acetate (3×40 mL). The combined organic layers were dried over anhydrous sodium sulfate, filtered and concentrated. The crude product was purified by column chromatography, eluting with 80:1 dichloromethane/methanol to afford the title compound as a brown oil (800 mg, 64%). MS (ESI): m/z=484.0 [M+H]$^+$.

tert-butyl-4-(5-carbamoyl-6-(4-(hydroxy(phenyl) methyl)phenyl)pyridin-2-yl)piperidine-1-carboxylate (5)

To a solution of tert-butyl 4-(6-(4-benzoylphenyl)-5-carbamoylpyridin-2-yl)-5,6-dihydropyridine-1(2H)-carboxylate 4 (800 mg, 1.65 mmol) in MeOH (15 mL) was added Pd/C (150 mg) under hydrogen atmosphere, and the mixture was degassed with hydrogen 6 times, then stirred for 16 h at ambient temperature under hydrogen atmosphere. The solution was filtered and the filtrate was evaporated to provide crude product as a white solid (500 mg, 62%). MS (ESI): m/z=488.1 [M+H]$^+$.

2-(4-(hydroxy(phenyl)methyl)phenyl)-6-(piperidin-4-yl)nicotinamide (6)

To a solution of tert-butyl 4-(5-carbamoyl-6-(4-(hydroxy(phenyl)methyl)phenyl)pyridin-2-yl)piperidine-1-carboxylate 5 (500 mg, 1.03 mmol) in dry dichloromethane (5 mL) was added TFA (2 mL), and the resulting mixture was stirred for 3 h at ambient temperature. The solvent was removed and the residue was partitioned between saturated aqueous sodium bicarbonate (30 mL) and ethyl acetate (20 mL). The organic phase was separated, dried over anhydrous sodium sulfate, filtered and concentrated to afford the title compound as a white solid (350 mg, 88%). MS (ESI): m/z=388.1 [M+H]$^+$.

Example 58

6-(1-acryloylpiperidin-4-yl)-2-(4-(hydroxy(phenyl) methyl)phenyl)nicotinamide

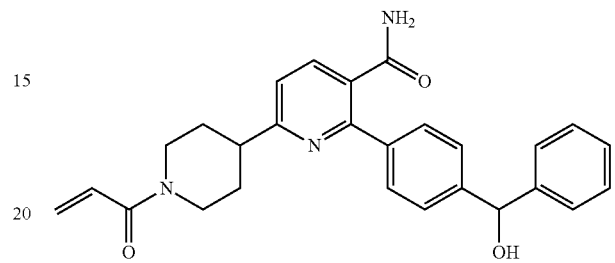

To a solution of 2-(4-(hydroxy(phenyl)methyl)phenyl)-6-(piperidin-4-yl) nicotinamide 6 (350 mg, 0.90 mmol) in DCM (10 mL) was added TEA (182 mg, 1.8 mmol) and acryloyl chloride (90 mg, 0.99 mmol) at 0° C. The mixture was stirred at 0° C. for 10 min. The solvent was removed and the residue was purified by Prep-HPLC to afford the title compound (150 mg, 38%) as white solid. $^1$H NMR (300 MHz, CDCl$_3$) δ 8.03 (d, J=7.9 Hz, 1H), 7.65 (d, J=7.1 Hz, 2H), 7.56-7.15 (m, 9H), 6.67-6.49 (m, 1H), 6.27 (d, J=16.6 Hz, 1H), 5.88 (s, 1H), 5.68 (d, J=10.1 Hz, 1H), 5.52 (d, J=27.1 Hz, 2H), 4.79-4.72 (m, 1H), 4.11-4.06 (m, 1H), 3.18-3.10 (m, 2H), 2.80-2.74 (m, 1H), 2.08-1.98 (m, 2H), 1.78 (d, J=10.5 Hz, 2H). MS (ESI, method F): m/z=441.8 [M+H]$^+$, t$_R$=1.268 min., HPLC: 100.0% (214 nm), 100.0% (254 nm).

Scheme 49

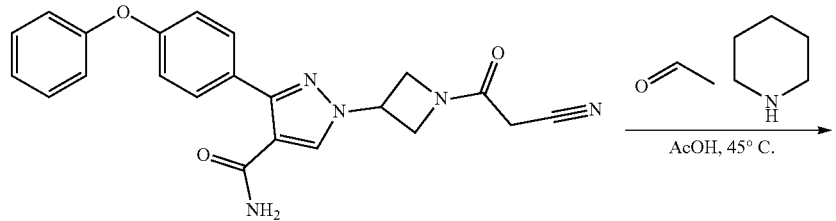

Example 50

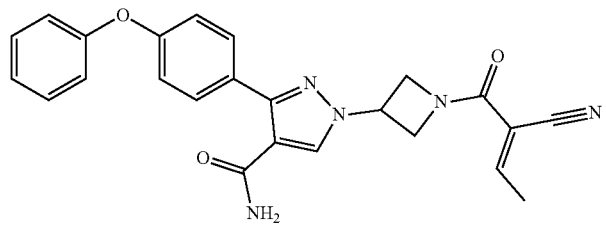

Example 59

Example 59

(E)-1-(1-(2-cyanobut-2-enoyl)azetidin-3-yl)-3-(4-phenoxyphenyl)-1H-pyrazole-4-carboxamide

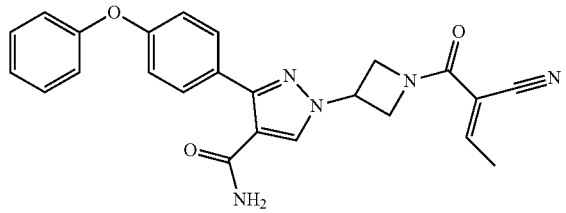 [SMILES: C/C=C(\C#N)C(=O)N1CC(n2cc(C(N)=O)c(-c3ccc(Oc4ccccc4)cc3)n2)C1]

To a solution of 1-(1-(2-cyanoacetyl)azetidin-3-yl)-3-(4-phenoxyphenyl)-1H-pyrazole-4-carboxamide (150 mg, 0.37 mmol) and piperidine (3 drops) in AcOH (10 mL) was added acetaldehyde (99 mg, 0.74 mmol), then stirred at 45° C. overnight. After the reaction was completed, sat. NaOH was added to the solution to pH=6-7. Then the solution was extracted with DCM (2×20 mL). The organic layer was combined and concentrated under vacuum to dryness. The residue was purified by Prep-HPLC (MeOH—H$_2$O=60-70, 0.1% FA) to afford the title compound (40 mg, 26%) as a white solid. $^1$H NMR (300 MHz, CDCl$_3$) δ 8.15 (s, 1H), 7.79-7.68 (m, 1H), 7.62-7.54 (m, 2H), 7.43-7.34 (m, 2H), 7.21-7.13 (m, 1H), 7.13-7.04 (m, 4H), 5.62 (s, 2H), 5.26-5.10 (m, 1H), 5.08-4.79 (m, 2H), 4.71-4.51 (m, 2H), 3.51-3.36 (m, 1H), 2.26-2.16 (m, 2H). MS (ESI, Method A): m/z=428.1 [M+H]$^+$, t$_R$=1.438 min. HPLC: 98.4% (214 nm), 98.4% (254 nm).

Scheme 50

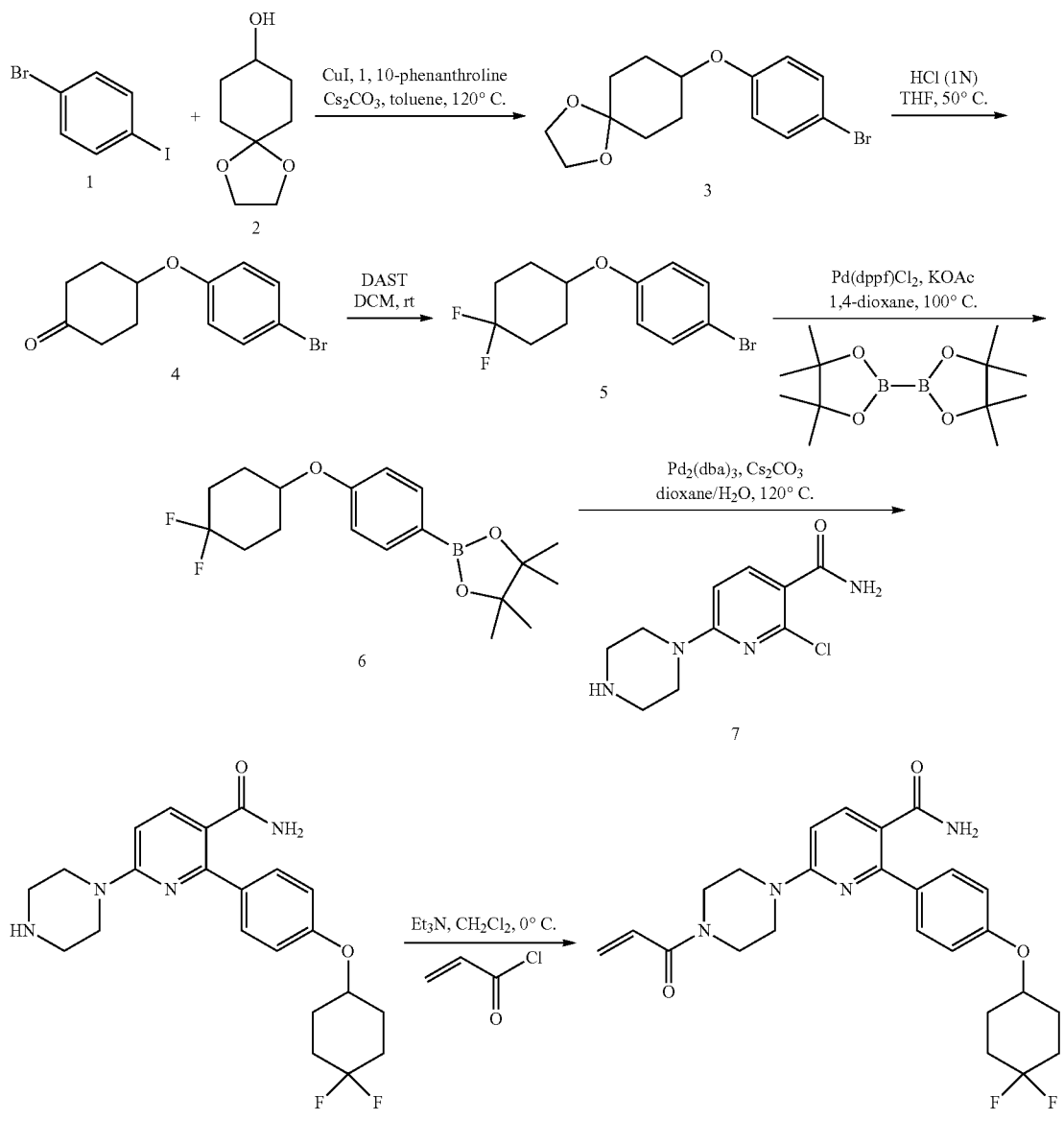

8-(4-bromophenoxy)-1,4-dioxaspiro[4.5]decane (3)

The title compound was obtained using a procedure analogous to the procedure described in 1-bromo-4-(cyclohexyloxy)benzene (see Scheme 17) as colorless oil (0.272 g, 87%).

4-(4-bromophenoxy)cyclohexanone (4)

A solution of 8-(4-bromophenoxy)-1,4-dioxaspiro[4.5]decane 3 (0.272 g, 0.87 mmol) in THF (5 mL) was treated with HCl (1 N, 5 mL) at 50° C. for 1 h. Then the mixture was neutralized with NaHCO$_3$ and extracted with EtOAc (5 mL×3). The combined organic phase was dried over Na$_2$SO$_4$, filtered and concentrated. The residue was purified by silica gel column chromatography eluting with 5:1 petroleum ether/EtOAc to give the title compound (147 mg, 63%) as white solid. $^1$H NMR (400 MHz, CDCl$_3$) δ 7.46-7.37 (m, 2H), 6.91-6.83 (m, 2H), 4.68 (s, 1H), 2.75-2.64 (m, 2H), 2.43-2.25 (m, 4H), 2.15-2.08 (s, 2H).

1-bromo-4-((4,4-difluorocyclohexyl)oxy)benzene (5)

To the solution of 4-(4-bromophenoxy)cyclohexanone 4 (0.538 g, 2.0 mmol) in dry DCM (5 mL) was added a solution of DAST (0.654 g, 4.0 mmol) in dry DCM (5 mL) at 0° C. and the resulting mixture was stirred at rt for 4 h. The reaction was quenched by ice water (5 mL), basified with saturated NaHCO$_3$ to pH=8 and extracted with EtOAc (10 mL×3). The combined organic phase was dried over Na$_2$SO$_4$, filtered and concentrated. The residue was purified by silica gel column chromatography eluting with 10:1 petroleum ether/EtOAc to afford the title compound (0.547 g, 94%) as yellow oil.

2-(4-((4,4-difluorocyclohexyl)oxy)phenyl)-4,4,5,5-tetramethyl-1,3,2-dioxaborolane (6)

The mixture of 1-bromo-4-((4,4-difluorocyclohexyl)oxy)benzene 5 (0.328 g, 1.13 mmol), bis(pinacolato)diboron (0.429 g, 1.69 mmol), Pd(dppf)Cl$_2$ (0.168 g, 0.23 mmol), KOAc (0.323 g, 3.29 mmol) and dry dioxane (3 mL) was stirred at 100° C. for 3 h. After cooled to rt, the mixture was poured into water (10 mL) and extracted with EtOAc (15 mL×3). The combined organic phase was dried over Na$_2$SO$_4$, filtered and concentrated. The residue was purified by silica gel column chromatography eluting with PE to afford the title compound (0.258 g, 68%) as a white solid.

2-(4-((4,4-difluorocyclohexyl)oxy)phenyl)-6-(piperazin-1-yl)nicotinamide (8)

The title compound was obtained using a procedure analogous to the procedure described in 6-(3-nitrophenyl)-2-(4-phenoxyphenyl)nicotinamide (see Scheme 1) as white solid (0.10 g, 31%). MS (ESI): m/z=417.1 [M+H]$^+$.

Example 60

6-(4-acryloylpiperazin-1-yl)-2-(4-((4,4-difluorocyclohexyl)oxy)phenyl)nicotinamide

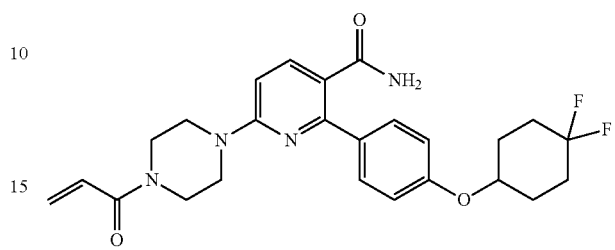

The title compound was obtained using a procedure analogous to the procedure described in Example 1 as white solid (6 mg, 11%). $^1$H NMR (400 MHz, DMSO-d6) δ 7.88 (d, J=8.7 Hz, 2H), 7.73 (d, J=8.6 Hz, 2H), 7.68 (d, J=8.7 Hz, 1H), 7.59 (s, 1H), 7.26 (s, 1H), 7.21-7.14 (m, 4H), 6.86 (dd, J=17.8, 9.3 Hz, 2H), 6.16 (dd, J=16.7, 2.2 Hz, 1H), 5.73 (dd, J=10.4, 2.2 Hz, 1H), 3.66-3.67 (m, 8H). MS (ESI, method A): m/z=471.2 [M+H]$^+$, $t_R$=1.753 (min). HPLC: 99.2% (214 nm), 99.2% (254 nm).

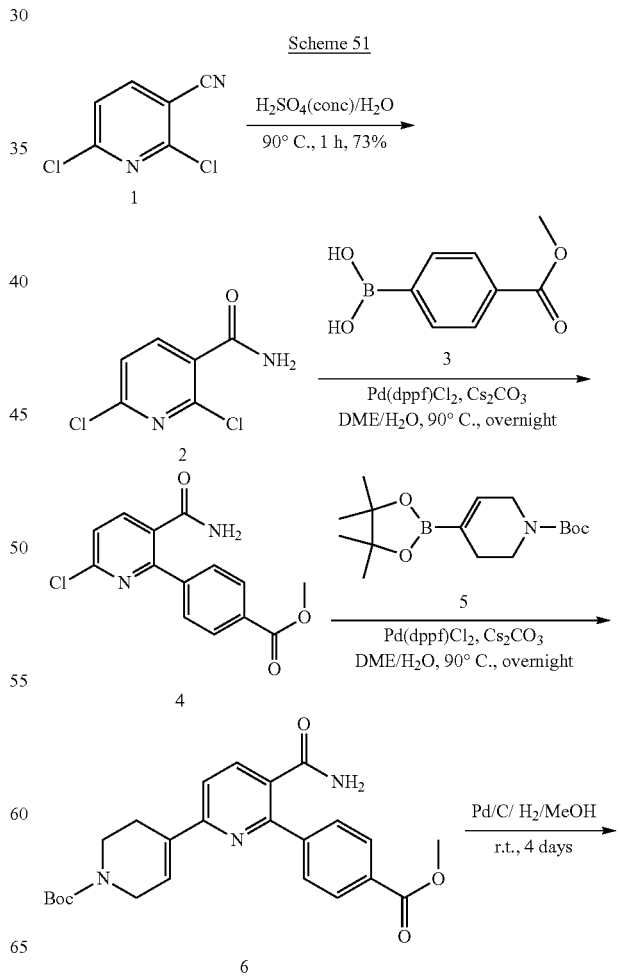

Scheme 51

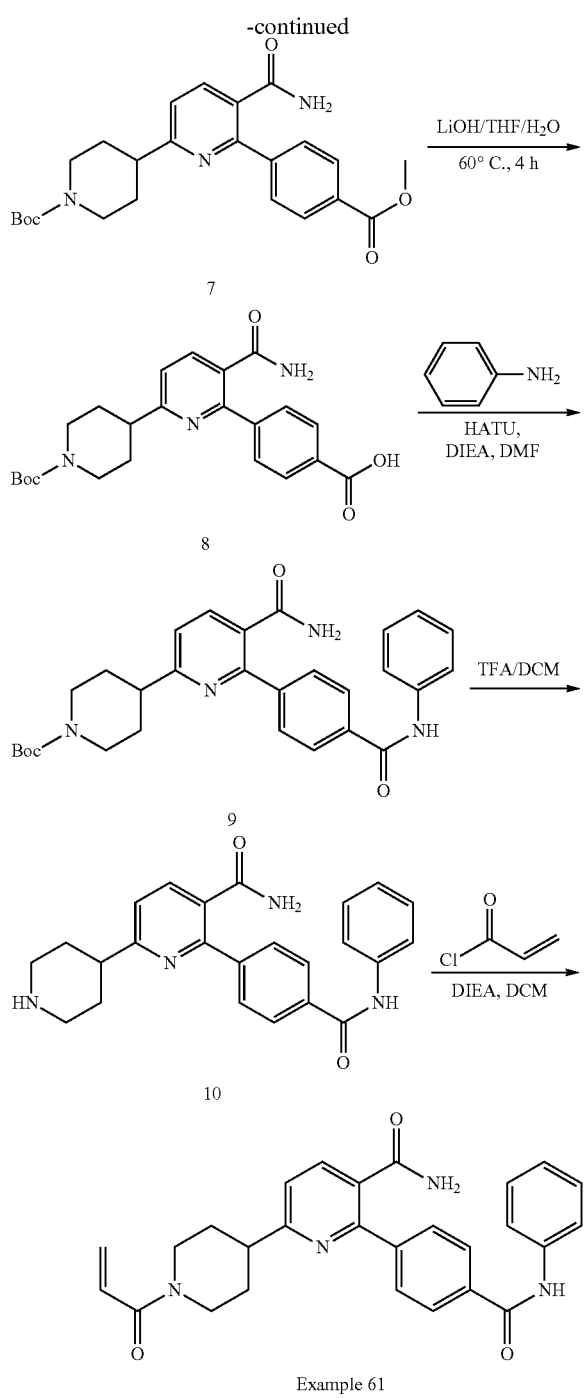

Example 61

2,6-dichloronicotinamide (2)

The title compound was synthesized using a procedure analogous to the procedure described in 2,6-dichloronicotinamide (see Scheme 51) (9.5 g, 81%) as a brown solid. MS (ESI): m/z=191.0 [M+H]$^+$.

methyl 4-(3-carbamoyl-6-chloropyridin-2-yl)benzoate (4)

To a solution of 2,6-dichloronicotinamide 2 (1.91 g, 10.0 mmol), 4-(methoxycarbonyl)phenylboronic acid 3 (1.8 g, 10.0 mmol) and Pd(dppf)Cl$_2$ (816 mg, 1.0 mmol) in DME/H$_2$O (20 mL/2 mL) was added Cs$_2$CO$_3$ (6.5 g, 20.0 mmol). The resulting solution was degassed with N$_2$ 6 times and stirred overnight at 90° C. under N$_2$ protection. After the reaction was completed, the solution was concentrated, diluted with ethyl acetate (30 mL) and washed with water (2×20 mL) and brine (2×20 mL). The organic layer was dried over anhydrous sodium sulfate, filtered and concentrated. The residue was purified by silica gel column diluted with 100:1 to 60:1 DCM/MeOH to afford the title compound (1.95 g, 67%) as a white solid. MS (ESI): m/z=291.1 [M+H]$^+$.

tert-butyl-4-(5-carbamoyl-6-(4-(methoxycarbonyl)phenyl)pyridin-2-yl)-5,6-dihydropyridine-1(2H)-carboxylate (6)

To a solution of methyl 4-(3-carbamoyl-6-chloropyridin-2-yl)benzoate 4 (170 mg, 0.59 mmol), tert-butyl 4-(4,4,5,5-tetramethyl-1,3,2-dioxaborolan-2-yl)-5,6-dihydropyridine-1(2H)-carboxylate 5 (200 mg, 0.65 mmol) and Pd(dppf)Cl$_2$ (50 mg, 0.06 mmol) in DME/H$_2$O (20 mL/2 mL) was added Cs$_2$CO$_3$ (390 mg, 1.2 mmol), the resulting solution was degassed with N$_2$ 6 times and stirred overnight at 90° C. under N$_2$. After the reaction was completed, the solution was concentrated, diluted with ethyl acetate (30 mL) and washed with water (2×20 mL) and brine (2×20 mL). The organic layer was dried over anhydrous sodium sulfate, filtered and concentrated. The residue was purified by silica gel column diluted with 50:1 to 10:1 DCM/MeOH to afford the title compound (145 mg, 56%) as brown oil. MS (ESI): m/z=438.2 [M+H]$^+$.

tert-butyl-4-(5-carbamoyl-6-(4-(methoxycarbonyl)phenyl)pyridin-2-yl)piperidine-1-carboxylate (7)

To a solution of tert-butyl 4-(5-carbamoyl-6-(4-(methoxycarbonyl)phenyl)pyridin-2-yl)-5,6-dihydropyridine-1(2H)-carboxylate 6 (145 mg, 0.33 mmol) in MeOH (10 mL) was added Pd/C (15 mg) and degassed with H$_2$ 6 times and stirred overnight at rt under H$_2$. After the reaction was completed, the solution was filtered and the filtrate was concentrated to afford the title compound (100 mg, 69%) as brown oil. MS (ESI): m/z=440.2 [M+H]$^+$.

4-(6-(1-(tert-butoxycarbonyl)piperidin-4-yl)-3-carbamoylpyridin-2-yl)benzoic acid (8)

To a solution of tert-butyl 4-(5-carbamoyl-6-(4-(methoxycarbonyl)phenyl)pyridin-2-yl)piperidine-1-carboxylate 7 (460 mg, 1.05 mmol) in THF/H$_2$O (20 mL/2 mL) was added LiOH (84 mg, 2.1 mmol), the resulting solution was stirred overnight at rt. After the reaction was complete, the solution was concentrated, added water (10 mL) and acidified with HCl (conc., 1 mL) to pH=5-6, diluted with ethyl acetate (30 mL) and washed with water (2×20 mL) and brine (2×20 mL). The organic layer was dried over anhydrous sodium sulfate, filtered and concentrated to afford the title compound (390 mg, 87%) as a yellow solid. MS (ESI): m/z=426.2 [M+H]$^+$.

tert-butyl-4-(5-carbamoyl-6-(4-(phenylcarbamoyl)phenyl)pyridin-2-yl)piperidine-1-carboxylate (9)

To a solution of 4-(6-(1-(tert-butoxycarbonyl)piperidin-4-yl)-3-carbamoylpyridin-2-yl)benzoic acid 8 (390 mg, 0.917 mmol), aniline (102 mg, 1.101 mmol) and HATU (418 mg, 1.101 mmol) in dry DMF (10 mL) was added DIEA (355 mg, 2.751 mmol), the resulting solution was stirred overnight at rt. The mixture was diluted with ethyl acetate (30 mL), and washed with water (2×20 mL) and brine (2×20 mL). The organic layer was dried over anhydrous sodium sulfate, filtered and concentrated. The residue was purified by Prep-TLC with 20:1 DCM/MeOH to get the title compound (120 mg, 27%) as a yellow solid. MS (ESI): m/z=501.2 [M+H]$^+$.

2-(4-(phenylcarbamoyl)phenyl)-6-(piperidin-4-yl)nicotinamide (10)

To a solution of tert butyl 4-(5-carbamoyl-6-(4-(phenylcarbamoyl)phenyl)pyridin-2-yl)piperidine-1-carboxylate 9 (120 mg, 0.24 mmol) in dry DCM (10 mL) was added TFA (3 mL), the resulting solution was stirred overnight at rt. The mixture was washed with NaHCO$_3$/H$_2$O (3×20 mL) and brine (3×20 mL). The organic layer was dried over anhydrous sodium sulfate, filtered and concentrated. The residue was concentrated to get the title compound (100 mg, 99%) as a yellow solid. MS (ESI): m/z=401.2 [M+H]$^+$.

Example 61

6-(1-acryloylpiperidin-4-yl)-2-(4-(phenylcarbamoyl)phenyl)nicotinamide

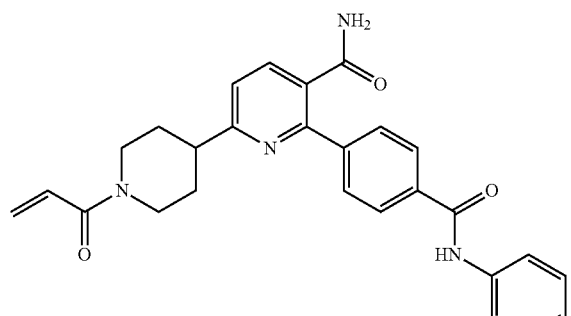

To a solution of 2-(4-(phenylcarbamoyl)phenyl)-6-(piperidin-4-yl)nicotinamide 10 (100 mg, 0.24 mmol) in dry DCM (15 mL) was added DIEA (95 mg, 0.72 mmol) and acryloyl chloride (35 mg, 0.36 mmol) at 0° C., and the resulting solution was stirred at 0° C. for 10 min. Water (10 mL) was added to quench the reaction. The mixture was diluted with DCM (20 mL), and washed with water (2×20 mL) and brine (2×20 mL). The organic layer was dried over anhydrous sodium sulfate, filtered and concentrated. The residue was purified by Prep-HPLC (ACN—H$_2$O=30-90, 0.1% FA) to afford the title compound (31 mg, 29%) as a white solid. $^1$H NMR (300 MHz, CDCl$_3$) δ 8.59 (s, 1H), 8.04-7.58 (m, 31H), 7.75-7.54 (m, 41H), 7.37-7.27 (m, 2H), 7.21-7.08 (m, 2H), 6.65-6.49 (m, 1H), 6.29-6.10 (m, 3H), 5.74-5.63 (m, 1H), 4.79-4.63 (m, 1H), 4.17-3.99 (m, 1H), 3.27-2.96 (m, 2H), 2.83-2.66 (m, 1H), 2.07-1.88 (in, 2H), 1.83-1.60 (m, 2H). MS (ESI): m/z=455.2 [M+H]$^+$, t$_R$=1.316 min. HPLC: 95.3% (214 nm), 93.0% (254 nm).

Scheme 52

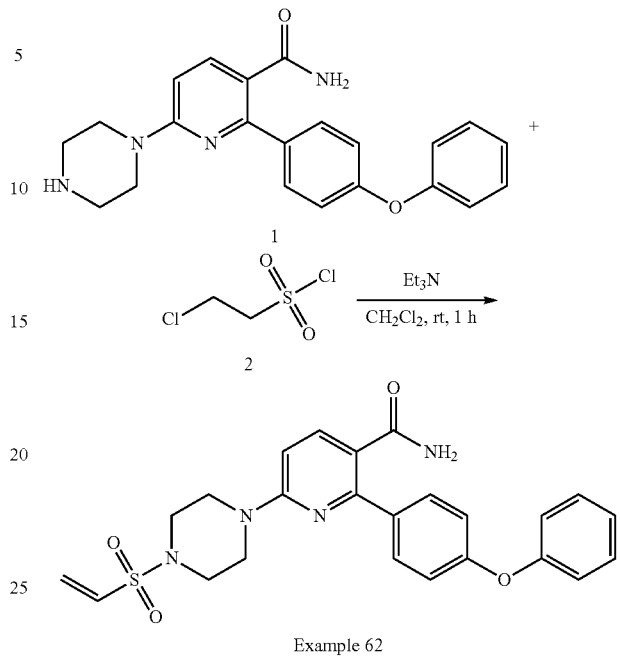

Example 62

2-(4-phenoxyphenyl)-6-(4-(vinylsulfonyl)piperazin-1-yl)nicotinamide

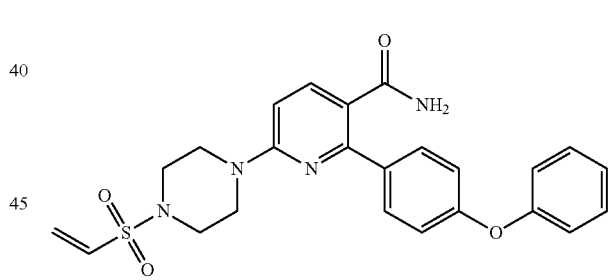

To a solution of 2-(4-phenoxyphenyl)-6-(piperazin-1-yl)nicotinamide 1 (200 mg, 0.53 mmol) in DCM (8 mL) was added TEA (161 mg, 1.59 mmol) and 2-chloroethanesulfonyl chloride (131 mg, 0.80 mmol) at rt. The mixture was stirred at rt for 1 h. The solution was poured into water (50 mL), and then extracted with CH$_2$Cl$_2$ (2×50 mL). The combined organic layers were dried over anhydrous sodium sulfate, filtered and concentrated, and the residue was purified by Prep-TLC eluting with 100:1 DCM/MeOH to afford the title compound (17 mg, 6.9%) as a white solid. $^1$H NMR (300 MHz, CDCl$_3$) δ 8.01 (d, J=8.8 Hz, 1H), 7.59 (d, J=8.6 Hz, 2H), 7.43-7.30 (m, 2H), 7.15 (t, J=7.4 Hz, 1H), 7.09-7.01 (m, 4H), 6.64 (d, J=8.8 Hz, 1H), 6.42 (dd, J=16.6, 9.7 Hz, 1H), 6.26 (d, J=16.5 Hz, 1H), 6.06 (d, J=9.7 Hz, 1H), 5.46 (br, 1H), 5.28 (br, 1H), 3.87-3.75 (m, 4H), 3.32-3.18 (m, 4H). MS (ESI, method F): m/z=465.1.0 [M+H]$^+$, t$_R$=1.546 min., HPLC: 99.5% (214 nm), 98.3% (254 nm).

Scheme 53

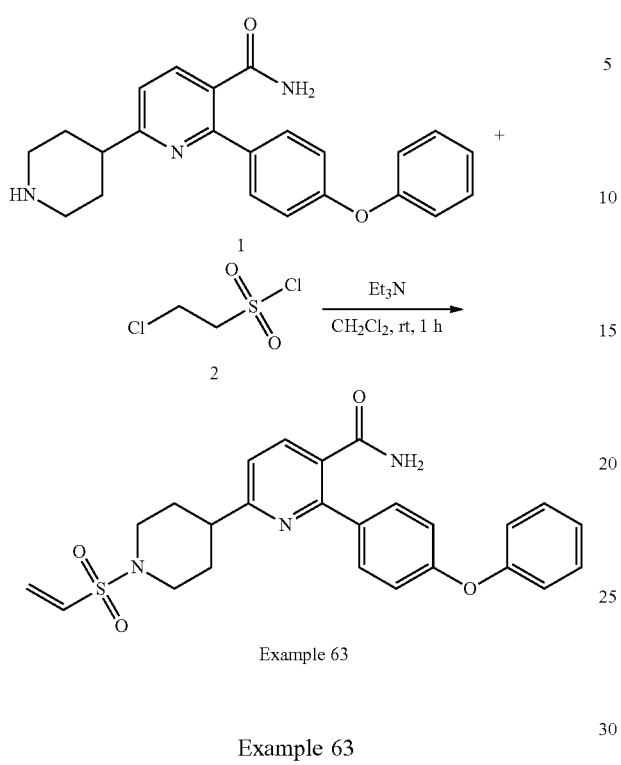

Example 63

2-(4-phenoxyphenyl)-6-(1-(vinylsulfonyl)piperidin-4-yl)nicotinamide

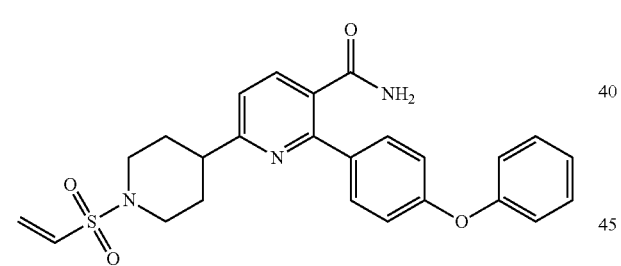

To a solution of 2-(4-phenoxyphenyl)-6-(piperidin-4-yl)nicotinamide 1 (200 mg, 0.54 mmol) in DCM (8 mL) was added TEA (164 mg, 1.62 mmol) and 2-chloroethanesulfonyl chloride (131 mg, 0.80 mmol) at rt. The mixture was stirred at rt for 1 h. The solution was poured into water (50 mL), and then extracted with ethyl acetate (2×50 mL). The combined organic layers were dried over anhydrous sodium sulfate, filtered and concentrated, and the residue was purified by Prep-HPLC to afford the title compound (40 mg, 16%) as a white solid. $^1$H NMR (300 MHz, CDCl$_3$) δ 8.03 (d, J=8.0 Hz, 1H), 7.71-7.61 (m, 2H), 7.43-7.31 (m, 2H), 7.17 (dd, J=15.6, 7.8 Hz, 2H), 7.10-7.01 (m, 4H), 6.46 (dd, J=16.6, 9.8 Hz, 1H), 6.26 (d, J=16.6 Hz, 1H), 6.04 (d, J=9.9 Hz, 1H), 5.60 (b, 1H), 5.41 (b, 1H), 3.94-3.82 (m, 2H), 2.97-2.86 (m, 1H), 2.80-2.71 (m, 2H), 2.11-1.92 (m, 4H). MS (ESI, method F): m/z=464.0 [M+H]$^+$, t$_R$=1.566 min., HPLC: 99.3% (214 nm), 100.0% (254 nm).

The following examples can be synthesized according to methods referenced below and utilizing ordinary skill in the art. These examples are believed to be useful as inhibitors of BTK based on the biological activities of the compounds described above.

Example 64

1-(1-acryloylpiperidin-3-yl)-3-(4-(phenylcarbamoyl)phenyl)-1H-pyrazole-4-carboxamide

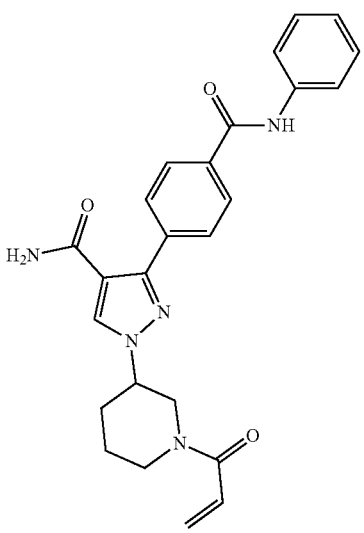 [SMILES: C=CC(=O)N1CCCC(n2cc(C(N)=O)c(-c3ccc(C(=O)Nc4ccccc4)cc3)n2)C1]

The title compound may be obtained using a procedure analogous to the procedures described in the General Scheme and Example 15.

Example 65

1-(1-acryloylpiperidin-3-yl)-3-(4-((4-(trifluoromethyl)pyridin-2-yl)carbamoyl)phenyl)-1H-pyrazole-4-carboxamide

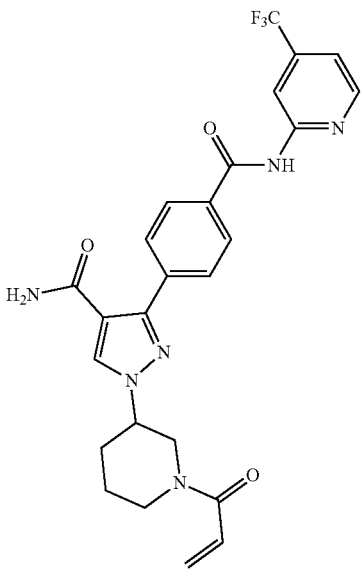 [SMILES: C=CC(=O)N1CCCC(n2cc(C(N)=O)c(-c3ccc(C(=O)Nc4cc(C(F)(F)F)ccn4)cc3)n2)C1]

The title compound may be obtained using a procedure analogous to the procedures described in the General Scheme and Example 15.

Example 66

6-(4-acrylamidophenyl)-2-(4-(phenylcarbamoyl)phenyl) nicotinamide

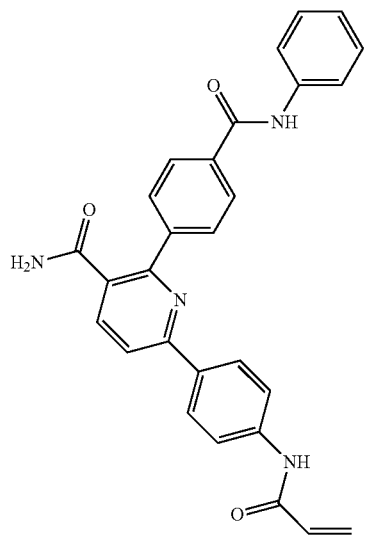 [SMILES: C=CC(=O)Nc1ccc(-c2ccc(C(N)=O)c(-c3ccc(C(=O)Nc4ccccc4)cc3)n2)cc1]

The title compound may be obtained using a procedure analogous to the procedures described in the General Scheme and Example 16.

Example 67

6-(4-acrylamidophenyl)-2-(4-((4-(trifluoromethyl)pyridin-2-yl)carbamoyl)phenyl)-nicotinamide

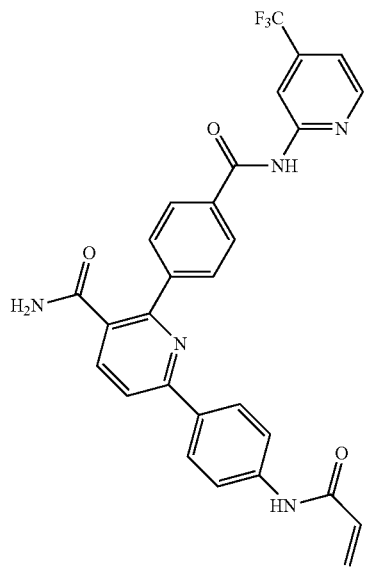 [SMILES: C=CC(=O)Nc1ccc(-c2ccc(C(N)=O)c(-c3ccc(C(=O)Nc4cc(C(F)(F)F)ccn4)cc3)n2)cc1]

The title compound may be obtained using a procedure analogous to the procedures described in the General Scheme and Example 16.

Example 68

1-(1-acryloylpiperidin-3-yl)-3-(4-(hydroxy(phenyl)methyl)phenyl)-1H-pyrazole-4-carboxamide

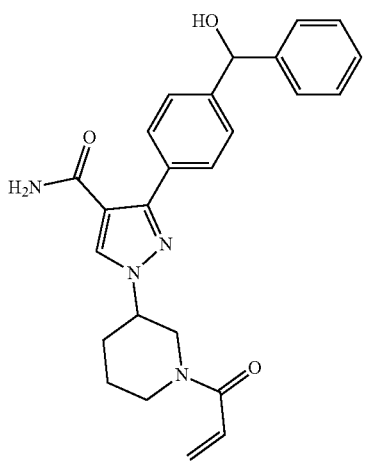 [SMILES: C=CC(=O)N1CCCC(n2cc(C(N)=O)c(-c3ccc(C(O)c4ccccc4)cc3)n2)C1]

The title compound may be obtained using a procedure analogous to the procedures described in the General Scheme and Examples 15 and 58.

Example 69

1-(1-acryloylpiperidin-3-yl)-3-(4-(methyl(phenyl)amino)phenyl)-1H-pyrazole-4-carboxamide

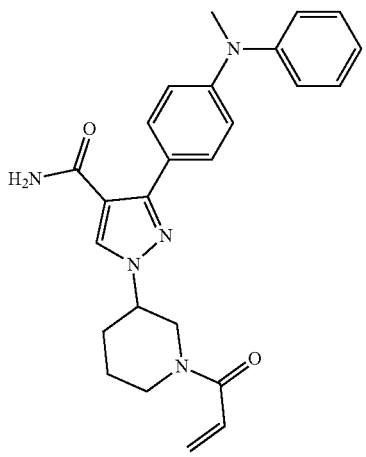 [SMILES: C=CC(=O)N1CCCC(n2cc(C(N)=O)c(-c3ccc(N(C)c4ccccc4)cc3)n2)C1]

The title compound may be obtained using a procedure analogous to the procedures described in the General Scheme and Example 15.

Example 70

6-(4-acrylamidophenyl)-2-(4-(1-hydroxy-1-phenyl-ethyl)phenyl)nicotinamide

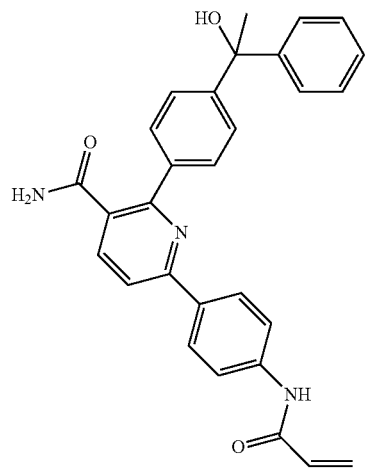 [SMILES: C=CC(=O)Nc1ccc(-c2ccc(C(N)=O)c(-c3ccc(C(C)(O)c4ccccc4)cc3)n2)cc1]

The title compound may be obtained using a procedure analogous to the procedures described in the General Scheme and Examples 16 and 58.

Example 71

6-(4-acrylamidophenyl)-2-(4-(difluoro(phenyl)methyl)phenyl)nicotinamide

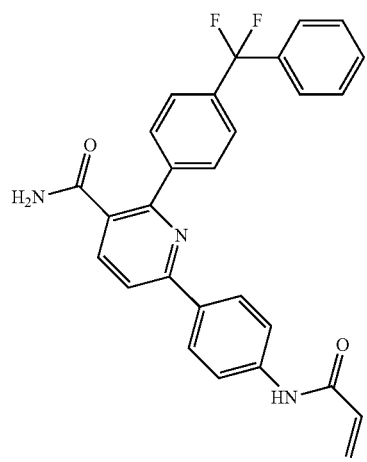 [SMILES: C=CC(=O)Nc1ccc(-c2ccc(C(N)=O)c(-c3ccc(C(F)(F)c4ccccc4)cc3)n2)cc1]

The title compound may be obtained using a procedure analogous to the procedures described in the General Scheme and Example 16.

Example 72

1-(1-acryloylpiperidin-3-yl)-3-(4-(phenylsulfonyl)phenyl)-1H-pyrazole-4-carboxamide

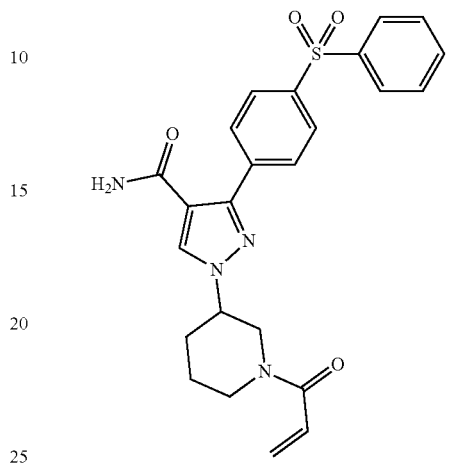

The title compound may be obtained using a procedure analogous to the procedures described in the General Scheme and Example 15.

Example 73

6-(4-acrylamidophenyl)-2-(4-(phenylsulfonyl)phenyl) nicotinamide

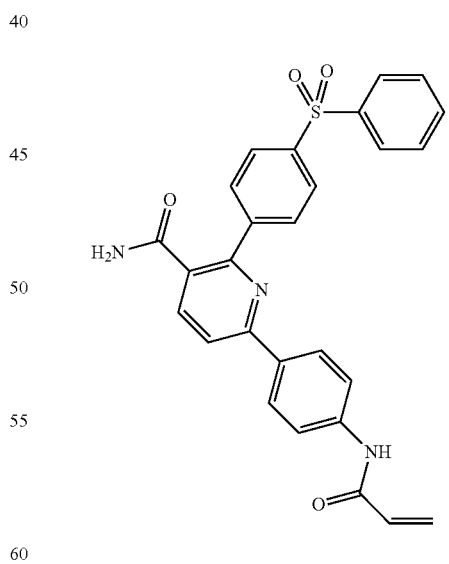

The title compound may be obtained using a procedure analogous to the procedures described in the General Scheme and Example 16.

Scheme A-1

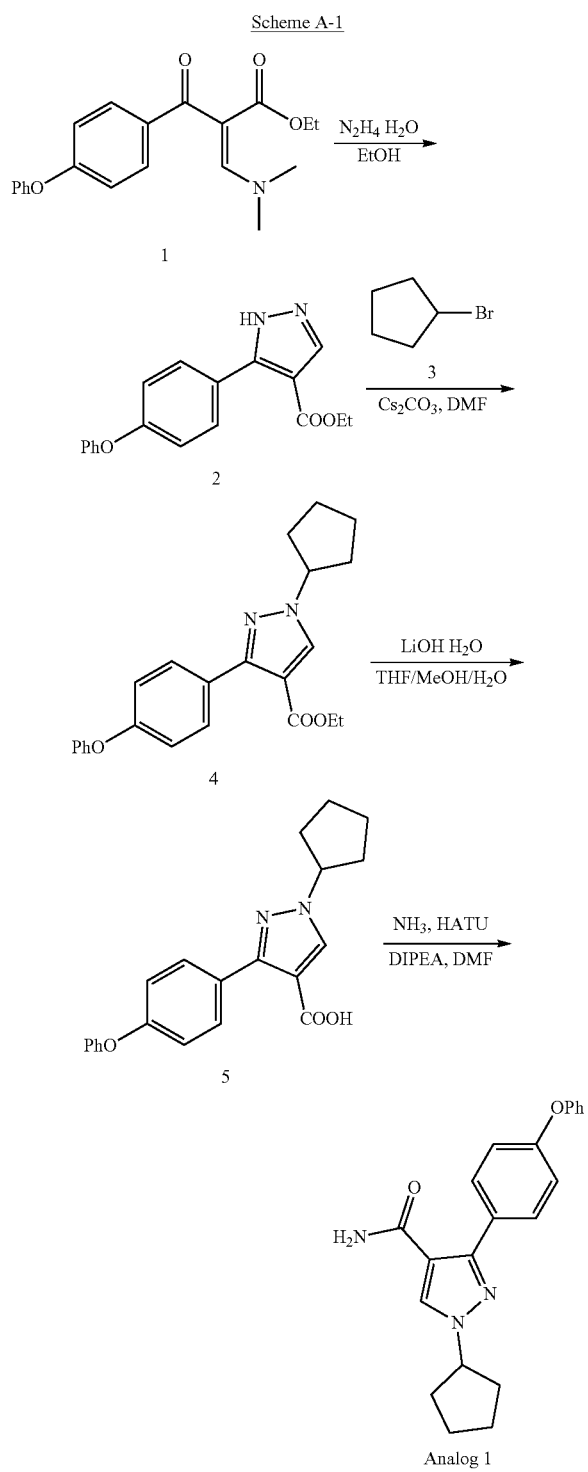

ethyl 5-(4-phenoxyphenyl)-1H-pyrazole-4-carboxylate (2)

The title compound was obtained using a procedure analogous to the procedure described in ethyl 3-(4-phenoxyphenyl)-1H-pyrazole-4-carboxylate (see Scheme 23) as yellow oil (0.3 g, 97%). MS (ESI): m/z=308.8 [M+H]$^+$.

ethyl 1-cyclopentyl-3-(4-phenoxyphenyl)-1H-pyrazole-4-carboxylate (4)

To a solution of ethyl 5-(4-phenoxyphenyl)-1H-pyrazole-4-carboxylate 2 (150 mg, 0.486 mmol) in DMF (10 mL) was added bromocyclopentane 3 (87 mg, 0.584 mmol) and Cs$_2$CO$_3$ (475.5 mg, 1.46 mmol). The mixture was stirred at 100° C. for 3 h. After finished, the mixture was extracted with ethyl acetate (2×30 mL), and washed with water (2×10 mL) and brine (3×10 mL). The organic layer was dried over Na$_2$SO$_4$, filtered and concentrated to give the title compound (0.13 g, 71%) as yellow oil. MS (ESI): m/z=376.9 [M+H]$^+$

1-cyclopentyl-3-(4-phenoxyphenyl)-1H-pyrazole-4-carboxylic acid (5)

The title compound was obtained using a procedure analogous to the procedure described in 5-(1-(tert-butoxycarbonyl)piperidin-4-yl)-1-(4-phenoxyphenyl)-1H-pyrazole-3-carboxylic acid (see Scheme 46) as yellow oil (0.12 g, 100%). MS (ESI): m/z=348.8 [M+H]$^+$.

Analog 1

1-cyclopentyl-3-(4-phenoxyphenyl)-1H-pyrazole-4-carboxamide

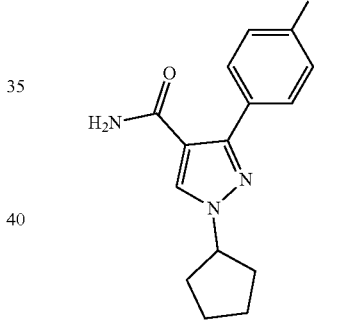

Analog 1

The title compound was obtained using a procedure analogous to the procedure described in tert-butyl 3-(5-carbamoyl-4-(4-phenoxyphenyl)thiazol-2-yl)pyrrolidine-1-carboxylate (see Scheme 31) as an off white solid (70 mg, 59%). $^1$H NMR (300 MHz, DMSO) δ 8.23 (s, 1H), 7.79 (d, J=8.5 Hz, 2H), 7.41 (t, J=7.0 Hz, 3H), 7.15 (t, J=7.1 Hz, 1H), 7.05 (d, J=7.6 Hz, 2H), 7.00 (s, 2H), 6.98 (d, J=1.4 Hz, 1H), 4.78-4.62 (m, 1H), 2.19-1.55 (m, 8H). MS (ESI, method F): m/z=347.9 [M+H]$^+$, t$_R$=1.589 (min). HPLC: 97.6% (214 nm), 98.0% (254 nm).

Scheme A-2

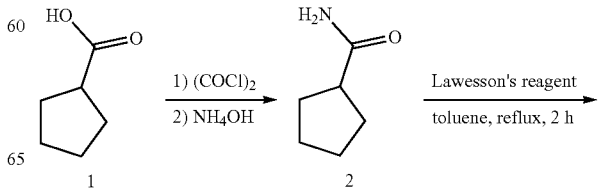

-continued

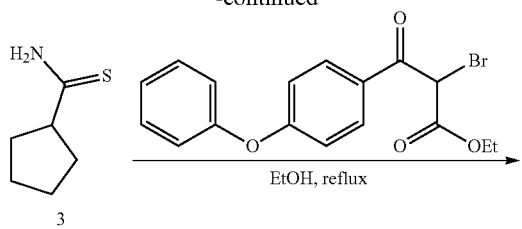

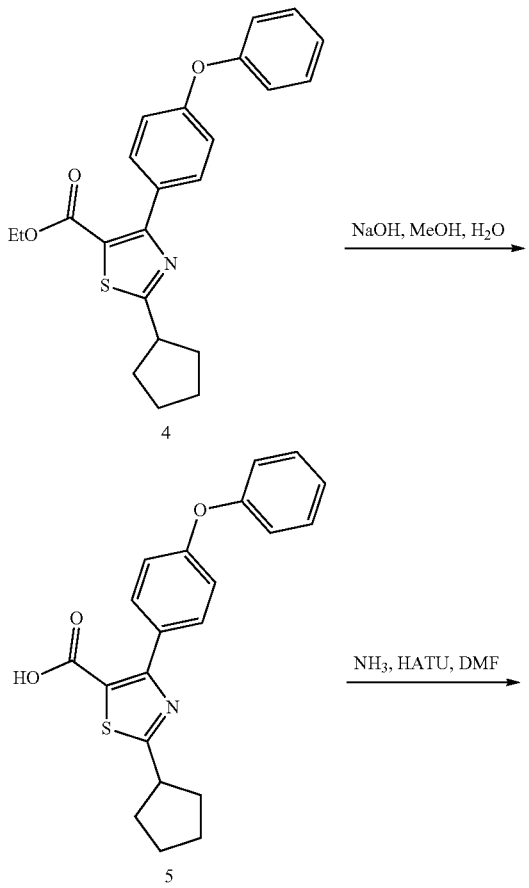

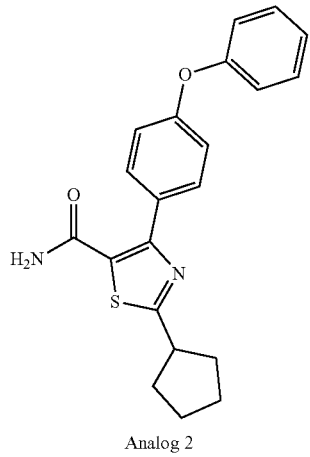

Analog 2

Cyclopentanecarboxamide (2)

To a mixture of cyclopentanecarboxylic acid 1 (2.85 g, 25 mmol) and DMF (3 drops) in DCM (60 mL) was added (COCl)$_2$ (3.2 g, 25 mmol) dropwise carefully at 0° C. under N$_2$. The resulting mixture was stirred at rt for 2 h, then NH$_4$OH (5 mL) was added dropwise to this mixture at 0° C. After the addition, the mixture was stirred at rt for another 1 h, which was diluted with DCM (50 mL). It was washed with water (50 mL), brine, dried over sodium sulfate, filtered and concentrated. This resulted in the title compound (1.8 g, 64%) as white solid. MS (ESI): m/z=114.8 [M+H]$^+$.

cyclopentanecarbothioamide (3)

A mixture of cyclopentanecarboxamide 2 (1.8 g, 15.9 mmol) and lawesson's reagent (3.2 g, 8.0 mmol) in toluene (40 mL) was stirred at 80° C. for 2 h under N$_2$ atmosphere. It was quenched with sat. NaHCO$_3$ (50 mL). which was extracted with EA (2×40 mL). The organic layers were combined, washed with brine, dried over sodium sulfate, filtered and concentrated. The residue was applied onto silica gel column eluting with 3:1 PE/EA to get the title compound (0.25 g, 12%) as yellow solid. MS (ESI): m/z=130.1 [M+H−56]$^+$.

ethyl 2-cyclopentyl-4-(4-phenoxyphenyl)thiazole-5-carboxylate (4)

A mixture of cyclopentanecarbothioamide 3 (150 mg, 1.16 mmol) and ethyl 2-bromo-3-oxo-3-(4-phenoxyphenyl) propanoate (422 mg, 1.16 mmol) in EtOH (15 mL) was refluxed for 2 h. The volatile phase was removed under reduced pressure. The residue was dissolved in EA (50 mL), which was washed with sat. NaHCO$_3$ (30 mL), brine, dried over sodium sulfate, filtered and concentrated. The residue was applied onto silica gel column eluting with 4:1 PE/EA to get the title compound (200 mg, 43%) as pale yellow oil. MS (ESI): m/z=394.1 [M+H]$^+$.

2-cyclopentyl-4-(4-phenoxyphenyl)thiazole-5-carboxylic acid (5)

The title compound was obtained using a procedure analogous to the procedure described in 5-(1-(tert-butoxycarbonyl)piperidin-4-yl)-4'-phenoxybiphenyl-2-carboxylic acid (see Scheme 45) as pale yellow solid (190 mg, 99%). MS (ESI): m/z=366.1 [M+H]$^+$.

Analog 2

2-cyclopentyl-4-(4-phenoxyphenyl)thiazole-5-carboxamide

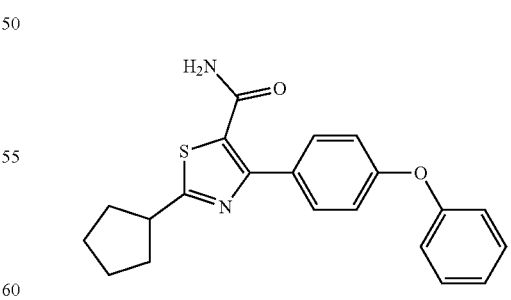

The title compound was obtained using a procedure analogous to the procedure described in tert-butyl 4-(6-carbamoyl-4'-phenoxybiphenyl-3-yl)piperidine-1-carboxylate (see Scheme 45) as white solid (70 mg, 38%). $^1$H NMR (300 MHz, CDCl$_3$) δ 7.66-7.56 (m, 2H), 7.43-7.33 (m, 2H), 7.17 (t, J=7.4 Hz, 1H), 7.12-7.00 (m, 4H), 5.73 (brs, 2H), 3.52-3.35 (m, 1H), 2.32-2.16 (m, 2H), 1.90-1.77 (m, 4H), 1.76-1.66 (m, 2H). MS (ESI, method A): m/z=365.1 [M+H]+, $t_R$=1.780 min. HPLC: 97% (214 nm), 96% (254 nm).

Analytical Conditions

Unless otherwise noted, all solvents, chemicals, and reagents were obtained commercially and used without purification. The 1H-NMR spectra were obtained in $CDCl_3$, DMSO-$d_6$, $CD_3OD$, or acetone-$d_6$ at 25° C. at 300 MHz or 400 MHz on an OXFORD (Varian) with chemical shift (δ, ppm) reported relative to TMS as an internal standard. HPLC-MS chromatograms and spectra were obtained with an Agilent 1200-6110 system. Prep-HPLC instruments were Gilson GX-281 (Gilson) and P230 Preparative Gradient System (Gradient: 95% water, 5% acetonitrile, 30-50 min gradient to 25% water, 75% acetonitrile). The microwave instrument was a CEM Discover SP.

Biological Properties: $IC_{50}$ Determination of BTK Inhibitors in ADP-Glo Kinase Biochemical Assay The activity of the Examples and Analogs described herein, as inhibitors of BTK are demonstrated and confirmed by pharmacological in vitro assays. Activity possessed by the compounds may be demonstrated in vivo. Those skilled in the art will appreciate that a variety of assay formats may be used to determine the activity of the compounds described herein.

Materials:

ADP-Glo™ Kinase Assay (cat. V9102, 10000 tests), components:
1×50 ml ADP-Glo™ Reagent,
1×100 ml Kinase Detection Buffer,
1×Kinase Detection Substrate (Lyophilized),
1×5 ml Ultra Pure ATP, 10 mM
1×5 ml ADP, 10 mM Reagents and Plate:

Tris·Hcl (Sigma cat. 154563), $MgCl_2$ (Sigma cat. M1028), $MnCl_2$ (Sigma, M3634), BSA (Sigma cat. 05470), BTK Substrate (Signalchem, P61-58), DTT (Sigma, D0632), DMSO (Sigma, S5879), BTK enzyme. (1.5 mg/ml, purity 75%, 90 ng/ul, made in house). 384 well assay plate (cat. 3674).

Assay Conditions:

Enzyme concentration: 8 ng/5 ul.
ATP concentration: 50 uM
Substrate (peptide) concentration: 0.2 mg/ml.
Reaction buffer composition: 40 mM Tris-HCl pH7.5, 10 mM $MgCl_2$, 2 mM $MnCl_2$, 0.1 mg/mL BSA, 0.05 mM DTT.
Test compound concentration: DMSO≤0.5%.

Methods:

Compound Dosage Gradient Solution Preparation:

A 3-fold serial dilution of test compound was made for 10 gradient points (100, 33.33, 11.11, 3.70, 1.23, 0.41, 0.14, 0.046, 0.015, 0.005 uM) in 100% DMSO. The intermediate dilution was done by adding 2 ul of diluted compound into 78 ul of assay buffer (containing 40 mM Tris·Hcl, pH 7.5 10 mM $MgCl_2$, 2 mM MnCl, 0.1 mg/mL BSA, 0.05 mM DTT), making the final compound concentration (1000, 333.33, 111.11, 37.04, 12.35, 4.12, 1.37, 0.46, 0.15, 0.05 nM) and DMSO concentration 0.5% percentage.

ADP-Glo Kinase Assay Protocol for BTK Inhibitors Testing:

1× and 2× assay buffer were made at first. BTK kinase was diluted with 1× assay buffer but substrate was diluted with 2× assay buffer. 1 ul of diluted compound was transferred into 384-well assay plate, and then 2.0 ul of enzyme solution was added, and spun at 2000 rpm for 1 min. This mixture was incubated at 24° C. for 30 mins. 2 ul of peptide substrate/ATP mixture was added into the assay plate to start the reaction. The mixture was mixed thoroughly and then the 384-well plate was spun and incubated at 24° C. for 60 mins. 5.0 ul of ADP-Glo Reagent was added to stop the kinase activity and deplete the ATP unconsumed, and the plate was mixed thoroughly and incubated at 24° C. for 40 min. Then, 10.0 ul of Kinase Detection reagent was added, and the plate was centrifuged and then kept at 24° C. for 30 min. The luminescence signal was read on Envision.

Data Analysis:

% inhibition of compounds at each different concentration is calculated from Equation (1):

% inhibition=100−100*(Signal−low control)/(High control−low control)  Equation(1)

$IC_{50}$ values of compounds were calculated from a 4-parameter fit using Equation (2):

Y=Bottom+(TOP−Bottom)/(1+((C/X)^hillslope))  Equation (2)

In Equation 2, Y represents % inhibition, X is the log value of the test compound concentration. $IC_{50}$ was the concentration of compound where half of maximal inhibition was achieved.

All data was analyzed with IDBS XLfit5 software (ID Business Solutions Ltd., UK). The $IC_{50}$ data is summarized in Table 1.

TABLE 1

| $IC_{50}$ BTK Activity Values For Examples 1-63 | |
|---|---|
| $IC_{50}$ (nM) | Examples |
| ≥1000 | 2, 4, 14, 27, 30, 33, 50, 53, 56 |
| ≥500 | 9, 24, 31 |
| ≤1000 | |
| ≥0 | 1, 3, 5, 6, 7, 8, 10, 11, 12, 13, 15, 16, 17, 18, 19, 20, |
| ≤500 | 21, 22, 23, 25, 26, 28, 29, 32, 34, 35, 36, 37, 38, 39, 40, 41, 42, 43, 44, 45, 46, 47, 48, 49, 51, 52, 54, 55, 57, 58, 59, 60, 61, 62, 63 |

Table 2 provides a comparison of Examples 3 and 5 to Analogs 1 and 2 in terms of in vitro BTK potency. Examples 3 and 5 demonstrate about a 100× improvement in potency over Analogs 1 and 2 when compared in head-to-head assays.

TABLE 2

| Comparison of Examples 3 and 5 to Analogs 1 and 2 | | | | |
|---|---|---|---|---|
| Target | Example 3 | Example 5 | Analog 1 | Analog 2 |
| BTK | 4.4 | 4.7 | 347.4 | 364.5 |

Examples 3 and 5 also demonstrate from 10×-100× differences in potency between BTK and Src and are thus selective for BTK over Src.

Furthermore, selectivity of Examples 3 and 5 was determined. Table 3 provides in vitro biochemical data demonstrating that Examples 3 and 5 are selective for BTK over Src.

TABLE 3

Selectivity Data for Examples 3 and 5

| Target | Example 3 % Inhibition @ 1000 nM | Example 5 % Inhibition @ 1000 nM |
|---|---|---|
| BTK | 99.35 | 99.7 |
| SRC | 23 | 33 |
| Fold Difference | >100× | >100× |

To obtain the data provided in Table 3, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 m) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific phage binding. Binding reactions were assembled by combining kinases, liganded affinity beads, and test compounds in 1× binding buffer (20% SeaBlock, 0.17×PBS, 0.05% Tween 20, 6 mM DTT).

Example compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

The compound(s) were screened at 1000 nM, and results for primary screen binding interactions are provided in Table 3 as "% Ctrl", where lower numbers indicate stronger hits. The % Ctrl is calculated according to Equation (1), below:

$$\left(\frac{\text{test compound signal} - \text{positive control signal}}{\text{negative control signal} - \text{positive control signal}}\right) \times 100 \quad (1)$$

Where:
test compound=Example
negative control=DMSO (100% Ctrl)
positive control=control compound (0% Ctrl)

Additional biological selectivity data for Examples 3 and 5 against each member of the SRC family of protein kinases as well as EGFR are provided in Table 4, below. The data in Table 4 was obtained using the same procedure as described above with respect to the data in Table 3.

TABLE 4

Selectivity Data for Examples 3 and 5

| Target | Example 3 % Inhibition @ 1000 nM | Example 5 % Inhibition @ 1000 nM |
|---|---|---|
| BLK | 51 | 46 |
| EGFR | 20 | 23 |
| FGR | 0 | 0 |
| FYN | 0 | 5 |
| HCK | 0 | 21 |
| LCK | 11 | 0 |
| LYN | 3 | 7 |
| YES | 8 | 6 |

Compositions:

The present invention includes pharmaceutical compositions comprising a compound or pharmaceutically acceptable salt thereof of the invention, which is formulated for a desired mode of administration with or without one or more pharmaceutically acceptable and useful carriers.

The compounds can also be included in pharmaceutical compositions in combination with one or more other therapeutically active compounds.

The pharmaceutical compositions of the invention comprise a compound of the invention (or a pharmaceutically acceptable salt thereof) as an active ingredient, optional pharmaceutically acceptable carrier(s) and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Compounds of the invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

A formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Compounds of the invention can be provided for formulation at high purity, for example at least about 90%, 95%, or 98% pure by weight.

Pharmaceutical compositions of the invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient.

Compositions containing a compound described by Formula I, or pharmaceutically acceptable salts thereof, may also be prepared in powder or liquid concentrate form.

Uses:

Compounds of the present invention inhibit the activity of BTK in animals, including humans, and are useful in the treatment and/or prevention of various diseases and conditions such as cancer, inflammation, fibrotic diseases, and autoimmune disease which are caused, mediated and/or propagated by BTK. In particular, compounds of the invention, and compositions thereof, are inhibitors of BTK, and are useful in treating conditions modulated, at least in part, by BTK.

In some aspects, the invention includes a method of treating cancer comprising administering to a mammal in need thereof a therapeutically effective amount of a compound or salt of the invention.

In some aspects, the invention includes a method of treating a cancer mediated at least in part by BTK comprising administering to a mammal in need thereof a therapeutically effective amount of a compound or salt of Formula I.

In some aspects, the invention includes a method of treating or a method of manufacturing a medicament for treating a cancer, such as those described herein, which is mediated at least in part by BTK, comprising administering to a mammal in need thereof a therapeutically effective amount of a compound or salt of the invention.

In some aspects, the invention includes a method of treating lymphocyte homing and inflammation mediated at least in part by BTK comprising administering to a mammal in need thereof a therapeutically effective amount of a compound or salt of Formula I.

In some aspects, the invention includes a method of treating or a method of manufacturing a medicament for treating lymphocyte homing and inflammation, such as those described herein, which is mediated at least in part by BTK, comprising administering to a mammal in need thereof a therapeutically effective amount of a compound or salt of the invention.

In some aspects, the invention includes a method of treating neuropathic pain comprising administering to a mammal in need thereof a therapeutically effective amount of a compound or salt of the invention.

In some aspects, the invention includes a method of treating neuropathic pain mediated at least in part by BTK comprising administering to a mammal in need thereof a therapeutically effective amount of a compound or salt of Formula I.

In some aspects, the invention includes a method of treating or a method of manufacturing a medicament for treating neuropathic pain, such as those described herein, which is mediated at least in part by BTK, comprising administering to a mammal in need thereof a therapeutically effective amount of a compound or salt of the invention.

In some aspects, the invention includes a method of treating fibrotic diseases comprising administering to a mammal in need thereof a therapeutically effective amount of a compound or salt of the invention.

In some aspects, the invention includes a method of treating fibrotic diseases mediated at least in part by BTK comprising administering to a mammal in need thereof a therapeutically effective amount of a compound or salt of Formula I.

In some aspects, the invention includes a method of treating or a method of manufacturing a medicament for treating a fibrotic disease, such as those described herein, which is mediated at least in part by BTK, comprising administering to a mammal in need thereof a therapeutically effective amount of a compound or salt of the invention.

In some aspects, the invention includes a method of treating thrombosis comprising administering to a mammal in need thereof a therapeutically effective amount of a compound or salt of the invention.

In some aspects, the invention includes a method of treating thrombosis mediated at least in part by BTK comprising administering to a mammal in need thereof a therapeutically effective amount of a compound or salt of Formula I.

In some aspects, the invention includes a method of treating or a method of manufacturing a medicament for treating thrombosis, such as those described herein, which is mediated at least in part by BTK, comprising administering to a mammal in need thereof a therapeutically effective amount of a compound or salt of the invention.

In some aspects, the invention includes a method of treating cholestatic pruritus comprising administering to a mammal in need thereof a therapeutically effective amount of a compound or salt of the invention.

In some aspects, the invention includes a method of treating cholestatic pruritus mediated at least in part by BTK comprising administering to a mammal in need thereof a therapeutically effective amount of a compound or salt of Formula I.

In some aspects, the invention includes a method of treating or a method of manufacturing a medicament for cholestatic pruritus, such as those described herein, which is mediated at least in part by BTK, comprising administering to a mammal in need thereof a therapeutically effective amount of a compound or salt of the invention.

The compounds of Formula I of the invention are useful in the treatment of a variety of cancers, including, but not limited to, solid tumors, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In some aspects, the above methods are used to treat one or more of bladder, colorectal, non-small cell lung, breast, or pancreatic cancer. In some aspects, the above methods are used to treat one or more of ovarian, gastric, head and neck, prostate, hepatocellular, renal, glioma, or sarcoma cancer.

In some aspects, the invention includes a method, including the above methods, wherein the compound is used to inhibit cellular epithelial to mesenchymal transition (EMT).

In some aspects, the method further comprises administering at least on additional active agent. In some aspects, the invention includes a method of treating cancer comprising administering to a mammal in need thereof a therapeutically effective amount of a compound or salt of the invention, wherein at least one additional active anti-cancer agent is used as part of the method.

In some aspects, the invention includes a method of treating the disease described herein mediated at least in part by BTK comprising administering to a mammal in need thereof a therapeutically effective regimen comprising a compound or salt of Formula I and at least one additional active agent. Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the Central Nervous System (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

General Definitions and Abbreviations:

Except where otherwise indicated, the following general conventions and definitions apply. Unless otherwise indicated herein, language and terms are to be given their broadest reasonable interpretation as understood by the skilled artisan. Any examples given are nonlimiting.

Any section headings or subheadings herein are for the reader's convenience and/or formal compliance and are non-limiting.

A recitation of a compound herein is open to and embraces any material or composition containing the recited compound (e.g., a composition containing a racemic mixture, tautomers, epimers, stereoisomers, impure mixtures, etc.). In that a salt, solvate, or hydrate, polymorph, or other complex of a compound includes the compound itself, a recitation of a compound embraces materials containing such forms. Isotopically labeled compounds are also encompassed except where specifically excluded. For example, hydrogen is not limited to hydrogen containing zero neutrons. For example, deuterium is referred to herein as "D" and means a hydrogen atom having one neutron.

The term "active agent" means a compound of the invention in any salt, polymorph, crystal, solvate, or hydrated form.

The term "substituted" and substitutions contained in formulas herein refer to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate.

In descriptions and claims where subject matter (e.g., substitution at a given molecular position) is recited as being selected from a group of possibilities, the recitation is specifically intended to include any subset of the recited group. In the case of multiple variable positions or substituents, any combination of group or variable subsets is also contemplated. Unless indicated otherwise, a substituent, diradical or other group referred to herein can be bonded through any suitable position to a referenced subject molecule. For example, the term "indolyl" includes 1-indolyl, 2-indolyl, 3-indolyl, etc.

The convention for describing the carbon content of certain moieties is "($C_{a-b}$)" or "$C_a$-$C_b$," meaning that the moiety can contain any number of from "a" to "b" carbon atoms. $C_0$alkyl means a single covalent chemical bond when it is a connecting moiety, and a hydrogen when it is a terminal moiety. Similarly, "x-y" can indicate a moiety containing from x to y atoms, e.g., $_{5-6}$heterocycloalkyl means a heterocycloalkyl having either five or six ring members. "$C_{x-y}$" may be used to define number of carbons in a group. For example, "$C_{0-12}$alkyl" means alkyl having 0-12 carbons, wherein $C_0$alkyl means a single covalent chemical bond when a linking group and means hydrogen when a terminal group. $C_{0-12}$alkyl includes various alternative embodiments, including, but not limited to, $C_{1-12}$alkyl, $C_{2-12}$alkyl, $C_{3-12}$alkyl, $C_{4-12}$alkyl, $C_{5-12}$alkyl, $C_{6-12}$alkyl, $C_{7-12}$alkyl, $C_{8-12}$alkyl, $C_{9-12}$alkyl, $C_{10-12}$alkyl, $C_{11-12}$alkyl, $C_{1-11}$alkyl, $C_{1-10}$alkyl, $C_{1-9}$alkyl, $C_{1-8}$alkyl, $C_{1-7}$alkyl, $C_{1-6}$alkyl, $C_1$-5alkyl, $C_{1-4}$alkyl, $C_{1-3}$alkyl, $C_{1-2}$alkyl, $C_1$alkyl, and $C_0$alkyl. $C_{0-12}$alkyl further includes any combination of "a" and "b" and/or "x" and "y" number of carbon atoms including, but not limited to, $C_{2-12}$alkyl, $C_{3-11}$alkyl, $C_{4-10}$alkyl, $C_{5-9}$alkyl, $C_{6-8}$alkyl and $C_7$alkyl.

The term "absent," as used herein to describe a structural variable (e.g., "—R— is absent") means that diradical R has no atoms, and merely represents a bond between other adjoining atoms, unless otherwise indicated.

Unless otherwise indicated (such as by a connecting "—"), the connections of compound name moieties are at the rightmost recited moiety. That is, the substituent name starts with a terminal moiety, continues with any bridging moieties, and ends with the connecting moiety. For example, "heteroarylthio$C_{1-4}$alkyl" is a heteroaryl group connected through a thio sulfur to a $C_{1-4}$alkyl, which alkyl connects to the chemical species bearing the substituent.

The term "aliphatic" means any hydrocarbon moiety, and can contain linear, branched, and cyclic parts, and can be saturated or unsaturated.

The term "alkyl" means any saturated hydrocarbon group that is straight-chain or branched. Examples of alkyl groups include methyl, ethyl, propyl, 2-propyl, n-butyl, iso-butyl, tert-butyl, pentyl, and the like.

The term "alkenyl" means any ethylenically unsaturated straight-chain or branched hydrocarbon group. Representative examples include, but are not limited to, ethenyl, 1-propenyl, 2-propenyl, 1-, 2-, or 3-butenyl, and the like.

The term "alkynyl" means any acetylenically unsaturated straight-chain or branched hydrocarbon group. Representative examples include, but are not limited to, ethynyl, 1-propynyl, 2-propynyl, 1-, 2-, or 3-butynyl, and the like.

The term "alkoxy" means —O-alkyl, —O-alkenyl, or —O-alkynyl. "Haloalkoxy" means an —O-(haloalkyl) group. Representative examples include, but are not limited to, trifluoromethoxy, tribromomethoxy, and the like.

"Haloalkyl" means an alkyl, preferably lower alkyl, that is substituted with one or more same or different halo atoms.

"Hydroxyalkyl" means an alkyl, preferably lower alkyl, that is substituted with one, two, or three hydroxy groups; e.g., hydroxymethyl, 1 or 2-hydroxyethyl, 1,2-, 1,3-, or 2,3-dihydroxypropyl, and the like.

The term "alkanoyl" means —C(O)-alkyl, —C(O)-alkenyl, or —C(O)-alkynyl.

"Alkylthio" means an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "cyclic" means any ring system with or without heteroatoms (N, O, or $S(O)_{0-2}$), and which can be saturated, partially saturated, or unsaturated. Ring systems can be bridged and can include fused rings. The size of ring systems may be described using terminology such as "$_{x-y}$cyclic," which means a cyclic ring system that can have from x to y ring atoms. For example, the term "9-10carbocyclic" means a 5,6 or 6,6 fused bicyclic carbocyclic ring system which can be saturated, unsaturated or aromatic. It also means a phenyl fused to one 5 or 6 membered saturated or unsaturated carbocyclic group. Nonlimiting examples of such groups include naphthyl, 1,2,3,4 tetrahydronaphthyl, indenyl, indanyl, and the like.

The term "carbocyclic" means a cyclic ring moiety containing only carbon atoms in the ring(s) without regard to aromaticity. A 3-10 membered carbocyclic means chemically feasible monocyclic and fused bicyclic carbocyclics having from 3 to 10 ring atoms. Similarly, a 4-6 membered carbocyclic means monocyclic carbocyclic ring moieties having 4 to 6 ring carbons, and a 9-10 membered carbocyclic means fused bicyclic carbocyclic ring moieties having 9 to 10 ring carbons.

The term "cycloalkyl" means a non-aromatic 3-12 carbon mono-cyclic, bicyclic, or polycyclic aliphatic ring moiety. Cycloalkyl can be bicycloalkyl, polycycloalkyl, bridged, or spiroalkyl. One or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

The term "unsaturated carbocyclic" means any cycloalkyl containing at least one double or triple bond. The term "cycloalkenyl" means a cycloalkyl having at least one double bond in the ring moiety.

The terms "bicycloalkyl" and "polycycloalkyl" mean a structure consisting of two or more cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" means a structure consisting of two cycloalkyl moieties that have exactly one atom in common. Examples include, but are not limited to, spiro[4.5]decyl, spiro[2.3]hexyl, and the like.

The term "aromatic" means a planar ring moieties containing 4n+2 pi electrons, wherein n is an integer.

The term "aryl" means aromatic moieties containing only carbon atoms in its ring system. Non-limiting examples include phenyl, naphthyl, and anthracenyl. The terms "arylalkyl" or "arylalkyl" or "aralkyl" refer to any alkyl that forms a bridging portion with a terminal aryl.

"Aralkyl" means alkyl that is substituted with an aryl group as defined above; e.g., —$CH_2$ phenyl, —$(CH_2)_2$phenyl, —$(CH_2)_3$ phenyl, $CH_3CH(CH_3)CH_2$phenyl, and the like and derivatives thereof.

The term "heterocyclic" means a cyclic ring moiety containing at least one heteroatom (N, O, or $S(O)_{0-2}$), including heteroaryl, heterocycloalkyl, including unsaturated heterocyclic rings.

The term "heterocycloalkyl" means a non-aromatic monocyclic, bicyclic, or polycyclic heterocyclic ring moiety of 3 to 12 ring atoms containing at least one ring having one or more heteroatoms. The rings may also have one or more double bonds. However, the rings do not have a completely conjugated pi-electron system. Examples, without limitation, of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diaza-spiro[4.5]decane, 6-oxa-2-thia-spiro[3.4]octane, octahydropyrrolo[1,2-a]pyrazine, 7-azabicyclo[2.2.1]heptane, 2-oxa-bicyclo[2.2.2]octane, and the like, are such heterocycloalkyls.

Examples of saturated heterocyclic groups include, but are not limited to oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl Non-aryl heterocyclic groups include saturated and unsaturated systems and can include groups having only 4 atoms in their ring system. The heterocyclic groups include benzo-fused ring systems and ring systems substituted with one or more oxo moieties. Recitation of ring sulfur is understood to include the sulfide, sulfoxide or sulfone where feasible. The heterocyclic groups also include partially unsaturated or fully saturated 4-10 membered ring systems, e.g., single rings of 4 to 8 atoms in size and bicyclic ring systems, including aromatic 6-membered aryl or heteroaryl rings fused to a non-aromatic ring. Also included are 4-6 membered ring systems ("4-6 membered heterocyclic"), which include 5-6 membered heteroaryls, and include groups such as azetidinyl and piperidinyl. Heterocyclics can be heteroatom-attached where such is possible. For instance, a group derived from pyrrole can be pyrrol-1-yl (N-attached) or pyrrol-3-yl (C-attached). Other heterocyclics include imidazo(4,5-b)pyridin-3-yl and benzoimidazol-1-yl.

Examples of heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and the like.

The term "unsaturated heterocyclic" means a heterocycloalkyl containing at least one unsaturated bond. The term "heterobicycloalkyl" means a bicycloalkyl structure in which at least one carbon atom is replaced with a heteroatom. The term "heterospiroalkyl" means a spiroalkyl structure in which at least one carbon atom is replaced with a heteroatom.

Examples of partially unsaturated heteroalicyclic groups include, but are not limited to: 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

The terms "heteroaryl" or "hetaryl" mean a monocyclic, bicyclic, or polycyclic aromatic heterocyclic ring moiety containing 5-12 atoms. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, indazole, imidazo[1,2-a]pyridine, 3-methyl-2-oxo-2,3-dihydrobenzo[d]oxazol-5-yl, 2-methyl-2H-indazol-5-yl, 3-methylimidazo[1,5-a]pyridine, 2-methyl-1H-benzo[d]imidazole, 1H-pyrrolo[2,3-b]pyridine, 3,4-Dihydro-2H-benzo[b][1,4]oxazine, 2-oxo-2,3-dihydrobenzo[d]oxazole, 3-oxo-3,4-dihydro-2H-benzo[b][1,4]oxazine, 2,3-Dihydrobenzo[b][1,4]dioxine, 2-methyl-[1,2,4]triazolo[1,5-a]pyridine, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

Heteroaryls include, e.g., 5 and 6 membered monocyclics such as pyrazinyl and pyridinyl, and 9 and 10 membered fused bicyclic ring moieties, such as quinolinyl. Other examples of heteroaryl include quinolin-4-yl, 7-methoxyquinolin-4-yl, pyridin-4-yl, pyridin-3-yl, and pyridin-2-yl. Other examples of heteroaryl include pyridinyl, imidazolyl, pyrimidinyl, pyrazolyl, triazolyl, pyrazinyl, tetrazolyl, furanyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. Examples of 5-6 membered heteroaryls include, thiophenyl, isoxazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2,5-triazinyl, 1,3,5-triazinyl, 6-oxo-1,6-dihydropyridine, and the like.

"Heteroaralkyl" group means alkyl, preferably lower alkyl, that is substituted with a heteroaryl group; e.g., —CH$_2$ pyridinyl, —(CH$_2$)$_2$pyrimidinyl, —(CH$_2$)$_3$imidazolyl, and the like, and derivatives thereof.

A pharmaceutically acceptable heteroaryl is one that is sufficiently stable to be attached to a compound of the invention, formulated into a pharmaceutical composition and subsequently administered to a patient in need thereof.

Examples of monocyclic heteroaryl groups include, but are not limited to: pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl tetrazolyl, pyridinyl, pyridazinyl, pyrimidinyl, pyrazinyl.

Examples of fused ring heteroaryl groups include, but are not limited to: benzoduranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, azaquinazoline, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrimido[2,3-b]pyrazinyl, pyrimido[4,5-d]pyrimidinyl.

"Arylthio" means an —S-aryl or an —S-heteroaryl group, as defined herein. Representative examples include, but are not limited to, phenylthio, pyridinylthio, furanylthio, thienylthio, pyrimidinylthio, and the like and derivatives thereof.

The term "9-10 membered heterocyclic" means a fused 5,6 or 6,6 bicyclic heterocyclic ring moiety, which can be saturated, unsaturated or aromatic. The term "9-10 membered fused bicyclic heterocyclic" also means a phenyl fused to one 5 or 6 membered heterocyclic group. Examples include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3 benzo[1,3]dioxolyl, 2H-chromanyl, isochromanyl, 5-oxo-2,3 dihydro-5H-[1,3]thiazolo[3,2-a]pyrimidyl, 1,3-benzothiazolyl, 1,4,5,6 tetrahydropyridazyl, 1,2,3,4,7,8hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3-ihydro-1H-indolyl, 1,3-dihydro-2H-isoindol-2-yl, 2,4,7-trioxo-1,2,3,4,7,8-hexahydropteridin-yl, thieno[3,2-d]pyrimidinyl, 4-oxo-4,7-dihydro-3H-pyrrolo[2,3-d]pyrimidin-yl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo-[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpyridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin4-yl, 4,5,6,7-tetrahydro-benzo[b]-thiophenyl-2-yl, 1,8-naphthyridinyl, 1,5-napthyridinyl, 1,6-naphthyridinyl, 1,7-napthyridinyl, 3,4-dihydro-2H-1,4-benzothiazine, 4,8-dihydroxy-quinolinyl, 1-oxo-1,2-dihydro-isoquinolinyl, 4-phenyl-[1,2,3]thiadiazolyl, and the like.

The term "aryloxy" means an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

The term "oxo" means a compound containing a carbonyl group. One in the art understands that an "oxo" requires a second bond from the atom to which the oxo is attached.

The term "halo" or "halogen" means fluoro, chloro, bromo, or iodo.

"Acyl" means a —C(O)R group, where R can be selected from the nonlimiting group of hydrogen or optionally substituted lower alkyl, trihalomethyl, unsubstituted cycloalkyl, aryl, or other suitable substituent.

"Thioacyl" or "thiocarbonyl" means a —C(S)R" group, with R as defined above.

The term "protecting group" means a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2d Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, CBZ, and various hydroxy protecting groups familiar to those skilled in the art including the groups referred to in Greene.

The term "linear structure" means a moiety having substituents that do not cyclize to form a ring system. A representative example includes, but is not limited to, a compound including —NR$^X$R$^Y$ where any atoms of "Rx" and any atoms of "R$^Y$" do not connect to form a ring.

As used herein, the term "pharmaceutically acceptable salt" means those salts which retain the biological effectiveness and properties of the parent compound and do not present safety or toxicity issues. The term "pharmaceutically acceptable salt(s)" is known in the art and includes salts of acidic or basic groups which can be present in the compounds and prepared or resulting from pharmaceutically acceptable bases or acids.

The term "pharmaceutical composition" means an active compound in any form suitable for effective administration to a subject, e.g., a mixture of the compound and at least one pharmaceutically acceptable carrier.

As used herein, a "physiologically/pharmaceutically acceptable carrier" means a carrier or diluent that does not cause significant irritation to an organism and does not abrogate the biological activity and properties of the administered compound.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "treat," "treatment," and "treating" means reversing, alleviating, inhibiting the progress of, or partially or completely preventing the disorder or condition to which such term applies, or one or more symptoms of such disorder or condition. "Preventing" means treating before an infection occurs.

"Therapeutically effective amount" means that amount of the compound being administered which will relieve to some extent one or more of the symptoms of the disorder being treated, or result in inhibition of the progress or at least partial reversal of the condition.

NMR Nuclear magnetic resonance
MDP(S) Mass-directed HPLC purification (system)
LC/MS Liquid chromatography mass spectrometry
LDA Lithium diisopropylamide
tert-BuOH tert-Butanol
AcOH Acetic acid
CDI 1,1'-Carbonyldiimidazole
DCE 1,1-Dichloroethane
DCM Dichloromethane
DMF Dimethylformamide
THF Tetrahydrofuran
MeOH Methanol
EtOH Ethanol
EtOAc Ethyl acetate
MeCN Acetonitrile
DMSO Dimethylsulfoxide
Boc tert-Butyloxycarbonyl
DME 1,2-Dimethoxyethane
DMF N,N-Dimethylformamide
DIPEA/DIEA Diisopropylethylamine
PS-DIEA Polymer-supported diisopropylethylamine
PS—PPh$_3$-Pd Polymer-supported Pd(PPh$_3$)$_4$
LAH Lithium aluminum hydride
EDC 1-(3-Dimethylaminopropyl)-3-ethylcarbodiimide
HATU: 1-[bis(dimethylamino)methylene]-1H-1,2,3-triazolo[4,5-b]pyridinium-3-oxide hexafluorophosphate
HOBt 1-Hydroxybenzotnazole
DMAP 4-Dimethylaminopyridine
SEM-Cl 2-(Trimethylsilyl)ethoxymethyl chloride
TBTU O-(Benzotriazol-1-yl)-N,N,N',N'-tetramethyluronium tetrafluoroborate
TEMPO 2,2,6,6-Tetramethylpiperidine-1-oxyl
TFA (A) Trifluoroacetic acid (anhydride)
TLC Thin layer chromatography
TMSCN Trimethylsilyl cyanide
Min Minute(s)
NMO N-Methylmorpholine N-oxide
h Hour(s)
d Day(s)
RT, R.T., r.t., r.t or rt Room temperature
t$_R$ Retention time
Conc. Concentrated

What is claimed is:

1. A method for reversing, alleviating, or inhibiting the progress of lymphoma, comprising administering to a subject in need thereof a therapeutic amount of 6-(1-acryloylpiperidin-4-yl)-2-(4-phenoxyphenyl)nicotinamide, or a pharmaceutically acceptable salt or solvate thereof:

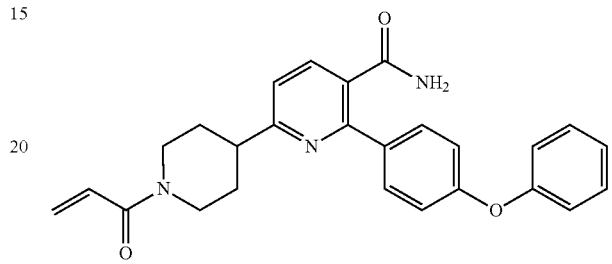

wherein the lymphoma is selected from the group consisting of: chronic lymphocytic leukemia (CLL), small lymphocytic lymphoma (SLL), mantle cell lymphoma (MCL), Waldenström's Macroglobulinemia (WM), marginal zone lymphoma (MZL), diffuse Large B-Cell Lymphoma (DLBCL), and central nervous system (CNS) lymphoma.

2. The method according to claim 1, wherein the cancer is CLL.

3. The method according to claim 1, wherein the cancer is SLL.

4. The method according to claim 1, wherein the cancer is MCL.

5. The method according to claim 1, wherein the cancer is WM.

6. The method according to claim 1, wherein the cancer is MZL.

7. The method according to claim 1, wherein the cancer is DLBCL.

8. The method according to claim 1, wherein the cancer is CNS lymphoma.

* * * * *